US009557856B2

(12) United States Patent
Send et al.

(10) Patent No.: US 9,557,856 B2
(45) Date of Patent: Jan. 31, 2017

(54) OPTICAL DETECTOR

(71) Applicant: BASF SE, Ludwigshafen (DE)

(72) Inventors: Robert Send, Karlsruhe (DE); Ingmar Bruder, Neuleiningen (DE); Stephan Irle, Siegen (DE); Erwin Thiel, Siegen (DE); Henrike Wonneberger, Mannheim (DE)

(73) Assignee: BASF SE, Ludwigshafen (DE)

( * ) Notice: Subject to any disclaimer, the term of this patent is extended or adjusted under 35 U.S.C. 154(b) by 127 days.

(21) Appl. No.: 14/460,540

(22) Filed: Aug. 15, 2014

(65) Prior Publication Data
US 2015/0286340 A1    Oct. 8, 2015

Related U.S. Application Data

(60) Provisional application No. 61/867,180, filed on Aug. 19, 2013, provisional application No. 61/906,430, (Continued)

(30) Foreign Application Priority Data

Mar. 6, 2014 (DE) .................. 10 2014 006 279
Jun. 10, 2014 (EP) .................... 14171759

(51) Int. Cl.
*G06F 3/042* (2006.01)
*G01J 4/04* (2006.01)
(Continued)

(52) U.S. Cl.
CPC ............ *G06F 3/0425* (2013.01); *G01B 11/25* (2013.01); *G01J 1/42* (2013.01); *G01J 4/04* (2013.01);
(Continued)

(58) Field of Classification Search
CPC ...... G06F 3/0425; G01S 17/026; G01S 17/42; G01S 17/46; G01S 17/66; G01S 17/936; G01S 7/499; G01S 7/4816; G01S 11/12; G01S 5/163; G01J 1/42; G01J 4/04; G06K 9/74; G06T 7/0042; G06T 2207/10016; G06T 2207/10152; G01N 30/74
(Continued)

(56) References Cited

U.S. PATENT DOCUMENTS 3,035,176 A    5/1962    Kis et al.
3,384,752 A    5/1968    Odone
(Continued)

FOREIGN PATENT DOCUMENTS

CA    2196563    12/1996
CN    1677053 A    10/2005
(Continued)

OTHER PUBLICATIONS

Paul Pargas, "Phenomena of Image Sharpness Recognition of CdS and CdSe Photoconductors" Journal of the Optical Society of America, vol. 54, No. 4, Apr. 1964, pp. 516-519.
(Continued)

*Primary Examiner* — Amare Mengistu
*Assistant Examiner* — Jennifer Zubajlo
(74) *Attorney, Agent, or Firm* — Oblon, McClelland, Maier & Neustadt, L.L.P.

(57) ABSTRACT

An optical detector (110) is disclosed, the optical detector (110) comprising:
at least one spatial light modulator (114) being adapted to modify at least one property of a light beam (136) in a spatially resolved fashion, having a matrix (132) of pixels (134), each pixel (134) being controllable to individually modify the at least one optical property of a portion of the light beam (136) passing the pixel (134);

(Continued)

at least one optical sensor (116) adapted to detect the light beam (136) after passing the matrix (132) of pixels (134) of the spatial light modulator (114) and to generate at least one sensor signal;

at least one modulator device (118) adapted for periodically controlling at least two of the pixels (134) with different modulation frequencies; and at least one evaluation device (120) adapted for performing a frequency analysis in order to determine signal components of the sensor signal for the modulation frequencies.

34 Claims, 19 Drawing Sheets

Related U.S. Application Data filed on Nov. 20, 2013, provisional application No. 61/914,402, filed on Dec. 11, 2013.

(51) Int. Cl.
*G01S 7/499* (2006.01)
*G01J 1/42* (2006.01)
*G01S 17/02* (2006.01)
*G01S 17/42* (2006.01)
*G01S 17/66* (2006.01)
*G01S 17/93* (2006.01)
*G01S 7/481* (2006.01)
*G01S 11/12* (2006.01)
*G06T 7/00* (2006.01)
*G01S 17/46* (2006.01)
*G01S 5/16* (2006.01)
*G06K 9/74* (2006.01)
*G01B 11/25* (2006.01)
*G01N 30/74* (2006.01)

(52) U.S. Cl.
CPC ............ *G01S 5/163* (2013.01); *G01S 7/4816* (2013.01); *G01S 7/499* (2013.01); *G01S 11/12* (2013.01); *G01S 17/026* (2013.01); *G01S 17/42* (2013.01); *G01S 17/46* (2013.01); *G01S 17/66* (2013.01); *G01S 17/936* (2013.01); *G06K 9/741* (2013.01); *G06T 7/0042* (2013.01); *G01N 30/74* (2013.01); *G06T 2207/10016* (2013.01); *G06T 2207/10152* (2013.01)

(58) Field of Classification Search
USPC ........................................................ 345/175
See application file for complete search history.

(56) References Cited

U.S. PATENT DOCUMENTS

| | | |
|---|---|---|
| 3,562,785 A | 2/1971 | Craig |
| 3,937,950 A | 2/1976 | Hosoe et al. |
| 3,954,340 A | 5/1976 | Blomqvist et al. |
| 4,023,033 A | 5/1977 | Bricot et al. |
| 4,053,240 A | 10/1977 | Aizawa et al. |
| 4,079,247 A | 3/1978 | Bricot et al. |
| 4,256,513 A | 3/1981 | Yoshida |
| 4,469,945 A | 9/1984 | Hoeberechts et al. |
| 4,524,276 A | 6/1985 | Ohtombe |
| 4,603,258 A | 7/1986 | Sher et al. |
| 4,647,193 A | 3/1987 | Rosenfeld |
| 4,675,535 A | 6/1987 | Tsunekawa et al. |
| 4,767,211 A | 8/1988 | Munakata et al. |
| 4,927,721 A | 5/1990 | Gratzel et al. |
| 5,216,476 A | 6/1993 | Lanckton |
| 5,350,644 A | 9/1994 | Graetzel et al. |
| 6,266,142 B1 | 7/2001 | Junkins et al. |
| 6,359,211 B1 | 3/2002 | Spitler et al. |
| 6,930,297 B1 | 8/2005 | Nakamura |
| 6,995,445 B2 | 2/2006 | Forrest et al. |
| 7,196,317 B1 | 3/2007 | Meissner et al. |
| 7,417,716 B2 | 8/2008 | Nagasaka et al. |
| 7,626,569 B2 | 12/2009 | Lanier |
| 7,677,742 B2 | 3/2010 | Hillmer et al. |
| 8,144,173 B2 | 3/2012 | Baba |
| 8,228,299 B1 | 7/2012 | Maloney et al. |
| 8,231,809 B2 | 7/2012 | Pschirer et al. |
| 8,563,855 B2 | 10/2013 | Pschirer et al. |
| 9,001,029 B2 | 4/2015 | Bruder et al. |
| 9,389,315 B2 | 7/2016 | Bruder et al. |
| 2001/0025938 A1 | 10/2001 | Imai |
| 2002/0011576 A1 | 1/2002 | Cho et al. |
| 2003/0017360 A1 | 1/2003 | Tai et al. |
| 2003/0094607 A1 | 5/2003 | Guenther et al. |
| 2003/0132391 A1 | 7/2003 | Agano |
| 2003/0227635 A1 | 12/2003 | Muller |
| 2004/0178325 A1 | 9/2004 | Forrest et al. |
| 2004/0216625 A1 | 11/2004 | Birnstock et al. |
| 2005/0052120 A1 | 3/2005 | Gupta et al. |
| 2005/0184301 A1 | 8/2005 | Nagasaka et al. |
| 2005/0217720 A1 | 10/2005 | Rey-Mermet et al. |
| 2005/0268957 A1 | 12/2005 | Enomoto et al. |
| 2005/0269616 A1 | 12/2005 | Andriessen |
| 2006/0049397 A1 | 3/2006 | Pfeiffer et al. |
| 2006/0082546 A1 | 4/2006 | Wey |
| 2007/0008515 A1 | 1/2007 | Otani et al. |
| 2007/0010924 A1 | 1/2007 | Otani et al. |
| 2007/0080925 A1 | 4/2007 | Radivojevic et al. |
| 2007/0122927 A1 | 5/2007 | Li et al. |
| 2007/0176165 A1 | 8/2007 | Forrest et al. |
| 2008/0080789 A1 | 4/2008 | Marks |
| 2008/0259310 A1 | 10/2008 | Wada |
| 2008/0269482 A1 | 10/2008 | Pschirer et al. |
| 2009/0097010 A1 | 4/2009 | Yamaguchi |
| 2009/0231582 A1 | 9/2009 | Aebischer |
| 2010/0091263 A1 | 4/2010 | Kumagai et al. |
| 2010/0141964 A1 | 6/2010 | Horsch |
| 2010/0194942 A1 | 8/2010 | Wada |
| 2010/0231513 A1 | 9/2010 | Deliwala |
| 2010/0258179 A1 | 10/2010 | Wieting |
| 2010/0279458 A1 | 11/2010 | Yeh |
| 2010/0282309 A1 | 11/2010 | Pschirer et al. |
| 2010/0283868 A1 | 11/2010 | Clark et al. |
| 2010/0297405 A1 | 11/2010 | Flores et al. |
| 2011/0055846 A1 | 3/2011 | Perez et al. |
| 2011/0096319 A1 | 4/2011 | Otani et al. |
| 2011/0099105 A1 | 4/2011 | Mennie et al. |
| 2011/0123188 A1 | 5/2011 | Cardwell et al. |
| 2011/0194097 A1 | 8/2011 | Yamaguchi et al. |
| 2011/0297235 A1 | 12/2011 | Bergmann |
| 2011/0306413 A1 | 12/2011 | Bickerstaff et al. |
| 2012/0206336 A1* | 8/2012 | Bruder .................. G01B 11/026 345/156 |
| 2012/0242867 A1 | 9/2012 | Shuster |
| 2012/0249998 A1 | 10/2012 | Eisele et al. |
| 2012/0250137 A1 | 10/2012 | Maxik et al. |
| 2012/0262365 A1 | 10/2012 | Mallinson |
| 2012/0289672 A1 | 11/2012 | Kastler et al. |
| 2013/0135604 A1 | 5/2013 | Gogolla et al. |
| 2013/0222551 A1* | 8/2013 | Shamir .................. G01B 11/25 348/47 |
| 2013/0271818 A1 | 10/2013 | Maxik et al. |
| 2014/0078376 A1 | 3/2014 | Shuster |
| 2014/0132724 A1 | 5/2014 | Choi et al. |
| 2014/0211295 A1 | 7/2014 | Maxik et al. |
| 2014/0291480 A1 | 10/2014 | Bruder et al. |
| 2015/0124268 A1 | 5/2015 | Bruder et al. |
| 2015/0286340 A1 | 10/2015 | Send et al. |
| 2016/0099429 A1 | 4/2016 | Bruder et al. |
| 2016/0124074 A1 | 5/2016 | Wonneberger et al. |

(56) References Cited

U.S. PATENT DOCUMENTS

| | | |
|---|---|---|
| 2016/0127664 A1 | 5/2016 | Bruder et al. |
| 2016/0139243 A1 | 5/2016 | Send et al. |

FOREIGN PATENT DOCUMENTS

| | | |
|---|---|---|
| CN | 1896686 A | 1/2007 |
| CN | 101290348 A | 10/2008 |
| CN | 101650173 A | 2/2010 |
| CN | 102096962 | 6/2011 |
| CN | 201897828 | 7/2011 |
| CN | 102549381 A | 7/2012 |
| CN | 102737435 | 10/2012 |
| CN | 103492835 | 1/2014 |
| DE | 2 417 854 | 10/1974 |
| DE | 25 01 124 A1 | 8/1975 |
| DE | 32 25 372 A1 | 2/1983 |
| DE | 10 2005 053 995 A1 | 5/2007 |
| DE | 10 2007 037 875 A1 | 2/2009 |
| EP | 0 185 450 A2 | 6/1986 |
| EP | 0 754 930 A2 | 1/1997 |
| EP | 1 176 646 | 1/2002 |
| EP | 1 191 819 A2 | 3/2002 |
| EP | 1 191 819 A3 | 3/2002 |
| EP | 1 330 117 A2 | 7/2003 |
| EP | 1 330 117 A3 | 7/2003 |
| EP | 1 667 246 A1 | 6/2006 |
| EP | 2 205 657 A1 | 7/2010 |
| EP | 2 220 141 A1 | 8/2010 |
| EP | 2 507 286 A2 | 10/2012 |
| EP | 2 527 866 A1 | 11/2012 |
| EP | 2 813 324 | 12/2014 |
| GB | 2 432 723 A | 5/2007 |
| JP | 8-159714 A | 6/1996 |
| JP | 10-221064 | 8/1998 |
| JP | 2005-241340 A | 9/2005 |
| WO | WO 99/09603 A1 | 2/1999 |
| WO | WO 01/29576 A1 | 4/2001 |
| WO | WO 02/101838 A1 | 12/2002 |
| WO | WO 2004/114112 A1 | 12/2004 |
| WO | WO 2005/106965 | 11/2005 |
| WO | WO 2006/134370 | 12/2006 |
| WO | WO 2007/054470 A1 | 5/2007 |
| WO | WO 2009/013282 A1 | 1/2009 |
| WO | WO 2009/053291 A1 | 4/2009 |
| WO | WO 2009/058115 A1 | 5/2009 |
| WO | WO 2010/088032 A2 | 8/2010 |
| WO | WO 2010/094636 A1 | 8/2010 |
| WO | WO 2011/067192 A2 | 6/2011 |
| WO | WO 2012/001628 A1 | 1/2012 |
| WO | WO 2012/046181 A1 | 4/2012 |
| WO | WO 2012/049038 A1 | 4/2012 |
| WO | WO 2012/085803 A1 | 6/2012 |
| WO | WO 2012/110924 A1 | 8/2012 |
| WO | WO 2012/139354 | 10/2012 |
| WO | 2012/152812 A1 | 11/2012 |
| WO | 2012/168395 A1 | 12/2012 |
| WO | WO 2013/091016 A1 | 6/2013 |
| WO | 2013/118037 A1 | 8/2013 |
| WO | WO 2013/144177 A1 | 10/2013 |
| WO | WO 2014/097181 A1 | 6/2014 |
| WO | 2014/198623 A1 | 12/2014 |
| WO | 2014/198625 A1 | 12/2014 |
| WO | 2014/198626 A1 | 12/2014 |

OTHER PUBLICATIONS

Paul Pargas, "A Lens Measuring Method Using Photoconductive Cells" Journal of the SMPTE, vol. 74, Jun. 1965, pp. 501-504.

Jack T. Billings, "An Improved Method for Critical Focus of Motion-Picture Optical Printers" Journal of the SMPTE, vol. 80, Aug. 1971, pp. 624-628.

International Search Report and Written Opinion issued Oct. 31, 2014 in PCT/EP2014/067466 filed Aug. 15, 2014.

Volker Viereck, et al., Large-area applications of optical MEMS: micromirror arrays guide daylight, optimize indoor illumination, Optical Components, Photonik International 2, 2009, pp. 48-49.

C.U. Murade, et al., "High speed adaptive liquid microlens array", Optics Express, vol. 20, No. 16, Jul. 2012, pp. 18180-18187.

Jason Heikenfeld, et al., "Recent Progress in Arrayed Electrowetting Optics", Optics & Photonics News, Jan. 2009, 7 pages, www.osa-opn.org.

Tao Peng, "Algorithms and models for 3-D shape measurement using digital fringe projections", Dissertation, University of Maryland (College Park, Md.), Jan. 16, 2007, 266 pages (http://drum.lib.umd.edu//handle/1903/6654; http://en.wikipedia.org/wiki/Gray_code; http://en.wikipedia.org/wiki/Structured-light_3D_scanner).

Jie-Ci Yang et al., "An Intelligent Automated Door Control System Based on a Smart", Sensors, 2013, 13(5), pp. 5923-5936; doi: 10.3390/s130505923 www.mdpi.com/journal/sensors.

Bin Peng et al., "Systematic investigation of the role of compact TiO2 layer in solid state dye-sensitized TiO2 solar cells", Coordination Chemistry Reviews, 248, 2004, pp. 1479-1489.

Brian O'Regan, et al., "A low-cost, high-efficiency solar cell based on dye-sensitized colloidal $TiO_2$ films", Nature vol. 353, (1991), pp. 737-740.

U. Bach, et al., Solid-state dye-sensitized mesoporous $TiO_2$ solar cells with high photon-to-electron conversion efficiencies, Nature vol. 395, Oct. 8, 1998, pp. 583-585 www.nature.com.

Lukas Schmidt-Mende et al., "Organic Dye for Highly Efficient Solid-State Dye-Sensitized Solar Cells", Advanced Materials, 2005, 17, No. 7, 3 pages.

V. P. S. Perera, et al., "Dye-Sensitized Solid-State Photovoltaic Cells Based on Dye Multilayer-Semiconductor Nanostructures", J. Phys. Chem., B., 2003, 107, pp. 13758-13761.

G.R.A. Kumara, et al., "Fabrication of Dye-Sensitized Solar Cells Using Triethylamine Hydrothiocyanate as a CuI Crystal Growth Inhibitor", Langmuir, 2002, 18, pp. 10493-10495.

Tobat P. I. Saragi, et al., "Comparison of Charge-Carrier Transport in Thin Films of Spiro-Linked Compounds and Their Corresponding Parent Compounds", DOI: 10.1002/adfm.200500361, Advanced Functional Materials, 2006, 16, 966-974.

Tomas Leijtens, et al., "Hole Transport Materials with Low Glass Transition Temperatures and High Solubility for Application in Solid-State Dye-Sensitized Solar Cells", ACS Nano, vol. 6, No. 2, 2012, pp. 1455-1462 www.acsnano.org.

DLP-Techoolgie, www.dlp.com/de/technology/how-dlp-works.

Leysop Ltd., Manufacturers and Suppliers of Electro-Optic Components, http://www.leysop.com/integrated_pockels_cell.htm.

Supplementary European Search Report issued Nov. 19, 2014, issued in corresponding European Patent Application No. EP 12 74 6808.

International Search Report and Written Opinion issued May 31, 2012 in PCT/IB2012/050592 filed on Feb. 9, 2012.

Atte Haapalinna, et al., "Measurement of the Absolute Linearity of Photodetectors with a Diode Laser," Meas. Sci. Technol., 10, (1999) 1075-1078.

Office Action issued Apr. 22, 2015 in Chinese Patent Application No. 201280018328.5 (submitting English translation only).

Extended Search Report issued Aug. 23, 2011 in Europe Application No. 11154531.5 (With English Translation of Category of Cited Documents).

Erwin Bacher, et al., "Synthesis and Characterization of Photo-Cross-Linkable Hole-Conducting Polymers", Macromolecules, vol. 38, 2005, pp. 1640-1647.

H. Bruce Goodbrand, et al., "Ligand-Accelerated Catalysis of the Ullmann Condensation: Application to Hole Conducting Triarylamines", J. Org. Chem., vol. 64, 1999, pp. 670-674.

Felix E. Goodson, et al., "Palladium-Catalyzed Synthesis of Pure, Regiodefined Polymeric Triarylamines", J. Am. Chem. Soc., vol. 121, 1999, pp. 7527-7539.

John F. Hartwig, "Transition Metal Catalyzed Synthesis of Arylamines and Aryl Ethers from Aryl Halides and Triflates: Scope and Mechanism", Angew. Chem. Int. Ed., vol. 37, 1998, pp. 2046-2067.

(56) References Cited

OTHER PUBLICATIONS

Sheila I. Hauck, et al., "Tetraazacyclophanes by Palladium-Catalyzed Aromatic Amination. Geometrically Defined, Stable, High-Spin Diradicals", Organic Letters, vol. 1, No. 13, 1999. pp. 2057-2060.

Ping-Hsin Huang, et al., "Synthesis and Characterization of new fluorescent two-photon absorption chromophores", J. Mater. Chem., vol. 16, 2006, pp. 850-857.

Qinglan Huang, et al., "Molecularly 'Engineered' Anode Adsorbates for Probing OLED Interfacial Structure-Charge Injection/Luminance Relationships: Large, Structure-Dependent Effects", J. Am. Chem. Soc., vol. 125, 2003, pp. 14704-14705.

A. Balionyte, et al., "Carbazolyl-substituted triphenyldiamine derivatives as novel photoconductive amorphous molecular materials", Journal of Photochemistry and Photobiology A: Chemistry, vol. 162, 2004, pp. 249-252.

G. R. A. Kumara, et al., "Fabrication of Dye-Sensitized Solar Cells Using Triethylamine Hydrothiocyanate as a CuI Crystal Growth Inhibitor", Langmuir, vol. 18, 2002, pp. 10493-10495.

Lukas Schmidt-Mende, et al., "Organic Dye for Highly Efficient Solid-State Dye-Sensitized Solar Cells", Adv. Mater., vol. 17, No. 7, 2005, pp. 813-815.

James Lindley, "Copper Assisted Nucleophilic Substitution of Aryl Halogen", Tetrahedron, vol. 40, No. 9, 1984, pp. 1433-1456.

Yunqi Liu, et al., "Synthesis and characterization of a novel bipolar polymer for light-emitting diodes", Chem. Commun., vol. 24, 1998, pp. 2747-2748.

Narukuni Hirata, et al., "Interface engineering for solid-state dye-sensitised nanocrystalline solar cells: the use of an organic redox cascade", Chem. Commun., vol. 5, 2006, pp. 535-537.

Qingjiang Yu, et al.. "High-Efficiency Dye-Sensitized Solar Cells: The Influence of Lithium Ions on Exciton Dissociation, Charge Recombination, and Surface States", ACS Nano, vol. 4, No. 10, 2010, pp. 6032-6038.

John P. Wolfe, et al., "Rational Development of Practical Catalysts for Aromatic Carbon—Nitrogen Bond Formation", Acc. Chem. Res. vol. 31, 1998, pp. 805-818.

Bryant H. Yang, et al., "Palladium-Catalyzed amination of aryl halides and sulfonates", Journal of Organometallic Chemistry, vol. 576, 1999, pp. 125-146.

Zhong Hui Li, et al., "Synthesis and Functional Properties of Strongly Luminescent Diphenylamino End-Capped Oligophenylenes", J. Org. Chem., vol. 69, 2004, pp. 921-927.

M. R. Andersen, et al., "Kinect Depth Sensor Evaluation for Computer Vision Applications",Electrical and Computer Engineering, Technical Report ECE-TR-6, Aarhus University, 2012, 39 pages.

Takumi Kinoshita, et al., "Wideband dye-sensitized solar cells employing a phosphine-coordinated ruthenium sensitizer". Nature Photonics, vol. 7, 2013, pp. 535-239.

International Search Report and Written Opinion of the International Searching Authority issued May 16, 2014 in PCT/IB2013/061095.

Lukas Schmidt-Mende, et al.. "Organic Dye for Highly Efficient Solid-State Dye-Sensitized Solar Cells", Adv. Mater., vol. 17, No. 7, 2005, pp. 813-815.

Seigo Ito, et al., "High-Efficiency Organic-Dye-Sensitized Solar Cells Controlled by Nanocrystalline-$TiO_2$ Electrode Thickness". Adv. Mater., vol. 18, 2006, pp. 1202-1205.

Hiura, S., et al., "Depth Measurement by the Multi-Focus Camera," Computer Vision and Pattern Recognition. 1998. Proceedings. 1998 IEEE Computer Society Conference on Santa Barbara, CA, USA, Jun. 23-25, 1998, pp. 953-959.

Kuthirumal, S., et al., "Flexible Depth of Field Photography," IEEE Transactions on Pattern Analysis and Machine Intelligence, vol. 33, No. 1 (2011), pp. 58-71.

Jiun Yi Shen, et al., "High Tg Blue Emitting Materials for Electroluminescent Devices," J. Mater. Chem., 2005, 15, 2455-2463.

"So funktioniert die DLP-Technologie" DLP-Technologie—www.dlp.com/de/technology/how-dlp-works, 2014, 2 Pages.

"New—Ultra-Compact Pockels Cells with Brewster Polarizer and Waveplate for Laser Q-Switching" Leysop Ltd, Manfacturers and Suppliers of Electro-Optic Components—http://www.leysop.com/integrated_pockels_cell.htm, Aug. 4, 2013, 2 Pages.

D. Scaramuzza, et al., "Extrinsic Self Calibration of a Camera and a 3D Laser Range Finder from Natural Scenes" 2007 IEEE/RSJ international Conference on Intelligent Robots and Systems, 2007, 8 pages.

Denis Klimentjew, et al., "Multi Sensor Fusion of Camera and 3D Laser Range Finder for Object Recognition" 2010 IEEE International Conference on Multisensor Fusion and Integration for Intelligent Systems, 2010, pp. 236-241.

U.S. Appl. No. 14/460,529, filed Aug. 15, 2014, Send, et al.
U.S. Appl. No. 15/099,717, filed Apr. 15, 2016, Bruder, et al.
U.S. Appl. No. 15/105,489, filed Jun. 16, 2016, Send, et al.

International Search Report and Written Opinion of the International Searching Authority Issued Mar. 12, 2015 in PCT/EP2014/078155 Filed Dec. 17, 2014.

International Search Report issued Aug. 28, 2015, in PCT/IB2015/052769, filed Apr. 16, 2015.

International Search Report and Written Opinion issued Nov. 21, 2014 in PCT/EP2014/067465.

Written Opinion of the International Searching Authority Issued Sep. 9, 2014 in PCT/EP2014/061688 filed Jun. 5, 2014.

International Search Report and Written Opinion issued Sep. 3, 2014 in PCT/EP2014/061691.

International Preliminary Report on Patentability issued Sep. 25, 2015 in PCT/EP2014/061691.

International Search Report issued Sep. 24, 2014 in PCT/EP2014/061682.

International Preliminary Report on Patentability and Written Opinion issued Dec. 15, 2015 in PCT/EP2014/061682.

International Preliminary Report on Patentability and Written Opinion issued Dec. 23, 2015 in PCT/EP2014/061695.

International Preliminary Report on Patentability and Written Opinion issued Dec. 23, 2015 in PCT/EP2014/061688.

International Search Report and Written Opinion issued Oct. 31, 2014 in PCT/EP2014/067466.

\* cited by examiner

OPTICAL DETECTOR

The present invention is based on previous U.S. provisional patent applications No. 61/867,180, dated Aug. 19, 2013, No. 61/906,430, dated Nov. 20, 2013 and No. 61/914,402, dated Dec. 11, 2013, and on German patent application number 10 2014 006 279.1, dated Mar. 6, 2014. The full content of these prior applications is herewith included by reference.

FIELD OF THE INVENTION

The invention relates to an optical detector, a detector system and a method of optical detection, specifically for determining a position of at least one object. The invention further relates to a human-machine interface for exchanging at least one item of information between a user and a machine, an entertainment device, a tracking system, a camera and various uses of the optical detector. The devices, systems, methods and uses according to the present invention specifically may be employed for example in various areas of daily life, gaming, traffic technology, production technology, security technology, photography such as digital photography or video photography for arts, documentation or technical purposes, medical technology or in the sciences. Additionally or alternatively, the application may be applied in the field of mapping of spaces, such as for generating maps of one or more rooms, one or more buildings or one or more streets. However, other applications are also possible.

PRIOR ART

A large number of optical detectors, optical sensors and photovoltaic devices are known from the prior art. While photovoltaic devices are generally used to convert electromagnetic radiation, for example, ultraviolet, visible or infrared light, into electrical signals or electrical energy, optical detectors are generally used for picking up image information and/or for detecting at least one optical parameter, for example, a brightness.

A large number of optical sensors which can be based generally on the use of inorganic and/or organic sensor materials are known from the prior art. Examples of such sensors are disclosed in US 2007/0176165 A1, U.S. Pat. No. 6,995,445 B2, DE 2501124 A1, DE 3225372 A1 or else in numerous other prior art documents. To an increasing extent, in particular for cost reasons and for reasons of large-area processing, sensors comprising at least one organic sensor material are being used, as described for example in US 2007/0176165 A1. In particular, so-called dye solar cells are increasingly of importance here, which are described generally, for example in WO 2009/013282 A1.

As a further example, WO 2013/144177 A1 discloses quinolinium dyes having a fluorinated counter anion, an electrode layer which comprises a porous film made of oxide semiconductor fine particles sensitized with these kinds of quinolinium dyes having a fluorinated counter anion, a photoelectric conversion device which comprises such a kind of electrode layer, and a dye sensitized solar cell which comprises such a photoelectric conversion device.

A large number of detectors for detecting at least one object are known on the basis of such optical sensors. Such detectors can be embodied in diverse ways, depending on the respective purpose of use. Examples of such detectors are imaging devices, for example, cameras and/or microscopes. High-resolution confocal microscopes are known, for example, which can be used in particular in the field of medical technology and biology in order to examine biological samples with high optical resolution. Further examples of detectors for optically detecting at least one object are distance measuring devices based, for example, on propagation time methods of corresponding optical signals, for example laser pulses. Further examples of detectors for optically detecting objects are triangulation systems, by means of which distance measurements can likewise be carried out.

In US 2007/0080925 A1, a low power consumption display device is disclosed. Therein, photoactive layers are utilized that both respond to electrical energy to allow a display device to display information and that generate electrical energy in response to incident radiation. Display pixels of a single display device may be divided into displaying and generating pixels. The displaying pixels may display information and the generating pixels may generate electrical energy. The generated electrical energy may be used to provide power to drive an image.

In EP 1 667 246 A1, a sensor element capable of sensing more than one spectral band of electromagnetic radiation with the same spatial location is disclosed. The element consists of a stack of sub-elements each capable of sensing different spectral bands of electromagnetic radiation. The sub-elements each contain a non-silicon semiconductor where the non-silicon semiconductor in each sub-element is sensitive to and/or has been sensitized to be sensitive to different spectral bands of electromagnetic radiation.

In WO 2012/110924 A1, the content of which is herewith included by reference, a detector for optically detecting at least one object is proposed. The detector comprises at least one optical sensor. The optical sensor has at least one sensor region. The optical sensor is designed to generate at least one sensor signal in a manner dependent on an illumination of the sensor region. The sensor signal, given the same total power of the illumination, is dependent on a geometry of the illumination, in particular on a beam cross section of the illumination on the sensor area. The detector furthermore has at least one evaluation device. The evaluation device is designed to generate at least one item of geometrical information from the sensor signal, in particular at least one item of geometrical information about the illumination and/or the object.

U.S. provisional applications 61/739,173, filed on Dec. 19, 2012, 61/749,964, filed on Jan. 8, 2013, and 61/867,169, filed on Aug. 19, 2013, and international patent application PCT/IB2013/061095, published under WO2014/097181 A1, filed on Dec. 18, 2013, the full content of all of which is herewith included by reference, disclose a method and a detector for determining a position of at least one object, by using at least one transversal optical sensor and at least one optical sensor. Specifically, the use of sensor stacks is disclosed, in order to determine a longitudinal position of the object with a high degree of accuracy and without ambiguity.

European patent application number EP 13171898.3, filed on Jun. 13, 2013, the full content of which is herewith included by reference, discloses an optical detector comprising an optical sensor having a substrate and at least one photosensitive layer setup disposed thereon. The photosensitive layer setup has at least one first electrode, at least one second electrode and at least one photovoltaic material sandwiched in between the first electrode and the second electrode. The photovoltaic material comprises at least one organic material. The first electrode comprises a plurality of first electrode stripes, and the second electrode comprises a plurality of second electrode stripes, wherein the first electrode stripes and the second electrode stripes intersect in such a way that a matrix of pixels is formed at intersections of the first electrode stripes and the second electrode stripes. The optical detector further comprises at least one readout device, the readout device comprising a plurality of electrical measurement devices being connected to the second electrode stripes and a switching device for subsequently connecting the first electrode stripes to the electrical measurement devices.

European patent application number EP 13171900.7, also filed on Jun. 13, 2013, the full content of which is herewith included by reference, discloses a detector device for determining an orientation of at least one object, comprising at least two beacon devices being adapted to be at least one of attached to the object, held by the object and integrated into the object, the beacon devices each being adapted to direct light beams towards a detector, and the beacon devices having predetermined coordinates in a coordinate system of the object. The detector device further comprises at least one detector adapted to detect the light beams traveling from the beacon devices towards the detector and at least one evaluation device, the evaluation device being adapted to determine longitudinal coordinates of each of the beacon devices in a coordinate system of the detector. The evaluation device is further adapted to determine an orientation of the object in the coordinate system of the detector by using the longitudinal coordinates of the beacon devices.

European patent application number EP 13171901.5, filed on Jun. 13, 2013, the full content of which is herewith included by reference, discloses a detector for determining a position of at least one object. The detector comprises at least one optical sensor being adapted to detect a light beam traveling from the object towards the detector, the optical sensor having at least one matrix of pixels. The detector further comprises at least one evaluation device, the evaluation device being adapted to determine a number N of pixels of the optical sensor which are illuminated by the light beam. The evaluation device is further adapted to determine at least one longitudinal coordinate of the object by using the number N of pixels which are illuminated by the light beam.

Despite the advantages implied by the above-mentioned devices and detectors, specifically by the detectors disclosed in WO 2012/110924 A1, U.S. 61/739,173, U.S. 61/749,964, EP 13171898.3, EP 13171900.7 and EP 13171901.5, several technical challenges remain. Thus, generally, a need exists for detectors for detecting a position of an object in space which is both reliable and may be manufactured at low cost. Specifically, a strong need exists for detectors having a high resolution, in order to generate images and/or information regarding a position of an object, which may be realized at high volume and at low cost and which, still, provide a high resolution and image quality.

PROBLEM TO BE SOLVED

It is, therefore, an object of the present invention to provide devices and methods facing the above-mentioned technical challenges of known devices and methods. Specifically, it is an object of the present invention to provide devices and methods which reliably may determine a position of an object in space, preferably at a low technical effort and with low requirements in terms of technical resources and cost.

SUMMARY OF THE INVENTION

This problem is solved by an optical detector, a detector system, a method of optical detection, a human-machine interface, an entertainment device, a tracking system, a camera and various uses of the optical detector, with the features of the independent claims. Preferred embodiments which might be realized in an isolated fashion or in any arbitrary combination are listed in the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of the present invention, an optical detector is disclosed. The optical detector comprises:
- at least one spatial light modulator being adapted to modify at least one property of a light beam in a spatially resolved fashion, having a matrix of pixels, each pixel being controllable to individually modify the at least one optical property of a portion of the light beam passing the pixel;
- at least one optical sensor adapted to detect the light beam after passing the matrix of pixels of the spatial light modulator and to generate at least one sensor signal;
- at least one modulator device adapted for periodically controlling at least two of the pixels with different modulation frequencies;
- at least one evaluation device adapted for performing a frequency analysis in order to determine signal components of the sensor signal for the modulation frequencies.

As used herein, an "optical detector" or, in the following, simply referred to as a "detector", generally refers to a device which is capable of generating at least one detector signal and/or at least one image, in response to an illumination by one or more light sources and/or in response to optical properties of a surrounding of the detector. Thus, the detector may be an arbitrary device adapted for performing at least one of an optical measurement and imaging process.

Specifically, as will be outlined in further detail below, the optical detector may be a detector for determining a position of at least one object. As used herein, the term position generally refers to at least one item of information regarding a location and/or orientation of the object and/or at least one part of the object in space. Thus, the at least one item of information may imply at least one distance between at least one point of the object and the at least one detector. As will be outlined in further detail below, the distance may be a longitudinal coordinate or may contribute to determining a longitudinal coordinate of the point of the object. Additionally or alternatively, one or more other items of information regarding the location and/or orientation of the object and/or at least one part of the object may be determined. As an example, at least one transversal coordinate of the object and/or at least one part of the object may be determined. Thus, the position of the object may imply at least one longitudinal coordinate of the object and/or at least one part of the object. Additionally or alternatively, the position of the object may imply at least one transversal coordinate of the object and/or at least one part of the object. Additionally or alternatively, the position of the object may imply at least one orientation information of the object, indicating an orientation of the object in space.

As used herein, a "light beam" generally is an amount of light traveling into more or less the same direction. Thus, preferably, a light beam may refer to a Gaussian light beam, as known to the skilled person. However, other light beams, such as non-Gaussian light beams, are possible. As outlined in further detail below, the light beam may be emitted and/or reflected by an object. Further, the light beam may be reflected and/or emitted by at least one beacon device which preferably may be one or more of attached or integrated into an object.

As further used herein, a "spatial light modulator", also referred to as a SLM, generally is a device adapted to modify at least one property, specifically at least one optical property, of a light beam in a spatially resolved fashion, specifically in at least one direction perpendicular to a direction of propagation of the light beam. Thus, as an example, the spatial light modulator may be adapted to modify the at least one optical property in a plane perpendicular to a local direction of propagation of the light beam in a controlled fashion. Thus, the spatial light modulator may be an arbitrary device which is capable of imposing some form of spatially varying modulation on the light beam, preferably in at least one direction perpendicular to the direction of propagation of the light beam. The spatial variation of the at least one property may be modified in a controlled fashion such that, at each controllable location in the plane perpendicular to the direction of propagation, the spatial light modulator may take at least two states which may modify the respective property of the light beam in different ways.

Spatial light modulators are generally known in the art, such as in the art of holography and/or in the art of projector devices. Simple examples of spatial light modulators generally known in the art are liquid crystal spatial modulators. Both transmissive and reflective liquid crystal spatial light modulators are known and may be used within the present invention. Further, micromechanical spatial light modulators are known based on an area of micro-mirrors which are individually controllable. Thus, reflective spatial light modulators may be used which are based on DLP® technology, available by Texas Instruments, having single-color or multi- or even full-color micro-mirrors. Further, micro-mirror arrays which may be used as spatial light modulators within the present invention are disclosed by V. Viereck et al., Photonik International 2 (2009), 48-49, and/or in U.S. Pat. No. 7,677,742 B2 (Hillmer et al.). Herein, micro-mirror arrays are shown which are capable of switching micro-mirrors between a parallel and a perpendicular position relative to an optical axis. These micro-mirror arrays generally may be used as a transparent spatial light modulator, similar to transparent spatial light modulator space on liquid crystal technology. The transparency of this type of spatial light modulators, however, generally is higher than the transparency of common liquid crystal spatial light modulators. Further, spatial light modulators may be based on other optical effects, such as acousto-optical effects and/or electro-optical effects such as the so-called Pockels effect and/or the so-called Kerr effect. Further, one or more spatial light modulators may be provided which are based on the use of interferometric modulation or IMOD technology. This technology is based on switchable interference effects within each pixel. The latter, as an example, is available by Qualcomm®, under the trade name "Mirasol™".

Further, additionally or alternatively, the at least one spatial light modulator used herein may be or may comprise at least one array of tunable optical elements, such as one or more of an array of focus-tunable lenses, an area of adaptive liquid micro-lenses, an array of transparent micro-prisms. Any combination of the named arrays of tunable optical elements may be used. The tuning of the optical elements of the array, as an example, may be performed electrically and/or optically. As an example, one or more arrays of tunable optical elements may be placed in a first image plane, such as in other spatial light modulators like DLP, LCDs, LCOS or other SLMs. The focus of the optical elements such as the micro-lenses and/or the refraction of the optical elements such as the micro-prisms may be modulated. This modulation may then be monitored by the at least one optical sensor and evaluated by the at least one evaluation device, by performing the frequency analysis, such as the demodulation.

Tunable optical elements such as focus-tunable lenses provide the additional advantage of being capable of correcting the fact that objects at different distances have different focal points. Focus-tunable lens arrays, as an example, are disclosed in US 2014/0132724 A1. The focus-tunable lens arrays disclosed therein may also be used in the SLM of the optical detector according to the present invention. Other embodiments, however, are feasible. Further, for potential examples of liquid micro-lens arrays, reference may be made to C. U. Murade et al., Optics Express, Vol. 20, No. 16, 18180-18187 (2012). Again, other embodiments are feasible. Further, for potential examples of microprisms arrays, such as arrayed electrowetting microprisms, reference may be made to J. Heikenfeld et al., Optics & Photonics News, January 2009, 20-26. Again, other embodiments of microprisms may be used.

Thus, as an example, one or more spatial light modulators may be used, selected from the group consisting of: a spatial light modulator or a reflective spatial light modulator. Further, as an example, one or more spatial light modulators may be used selected from the group consisting of: a spatial light modulator based on liquid crystal technology, such as one or more liquid crystal spatial light modulators; a spatial light modulator based on a micromechanical system, such as a spatial light modulator based on a micro-mirror system, specifically a micro-mirror array; a spatial light modulator based on interferometric modulation; a spatial light modulator based on an acousto-optical effect; a spatial light modulator based on an electro-optical effect, specifically based on the Pockels-effect and/or the Kerr-effect; a spatial light modulator comprising at least one array of tunable optical elements, such as one or more of an array of focus-tunable lenses, an area of adaptive liquid micro-lenses, an array of transparent micro-prisms. Typical spatial light modulators known in the art are adapted to modulate the spatial distribution of the intensity of the light beam, such as in a plane perpendicular to the direction of propagation of the light beam. However, as will be outlined in further detail below, additionally or alternatively, other optical properties of the light beam may be varied, such as a phase of the light beam and/or a color of the light beam. Other potential spatial light modulators will be explained in more detail below.

Generally, the spatial light modulator may be computer-controllable such that the state of variation of the at least one property of the light beam may be adjusted by a computer. The spatial light modulator may be an electrically addressable spatial light modulator, an optically addressable spatial light modulator or any other type of spatial light modulator.

As outlined above, the spatial light modulator comprises a matrix of pixels, each pixel being controllable to individually modify the at least one optical property of a portion of the light beam passing the pixel, i.e. interacting with the pixels by passing through the pixel, being reflected by the pixel or other ways of interaction. As used herein, a "pixel" thus generally refers to a unitary element of the spatial light modulator adapted to modify the at least one optical property of the portion of the light beam passing the pixel. Consequently, a pixel may be the smallest unit of the spatial light modulator which is adapted to modify the at least one optical property of the portion of the light beam passing the pixel. As an example, each pixel may be a liquid crystal cell and/or a micro-mirror. Each pixel is individually controllable.

As used herein, the term "control" generally refers to the fact that the way the pixel modifies the at least one optical property may be adjusted to assume at least two different states. The adjustment may take place by any type of control, preferably by electrical adjustment. Thus, preferably, each pixel may be individually addressable electrically in order to adjust the state of the respective pixel, such as by applying a specific voltage and/or a specific electric current to the pixel.

As further used herein, the term "individually" generally refers to the fact that one pixel of the matrix may be addressed at least substantially independently from addressing other pixels, such that a state of the pixel and, thus, the way the respective pixel influences the respective portion of the light beam, may be adjusted independently from an actual state of one or more or even all of the other pixels.

As further used herein, the term "modify at least one property of the light beam" generally refers to the fact that the pixel is capable of changing the at least one property of the light beam for the portion of the light beam passing the pixel by at least some degree. Preferably, the degree of change of the property may be adjusted to assume at least two different values including the possibility that one of the at least two different values implies unchanged passing of the portion of the light beam. The modification of the at least one property of the light beam may take place in any feasible way by any feasible interaction of the pixels with the light beam, including one or more of absorption, transmission, reflection, phase change or other types of optical interaction. Thus, as an example, each pixel may take at least two different states, wherein the actual state of the pixel may be adjustable in a controlled fashion, wherein the at least two states, for each pixel, differ with regard to their interaction of the respective pixel with the portion of the light beam passing the respective pixel, such as differing with regard to one or more of the absorption, the transmission, the reflection, the phase change or any other type of interaction of the pixel with the portion of the light beam.

Thus, a "pixel" generally may refer to a minimum uniform unit of the spatial light modulator adapted to modify the at least one property of a portion of the light beam in a controlled fashion. As an example, each pixel may have an area of interaction with the light beam, also referred to as a pixel area, of 1 $\mu m^2$ to 5 000 000 $\mu m^2$, preferably 100 $\mu m^2$ to 4 000 000 $\mu m^2$, preferably 1 000 $\mu m^2$ to 1 000 000 $\mu m^2$ and more preferably 2 500 $\mu m^2$ to 50 000 $\mu m^2$. Still, other embodiments are feasible.

The expression "matrix" generally refers to an arrangement of a plurality of the pixels in space, which may be a linear arrangement or an areal arrangement. Thus, generally, the matrix preferably may be selected from the group consisting of a one-dimensional matrix and a two-dimensional matrix. The pixels of the matrix may be arranged to form a regular pattern, which may be at least one of a rectangular pattern, a polygonal pattern, a hexagonal pattern, a circular pattern or another type of pattern. Thus, as an example, the pixels of the matrix may be arranged independently equidistantly in each dimension of a Cartesian coordinate system and/or in a polar coordinate system. As an example, the matrix may comprise 100 to 100 000 000 pixels, preferably 1 000 to 1 000 000 pixels and, more preferably, 10 000 to 500 000 pixels. Most preferably, the matrix is a rectangular matrix having pixels arranged in rows and columns.

As will be outlined in further detail below, the pixels of the matrix may be identical or may vary. Thus, as an example, all pixels of the matrix may have the same spectral properties and/or may have the same states. As an example, each pixel may have an on-state and an off-state, wherein the light, in the on-state, may pass through the pixel or may be reflected by the pixel into a direction of passing or a direction of the optical sensor, and wherein, in the off-state, the light is blocked or attenuated by the pixel or is reflected into a blocking direction, such as to a beam dump away from the optical sensor. Further, the pixels may have differing properties, such as differing states. As an example which will be outlined in further detail below, the pixels may be colored pixels including differing spectral properties, such as differing filter properties with regard to a transmission wavelength and/or a reflection wavelength of the light. Thus, as an example, the matrix may be a matrix having red, green and blue pixels or other types of pixels having different colors. As an example, the SLM may be a full-color SLM such as a full-color liquid crystal device and/or a micro-mirror device having mirrors of differing spectral properties.

As further used herein, the term "optical sensor" generally refers to a light-sensitive device for detecting a light beam and/or a portion thereof, such as for detecting an illumination and/or a light spot generated by a light beam. The optical sensor, in conjunction with the evaluation device, may be adapted, as outlined in further detail below, to determine at least one longitudinal coordinate of the object and/or of at least one part of the object, such as at least one part of the object from which the at least one light beam travels towards the detector.

The optical detector may comprise one or more optical sensors. In case a plurality of optical sensors is comprised, the optical sensors may be identical or may be different such that at least two different types of optical sensors may be comprised. As outlined in further detail below, the at least one optical sensor may comprise at least one of an inorganic optical sensor and an organic optical sensor. As used herein, an organic optical sensor generally refers to an optical sensor having at least one organic material included therein, preferably at least one organic photosensitive material. Further, hybrid optical sensors may be used including both inorganic and organic materials.

The at least one optical sensor specifically may be or may comprise at least one longitudinal optical sensor and/or at least one transversal optical sensor. For potential definitions of the terms "longitudinal optical sensor" and "transversal optical sensor", as well as for potential embodiments of these sensors, reference may be made, as an example, to the at least one longitudinal optical sensor and/or to the at least one transversal optical sensor as shown in WO2014/097181 A1. Other setups are feasible.

The at least one optical sensor is adapted to detect the light beam after passing the matrix of pixels of the spatial light modulator, i.e. after being transmitted by the spatial light modulator and/or being reflected by the spatial light modulator. As used herein, the term "detect" generally refers to the fact that the optical sensor is adapted to generate the at least one sensor signal depending on at least one property of the light beam in directing with the optical sensor, preferably depending on an intensity of the light beam. As will be outlined in further detail below, however, the sensor signal may, additionally or alternatively, depend on other properties of the light beam such as a width of the light beam. The sensor signal preferably may be an electrical signal, such as an electrical current and/or an electric voltage. The sensor signal may be a continuous or discontinuous signal. Further, the sensor signal may be an analogue signal or a digital signal. Further, the optical sensor, by itself and/or in conjunction with other components of the optical detector, may be adapted to process or preprocess the detector signal, such as by filtering and/or averaging, in order to provide a processed detector signal. Thus, as an example, a bandpass filter may be used in order to transmit only detector signals of a specific frequency range. Other types of preprocessing are feasible. In the following, when referring to the detector signal, no difference will be made between the case in which the raw detector signal is used and the case in which a preprocessed detector signal is used for further evaluation.

As used within the present invention, a "modulator device" generally refers to a device which is adapted to control two or more or even all of the pixels of the matrix, in order to adjust the respective pixels to assume one out of at least two different states for each pixel, each state having a specific type of interaction of the pixel with the portion of the light beam passing the respective pixel. Thus, as an example, the modulator device may be adapted to selectively apply two different types of voltages and/or at least two different types of electric currents to each of the pixels controlled by the modulator device.

The at least one modulator device is adapted for periodically controlling at least two of the pixels, preferably more of the pixels or even all of the pixels of the matrix with different modulation frequencies. As used herein, the term "modulation frequency" generally refers to one or both of a frequency f of a modulation and a phase φ of modulation of the control of the pixels. Thus, one or both of the frequency and/or the phase of the periodic control or modulation may be used for encoding and/or decoding optical information, as will be discussed in further detail below.

As used herein, the term "periodically control" generally refers to the fact that the modulator device is adapted to periodically switch between at least two different states of the respective pixel, wherein the at least two different states of the respective pixel differ with regard to their way of interacting with the portion of the light beam passing the pixel and, thus, differ with regard to their degree or way of modifying the portion of the light beam passing the pixels. The modulation frequency generally is selected from the group consisting of the frequency and/or the phase of the periodic switching between the at least two states of the respective pixel. The switching generally may be a stepwise switching or digital switching or may be a continuous switching in which the state of the respective pixel is continuously changed between a first state and a second state. As a most common example, the pixels may periodically be switched on or off at the respective modulation frequencies, i.e. at a specific frequency f and/or at a specific phase φ.

As further used herein, the term "evaluation device" generally refers to an arbitrary device adapted to perform the named operations. The evaluation device may contain one or more sub-devices such as one or more of a measurement device, a frequency analyzer, preferably a phase-sensitive frequency analyzer, a Fourier analyzer, and a demodulation device. Thus, as an example, the evaluation device may comprise at least one frequency mixing device adapted for mixing a specific modulation frequency with the detector signal. The mixed-signal obtained this way may be filtered by using a low-pass filter in order to obtain a demodulated signal. By using a set of frequencies, demodulated signals for various frequencies may be generated by the evaluation device, thus providing a frequency analysis. The frequency analysis may be a full frequency analysis over a range of frequency or phases or may be a selective frequency analyzer for one, two or more predetermined or adjustable frequencies and/or phases.

As used herein, the term "frequency analysis" generally refers to the fact that the evaluation device is adapted to evaluate the detector signal in a frequency-selective way, thus separating the signal components of the sensor signal at least two different frequencies and/or phases, i.e. according to their frequency f and/or according to their phase φ. Thus, the signal components may be separated according to their frequency f and/or phase φ, the latter even in case these signal components may have the same frequency f. Thus, the frequency analysis generally may be adapted to separate the signal components according to one or more of a frequency and a phase. Consequently, for each modulation frequency, one or more signal components may be determined by the frequency analysis. Thus, generally, the frequency analysis may be performed in a phase-sensitive way or in a non-phase-sensitive way.

The frequency analysis may take place at one, two or more different frequencies, thus obtaining the signal components of the sensor signal at these one, two or more different frequencies. The two or more different frequencies may be discrete frequencies or may be a continuous frequency range, such as a continuous frequency range in a frequency interval. Frequency analyzers generally are known in the art of high-frequency electronics.

Preferably, the evaluation device is adapted to perform the frequency analysis for the modulation frequencies. Thus, preferably, the evaluation device at least is adapted to determine the frequency components of the sensor signal for the different modulation frequencies used by the modulator device. In fact, the modulator device may even fully or partially be part of the evaluation device or vice versa. Thus, as an example, one or more signal generators may be provided which both provide the modulation frequencies used by the modulator device and the frequencies for frequency analysis. As an example, the at least one signal generated may be used both for providing a set of modulation frequencies for periodically controlling the at least two pixels, preferably more or even all of the pixels, and for providing the same set of modulation frequencies for frequency analysis. Thus, each modulation frequency of the set of modulation frequencies may be provided to a respective pixel. Further, each modulation frequency of the set of modulation frequencies may be provided to a demodulation device of the evaluation device in order to demodulate the sensor signal with the respective modulation frequency, thereby obtaining a signal component for the respective modulation frequency. Thus, a set of signal components may be generated by the evaluation device, each signal component of the set of signal components corresponding to a respective modulation frequency of the set of modulation frequencies and, thus, corresponding to a respective pixel of the matrix. Thus, preferably, the evaluation device may be adapted to establish an unambiguous correlation between each of the signal components and a pixel of the matrix of pixels of the spatial light modulator. In other words, the evaluation device may be adapted to separate the sensor signal provided by the at least one optical sensor into signal components which are generated by the light portions passing the respective pixel and/or to assign signal components to specific pixels of the matrix.

In case a plurality of optical sensors are provided, the evaluation device may be adapted to perform the above-mentioned frequency analysis for each of the optical sensors individually or in common or may be adapted to perform the above-mentioned frequency analysis for only one or more of the optical sensors As will be outlined in further detail below, the evaluation device may comprise at least one data processing device, such as at least one microcontroller or processor. Thus, as an example, the at least one evaluation device may comprise at least one data processing device having a software code stored thereon comprising a number of computer commands. Additionally or alternatively, the evaluation device may comprise one or more electronic components, such as one or more frequency mixing devices and/or one or more filters, such as one or more bandpass filters and/or one or more low-pass filters. Thus, as an example, the evaluation device may comprise at least one Fourier analyzer and/or at least one lock-in amplifier or, preferably, a set of lock-in amplifiers, for performing the frequency analysis. Thus, as an example, in case a set of modulation frequencies is provided, the evaluation device may comprise a separate lock-in amplifier for each modulation frequency of the set of modulation frequencies or may comprise one or more lock-in amplifiers adapted for performing a frequency analysis for two or more of the modulation frequencies, such as sequentially or simultaneously. Lock-in amplifiers of this type generally are known in the art.

The evaluation device can be connected to or may comprise at least one further data processing device that may be used for one or more of displaying, visualizing, analyzing, distributing, communicating or further processing of information, such as information obtained by the optical sensor and/or by the evaluation device. The data processing device, as an example, may be connected or incorporate at least one of a display, a projector, a monitor, an LCD, a TFT, an LED pattern, or a further visualization device. It may further be connected or incorporate at least one of a communication device or communication interface, a connector or a port, capable of sending encrypted or unencrypted information using one or more of email, text messages, telephone, bluetooth, Wi-Fi, infrared or internet interfaces, ports or connections. The data processing device, as an example, may use communication protocols of protocol families or suites to exchange information with the evaluation device or further devices, wherein the communication protocol specifically may be one more of: TCP, IP, UDP, FTP, HTTP, IMAP, POP3, ICMP, IIOP, RMI, DOOM, SOAP, DDE, NNTP, PPP, TLS, E6, NTP, SSL, SFTP, HTTPs, Telnet, SMTP, RTPS, ACL, SCO, L2CAP, RIP, or a further protocol. The protocol families or suites specifically may be one or more of TCP/IP, IPX/SPX, X.25, AX.25, OSI, AppleTalk or a further protocol family or suite. The data processing device may further be connected or incorporate at least one of a processor, a graphics processor, a CPU, an Open Multimedia Applications Platform (OMAP™), an integrated circuit, a system on a chip such as products from the Apple A series or the Samsung S3C2 series, a microcontroller or microprocessor, one or more memory blocks such as ROM, RAM, EEPROM, or flash memory, timing sources such as oscillators or phase-locked loops, counter-timers, real-time timers, or power-on reset generators, voltage regulators, power management circuits, or DMA controllers. Individual units may further be connected by buses such as AMBA buses.

The evaluation device and/or the data processing device may be connected by or have further external interfaces or ports such as one or more of serial or parallel interfaces or ports, USB, Centronics Port, FireWire, HDMI, Ethernet, Bluetooth, RFID, Wi-Fi, USART, or SPI, or analog interfaces or ports such as one or more of ADCs or DACs, or a standardized interfaces or ports to further devices such as a 2D-camera device using an RGB-interface such as Camera-Link. The evaluation device and/or the data processing device may further be connected by one or more of inter-processor interfaces or ports, FPGA-FPGA-interfaces, or serial or parallel interfaces ports. The evaluation device and the data processing device may further be connected to one or more of an optical disc drive, a CD-RW drive, a DVD+RW drive, a flash drive, a memory card, a disk drive, a hard disk drive, a solid state disk or a solid state hard disk.

The evaluation device and/or the data processing device may be connected by or have one or more further external connectors such as one or more of phone connectors, RCA connectors, VGA connectors, hermaphrodite connectors, USB connectors, HDMI connectors, 8P8C connectors, BCN connectors, IEC 60320 C14 connectors, optical fiber connectors, D-subminiature connectors, RF connectors, coaxial connectors, SCART connectors, XLR connectors, and/or may incorporate at least one suitable socket for one or more of these connectors.

Possible embodiments of a single device incorporating one or more of the optical detector according to the present invention, the evaluation device or the data processing device, such as incorporating one or more of the optical sensor, optical systems, evaluation device, communication device, data processing device, interfaces, system on a chip, display devices, or further electronic devices, are: mobile phones, personal computers, tablet PCs, televisions, game consoles or further entertainment devices. In a further embodiment, the 3D-camera functionality which will be outlined in further detail below may be integrated in devices that are available with conventional 2D-digital cameras, without a noticeable difference in the housing or appearance of the device, where the noticeable difference for the user may only be the functionality of obtaining and or processing 3D information.

Specifically, an embodiment incorporating the optical detector and/or a part thereof such as the evaluation device and/or the data processing device may be: a mobile phone incorporating a display device, a data processing device, the optical sensor, optionally the sensor optics, and the evaluation device, for the functionality of a 3D camera. The optical detector according to the present invention specifically may be suitable for integration in entertainment devices and/or communication devices such as a mobile phone.

A further embodiment of the present invention may be an incorporation of the optical detector or a part thereof such as the evaluation device and/or the data processing device in a device for use in automotive, for use in autonomous driving or for use in car safety systems such as Daimler's Intelligent Drive system, wherein, as an example, a device incorporating one or more of the optical sensor, optionally one or more optical systems, the evaluation device, optionally a communication device, optionally a data processing device, optionally one or more interfaces, optionally a system on a chip, optionally one or more display devices, or optionally further electronic devices may be part of a vehicle, a car, a truck, a train, a bicycle, an airplane, a ship, a motorcycle. In automotive applications, the integration of the device into the automotive design may necessitate the integration of the optical sensor, optionally optics, or device at minimal visibility from the exterior or interior. The optical detector or a part thereof such as the evaluation device and/or the data processing device may be especially suitable for such integration into automotive design.

The present invention basically may use a frequency analysis for assigning frequency components to specific pixels of the spatial light modulator. Generally, sophisticated display technology and appropriate sophisticated spatial light modulators having a high resolution and/or a high quality are widely available at low cost, whereas a spatial resolution of optical sensors generally is technically challenging. Consequently, instead of using a pixelated optical sensor, the present invention provides the advantage of possibly using a large-area optical sensor or an optical sensor having a low resolution, in combination with a pixelated spatial light modulator, in conjunction with assigning signal components of the sensor signal to the respective pixels of the pixelated spatial light modulator via frequency analysis. Consequently, low cost optical sensors may be used, or optical sensors may be used which may be optimized with regard to other parameters instead of resolution, such as transparency, low noise and high signal quality or color. The spatial resolution and the technical challenges imposed thereby may be transferred from the optical sensor to the spatial light modulator.

The at least one spatial light modulator may further be adapted and/or controlled to provide one or more light patterns. Thus, the at least one spatial light modulator may be controlled in such a fashion that one or more light patterns are reflected and/or transmitted towards the at least one optical sensor, such as stewards the at least one longitudinal optical sensor. The at least one light pattern generally may be or may comprise at least one generic light pattern and/or may be or may comprise at least one light pattern dependent on a space or scene captured by the optical detector and/or may be dependent on a specific analysis of a scene captured by the optical detector. Examples for generic patterns are: patterns based on fringes (see e.g. T. Peng: "Algorithms and models for 3-D shape measurement using digital fringe projections", Dissertation, University of Maryland (College Park, Md.), 16 Jan. 2007—available online under http://drum.lib.umd.edu//handle/1903/6654) and/or patterns based on gray codes (see e.g. http://en.wikipedia.org/wiki/Gray_code). These types of patterns are commonly used in structured light illumination based 3D-recognition (see e.g. http://en.wikipedia.org/wiki/Structured-light_3D_scanner) or fringe projection).

The spatial light modulator and the optical sensor may be spatially separated, such as by establishing these components as separate components of the optical detector. As an example, along an optical axis of the optical detector, the spatial light modulator may be separated from the at least one optical sensor by at least 0.5 mm, preferably by at least 1 mm and, more preferably, by at least 2 mm. However, other embodiments are feasible, such as by fully or partially integrating the spatial light modulator into the optical sensor.

The optical detector according to this basic principle of the present invention may be further developed by various embodiments which may be used in isolation or in any feasible combination.

Thus, as outlined above, the evaluation device may further be adapted to assign each signal component to a respective pixel in accordance with its modulation frequency. For further details, reference may be made to the embodiments given above. Thus, as an example, a set of modulation frequencies may be used, each modulation frequency being assigned to a specific pixel of the matrix, wherein the evaluation device may be adapted to perform the frequency analysis of the sensor signal at least for the modulation frequencies of the set of modulation frequencies, thereby deriving the signal components at least for these modulation frequencies. As outlined above, the same signal generator may be used both for the modulator device and for the frequency analysis. Preferably, the modulator device is adapted such that each of the pixels is controlled at a unique modulation frequency. Thus, by using unique modulation frequencies, a well-defined relationship between the modulation frequency and the respective pixel may be established such that each signal component may be assigned to a respective pixel via the modulation frequency. Still, other embodiments are feasible, such as by subdividing the optical sensor and/or the spatial light modulator into two or more regions. Therein, each region of the spatial light modulator in conjunction with the optical sensor and/or a part thereof, may be adapted to perform the above-mentioned assignment. Thus, as an example, the set of modulation frequencies may both be provided to a first region of the spatial light modulator and to at least one second region of the spatial light modulator. An ambiguity in the signal components of the sensor signal between the sensor signals generating from the first region and sensor signals generating from the second region may be resolved by other means, such as by using additional modulation.

Thus, generally, the modulator device may be adapted for controlling the at least two pixels, preferably more of the pixels or even all of the pixels of the matrix each with precisely one modulation frequency or each with two or more modulation frequencies. Thus, a single pixel may be modulated with one modulation frequency, two modulation frequencies or even more modulation frequencies. These types of multi-frequency modulation generally are known in the art of high-frequency electronics.

As outlined above, the modulator device may be adapted for periodically modulating the at least two pixels with the different modulation frequencies. More preferably, as discussed above, the modulator device may provide or may make use of a set of modulation frequencies, each modulation frequency of the set of modulation frequencies being assigned to a specific pixel. As an example, the set of modulation frequencies may comprise at least two modulation frequencies, more preferably at least five modulation frequencies, most preferably at least 10 modulation frequencies, at least 50 modulation frequencies, at least 100 modulation frequencies, at least 500 modulation frequencies or at least 1000 modulation frequencies. Other embodiments are feasible.

As outlined in further detail above, the evaluation device preferably may be adapted for performing the frequency analysis by demodulating the sensor signal with different modulation frequencies. For this purpose, the evaluation device may contain one or more demodulation devices, such as one or more frequency mixing devices, one or more frequency filters such as one or more low-pass filters or one or more lock-in amplifiers and/or Fourier-analyzers. The evaluation device preferably may be adapted to perform a discrete or continuous Fourier analysis over a predetermined and/or adjustable range of frequencies.

As discussed above, the evaluation device preferably may be adapted to use the same set of modulation frequencies which is also used by the modulator device such that the modulation of the spatial light modulator by the modulator device and the demodulation of the sensor signals by the evaluation device preferably take place with the same set of modulation frequencies.

Further preferred embodiments relate to the at least one property, preferably the at least one optical property, of the light beam which is modified in a spatially resolved fashion by the spatial light modulator. Thus, preferably, the at least one property of the light beam modified by the spatial light modulator in a spatially resolved fashion is at least one property selected from the group consisting of: an intensity of the portion of the light beam; a phase of the portion of the light beam; a spectral property of the portion of the light beam, preferably a color; a polarization of the portion of the light beam; a direction of propagation of the portion of the light beam. As an example, as outlined above, the spatial light modulator, for each pixel, may be adapted to switch on or off the portion of light passing the respective pixel, i.e. being adapted to switch between a first state in which the portion of light may proceed towards the optical sensor and a second state in which the portion of light is prevented from proceeding towards the optical sensor. Still, other options are feasible, such as an intensity modulation between a first state having a first transmission of the pixel and a second state having a second transmission of the pixel being different from the first transmission. Other options are feasible.

The at least one spatial light modulator preferably may comprise at least one spatial light modulator selected from the group consisting of: a spatial light modulator based on liquid crystal technology, such as one or more liquid crystal spatial light modulators; a spatial light modulator based on a micromechanical system, such as a spatial light modulator based on a micro-mirror system, specifically a micro-mirror array; a spatial light modulator based on interferometric modulation; a spatial light modulator based on an acousto-optical effect; a spatial light modulator based on an electro-optical effect, specifically based on the Pockels-effect and/or the Kerr-effect; a transmissive spatial light modulator, wherein the light beam passes through the matrix of pixels and wherein the pixels are adapted to modify the optical property for each portion of the light beam passing through the respective pixel in an individually controllable fashion; a reflective spatial light modulator, wherein the pixels have individually controllable reflective properties and are adapted to individually change a direction of propagation for each portion of the light beam being reflected by the respective pixel; a transmissive spatial light modulator, wherein the pixels have individually controllable reflective properties and are adapted to individually change a transmission for each pixel by controlling a position of a micro-mirror assigned to the respective pixel; a spatial light modulator based on interferometric modulation, wherein the light beam passes through the matrix of pixels and wherein the pixels are adapted to modify the optical property for each portion of the light beam passing through the respective pixel by modifying interferometric effects of the pixels; an electrochromic spatial light modulator, wherein the pixels have controllable spectral properties individually controllable by an electric voltage applied to the respective pixel; an acousto-optical spatial light modulator, wherein a birefringence of the pixels is controllable by acoustic waves; an electro-optical spatial light modulator, wherein a birefringence of the pixels is controllable by electric fields, preferably a spatial light modulator based on the Pockels effect and/or on the Kerr effect; a spatial light modulator comprising at least one array of tunable optical elements, such as one or more of an array of focus-tunable lenses, an area of adaptive liquid micro-lenses, an array of transparent microprisms. These types of spatial light modulator generally are known to the skilled person and, at least partially, are commercially available. Thus, as an example, the at least one spatial light modulator may comprise at least one spatial light modulator selected from the group consisting of: a liquid crystal device, preferably an active matrix liquid crystal device, wherein the pixels are individually controllable cells of the liquid crystal device; a micro-mirror device, wherein the pixels are micro-mirrors of the micro-mirror device individually controllable with regard to an orientation of their reflective surfaces; an electrochromic device, wherein the pixels are cells of the electrochromic device having spectral properties individually controllable by an electric voltage applied to the respective cell; an acousto-optical device, wherein the pixels are cells of the acousto-optical device having a birefringence individually controllable by acoustic waves applied to the cells; an electro-optical device, wherein the pixels are cells of the electro-optical device having a birefringence individually controllable by electric fields applied to the cells. Combinations of two or more of the named technologies are feasible. Micro-mirror devices generally are commercially available, such as micro-mirror devices implementing the so-called DLP® technology.

As outlined above, the capability of the pixels to modify the at least one property of the light beam may be uniform over the matrix of pixels. Alternatively, the capability of the pixels to modify the at least one property may differ between the pixels, such that at least one first pixel of the matrix of pixels has a first capability of modifying the property, and at least one second pixel of the matrix of pixels has a second capability of modifying the property. Further, more than one property of the light beam may be modified by the pixels. Again, the pixels may be capable of modifying the same property of the light beam or different types of properties of the light beam. Thus, as an example, at least one first pixel may be adapted to modify a first property of the light beam, and at least one second pixel may be adapted to modify a second property of the light beam being different from the first property of the light beam. Further, the capability of the pixels to modify the at least one optical property of the portion of the light beam passing the respective pixel may be dependent on the spectral properties of the light beam, specifically of the color of the light beam. Thus, as an example, the capability of the pixels to modify the at least one property of the light beam may be dependent on a wavelength of the light beam and/or of a color of a light beam, wherein the term "color" generally refers to the spectral distribution of the intensities of the light beam. Again, the pixels may have uniform properties or differing properties. Thus, as an example, at least one first pixel or at least one first group of pixels may have filtering properties with a high transmission in a blue spectral range, a second group of pixels may have filtering properties with a high transmission in a red spectral range, and a third group of pixels may have filtering properties with a high transmission in a green spectral range. Generally, at least two groups of pixels may be present having filtering properties for the light beam with differing transmission ranges, wherein the pixels within each group, additionally, may be switched between at least one low transmission state and at least one high transmission state. Other embodiments are feasible.

As outlined above, the spatial light modulator may be a transparent spatial light modulator or an intransparent or opaque spatial light modulator. In the latter case, preferably, the spatial light modulator is a reflective spatial light modulator such as a micro-mirror device having a plurality of micro-mirrors, each micro-mirror forming a pixel of the micro-mirror device, wherein each micro-mirror is individually switchable between at least two orientations. Thus, as an example, a first orientation of each micro-mirror may be an orientation in which the portion of the light beam passing the micro-mirror, i.e. impinging on the micro-mirror, is directed towards the optical sensor, and a second orientation may be an orientation in which the portion of the light beam passing the micro-mirror, i.e. impinging on the micro-mirror, is directed towards another direction and does not reach the optical sensor, e.g. by being directed into a beam dump.

Additionally or alternatively, the spatial light modulator may be a transmissive spatial light modulator, preferably a transmissive spatial light modulator in which a transmissivity of the pixels is switchable, preferably individually. Thus, as an example, the spatial light modulator may comprise at least one transparent liquid crystal device, such as a liquid crystal device widely used for projecting purposes, e.g. in beamers used for presentation purposes. The liquid crystal device may be a monochrome liquid crystal device having pixels of identical spectral properties or may be a multichrome or even full-color liquid crystal device having pixels of differing spectral properties, such as red green and blue pixels.

As outlined above, the evaluation device preferably is adapted to assign each of the signal components to a pixel of the matrix. The evaluation device may further be adapted to determine which pixels of the matrix are illuminated by the light beam by evaluating the signal components. Thus, since each signal component may correspond to a specific pixel via a unique correlation, an evaluation of the spectral components may lead to an evaluation of the illumination of the pixels. As an example, the evaluation device may be adapted to compare the signal components with at least one threshold in order to determine the illuminated pixels. The at least one threshold may be a fixed threshold or predetermined threshold or may be a variable or adjustable threshold. As an example, a predetermined threshold above typical noise of the signal components may be chosen, and, in case a signal component of a respective pixel exceeds the threshold, an illumination of the pixel may be determined. The at least one threshold may be a uniform threshold for all signal components or may be an individual threshold for the respective signal component. Thus, in case different signal components are prone to show different degrees of noise, an individual threshold may be chosen in order to take account of these individual noises.

The evaluation device may further be adapted to identify at least one transversal position of the light beam and/or an orientation of the light beam, such as an orientation with regard to an optical axis of the detector, by identifying a transversal position of pixels of the matrix illuminated by the light beam. Thus, as an example, a center of the light beam on the matrix of pixels may be identified by identifying the at least one pixel having the highest illumination by evaluating the signal components. The at least one pixel having the highest illumination may be located at a specific position of the matrix which again may then be identified as the transversal position of the light beam. In this regard, generally, reference may be made to the principle of determining a transversal position of the light beam as disclosed in European patent application number EP 13171901.5, even though other options are feasible.

Generally, as will be used in the following, several directions of the detector may be defined. Thus, a position and/or orientation of an object may be defined in a coordinate system, which, preferably, may be a coordinate system of the detector. Thus, the detector may constitute a coordinate system in which an optical axis of the detector forms the z-axis and in which, additionally, an x-axis and a y-axis may be provided which are perpendicular to the z-axis and which are perpendicular to each other. As an example, the detector and/or a part of the detector may rest at a specific point in this coordinate system, such as at the origin of this coordinate system. In this coordinate system, a direction parallel or antiparallel to the z-axis may be regarded as a longitudinal direction, and a coordinate along the z-axis may be considered a longitudinal coordinate. An arbitrary direction perpendicular to the longitudinal direction may be considered a transversal direction, and an x- and/or y-coordinate may be considered a transversal coordinate.

Alternatively, other types of coordinate systems may be used. Thus, as an example, a polar coordinate system may be used in which the optical axis forms a z-axis and in which a distance from the z-axis and a polar angle may be used as additional coordinates. Again, a direction parallel or antiparallel to the z-axis may be considered a longitudinal direction, and a coordinate along the z-axis may be considered a longitudinal coordinate. Any direction perpendicular to the z-axis may be considered a transversal direction, and the polar coordinate and/or the polar angle may be considered a transversal coordinate.

The center of the light beam on the matrix of pixels, which may be a central spot or a central area of the light beam on the matrix of pixels, may be used in various ways. Thus, at least one transversal coordinate for the center of the light beam may be determined, which, in the following, will also be referred to as the xy-coordinate of the center of the light beam.

Further, the position of the center of the light beam may allow for obtaining information regarding a transversal position and/or a relative direction of an object from which the light beam propagates towards the detector. Thus, the transversal position of the pixels of the matrix illuminated by the light beam is determined by determining one or more pixels having the highest illumination by the light beam. For this purpose, known imaging properties of the detector may be used. As an example, a light beam propagating from the object with the detector may directly impinge on a specific area, and from the location of this area or specifically from the position of the center of the light beam, a transversal position and/or a direction of the object may be derived. Optionally, the detector may comprise at least one transfer device, such as at least one lens or lens system, having optical properties. Since, typically, the optical properties of the transfer device are known, such as by using known imaging equations and/or geometric relationships known from ray optics or matrix optics, the position of the center of the light beam on the matrix of pixels may also be used for deriving information on a transversal position of the object in case one or more transfer devices are used. Thus, generally, the evaluation device may be adapted to identify one or more of a transversal position of an object from which the light beam propagates towards the detector and a relative direction of the object from which the light beam propagates towards the detector, by evaluating at least one of the transversal position of the light beam and the orientation of the light beam. In this regard, as an example, reference may also be made to one or more of the transversal optical sensors as disclosed in one or more of European patent application number EP 13171901.5, U.S. provisional application No. 61/739,173 or U.S. provisional application No. 61/749,964. Still, other options are feasible.

The evaluation device may further be adapted to derive one or more other items of information relating to the light beam and/or relating to a position of an object from which the light beam propagates towards the detector by further evaluating the results of the spectral analysis, specifically by evaluating the signal components. Thus, as an example, the evaluating device may be adapted to derive one or more items of information selected from the group consisting of: a position of an object from which the light beam propagates towards the detector; a transversal position of the light beam on the matrix of pixels of the spatial light modulator; a width of the light beam at the position of the matrix of the pixels of the spatial light modulator; a color of the light beam and/or spectral properties of the light beam; a longitudinal coordinate of the object from which the light beam propagates towards the detector. Examples of these items of information and deriving these items of information will be given in further detail below.

Thus, as an example, the evaluation device may be adapted to determine a width of the light beam by evaluating the signal components. Generally, as used herein, the term "width of the light beam" refers to an arbitrary measure of a transversal extension of a spot of illumination generated by the light beam on the matrix of pixels, specifically in a plane perpendicular to a local direction of propagation of the light beam, such as the above-mentioned z-axis. Thus, as an example, the width of the light beam may be specified by providing one or more of an area of the light spot, a diameter of the light spot, an equivalent diameter of the light spot, a radius of the light spot or an equivalent radius of the light spot. As an example, the so-called beam waist may be specified in order to determine the width of the light beam at the position of the spatial light modulator, as will be outlined in further detail below. Specifically, the evaluation device may be adapted to identify the signal components assigned to pixels being illuminated by the light beam and to determine the width of the light beam at the position of the spatial light modulator from known geometric properties of the arrangement of the pixels. Thus, specifically, in case the pixels of the matrix are located at known positions of the matrix, which typically is the case, the signal components of the respective pixels as derived by the frequency analysis may be transformed into a spatial distribution of illumination of the spatial light modulator by the light beam, thereby being able to derive at least one item of information regarding the width of the light beam at the position of the spatial light modulator.

In case the width of the light beam is known, the width may be used for deriving one or more items of information regarding the position of the object from which the light beam travels towards the detector. Thus, the evaluation device, using a known or determinable relationship between the width of the light beam and the distance between an object from which the light beam propagates towards the detector, may be adapted to determine a longitudinal coordinate of the object. For the general principle of deriving a longitudinal of an object by evaluating a width of a light beam, reference may be made to one or more of WO 2012/110924 A1, EP 13171901.5, U.S. provisional application No. 61/739,173 or U.S. provisional application No. 61/749,964.

Thus, as an example, the evaluation device may be adapted to compare, for each of the pixels, the signal component of the respective pixel to at least one threshold in order to determine whether the pixel is an illuminated pixel or not. This at least one threshold may be an individual threshold for each of the pixels or may be a threshold which is a uniform threshold for the whole matrix. As will be outlined above, the threshold may be predetermined and/or fixed. Alternatively, the at least one threshold may be variable. Thus, the at least one threshold may be determined individually for each measurement or groups of measurements. Thus, at least one algorithm may be provided adapted to determine the threshold.

The evaluation device generally may be adapted to determine at least one pixel having the highest illumination out of the pixels by comparing the signals of the pixels. Thus, the detector generally may be adapted to determine one or more pixels and/or an area or region of the matrix having the highest intensity of the illumination by the light beam. As an example, in this way, a center of illumination by the light beam may be determined.

The highest illumination and/or the information about the at least one area or region of highest illumination may be used in various ways. Thus, as outlined above, the at least one above-mentioned threshold may be a variable threshold. As an example, the evaluation device may be adapted to choose the above-mentioned at least one threshold as a fraction of the signal of the at least one pixel having the highest illumination. Thus, the evaluation device may be adapted to choose the threshold by multiplying the signal of the at least one pixel having the highest illumination with a factor of $1/e^2$. As will be outlined in further detail below, this option is particularly preferred in case Gaussian propagation properties are assumed for the at least one light beam, since the threshold $1/e^2$ generally determines the borders of a light spot having a beam radius or beam waist w generated by a Gaussian light beam on the optical sensor.

The evaluation device may be adapted to determine the longitudinal coordinate of the object by using a predetermined relationship between the width of the light beam or, which is equivalent, the number N of the pixels which are illuminated by the light beam, and the longitudinal coordinate of the object. Thus, generally, the diameter of the light beam, due to propagation properties generally known to the skilled person, changes with propagation, such as with a longitudinal coordinate of the propagation. The relationship between the number of illuminated pixels and the longitudinal coordinate of the object may be an empirically determined relationship and/or may be analytically determined.

Thus, as an example, a calibration process may be used for determining the relationship between the width of the light beam and/or the number of illuminated pixels and the longitudinal coordinate. Additionally or alternatively, as mentioned above, the predetermined relationship may be based on the assumption of the light beam being a Gaussian light beam. The light beam may be a monochromatic light beam having a precisely one wavelength λ or may be a light beam having a plurality of wavelengths or a wavelength spectrum, wherein, as an example, a central wavelength of the spectrum and/or a wavelength of a characteristic peak of the spectrum may be chosen as the wavelength λ of the light beam.

As an example of an analytically determined relationship, the predetermined relationship, which may be derived by assuming Gaussian properties of the light beam, may be:

$$N \sim \pi \cdot w_0^2 \cdot \left(1 + \left(\frac{z}{z_0}\right)^2\right), \quad (1)$$

wherein z is the longitudinal coordinate,
wherein $w_0$ is a minimum beam radius of the light beam when propagating in space,
wherein $z_0$ is a Rayleigh-length of the light beam with $z_0 = \pi \cdot w_0^2/\lambda$, λ being the wavelength of the light beam.

This relationship may generally be derived from the general equation of an intensity I of a Gaussian light beam traveling along a z-axis of a coordinate system, with r being a coordinate perpendicular to the z-axis and E being the electric field of the light beam:

$$I(r,z) = |E(r,z)|^2 = I_0 \cdot (w_0/w(z))^2 \cdot e^{-2r^2/w(z)^2} \quad (2)$$

The beam radius w of the transversal profile of the Gaussian light beam generally representing a Gaussian curve is defined, for a specific z-value, as a specific distance from the z-axis at which the amplitude E has dropped to a value of 1/e (approx. 36%) and at which the intensity I has dropped to $1/e^2$. The minimum beam radius, which, in the Gaussian equation given above (which may also occur at other z-values, such as when performing a z-coordinate transformation), occurs at coordinate z=0, is denoted by $w_0$. Depending on the z-coordinate, the beam radius generally follows the following equation when light beam propagates along the z-axis:

$$w(z) = w_0 \cdot \sqrt{1 + \left(\frac{z}{z_0}\right)^2} \quad (3)$$

With the number N of illuminated pixels being proportional to the illuminated area A of the optical sensor:

$$N \sim A \quad (4)$$

or, in case a plurality of spatial light modulators i=1, ..., n is used, with the number $N_i$ of illuminated pixels for each spatial light modulator being proportional to the illuminated area $A_i$ of the respective optical sensor $$N_i \sim A_i \quad (4')$$

and the general area of a circle having a radius w:

$$A = \pi \cdot w^2, \quad (5)$$

the following relationship between the number of illuminated pixels and the z-coordinate may be derived:

$$N \sim \pi \cdot w_0^2 \cdot \left(1 + \left(\frac{z}{z_0}\right)^2\right) \quad (6)$$

or $$N_i \sim \pi \cdot w_0^2 \cdot \left(1 + \left(\frac{z}{z_0}\right)^2\right), \quad (6')$$

respectively, with $z_0 = \pi \cdot w_0^2/\lambda$, as mentioned above. Thus, with N or $N_i$, respectively, being the number of pixels within a circle being illuminated at an intensity o $I \geq I_0/e^2$, as an example, N or $N_i$ may be determined by simple counting of pixels and/or other methods, such as a histogram analysis. In other words, a well-defined relationship between the z-coordinate and the number of illuminated pixels N or $N_i$, respectively, may be used for determining the longitudinal coordinate z of the object and/or of at least one point of the object, such as at least one longitudinal coordinate of at least one beacon device being one of integrated into the object and/or attached to the object.

In the equations given above, such as in equation (1), it is assumed that the light beam has a focus at position z=0. It shall be noted, however, that a coordinate transformation of the z-coordinate is possible, such as by adding and/or subtracting a specific value. Thus, as an example, the position of the focus typically is dependent on the distance of the object from the detector and/or on other properties of the light beam. Thus, by determining the focus and/or the position of the focus, a position of the object, specifically a longitudinal coordinate of the object, may be determined, such as by using an empirical and/or an analytical relationship between a position of the focus and a longitudinal coordinate of the object and/or the beacon device. Further, imaging properties of the at least one optional transfer device, such as the at least one optional lens, may be taken into account. Thus, as an example, in case beam properties of the light beam being directed from the object towards the detector are known, such as in case emission properties of an illuminating device contained in a beacon device are known, by using appropriate Gaussian transfer matrices representing a propagation from the object to the transfer device, representing imaging of the transfer device and representing beam propagation from the transfer device to the at least one optical sensor, a correlation between a beam waist and a position of the object and/or the beacon device may easily be determined analytically. Additionally or alternatively, a correlation may empirically be determined by appropriate calibration measurements.

As outlined above, the matrix of pixels preferably may be a two-dimensional matrix. However, other embodiments are feasible, such as one-dimensional matrices. More preferably, as outlined above, the matrix of pixels is a rectangular matrix.

As outlined above, the information derived by the frequency analysis may further be used to derive other types of information regarding the object and/or the light beam. As a further example of information which may be derived additionally or alternatively to transversal and/or longitudinal position information, color and/or spectral properties of the object and/or the light beam may be named.

Thus, the capability of the pixels to modify the at least one optical property of the portion of the light beam passing the respective pixel may be dependent on the spectral properties of the light beam, specifically of the color of the light beam. The evaluation device specifically may be adapted to assign the signal components to components of the light beam having differing spectral properties. Thus, as an example, one or more first signal components may be assigned to one or more pixels adapted to transmit or reflect portions of the light beam in a first spectral range, one or more second signal components may be assigned to one or more pixels adapted to transmit or reflect portions of the light beam in a second spectral range, and one or more third signal components may be assigned to one or more pixels adapted to transmit or reflect portions of the light beam in a third spectral range. Thus, the matrix of pixels may have at least two different groups of pixels having different spectral properties, and the evaluation device may be adapted to distinguish between signal components of these groups, thereby allowing for a full or partial spectral analysis of the light beam. As an example, the matrix may have red, green and blue pixels, which each may be controlled individually, and the evaluation device may be adapted to assign signal components to one of the groups. For example, a full-color liquid crystal SLM may be used for this purpose.

Thus, generally, the evaluation device may be adapted to determine a color of the light beam by comparing signal components being assigned to components of the light beam having differing spectral properties, specifically being assigned to components of the light beam having differing wavelengths. The matrix of pixels may comprise pixels having differing spectral properties, preferably having differing color, wherein the evaluation device may be adapted to assign signal components to the respective pixels having differing spectral properties. The modulator device may be adapted to control pixels having a first color in a different way than pixels having a second color.

As outlined above, one of the advantages of the present invention resides in the fact that a fine pixelation of the optical sensor may be avoided. Instead, the pixelated SLM may be used, thereby, in fact, transferring the pixelation from the actual optical sensor to the SLM. Specifically, the at least one optical sensor may be or may comprise at least one large-area optical sensor being adapted to detect a plurality of portions of the light beam passing through a plurality of the pixels. Thus, the at least one optical sensor may provide a single, non-segmented unitary sensor region adapted to provide a unitary sensor signal, wherein the sensor region is adapted to detect all portions of the light beam passing the SLM, at least for light beams entering the detector and passing the parallel to the optical axis. As an example, the unitary sensor region may have a sensitive area of at least 25 mm$^2$, preferably of at least 100 mm$^2$ and more preferably of at least 400 mm$^2$. Still, other embodiments are feasible, such as embodiments having two or more sensor regions. Further, in case two or more optical sensors are used, the optical sensors do not necessarily have to be identical. Thus, one or more large-area optical sensors may be combined with one or more pixelated optical sensors, such as with one or more camera chips, e.g. one or more CCD- or CMOS-chips, as will be outlined in further detail below.

The at least one optical sensor or, in case a plurality of optical sensors is provided, at least one of the optical sensors preferably may be fully or partially transparent. Thus, generally, the at least one optical sensor may comprise at least one at least partially transparent optical sensor such that the light beam at least partially may pass through the parent optical sensor. As used herein, the term "at least partially transparent" may both refer to the option that the entire optical sensor is transparent or a part (such as a sensitive region) of the optical sensor is transparent and/or to the option that the optical sensor or at least a transparent part of the optical sensor may transmit the light beam in an attenuated or non-attenuated fashion. Thus, as an example, the transparent optical sensor may have a transparency of at least 10%, preferably at least 20%, at least 40%, at least 50% or at least 70%. The transparency may depend on the wavelength of the light beam, and the given transparencies may be valid for at least one wavelength in at least one of the infra-red spectral range, the visible spectral range and the ultraviolet spectral range. Generally, as used herein, the infrared spectral range refers to a range of 780 nm to 1 mm, preferably to a range of 780 nm to 50 μm, more preferably to a range of 780 nm to 3.0 μm. The visible spectral range refers to a range of 380 nm to 780 nm. Therein, the blue spectral range, including the violet spectral range, may be defined as 380 nm to 490 nm, wherein the pure blue spectral range may be defined as 430 to 490 nm. The green spectral range, including the yellow spectral range, may be defined as 490 nm to 600 nm, wherein the pure green spectral range may be defined as 490 nm to 470 nm. The red spectral range, including the orange spectral range, may be defined as 600 nm to 780 nm, wherein the pure red spectral range may be defined as 640 to 780 nm. The ultraviolet spectral range may be defined as 1 nm to 380 nm, preferably 50 nm to 380 nm, more preferably 200 nm to 380 nm.

In order to provide a sensory effect, generally, the optical sensor typically has to provide some sort of interaction between the light beam and the optical sensor which typically results in a loss of transparency. The transparency of the optical sensor may be dependent on a wavelength of the light beam, resulting in a spectral profile of a sensitivity, an absorption or a transparency of the optical sensor. As outlined above, in case a plurality of optical sensors is provided, the spectral properties of the optical sensors do not necessarily have to be identical. Thus, one of the optical sensors may provide a strong absorption (such as one or more of an absorbance peak, an absorptivity peak or an absorption peak) in the red spectral region, another one of the optical sensors may provide a strong absorption in the green spectral region, and another one may provide a strong absorption in the blue spectral region. Other embodiments are feasible.

As outlined above, in case a plurality of optical sensors is provided, the optical sensors may form a stack. Thus, the at least one optical sensor comprises a stack of at least two optical sensors. At least one of the optical sensors of the stack may be an at least partially transparent optical sensor. Thus, preferably, the stack of optical sensors may comprise at least one at least partially transparent optical sensor and at least one further optical sensor which may be transparent or intransparent. Preferably, at least two transparent optical sensors are provided. Specifically, an optical sensor on a side furthest away from the spatial light modulator may also be an intransparent optical sensor, such as an opaque sensor, wherein organic or inorganic optical sensors may be used, such as inorganic semiconductor sensors like CCD or CMOS chips.

The stack may be partially or fully immersed in an oil and/or liquid to avoid and/or decrease reflections at interfaces. Thus, at least one of the optical sensors of the stack may fully or partially be immersed in the oil and/or the liquid.

As outlined above, the at least one optical sensor necessarily has to be a pixelated optical sensor. Thus, by using the general idea of performing the frequency analysis, a pixelation may be omitted. Still, specifically in case a plurality of optical sensors is provided, one or more pixelated optical sensors may be used. Thus, specifically in case a stack of optical sensors is used, at least one of the optical sensors of the stack may be a pixelated optical sensor having a plurality of light-sensitive pixels. As an example, the pixelated optical sensor may be a pixelated organic and/or inorganic optical sensor. Most preferably, specifically due to their commercial availability, the pixelated optical sensor may be an inorganic pixelated optical sensor, preferably a CCD chip or a CMOS chip. Thus, as an example, the stack may comprise one or more transparent large-area non-pixelated optical sensors, such as one or more DSCs and more preferably sDSCs (as will be outlined in further detail below), and at least one inorganic pixelated optical sensor, such as a CCD chip or a CMOS chip. As an example, the at least one inorganic pixelated optical sensor may be located on a side of the stack furthest away from the spatial light modulator. Specifically, the pixelated optical sensor may be a camera chip and, more preferably, a full-color camera chip. Generally, the pixelated optical sensor may be color-sensitive, i.e. may be a pixelated optical sensor adapted to distinguish between color components of the light beam, such as by providing at least two different types of pixels, more preferably at least three different types of pixels, having a different color sensitivity. Thus, as an example, the pixelated optical sensor may be a full-color imaging sensor.

Preferably, the at least one optical sensor contains at least one longitudinal optical sensor, i.e. an optical sensor which is adapted to determine a longitudinal position of at least one object, such as at least one z-coordinate of an object. Preferably, the optical sensor or, in case a plurality of optical sensors is provided, at least one of the optical sensors may have a setup and/or may provide the functions of the optical sensor as disclosed in WO 2012/110924 A1. Thus, preferably, the at least one optical sensor and/or one or more of the optical sensors may have at least one sensor region, wherein the sensor signal of the optical sensor is dependent on an illumination of the sensor region by the light beam, wherein the sensor signal, given the same total power of the illumination, is dependent on a geometry, specifically a width, of the light beam in the sensor region, wherein the evaluation device is adapted to determine the width by evaluating the sensor signal. In the following, this effect generally will be referred to as the FiP-effect, since, given the same total power p of illumination, the sensor signal i is dependent on a flux F of photons, i.e. the number of photons per unit area. It shall be noted, however, that a detector based on the FiP-effect is simply a preferred embodiment of a longitudinal optical sensor. Additionally or alternatively, one or more other types of longitudinal optical sensors may be used. Thus, in the following, in case reference is made to a FiP sensor, it shall be noted that, generally, other types of longitudinal optical sensors may be used instead. Still, due to the superior properties and due to the advantages of FiP sensors, the use of at least one FiP sensor is preferred.

The FiP-effect, which is further disclosed in U.S. provisional applications 61/739,173 and 61/749,964, may be used for determining a longitudinal position of an object from which the light beam travels towards the detector. Thus, since the beam with the light beam on the sensor region, which preferably may be a non-pixelated sensor region, depends on a width, such as a diameter or radius, of the light beam which again depends on a distance between the detector and the object, the sensor signal may be used for determining a longitudinal coordinate of the object. Thus, as an example, the evaluation device may be adapted to use a predetermined relationship between a longitudinal coordinate of the object and a sensor signal in order to determine the longitudinal coordinate. The predetermined relationship may be derived by using empiric calibration measurements and/or by using known beam propagation properties, such as Gaussian beam propagation properties. For further details, reference may be made to WO 2012/110924 A1 and/or U.S. provisional applications 61/739,173 and 61/749,964.

Preferably, in case a plurality of optical sensors is provided, such as a stack of optical sensors, at least two of the optical sensors may be adapted to provide the FiP-effect. Specifically, one or more optical sensors may be provided which exhibit the FiP-effect, wherein, preferably, the optical sensors exhibiting the FiP-effect are large-area optical sensors having a uniform sensor surface rather than being pixelated optical sensors.

Thus, by evaluating signals from optical sensors which subsequently are illuminated by the light beam, such as subsequent optical sensors of a sensor stack, and by using the above-mentioned FiP-effect, ambiguities in a beam profile may be resolved. Thus, Gaussian light beams may provide the same beam width at a distance z before and after a focal point. By measuring the beam width along at least two positions, this ambiguity may be resolved, by determining whether the light beam still is narrowing or widening. Thus, by providing two or more optical sensors having the FiP-effect, a higher accuracy may be provided. The evaluation device may be adapted to determine the widths of the light beam in the sensor regions of the at least two optical sensors, and the evaluation device may further be adapted to generate at least one item of information on a longitudinal position of an object from which the light beam propagates towards the optical detector, by evaluating the widths.

Specifically in case the at least one optical sensor or one or more of the optical sensors provide the above-mentioned FiP-effect, the sensor signal of the optical sensor may be dependent on a modulation frequency of the light beam. As an example, the FiP-effect may function as modulation frequencies of 0.1 Hz to 10 kHz.

Thus, generally, the light beam may be modulated by one or more modulation devices. The modulation for enhancing and/or enabling the FiP-effect may be the same modulation as used by the modulator device controlling the pixels of the spatial light modulator and/or may be a different modulation. Thus, the spatial light modulator may provide the modulation enabling and/or enhancing the FiP-effect. Additionally or alternatively, an additional modulation may be provided, such as by using one or more illumination sources being adapted to emit the light beam in a modulated way. Thus, as an example, the modulation used by the modulator device and the pixels of the spatial light modulator may be in a first frequency range, such as in a range of 1 Hz to 100 Hz, whereas, additionally, the light beam itself may optionally additionally be modulated by a at least one second modulation frequency, such as a frequency in a second frequency range of 100 Hz to 10 kHz. Thus, for example, more than one modulation may be used, wherein at least one first modulation generated by the spatial light modulator and the modulator device may be used for assigning a signal component to one or more specific pixels of the spatial light modulator and wherein at least one further modulation may be used for one or more different purposes, such as for enhancing and/or enabling the FiP-effect and/or for identifying one or more illumination sources emitting at a specific modulation frequency. The latter purpose may be used for distinguishing between two or more different types of beacon devices emitting modulated light beams at different modulation frequencies. For further details, reference may be made to EP 13171900.7, filed on Jun. 13, 2013.

As outlined above, the at least one optical sensor or, in case a plurality of optical sensors is provided, one or more of the optical sensors preferably may be or may comprise at least one organic semiconductor detector and/or at least one inorganic semiconductor detector. Thus, generally, the optical detector may comprise at least one semiconductor detector. Most preferably, the semiconductor detector or at least one of the semiconductor detectors may be an organic semiconductor detector comprising at least one organic material. Thus, as used herein, an organic semiconductor detector is an optical detector comprising at least one organic material, such as an organic dye and/or an organic semiconductor material. Besides the at least one organic material, one or more further materials may be comprised, which may be selected from organic materials or inorganic materials. Thus, the organic semiconductor detector may be designed as an all-organic semiconductor detector comprising organic materials only, or as a hybrid detector comprising one or more organic materials and one or more inorganic materials. Still, other embodiments are feasible. Thus, combinations of one or more organic semiconductor detectors and/or one or more inorganic semiconductor detectors are feasible.

Preferably, the semiconductor detector may be selected from the group consisting of an organic solar cell, a dye solar cell, a dye-sensitized solar cell, a solid dye solar cell, a solid dye-sensitized solar cell.

Preferably, specifically in case one or more of the optical sensors provide the above-mentioned FiP-effect, the at least one optical sensor or, in case a plurality of optical sensors is provided, one or more of the optical sensors, may be or may comprise a dye-sensitized solar cell (DSC), preferably a solid dye-sensitized solar cell (sDSC). As used herein, a DSC generally refers to a setup having at least two electrodes, wherein at least one of the electrodes is at least partially transparent, wherein at least one n-semiconducting metal oxide, at least one dye and at least one electrolyte or p-semiconducting material is embedded in between the electrodes. In an sDSC, the electrolyte or p-semiconducting material is a solid material. Generally, for potential setups of sDSCs which may also be used for one or more of the optical sensors within the present invention, reference may be made to one or more of WO 2012/110924 A1, U.S. provisional applications 61/739,173 and 61/749,964, EP 13171898.3, EP 13171900.7 or EP 13171901.5. Other embodiments are feasible. The above-mentioned FiP-effect, as demonstrated in WO 2012/110924 A1, specifically may be present in sDSCs.

Thus, generally, the at least one optical sensor may comprise at least one optical sensor having a layer setup comprising at least one first electrode, at least one n-semiconducting metal oxide, at least one dye, at least one p-semiconducting organic material, preferably a solid p-semiconducting organic material, and at least one second electrode. As outlined above, at least one of the first electrode and the second electrode may be transparent. Most preferably, specifically in case a transparent optical sensor shall be provided, both the first electrode and the second electrode may be transparent.

As outlined above, the optical detector may contain one or more further devices, specifically one or more further optical devices such as one or more lenses and/or one or more reflecting devices. Thus, most preferably, the optical detector may comprise a setup, such as a setup arranged in a tubular fashion, the setup having the at least one spatial light modulator and at least one optical sensor, preferably a stack of at least two optical sensors, located behind the spatial light modulator such that a light beam having passed the spatial light modulator subsequently passes the one or more optical sensors. Preferably before passing the spatial light modulator, the light beam may pass one or more optical devices such as one or more lenses, preferably one or more optical devices adapted for influencing a beam shape and/or a beam widening or narrowing in a well-defined fashion. Additionally or alternatively, one or more optical devices such as one or more lenses may be placed in between the spatial light modulator and the at least one optical sensor.

The one or more optical devices generally may be referred to as a transfer device, since one of the purposes of the transfer device may reside in a well-defined transfer of the light beam into the optical detector. As used herein, consequently, the term "transfer device" generally refers to an arbitrary device or combination of devices adapted for guiding and/or feeding the light beam onto one or more of the spatial light modulator or the optical sensor, preferably by influencing one or more of a beam shape, a beam width or a widening angle of the light beam in a well-defined fashion, such as a lens or a curved mirror do.

Thus, generally, the optical detector may further comprise at least one transfer device adapted for feeding light into the optical detector. The transfer device may be adapted to focus and/or collimate light onto one or more of the spatial light modulator and the optical sensor. The transfer device specifically may comprise one or more devices selected from the group consisting of: a lens, a focusing mirror, a defocusing mirror, a reflector, a prism, an optical filter, a diaphragm. Other embodiments are feasible.

A further aspect of the present invention may refer to the option of image recognition, pattern recognition and individually determining z-coordinates of different regions of an image captured by the optical detector. Thus, generally, as outlined above, the optical detector may be adapted to capture at least one image, such as a 2D-image. For this purpose, as outlined above, the optical detector may comprise at least one imaging device such as at least one pixelated optical sensor. As an example, the at least one pixelated optical sensor may comprise at least one CCD sensor and/or at least one CMOS sensor. By using this at least one imaging device, the optical detector may be adapted to capture at least one regular two-dimensional image of a scene and/or at least one object. The at least one image may be or may comprise at least one monochrome image and/or at least one multi-chrome image and/or at least one full-color image. Further, the at least one image may be or may comprise a single image or may comprise a series of images.

Further, as outlined above, the optical detector may comprise at least one distance sensor adapted for determining a distance of at least one object from the optical detector, also referred to as a z-coordinate. Thus, specifically, the so-called FiP-effect may be used, as outlined above and as disclosed e.g. in WO 2012/110924 A1 and/or in one or more of U.S. provisional applications 61/739,173 and 61/749,964. Thus, the at least one optical sensor or, in case a plurality of optical sensors is comprised, at least one of the optical sensors, may be embodied as a so-called FiP-sensor, i.e. a sensor having at least one sensor region, wherein the sensor signal of the FiP-sensor is dependent on an illumination of the sensor region by the light beam, wherein the sensor signal, given the same total power of the illumination, is dependent on a width of the light beam in the sensor region. Thus, generally, in FiP-sensors, a known relationship between the sensor signal and a z-coordinate of an object from which the light beam travels towards the optical detector may be used for determining the z-coordinate of the object and/or a part thereof. The optical detector generally may comprise one or more FiP-sensors, preferably a stack of FiP-sensors.

By using a combination of regular 2D-image capturing and the possibility of determining z-coordinates, 3D-imaging is feasible.

In order to individually evaluate one or more objects and/or components contained within a scene captured within the at least one image, the at least one image may be subdivided into two or more regions, wherein the two or more regions or at least one of the two or more regions may be evaluated individually. For this purpose, a frequency selective separation of the signals corresponding to the at least two regions may be performed.

Thus, the optical detector generally may be adapted to capture at least one image, preferably a 2D-image. Further, the optical detector, preferably the at least one evaluation device, may be adapted to define at least two regions in the image and to assign corresponding superpixels of the matrix of pixels of the spatial light modulator to at least one of the regions, preferably to each of the regions. As used herein, a region generally may be an area of the image or group of pixels of an imaging device capturing the image corresponding to the area, wherein, within the area, an identical or similar intensity or color may be present. Thus, generally, a region may be an image of at least one object, the image of the at least one object forming a partial image of the image captured by the optical detector. Thus, the optical detector may acquire an image of a scene, wherein, within the scene, at least one object is present, wherein the object is imaged onto a partial image.

Thus, within the image, at least two regions may be identified, such as by using an appropriate algorithm as will be outlined in further detail below. Since, generally, the imaging properties of the optical detector are known, such as by using known imaging equations and/or matrix optics, the regions of the image may be assigned to corresponding pixels of the spatial light modulator. Thus, components of the at least one light beam passing specific pixels of the matrix of pixels of the spatial light modulator subsequently may hit corresponding pixels of the imaging device. Thus, by subdividing the image into two or more regions, the matrix of pixels of the spatial light modulator may be subdivided into two or more superpixels, each superpixel corresponding to a respective region of the image.

As outlined above, one or more image recognition algorithms may be used for determining the at least two regions. Thus, generally, the optical detector, preferably the at least one evaluation device, may be adapted to define the at least two regions in the image by using at least one image recognition algorithm. Means and algorithms for image recognition generally are known to the skilled person. Thus, as an example, the at least one image recognition algorithm may be adapted to define the at least two regions by recognizing boundaries of at least one of: contrast, color or intensity. As used herein, a boundary generally is a line along which a significant change in at least one parameter occurs when crossing the line. Thus, as an example, gradients of one or more parameters may be determined and, as an example, may be compared to one or more threshold values. Specifically, the at least one image recognition algorithm may be selected from the group consisting of: Felzenszwalb's efficient graph based segmentation; Quick-shift image segmentation; SLIC—K-Means based image segmentation; Energy-Driven sampling; an edge detection algorithm such as a Canny algorithm; a Mean-shift algorithm, such as a Cam shift algorithm (Cam: Continuously Adaptive Mean shift); a Contour extraction algorithm. Additionally or alternatively, other algorithms may be used, such as one or more of: algorithms for edge, ridge, corner, blob, or feature detection; algorithms for dimensionality reduction; algorithms for texture classification; algorithms for texture segmentation. These algorithms are generally known to the skilled person. In the context of the present invention, these algorithms may be referred to as an image recognition algorithm, and image partitioning algorithm or a superpixel algorithm. As outlined above, the at least one image recognition algorithm is adapted to recognize one or more objects in the image. Thereby, as an example, one or more objects of interest and/or one or more regions of interest may be determined, for further analysis, such as for determination of corresponding z-coordinates.

As outlined above, the superpixels may be chosen such that the superpixels and their corresponding regions are illuminated by the same components of the light beam. Thus, the optical detector, preferably the at least one evaluation device, may be adapted to assign the superpixels of the matrix of pixels of the spatial light modulator to at least one of the regions, preferably to each of the regions such that each component of the light beam passing a specific pixel of the matrix of pixels, the specific pixel belonging to a specific superpixel, subsequently hits the specific region of the at least two regions, the specific region corresponding to the specific superpixel.

As indicated above, the assignment of superpixels may be used for simplifying the modulation. Thus, by assigning superpixels to corresponding regions of the image, the number of modulation frequencies may be reduced, thereby allowing for using a lower number of modulation frequencies as compared to a process in which individual modulation frequencies are used for each of the pixels. Thus, as an example, the optical detector, preferably the at least one evaluation device, may be adapted to assign at least one first modulation frequency to at least a first superpixel of the superpixels and at least one second modulation frequency to at least a second superpixel of the superpixels, wherein the first modulation frequency is different from the second modulation frequency, and wherein the at least one modulator device is adapted for periodically controlling the pixels of the first superpixel with the at least one first modulation frequency and for periodically controlling the pixels of the second superpixel with the at least one second modulation frequency. Thereby, the pixels of a specific superpixel may be modulated by using a uniform modulation frequency assigned to the specific superpixel. Further, optionally, the superpixel may be subdivided into sub-pixels and/or additionally modulations may be applied within the superpixel. Using a uniform modulation frequency e.g. for a superpixel corresponding to an identified object within the image greatly simplifies the evaluation, since, as an example, a determination of a z-coordinate of the object may be performed by evaluating the at least one sensor signal (such as at least one sensor signal of at least one FiP-sensor or a stack of FiP-sensors of the optical detector) in a frequency-selective way, by selectively evaluating the sensor signals having the respective modulation frequency assigned to the superpixel of the object. Thereby, within a scene captured by the optical detector, the object may be identified within the image, at least one superpixel may be assigned to the object, and, by using at least one optical sensor adapted for determining a z-coordinate and by evaluating the at least one sensor signal of said optical sensor in a frequency-selective way, the z-coordinate of the object may be determined.

Thus, generally, as outlined above, the optical detector, preferably the at least one evaluation device, may be adapted to individually determine z-coordinates for each of the regions or for at least one of the regions, such as for a region within the image which is recognized as a partial image, such as the image of an object. For determining the at least one z-coordinate, the FiP-effect may be used, as outlined in one or more of the above-mentioned prior art documents referring to the FiP-effect. Thus, the optical detector may comprise at least one FiP-sensor, at least one optical sensor having at least one sensor region, wherein the sensor signal of the optical sensor is dependent on an illumination of the sensor region by the light beam, wherein the sensor signal, given the same total power of the illumination, is dependent on a width of the light beam in the sensor region. An individual FiP-sensor may be used or, preferably, a stack of FiP-sensors, i.e. a stack of optical sensors having the named properties. The evaluation device of the optical detector may be adapted to determine the z-coordinates for at least one of the regions or for each of the regions, by individually evaluating the sensor signal in a frequency-selective way.

In order to make use of at least one FiP-sensor within the optical detector, various setups may be used for combining the spatial light modulator, the at least one FiP-sensor and the at least one imaging device such as the at least one pixelated sensor, preferably the at least one CCD or CMOS sensor. Thus, generally, the named elements may be arranged in one and the same beam path of the optical detector or may be distributed over two or more partial beam paths. As outlined above, optionally, the optical detector may contain at least one beam-splitting element adapted for dividing a beam path of the light beam into at least two partial beam paths. Thereby, the at least one imaging device for capturing the 2D image and the at least one FiP-sensor may be arranged in different partial beam paths. Thus, the at least one optical sensor having the at least one sensor region, the sensor signal of the optical sensor being dependent on the illumination of the sensor region by the light beam, the sensor signal, given the same total power of the illumination, being dependent on the width of the light beam in the sensor region, (i.e. the at least one FiP-sensor) may be arranged in a first partial beam path of the beam paths, and at least one pixelated optical sensor for capturing the at least one image (i.e. the at least one imaging device), preferably the at least one inorganic pixelated optical sensor and more preferably the at least one of a CCD sensor and/or CMOS sensor, may arranged in a second partial beam path of the beam paths.

The above-mentioned optional definition of the at least two regions and/or the definition of the at least two superpixels may be performed once or more than once. Thus, specifically, the definition of at least one of the regions and/or of at least one of the superpixels may be performed in an iterative way. The optical detector, preferably the at least one evaluation device, may be adapted to iteratively refine the at least two regions in the image or at least one of the at least two regions within the image and, consequently, to refine the at least one corresponding superpixel. By this iterative procedure, as an example, at least one specific superpixel assigned to at least one object within a scene captured by the detector may be refined by identifying two or more sub-pixels, such as sub pixels corresponding to different parts of the at least one object having different z-coordinates. Thereby, by this iterative procedure, a refined 3D image of at least one object may be generated, since, typically, an object comprises a plurality of parts having different orientations and/or locations in space.

The above-mentioned embodiments of the optical sensor being adapted for defining two or more superpixels provide a large number of advantages. Thus, specifically, in a typical setup, a limited number of modulation frequencies is available. Consequently, only a limited number of pixels and/or modulation frequencies may be resolved by the optical detector and may be available for distance sensing. Further, in typical applications, boundary regions of high contrast are necessary for accurate distance sensing. By defining two or more superpixels and, thus, by partitioning (also referred to as tessellating) the matrix of pixels of the spatial light modulator into superpixels, the imaging process may be adapted to the scene to be recorded.

The spatial light modulator specifically may have a rectangular matrix of pixels. Several pixels which may or may not be direct neighbors and which may form a connected area may form a superpixel. The 2D image recorded by the pixelated sensor, such as the CMOS and/or CCD, may be analyzed, such as by an appropriate software, such as an image recognition software running on the evaluation device, and, consequently, the image may be partitioned into two or more regions. The tessellation of the spatial light modulator may take place in accordance with this subdividing of the image into two or more regions. As an example, a large or very large superpixel may correspond to specific objects within the scene recorded, such as a wall, a building, the sky, etc. Further, many small pixels or superpixels may be used to partition a face, etc. In case a sufficient amount of superpixels are available, larger superpixels may further be partitioned into sub-pixels. The at least two superpixels generally may differ with regard to the number of pixels of the spatial light modulator belonging to the respective superpixels. Thus, two different superpixels not necessarily have to comprise the same number of pixels.

Generally, boundaries of the regions or superpixels may be set by arbitrary means generally known in the field of image processing and image recognition. Thus, as an example, boundaries may be chosen by contrast, color or intensity edges.

The definition of the two or more regions and/or the two or more superpixels may later on also be used for further image analysis, such as gesture analysis, body recognition or object recognition. Exemplary algorithms for segmentation are Felzenszwalb's efficient graph based segmentation, Quickshift image segmentation, SLIC—K-Means based image segmentation, superpixels extracted via energy driven sampling, superpixels extracted via one or more edge detection algorithms such as a Canny algorithm, superpixels extracted via a Mean-shift algorithm such as a Cam shift algorithm, superpixels extracted via a Contour extraction algorithm, superpixels extracted via edge, ridge, corner, blob, or feature detection, superpixels extracted via dimensionality reduction, superpixels obtained by texture classification and superpixels obtained by using texture segmentation. Combinations of the named techniques and/or other techniques are possible.

The superpixelation may also change during image recording. Thus, a rough pixelation into superpixels may be chosen for quick distance sensing. A finer grid or superpixelation may then be chosen for a more detailed analysis and/or in case high distance gradients are recognized in between two neighboring superpixels and/or in case high gradients in one or more of contrast, color, intensity or the like are noticed in between two neighboring superpixels. A high resolution 3D-image may thus be recorded in an iterative approach where the first image has a rough resolution, the next image has a refined resolution etc.

The above-mentioned options of determining one or more regions and assigning one or more superpixels to these regions may further be used for eye tracking. Thus, in many applications such as safety applications and/or entertainment applications, determining the position and/or orientation of eyes of a user, another person or another creature may play an important role. As an example, in entertainment applications, the perspective of the viewer plays a role. For instance 3D-vision applications, the perspective of the viewer may change the setup of an image. Therefore, it may be a significant interest to know and/or track the viewing position of an observer. In safety applications such as automotive safety applications, the detection of animals is of importance, in order to avoid collisions.

The above-mentioned definition of one, two or more superpixels may further be used to improve or even optimize light conditions. Thus, generally, the frequency response of an optical sensor typically leads to weaker sensor signals when higher modulation frequencies are used, such as higher modulation frequencies of the SLM, specifically of the DLP. Areas with high light intensities within the image and/or scene may therefore be modulated with high frequencies, whereas areas with low light intensities may be modulated with low frequencies.

In order to make use of this effect, the optical detector may be adapted to detect at least one first area within the image, the first area having a first illumination, such as a first average illumination, and the optical detector may further be adapted to detect at least one second area within the image, the second area having a second illumination, such as a second average illumination, wherein the second illumination is lower than the first illumination. The first area may be assigned to at least one first superpixel, and the second area may be assigned to at least one second superpixel. In other words, the optical detector may be adapted to choose at least two superpixels according to the illumination of a scene or an image of the scene captured by the optical detector.

The optical detector may further be adapted to modulate the pixels of the at least two superpixels according to their illumination. Thus, superpixels having a higher illumination may be modulated at higher modulation frequencies, and superpixels having a lower illumination may be modulated at lower modulation frequencies. In other words, the optical detector may further be adapted to modulate the pixels of the first superpixel with at least one first modulation frequency, and the optical detector may further be adapted to modulate the pixels of the second superpixel with at least one second modulation frequency, wherein the first modulation frequency is higher than the second modulation frequency. Other embodiments are feasible.

The optical detector according to the present invention may therefore be adapted to detect at least one eye and preferably to track the position and/or orientation of at least one eye or of eyes.

A simple solution to detect the viewing position of an observer or the position of an animal is to make use of a modulated eye reflection. A large number of mammals possess a reflective layer behind the retina, the so-called tapetum lucidum. The tapetum lucidum reflection is of slightly different color appearance for different animals, but most reflect well in the green visible range. The tapetum lucidum reflection generally allows for making animals visible in the dark over far distances, using simple diffuse light sources.

Humans generally do not possess a tapetum lucidum. However, in photographs, the so-called heme-emission induced by a photography flash is often recorded, also referred to as the "red-eye effect". This effect may also be used for eye detection of human beings, even though it is not directly visible to the human eye, due to the human eye's low sensitivity in the spectral range beyond 700 nm. The red-eye effect may specifically be induced by modulated red illumination and sensed by at least one optical sensor of the optical detector, such as at least one FiP-sensor, wherein the at least one optical sensor is sensitive at the heme-emission wavelength.

The optical detector according to the present invention may therefore comprise at least one illumination source, also referred to as at least one light source, which may be adapted to fully or partially illuminate a scene captured by the optical detector, wherein the light source is adapted to evoke reflections in a mammal, such as in a tapetum lucidum of a mammal and/or is adapted to evoke the above-mentioned red-eye effect in human eyes. Specifically, the light in the infrared spectral range, the red spectral range, the yellow spectral range, the green spectral range, the blue spectral range or simply white light may be used. Still, other spectral ranges and/or broadband light sources may be used additionally or alternatively.

Additionally or alternatively, the eye detection may also take place without a dedicated illumination source. As an example, ambient light or other light from light sources such as lanterns, streetlights or headlights of a car or other vehicle may be used and may be reflected by the eye.

In case at least one illumination source is used, the at least one illumination source may continuously emit light or may be a modulated light source. Thus, specifically, at least one modulated active light source may be used.

The reflection specifically may be used in order to detect animals and/or humans over large distances, such as by using a modulated active light source. The at least one optical sensor, specifically the at least one FiP sensor, may be used for measuring at least one longitudinal coordinate of the eye, such as by evaluating the above mentioned FiP-effect of the eye reflections. This effect specifically may be used in car safety applications, such as in order to avoid collisions with humans or animals. A further possible application is the positioning of observers for entertainment devices, especially if using 3D-vision, especially if the 3D-vision is dependent on the viewing angle of the observer.

As outlined above or as outlined in further detail in the following, the devices according to the present invention, such as the optical detector, may be adapted to identify and/or track one or more objects within an image and/or within a scene captured by the optical detector, specifically by assigning one or more superpixels to the at least one object. Further, two or more parts of the object may be identified, and by determining and/or tracking the longitudinal and/or transversal position of these parts within the image, such as the relative longitudinal and/or transversal position, at least one orientation of the object may be determined and/or tracked.

Thus, as an example, by determining two or more wheels of a vehicle within the image and by determining and/or tracking the position, specifically the relative position, of these wheels, an orientation of the vehicle and/or a change of orientation of the vehicle may be determined, such as calculated, and/or tracked. For example, in a car, the distance between the wheels is generally known or it is known that the distance between the wheels does not change. Further it is generally known that the wheels are aligned on a rectangle. Detecting the position of the wheels thus allows calculating the orientation of the vehicle such as a car, a plane or the like.

In a further example, as outlined above, the position of eyes may be determined and/or tracked. Thus, the distance and/or position of the eyes or parts thereof, such as the pupils, and/or other facial features can be used for eye trackers or to determine in which direction a face is oriented.

As outlined above, the at least one light beam may fully or partially originate from the object itself and/or from at least one additional illumination source, such as an artificial illumination source and/or a natural illumination source. Thus, the object may be illuminated with at least one primary light beam, and the actual light beam propagating towards the optical detector may be or may comprise a secondary light beam generated by reflection, such as elastic and/or inelastic reflection, of the primary light beam at the object and/or by scattering. Non-limiting examples of objects which are detectable by reflections are reflections of sunlight, artificial light in eyes, on surfaces, etc. Non-limiting examples of objects from which the at least one light beam originates fully or partially from the object itself are engine exhausts in cars or planes. As outlined above, eye reflections might be especially useful for eye-trackers.

Further, as outlined above, the optical detector comprises at least one modulator device, such as an SLM. The optical detector, however, additionally or alternatively may make use of a given modulation of the light beam. Thus, in many instances, the light beam already exhibits a given modulation. The modulation, as an example, may originate from a movement of the object, such as a periodic modulation, and/or from a modulation of a light source or illumination source generating the light beam. Thus, as non-limiting examples for moving objects adapted to generate modulated light such as by reflection and/or scattering are objects that are modulated by itself, such as rotors of wind turbines or planes. Non-limiting examples of illumination sources adapted to generate modulated light are fluorescent lamps or reflections of fluorescent lamps.

The optical detector may be adapted to detect given modulations of the at least one light beam. As an example, the optical detector may be adapted to determine at least one object or at least one part of an object within an image or a scene captured by the optical detector that emits or reflects modulated light, such as light having, by itself and without any influence of the SLM, at least one modulation frequency. If this is the case, the optical detector may be adapted to make use of this given modulation, without additionally modulating the already modulated light. As an example, the optical detector may be adapted to determine if at least one object within an image or a scene captured by the optical detector emits or reflects modulated light. The optical detector, especially the evaluation device, may further be adapted to assign at least one superpixel to said object, wherein the pixels of the superpixel specifically may not be modulated, in order to avoid a further modulation of light originating or being reflected by said object. The optical detector, specifically the evaluation device, may further be adapted to determine and/or track the position and/or orientation of said object by using the modulation frequency. Thus, as an example, the detector may be adapted to avoid modulation for the object, such as by switching the modulation device to an "open" position. The evaluation device could then track the frequency of the lamp.

The spatial light modulator may be used for a simplified image analysis of at least one image captured by an image detector and/or for an analysis of a scene captured by the optical detector. Thus, generally, a combination of the at least one spatial light modulator and at least one longitudinal optical sensor may be used, such as a combination of at least one FiP sensor and at least one spatial light modulator such as a DLP. The analysis may be performed by using an iterative scheme. If a focus point causing a FiP-signal is part of a larger region on the longitudinal optical sensor, the FiP signal may be detected. The spatial light modulator may separate an image or a scene captured by the optical detector into two or more regions. If a FiP-effect is measured in at least one of the regions, the regions may further be subdivided. This subdivision may be continued until a maximum number of possible regions, which may be limited by the maximum number of available modulation frequencies of the spatial light modulator, is reached. More complex patterns are also possible.

As outlined above, the optical detector generally may comprise at least one imaging device and/or may be adapted to capture at least one image, such as at least one image of a scene within a field of view of the optical detector. By using one or more image evaluation algorithms, such as generally known pattern detection algorithms and/or software image evaluation means generally known to the skilled person, the optical detector may be adapted to detect at least one object in the at least one image. Thus, as an example, in traffic technology, the detector and, more specifically, the evaluation device, may be adapted to search for specific predefined patterns within an image, such as one or more of the following: the contour of a car; the contour of another vehicle; the contour of a pedestrian; street signs; signals; landmarks for navigation. The detector may also be used in combination with global or local positioning systems. Similarly, for biometrical purposes such as for the purpose of recognition and/or tracking of persons, the detector and, more specifically, the evaluation device, may be adapted for searching a contour of a face, eyes, earlobes, lips, noses or profiles thereof. Other embodiments are feasible.

In case one or more objects are detected, the optical detector might be adapted to track the object in a series of images, such as an ongoing movie or film of the scene. Thus, generally, the optical detector, specifically the evaluation device, may be adapted to track and/or follow the at least one object within a series of images, such as a series of subsequent images.

For the purpose of object following, the optical detector may be adapted to assign the at least one object to a region within the image or series of images, as described above. As discussed earlier, the optical detector, preferably the at least one evaluation device, may be adapted to assign at least one superpixel of the matrix of pixels of the spatial light modulator to the at least one region corresponding to the at least one object. By modulating the pixels of the superpixels in a specific way, such as by using a specific modulation frequency, the object may be tracked, and the at least one z-coordinates of the at least one object may be followed by using the at least one optional longitudinal sensor, such as the at least one FiP-detector, and demodulating or isolating the corresponding signals of the longitudinal sensor, such as the at least one FiP-detector, according to this specific modulation frequency. The optical detector may be adapted to adjust the assignment of the at least one superpixel for the images of the series of images. Thus, as an example, the imaging device may continuously acquire images of the scene and, for each image, the at least one object may be recognized. Subsequently, the at least one superpixel may be assigned to the object, and the z-coordinate of the object may be determined by using the at least one longitudinal optical sensor, specifically the at least one FiP-sensor, before turning to the next image. Thus, the at least one object may be followed in space.

This embodiment allows for a greatly simplified setup of the optical detector. The optical detector may be adapted to perform an analysis of a scene captured by the imaging device, such as a standard 2D-CCD camera. A picture analysis of the scene can be used to recognize positions of active and/or passive objects. The optical detector may be trained to recognize specific objects, such as predetermined patterns or similar patterns. In case one or more objects are recognized, the spatial light modulator may be adapted to modulate only the regions in which the one or more objects are located and/or to modulate these regions in a specific fashion. The remaining area may remain unmodulated and/or may be modulated in a different way, which may generally be known to the longitudinal sensor and/or to the evaluation device.

By using this effect, the number of modulation frequencies used by the spatial light modulator may be greatly reduced. Typically, only a limited number of modulation frequencies is available to analyze the full scene. If only the important or recognized objects are followed, a very small number of frequencies are necessary.

The longitudinal optical sensor or distance sensor can then be used as unpixelated large area sensor or as a large area sensor having only a small number of superpixels, such as at least one superpixel corresponding to the at least one object and a remaining superpixel corresponding to the surrounding area, wherein the latter may remain unmodulated. Thus, the number of modulation frequencies and thus the complexity of the data analysis of the sensor signal may greatly be reduced as compared to the basic SLM detector of the present invention.

As outlined above, this embodiment specifically may be used in traffic technology and/or for biometric purposes, such as identification and/or of persons and/or for the purpose of eye tracking. Other applications are feasible.

The optical detector according to the present invention may further be embodied to acquire three-dimensional images. Thus, specifically, a simultaneous acquisition of images in different planes perpendicular to an optical axis may be performed, i.e. an acquisition of images in different focal planes. Thus, specifically, the optical detector may be embodied as a light-field camera adapted for acquiring images in multiple focal planes, such as simultaneously. The term light-field, as used herein, generally refers to the spatial light propagation of light inside the camera. Contrarily, in commercially available plenoptic or light-field cameras, micro-lenses may be placed on top of an optical detector. These micro-lenses allow for recording a direction of light beams, and, thus, for recording pictures in which a focus may be changed a posteriori. However, the resolution of a camera with micro-lenses is generally reduced by approximately a factor of ten as compared to conventional cameras. A post-processing of the images is required in order to calculate pictures which are focused on various distances. Another disadvantage of current light-field cameras is the necessity of using a large number of micro-lenses which typically have to be manufactured on top of an imaging chip such as a CMOS chip.

By using the optical detector according to the present invention, a greatly simplified light-field camera may be produced, without the necessity of using micro-lenses. Specifically, a single lens or lens system may be used. The evaluation device may be adapted for intrinsic depth-calculation and simple and intrinsic creation of a picture that is focused on a plurality of levels or even on all levels.

These advantages may be achieved by using a multiplicity of the optical sensors. Thus, as outlined above, the optical detector may comprise at least one stack of optical sensors. The optical sensors of the stack or at least several of the optical sensors of the stack preferably are at least partially transparent. Thus, as an example, pixelated optical sensors or large area optical sensors may be used within the stack. As an example for potential embodiments of optical sensors, reference may be made to the organic optical sensors, specifically to the organic solar cells and, more specifically, to the DSC optical sensors or sDSC optical sensors as disclosed above or as disclosed in further detail below. Thus, as an example, the stack may comprise a plurality of FiP sensors as disclosed e.g. in WO 2012/110924 A1 or in any other of the FiP-related documents discussed above, i.e. a plurality of optical sensors with photon density-dependent photocurrents for depth detection. Thus, specifically, the stack may be a stack of transparent dye-sensitized organic solar cells. As an example, the stack may comprise at least two, preferably at least three, more preferably at least four, at least five, at least six or even more optical sensors, such as 2-30 optical sensors, preferably 4-20 optical sensors. Other embodiments are feasible. By using the stack of optical sensors, the optical detector, specifically the at least one evaluation device, may be adapted to acquire a three-dimensional image of a scene within a field of view of the optical detector, such as by acquiring images at different focal depths, preferably simultaneously, wherein the different focal depths generally may be defined by a position of the optical sensors of the stack along an optical axis of the optical detector. Even though a pixelation of the optical sensors generally may be present, a pixelation is, however, generally unnecessary due to the fact that the use of the at least one spatial light modulator allows for a virtual pixelation, as outlined above. Thus, as an example, a stack of organic solar cells, such as a stack of sDSCs, may be used, without the necessity of subdividing the organic solar cells into pixels.

Thus, specifically for use as a light-field camera and/or for acquisition of three-dimensional images, the optical detector may comprise the at least one stack of optical sensors and the at least one spatial light modulator, the latter of which may be or may comprise at least one transparent spatial light modulator and/or at least one reflective spatial light modulator, as outlined above. Further, the optical detector may comprise at least one transfer device, specifically at least one lens or lens system. Thus, as an example, the optical detector may comprise at least one camera lens, specifically at least one camera lens for imaging a scene, as known in the field of photography.

The setup of the optical detector as disclosed above specifically may be arranged and ordered as follows (listed in a direction towards the object or scene to be detected):

(1) at least one stack of optical sensors, such as a stack of transparent or semitransparent optical sensors, more specifically a stack of solar cells, such as organic solar cells like sDSCs, preferably without pixels with photon density-dependent photocurrents for depth detection;

(2) at least one spatial light modulator, preferably with high resolution pixels and high frequency for switching pixels, such as a transparent or reflective spatial light modulator;

(3) at least one transfer device, such as at least one lens or lens system, more preferably at least one suitable camera lens system.

Additional devices may be comprised, such as one or more beam splitters. Further, as outlined above, in this embodiment or other embodiments, the optical detector may comprise one or more optical sensors embodied as an imaging device, wherein monochrome, multi-chrome or full-color imaging devices may be used. Thus, as an example, the optical detector may further comprise at least one imaging device such as at least one CCD chip and/or at least one CMOS chip. The at least one imaging device, as outlined above, specifically may be used for acquiring two-dimensional images and/or for recognition of objects within a scene captured by the optical detector.

As outlined in further detail above, the pixels of the spatial light modulator may be modulated. Therein, the pixels may be modulated at different frequencies and/or the pixels may be grouped into at least two groups of pixels corresponding to the scene, such as for the purpose of forming superpixels. In this regard, reference may be made to the possibilities disclosed above. The information for the pixels may be attained by using differing modulation frequencies. For details, reference may be made to the possibilities discussed above.

In general, a depth map may be recorded by using signals produced by the stack of optical sensors and, additionally, by recording a two-dimensional image by using the at least one optional imaging device. A plurality of two-dimensional images at different distances from the transfer device, such as from the lens, may be recorded. Thus, a depth map may be recorded by a stack of solar cells, such as a stack of organic solar cells, and by further recording a two-dimensional image by using the imaging device such as the at least one optional CCD chip and/or CMOS chip. The two-dimensional image may then be matched with the signals of the stack in order to obtain a three-dimensional image. Additionally or alternatively, however, the recording of a three-dimensional image may also take place without the use of an imaging device such as a CCD chip and/or a CMOS chip. Thus, each optical sensor or two or more of the optical sensors of the stack of optical sensors may be used for recording two-dimensional images each, by using the above-mentioned process implying the spatial light modulator. This is possible, since by SLM-modulation, information on pixel position, size and brightness may be known. By evaluating sensor signals of the optical sensors, such as by demodulating the sensor signals and/or by performing a frequency analysis as discussed above, two-dimensional pictures may be derived from each optical sensor signal. Thereby, a two-dimensional image for each of the optical sensors may be reconstructed. Using a stack of optical sensors, such as a stack of transparent solar cells, therefore allows for recording two-dimensional images acquired at different positions along an optical axis of the optical detector, such as at different focal positions. The acquisition of the plurality of two-dimensional optical images may be performed simultaneously and/or instantaneously. Thus, by using the stack of optical sensors in combination with the spatial light modulator, a simultaneous "tomography" of the optical situation may be acquired. Thereby, a light-field camera without micro-lenses may be realized.

The optical detector even allows for further post-processing of the information acquired by using the spatial light modulator and the stack of optical sensors. As compared to other sensors, however, for obtaining a three-dimensional image of a scene, little post-processing or even no post-processing may be required. Still, fully focused pictures can be obtained.

Further, use may be made of the possibility that one, more than one or even all of the optical sensors of the stack of optical sensors may be FiP sensors, i.e. optical sensors having a photon-density dependent sensor signal, i.e. optical sensors providing sensor signals being dependent on an illumination of a sensor region by a light beam, wherein the sensor signal, given the same total power of the illumination, is dependent on a width of the light beam in the sensor region. When changing the focus of a light beam illuminating the sensor region, the sensor signal, such as the photocurrent, for the respective optical sensor being designed as a FiP sensor reaches a maximum for a minimum diameter of the spot of illumination, i.e. as soon as the light beam is focused in the sensor region. Thus, the sensor signals of the optical sensors of the stack of optical sensors may indicate a focal position of a light beam since, generally, the optical sensor having the largest sensor signal may indicate a focal plane for the light beam. In case the light beam is emitted by an object within a scene captured by the optical detector, the light beam optionally will be imaged by the at least one optional transfer device such as the at least one lens or lens system and finally may be focused onto a position within the stack of optical sensors. By evaluating and comparing the sensor signals, such as by detecting the maximum sensor signal, the focal position may be determined. Generally, if a picture is constructed from the pixel information having a maximum in the sensor signal, corresponding to a maximum of the FIP-curve, the reconstructed picture may be focused in all image planes.

Further, the optical detector according to the present invention may avoid or at least partially circumvent typical problems of correcting imaging errors such as lens errors. Thus, in many optical devices such as microscopes or telescopes, lens errors may cause significant problems. As an example, in microscopes, a common lens error is the well-known error of spherical aberration, which leads to the phenomenon that the refraction of light rays may depend on the distance from an optical axis. Further, temperature effects may occur, such as a temperature-dependency of a focal position in a telescope. Static errors generally may be corrected by determining the error once and using a fixed set of SLM-pixel/solar cell combinations to construct a focused image. In case the optical system remains identical, in many cases, a software adjustment may be sufficient. Still, specifically in cases of errors changing over time, these conventional corrections may not be sufficient any longer. In this case, by using the optical detector according to the present invention having at least one spatial light modulator and at least one stack of optical sensors may be used for intrinsically correcting the error, specifically automatically, by acquiring an image in the correct focal plane.

The above-mentioned concept of the optical detector having a stack of optical sensors at different z-positions provides further advantages over current light-field cameras. Thus, typical light-field cameras are picture-based or pixel-based, in that a picture at a certain distance from the lens is reconstructed. The information to be stored typically is linearly dependent on the number of pixels and on the number of pictures. Contrarily, the optical detector according to the present invention, specifically having a stack of optical sensors in combination with at least one spatial light modulator, may have the capability of directly recording a light-field within the optical detector or camera, such as behind a lens. Thus, the optical detector generally may be adapted for recording one or more beam parameters for one or more light beams entering the optical detector. As an example, for each of the light beams, one or more beam parameters such as Gaussian beam parameters may be recorded, such as a focal point, a direction, and a spread-function width. Therein, the focal point may be the point or coordinate at which the beam is focused, and the direction may provide information regarding the spreading or propagation of the light beam. Other beam parameters may be used alternatively or additionally. The spread-function width may be the width of the function that describes the beam outside its focal point. The spread function may be a Gaussian function in simple cases, and the width parameter may be the exponent of the Gaussian function or a part of the exponent.

Thus, generally, the optical detector according to the present invention may allow for directly recording one or more beam parameters of the at least one light beam, such as at least one focal point of light beams, their propagation direction and their spread parameters. These beam parameters may directly be derived from an analysis of one or more sensor signals of the optical sensors of the stack of optical sensors, such as from an analysis of the FiP-signals. The optical detector, which specifically may be designed as a camera, thus may record a vector representation of the light-field which may be compact and scalable, and, thus, may include more information as compared to a two-dimensional picture and a depth map.

Thus, a focal stacking camera and/or a focal sweep camera may record pictures at different cut-planes of the light-field. The information may be stored as number of pictures times a number of pixels. Contrarily, the optical detector according to the present invention, specifically the optical detector comprising a stack of optical sensors and at least one spatial light modulator, more specifically a stack of FiP-sensors and a spatial light modulator, may be adapted for storing the information as number of beam parameters, such as the above-mentioned at least one spread parameter, the focal point, and the propagation direction, for each light beam. Thus, generally, pictures in between the optical sensors may be calculated from the vector representation. Thus, generally, an interpolation or extrapolation may be avoided. A vector representation generally has very low need for data storage space, as compared e.g. to the storage space required for known light-field cameras based on a pixel representation. Further, the vector representation may be combined with image compression methods known to the person skilled in the art. Such a combination with image compressing methods may further reduce the storage requirements for the recorded light-field. Compression methods may be one or more of color space transformation, down-sampling, chain codes, Fourier-related transforms, block splitting, discrete cosine transform, fractal compression, chroma sub-sampling, quantization, deflation, DPCM, LZW, entropy coding, wavelet transform, jpeg compression or further lossless or lossy compression methods.

Consequently, the optical detector including the at least one spatial light modulator and the stack of optical sensors may be adapted to determine at least one, preferably at least two or more beam parameters for at least one light beam, preferably for two beams or more than two light beams, and may be adapted to store these beam parameters for further use. Further, the optical detector, specifically the evaluation device, may be adapted for calculating images or partial images of a scene captured by the optical detector by using these beam parameters, such as by using the above-mentioned vector representation. Due to the vector representation, the optical detector designed as a light-field camera may also detect and/or calculate the field between the picture planes defined by the optical sensors.

Further, the optical detector, specifically the evaluation device, may be designed to take into account the position of an observer and/or a position of the optical detector itself. This is due to the fact that all information or almost all information entering the detector through the transfer device such as through the at least one lens may be detected by the optical detector, such as the light-field camera. Similar to a hologram, providing insight into part of a space behind an object, the light-field as detected or detectable by the optical detector having the stack of optical sensors and the at least one spatial light modulator, specifically given the above-mentioned beam parameter or vector representation, may contain additional information such as information regarding a situation in which an observer moves with respect to a fixed camera lens. Thus, due to the known properties of the light-field, a cross-sectional plane through the light-field may be moved and/or tilted. Additionally or alternatively, even non-planar cross-sections through the light-field may be generated. The latter specifically may be beneficial for correcting lens errors. When a position of an observer is moved, such as a position of an observer in a coordinate system of the optical detector, the visibility of one or more objects may change, such as in case a second object becomes visible behind a first object.

The optical detector, as outlined above, may be a monochrome, a multi-chrome or even a full-color optical detector. Thus, as outlined above, color sensitivity may be generated by using at least one multi-chrome or full-color spatial light modulator. Additionally or alternatively, in case two or more optical sensors are comprised, the two or more optical sensors may provide different spectral sensitivities. Specifically, in case a stack of optical sensors is used, specifically a stack of one or more optical sensors selected from the group consisting of solar cells, organic solar cells, dye sensitized solar cells, solid dye sensitized solar cells or FiP sensors in general, color sensitivity may be generated by using optical sensors having differing spectral sensitivities. Specifically in case a stack of optical sensors is used, comprising two or more optical sensors, the optical sensors may have differing spectral sensitivities such as differing absorption spectra.

Thus, generally, the optical detector may comprise a stack of optical sensors, wherein the optical sensors of the stack have differing spectral properties. Specifically, the stack may comprise at least one first optical sensor having a first spectral sensitivity and at least one second optical sensor having a second spectral sensitivity, wherein the first spectral sensitivity and the second spectral sensitivity are different. The stack, as an example, may comprise optical sensors having differing spectral properties in an alternating sequence. The optical detector may be adapted to acquire a multicolor three-dimensional image, preferably a full-color three-dimensional image, by evaluating sensor signals of the optical sensors having differing spectral properties.

This option of color resolution provides a large number of advantages over known color sensitive camera setups. Thus, by using optical sensors in a stack, the optical sensors having differing spectral sensitivities, the full sensor area of each sensor may be used for detection, as compared to a pixelated full-color camera such as full-color CCD or CMOS chips. Thereby, the resolution of the images may significantly be increased, since typical pixelated full-color camera chips may only use one third or one fourth or even less of the chip surface for imaging, due to the fact that colored pixels have to be provided in a neighboring arrangement.

The at least two optical sensors having differing spectral sensitivities may contain different types of dyes, specifically when using organic solar cells, more specifically sDSCs. Therein, stacks containing two or more types of optical sensors, each type having a uniform spectral sensitivity, may be used. Thus, the stack may contain at least one optical sensor of a first type, having a first spectral sensitivity, and at least one optical sensor of a second type, having a second spectral sensitivity. Further, the stack may optionally contain a third type and optionally even a fourth type of optical sensors having third and fourth spectral sensitivities, respectively. The stack may contain optical sensors of the first and second type in an alternating fashion, optical sensors of the first, second and third type in an alternating fashion or even sensors of the first, second, third and fourth type in an alternating fashion.

As it turns out, a color detection or even an acquisition of full-color images may be possible with optical sensors of a first type and a second type, only, such as in an alternating fashion. Thus, as an example, the stack may contain organic solar cells, specifically sDSCs, of a first type, having a first absorbing dye, and organic solar cells, specifically sDSCs, of a second type, having a second absorbing dye. The organic solar cells of the first and second type may be arranged in an alternating fashion within the stack. The dyes specifically may be broadly absorbing, such as by providing an absorption spectrum having at least one absorption peak and the broad absorption covering a range of at least 30 nm, preferably of at least 100 nm, of at least 200 nm or of at least 300 nm, such as having a width of 30-200 nm and/or a width of 60-300 nm and or a width of 100-400 nm.

Thus, two broadly absorbing dyes may be sufficient for color detection. Using two broadly absorbing dyes with different absorption profiles in a transparent or semi-transparent solar cell, different wavelengths will cause different sensor signals such as different currents, due to the complex wavelength dependency of the photon-to-current efficiency (PCE). The color can be determined by comparing the currents of two solar cells with different dyes.

Thus, generally, the optical detector having the stack of optical sensors with at least two optical sensors having different spectral sensitivities, may be adapted to determine at least one color and/or at least one item of color information by comparing sensor signals of the at least two optical sensors having different spectral sensitivities. As an example, an algorithm may be used for determining the color of color information from the sensor signals. Additionally or alternatively, other ways of evaluating the sensor signals may be used, such as a lookup tables. As an example, a look-up table can be created in which, for each pair of sensor signals, such as for each pair of currents, a unique color is listed. Additionally or alternatively, other evaluation schemes may be used, such as by forming a quotient of the optical sensor signals and deriving a color, a color information or color coordinate thereof.

By using a stack of optical sensors having differing spectral sensitivities, such as a stack of pairs of optical sensors having two different spectral sensitivities, a variety of measurements may be taken. Thus, as an example, by using the stack, a recording of a three-dimensional multi-color or even full-color image is feasible, and/or a recording of an image in several focal planes. Further, depth images can be calculated using depth from-defocus algorithms.

By using two types of optical sensors having differing spectral sensitivities, a missing color information may be extrapolated between surrounding color points. A smoother function can be obtained by taking more than only surrounding points into account. This may also be used for reducing measurement errors, while computational costs for post-processing increase.

Generally, the optical detector according to the present invention may thus be designed as a multicolor or full-color or color-detecting light-field camera. A stack of alternatingly colored optical sensors, such as transparent or semi-transparent solar cells, specifically organic solar cells and more specifically sDSCs, may be used. These optical detectors are used in combination with the at least one spatial light-modulator, such as for the purpose of providing a virtual pixelation. Thus, the optical detectors may be large-area optical detectors without pixelation, wherein the pixelation is virtually created by the spatial light modulator and an evaluation, specifically a frequency analysis, of the sensor signals of the optical sensors.

Color information in-plane may be obtained from sensor signals of two neighboring optical sensors of the stack, neighboring optical sensors having different spectral sensitivity, such as different colors, more specifically different types of dyes. As outlined above, the color information may be generated by an evaluation algorithm evaluating the sensor signals of the optical sensors having different wavelength sensitivities, such as by using one or more look-up tables. Further, a smoothing of the color information may be performed, such as in a post-processing step, by comparing colors of neighboring areas.

The color information in z-direction, i.e. along the optical axis, can also be obtained by comparing neighboring optical sensors and the stack, such as neighboring solar cells in the stack. Smoothing of the color information can be done using color information from several optical sensors.

The optical detector according to the present invention, comprising at least one spatial light modulator and at least one optical sensor, may further be combined with one or more other types of sensors or detectors. Thus, the optical detector may further comprise at least one additional detector. The at least one additional detector may be adapted for detecting at least one parameter, such as at least one of: a parameter of a surrounding environment, such as a temperature and/or a brightness of a surrounding environment; a parameter regarding a position and/or orientation of the detector; a parameter specifying a state of the object to be detected, such as a position of the object, e.g. an absolute position of the object and/or an orientation of the object in space. Thus, generally, the principles of the present invention may be combined with other measurement principles in order to gain additional information and/or in order to verify measurement results or reduce measurement errors or noise.

Specifically, the optical detector according to the present invention may further comprise at least one time-of-flight (ToF) detector adapted for detecting at least one distance between the at least one object and the optical detector by performing at least one time-of-flight measurement. As used herein, a time-of-flight measurement generally refers to a measurement based on a time a signal needs for propagating between two objects or from one object to a second object and back. In the present case, the signal specifically may be one or more of an acoustic signal or an electromagnetic signal such as a light signal. A time-of-flight detector consequently refers to a detector adapted for performing a time-of-flight measurement. Time of flight measurements are well-known in various fields of technology such as in commercially available distance measurement devices or in commercially available flow meters, such as ultrasonic flow meters. Time-of-flight detectors even may be embodied as time-of-flight cameras. These types of cameras are commercially available as range-imaging camera systems, capable of resolving distances between objects based on the known speed of light.

Presently available ToF detectors generally are based on the use of a pulsed signal, optionally in combination with one or more light sensors such as CMOS-sensors. A sensor signal produced by the light sensor may be integrated. The integration may start at two different points in time. The distance may be calculated from the relative signal intensity between the two integration results.

Further, as outlined above, ToF cameras are known and may generally be used, also in the context of the present invention. These ToF cameras may contain pixelated light sensors. However, since each pixel generally has to allow for performing two integrations, the pixel construction generally is more complex and the resolutions of commercially available ToF cameras is rather low (typically 200×200 pixels). Distances below ~40 cm and above several meters typically are difficult or impossible to detect. Furthermore, the periodicity of the pulses leads to ambiguous distances, as only the relative shift of the pulses within one period is measured.

ToF detectors, as standalone devices, typically suffer from a variety of shortcomings and technical challenges. Thus, in general, ToF detectors and, more specifically, ToF cameras suffer from rain and other transparent objects in the light path, since the pulses might be reflected too early, objects behind the raindrop are hidden, or in partial reflections the integration will lead to erroneous results. Further, in order to avoid errors in the measurements and in order to allow for a clear distinction of the pulses, low light conditions are preferred for ToF-measurements. Bright light such as bright sunlight can make a ToF-measurement impossible. Further, the energy consumption of typical ToF cameras is rather high, since pulses must be bright enough to be back-reflected and still be detectable by the camera. The brightness of the pulses, however, may be harmful for eyes or other sensors or may cause measurement errors when two or more ToF measurements interfere with each other. In summary, current ToF detectors and, specifically, current ToF-cameras suffer from several disadvantages such as low resolution, ambiguities in the distance measurement, limited range of use, limited light conditions, sensitivity towards transparent objects in the light path, sensitivity towards weather conditions and high energy consumption. These technical challenges generally lower the aptitude of present ToF cameras for daily applications such for safety applications in cars, cameras for daily use or human-machine-interfaces, specifically for use in gaming applications.

In combination with the detector according to the present invention, providing at least one spatial light modulator and at least one optical sensor as well as the above-mentioned principle of evaluating the sensor signal by frequency analysis, the advantages and capabilities of both systems may be combined in a fruitful way. Thus, the SLM detector, i.e. the combination of the at least one spatial light modulator and the at least one optical sensor, specifically the at least one stack of optical sensors, may provide advantages at bright light conditions, while the ToF detector generally provides better results at low-light conditions. A combined device, i.e. an optical detector according to the present invention further including at least one ToF detector, therefore provides increased tolerance with regard to light conditions as compared to both single systems. This is especially important for safety applications, such as in cars or other vehicles.

Specifically, the optical detector may be designed to use at least one ToF measurement for correcting at least one measurement performed by using the SLM detector and vice a versa. Further, the ambiguity of a ToF measurement may be resolved by using the SLM detector. An SLM measurement specifically may be performed whenever an analysis of ToF measurements results in a likelihood of ambiguity. Additionally or alternatively, SLM measurements may be performed continuously in order to extend the working range of the ToF detector into regions which are usually excluded due to the ambiguity of ToF measurements. Additionally or alternatively, the SLM detector may cover a broader or an additional range to allow for a broader distance measurement region. The SLM detector, specifically the SLM camera, may further be used for determining one or more important regions for measurements to reduce energy consumption or to protect eyes. Thus, as outlined above, the SLM detector may be adapted for detecting one or more regions of interest. Additionally or alternatively, the SLM detector may be used for determining a rough depth map of one or more objects within a scene captured by the optical detector, wherein the rough depth map may be refined in important regions by one or more ToF measurements. Further, the SLM detector may be used to adjust the ToF detector, such as the ToF camera, to the required distance region. Thereby, a pulse length and/or a frequency of the ToF measurements may be pre-set, such as for removing or reducing the likelihood of ambiguities in the ToF measurements. Thus, generally, the SLM detector may be used for providing an autofocus for the ToF detector, such as for the ToF camera.

As outlined above, a rough depth map may be recorded by the SLM detector, such as the SLM camera. Further, the rough depth map, containing depth information or z-information regarding one or more objects within a scene captured by the optical detector, may be refined by using one or more ToF measurements. The ToF measurements specifically may be performed only in important regions. Additionally or alternatively, the rough depth map may be used to adjust the ToF detector, specifically the ToF camera.

Further, the use of the SLM detector in combination with the at least one ToF detector may solve the above-mentioned problem of the sensitivity of ToF detectors towards the nature of the object to be detected or towards obstacles or media within the light path between the detector and the object to be detected, such as the sensitivity towards rain or weather conditions. A combined SLM/ToF measurement may be used to extract the important information from ToF signals, or measure complex objects with several transparent or semi-transparent layers. Thus, objects made of glass, crystals, liquid structures, phase transitions, liquid motions, etc. may be observed. Further, the combination of an SLM detector and at least one ToF detector will still work in rainy weather, and the overall optical detector will generally be less dependent from weather conditions. As an example, measurement results provided by the SLM detector may be used to remove the errors provoked by rain from ToF measurement results, which specifically renders this combination useful for safety applications such as in cars or other vehicles.

The implementation of at least one ToF detector into the optical detector according to the present invention may be realized in various ways. Thus, the at least one SLM detector and the at least one ToF detector may be arranged in a sequence, within the same light path. As an example, at least one transparent SLM detector may be placed in front of at least one ToF detector. Additionally or alternatively, separate light paths or split light paths for the SLM detector and the ToF detector may be used. Therein, as an example, light paths may be separated by one or more beam-splitting elements, such as one or more of the beam splitting elements listed above listed in further detail below. As an example, a separation of beam paths by wavelength-selective elements may be performed. Thus, e.g., the ToF detector may make use of infrared light, whereas the SLM detector may make use of light of a different wavelength. In this example, the infrared light for the ToF detector may be separated off by using a wavelength-selective beam splitting element such as a hot mirror. Additionally or alternatively, light beams used for the SLM measurement and light beams used for the ToF measurement may be separated by one or more beam-splitting elements, such as one or more semitransparent mirrors, beam-splitter cubes, polarization beam splitters or combinations thereof. Further, the at least one SLM detector and the at least one ToF detector may be placed next to each other in the same device, using distinct optical pathways. Various other setups are feasible.

As outlined above, the optical detector according to the present invention as well as one or more of the other devices as proposed within the present invention may be combined with one or more other types of measurement devices. Thus, the optical detector according to the present invention, comprising at least one spatial light modulator and at least one optical sensor, may be combined with one or more other types of sensors or detectors, such as the above-mentioned ToF detector. When combining the optical detector according to the present invention with one or more other types of sensors or detectors, the optical detector and the at least one further sensor or detector may be designed as independent devices, with the at least one optical sensor and the spatial light modulator of the optical detector being separate from the at least one further sensor or detector. Alternatively, one or more of these components may fully or partially be used for the further sensor or detector, too, or the optical sensor as well as the spatial light modulator and the at least one further sensor or detector may be fully or partially combined in another way.

Thus, as a non-limiting example, the optical detector, as an example, may further comprise at least one distance sensor other than the above-mentioned ToF detector, in addition or as alternatives to the at least one optional ToF detector. The distance sensor, for instance, may be based on the above-mentioned FiP-effect. Consequently, the optical detector may further comprise at least one active distance sensor. As used herein, an "active distance sensor" is a sensor having at least one active optical sensor and at least one active illumination source, wherein the active distance sensor is adapted to determine a distance between an object and the active distance sensor. The active distance sensor comprises at least one active optical sensor adapted to generate a sensor signal when illuminated by a light beam propagating from the object to the active optical sensor, wherein the sensor signal, given the same total power of the illumination, is dependent on a geometry of the illumination, in particular on a beam cross section of the illumination on the sensor area. The active distance sensor further comprises at least one active illumination source for illuminating the object. Thus, the active illumination source may illuminate the object, and illumination light or a primary light beam generated by the illumination source may be reflected or scattered by the object or parts thereof, thereby generating a light beam propagating towards the optical sensor of the active distance sensor.

For possible setups of the at least one active optical sensor of the active distance sensor, reference may be made to one or more of WO 2012/110924 A1 or WO2014/097181 A1, the full content of which is herewith included by reference. The at least one longitudinal optical sensor disclosed in one or both of these documents may also be used for the optional active distance sensor which may be included into the optical detector according to the present invention. Thus, a single optical sensor may be used or a combination of a plurality of optical sensors, such as a sensor stack.

As outlined above, the active distance sensor and the remaining components of the optical detector may be separate components or may come alternatively, fully or partially integrated. Consequently, the at least one active optical sensor of the active distance sensor may fully or partially be separate from the at least one optical sensor or may fully or partially be identical to the at least one optical sensor of the optical detector. Similarly, the at least one active illumination source may fully or partially be separate from the illumination source of the optical detector or may fully or partially be identical.

The at least one active distance sensor may further comprise at least one active evaluation device which may fully or partially be identical to the evaluation device of the optical detector or which may be a separate device. The at least one active evaluation device may be adapted to evaluate the at least one sensor signal of the at least one active optical sensor and to determine a distance between the object and the active distance sensor. For this evaluation, a predetermined or determinable relationship between the at least one sensor signal and the distance may be used, such as a predetermined relationship determined by empirical measurements and/or a predetermined relationship fully or partially based on a theoretical dependency of the sensor signal on the distance. For potential embodiments of this evaluation, reference may be made to one or more of WO 2012/110924 A1 or WO2014/097181 A1, the full content of which is herewith included by reference.

The at least one active illumination source may be a modulated illumination source or a continuous illumination source. For potential embodiments of this active illumination source, reference may be made to the options disclosed above in the context of the illumination source. Specifically, the at least one active optical sensor may be adapted such that the sensor signal generated by this at least one active optical sensor is dependent on a modulation frequency of the light beam.

The at least one active illumination source may illuminate the at least one object in an on-axis fashion, such that the illumination source propagates towards the object on an optical axis of the optical detector and/or the active distance sensor. Additionally or alternatively, the at least one illumination source may be adapted to illuminate the at least one object in an off-axis fashion, such that the illumination light propagating towards the object and the light beam propagating from the object to the active distance sensor are oriented in a nonparallel fashion.

The active illumination source may be a homogeneous illumination source or may be a patterned or structured illumination source. Thus, as an example, the at least one active illumination source may be adapted to illuminate a scene or a part of a scene captured by the optical detector with homogeneous light and/or with patterned light. Thus, as an example, one or more light patterns may be projected into the scene and/or into a part of the scene, whereby a contrast of detection of the at least one object may be increased. As an example, line patterns or point patterns, such as rectangular line patterns and/or a rectangular matrix of light points may be projected into the scene or into a part of the scene. For generating light patterns, the at least one active illumination source by itself may be adapted to generate patterned light and/or one or more light-patterning devices may be used, such as filters, gratings, mirrors or other types of light-patterning devices. Further, additionally or alternatively, one or more light-patterning devices having a spatial light modulator may be used. The spatial light modulator of the active distance sensor may be separate and distinct from the above-mentioned spatial light modulator or may fully or partially be identical. Thus, for generating patterned light, micro-mirrors may be used, such as the above-mentioned DLPs. Additionally or alternatively, other types of patterning devices may be used.

The combination of the optical detector having the optical sensor and the spatial light modulator with the at least one optional active distance sensor provides a plurality of advantages. Thus, a combination with a structured active distance sensor, such as an active distance sensor having at least one patterned or structured active illumination source, may render the overall system more reliable. As an example, when the above-mentioned principle of the optical detector, using the optical sensor, the spatial light modulator and the modulation of the pixels, should fail to work properly, such as due to low contrast of the scene captured by the optical detector, the active distance sensor may be used. Contrarily, when the active distance sensor fails to work properly, such as due to reflections of the at least one active illumination source on transparent objects due to fog or rain, the basic principle of the optical detector using the spatial light modulator and the modulation of pixels may still resolve objects with proper contrast. Consequently, as for the time-of-flight detector, the active distance sensor may improve reliability and stability of measurements generated by the optical detector.

As outlined above, the optical detector may comprise one or more beam-splitting elements adapted for splitting a beam path of the optical detector into two or more partial beam paths. Various types of beam-splitting elements may be used, such as prisms, gratings, semi-transparent mirrors, beam-splitter cubes, a reflective spatial light modulator, or combinations thereof. Other possibilities are feasible.

The beam-splitting element may be adapted to divide the light beam into at least two portions having identical intensities or having different intensities. In the latter case, the partial light beams and their intensities may be adapted to their respective purposes. Thus, in each of the partial beam paths, one or more optical elements, such as one or more optical sensors may be located. By using at least one beam-splitting element adapted for dividing the light beam into at least two portions having different intensities, the intensities of the partial light beams may be adapted to the specific requirements of the at least two optical sensors.

The beam-splitting element specifically may be adapted to divide the light beam into a first portion traveling along a first partial beam path and at least one second portion traveling along at least one second partial beam path, wherein the first portion has a lower intensity than the second portion. The optical detector may contain at least one imaging device, preferably an inorganic imaging device, more preferably a CCD chip and/or a CMOS chip. Since, typically, imaging devices require lower light intensities as compared to other optical sensors, e.g. as compared to the at least one longitudinal optical sensor, such as the at least one FiP sensor, the at least one imaging device specifically may be located in the first partial beam path. The first portion, as an example, may have an intensity of lower than one half the intensity of the second portion. Other embodiments are feasible.

The intensities of the at least two portions may be adjusted in various ways, such as by adjusting a transmissivity and/or reflectivity of the beam-splitting element, by adjusting a surface area of the beam splitting-element or by other ways. The beam-splitting element generally may be or may comprise a beam-splitting element which is indifferent regarding a potential polarization of the light beam. Still, however, the at least one beam-splitting element also may be or may comprise at least one polarization-selective beam-splitting element. Various types of polarization-selective beam-splitting elements are generally known in the art. Thus, as an example, the polarization-selective beam-splitting element may be or may comprise a polarization beam-splitting cube. Polarization-selective beam-splitting elements generally are favorable in that a ratio of the intensities of the partial light beams may be adjusted by adjusting a polarization of the light beam entering the polarization-selective beam-splitting element.

The optical detector may be adapted to at least partially back-reflect one or more partial light beams traveling along the partial beam paths towards the beam-splitting element. Thus, as an example, the optical detector may comprise one or more reflective elements adapted to at least partially back-reflect a partial light beam towards the beam-splitting element. The at least one reflective element may be or may comprise at least one mirror. Additionally or alternatively, other types of reflective elements may be used, such as reflective prisms and/or the at least one spatial light modulator which, specifically, may be a reflective spatial light modulator and which may be arranged to at least partially back-reflect a partial light beam towards the beam-splitting element. The beam-splitting element may be adapted to at least partially recombine the back-reflected partial light beams in order to form at least one common light beam. The optical detector may be adapted to feed the re-united common light beam into at least one optical sensor, preferably into at least one longitudinal optical sensor, specifically at least one FiP sensor, more preferably into a stack of optical sensors such as a stack of FiP sensors.

The optical detector may comprise one or more spatial light modulators. In case a plurality of spatial light modulators is comprised, such as two or more spatial light modulators, the at least two spatial light modulators may be arranged in the same beam path or may be arranged in different partial beam paths. In case the spatial light modulators are arranged in different beam paths, the optical detector, specifically the at least one beam-splitting element, may be adapted to recombine partial light beams passing the spatial light modulators to form a common light beam.

In a further aspect of the present invention, a detector system for determining a position of at least one object is disclosed. The detector system comprises at least one optical detector according to the present invention, such as according to one or more of the embodiments disclosed above or disclosed in further detail below. The detector system further comprises at least one beacon device adapted to direct at least one light beam towards the optical detector, wherein the beacon device is at least one of attachable to the object, holdable by the object and integratable into the object.

As used herein, a "detector system" generally refers to a device or arrangement of devices interacting to provide at least one detector function, preferably at least one optical detector function, such as at least one optical measurement function and/or at least one imaging off-camera function. The detector system may comprise at least one optical detector, as outlined above, and may further comprise one or more additional devices. The detector system may be integrated into a single, unitary device or may be embodied as an arrangement of a plurality of devices interacting in order to provide the detector function.

As outlined above, the detector system comprises at least one beacon device adapted to direct at least one light beam towards the detector. As used herein and as will be disclosed in further detail below, a "beacon device" generally refers to an arbitrary device adapted to direct at least one light beam towards the detector. The beacon device may fully or partially be embodied as an active beacon device, comprising at least one illumination source for generating the light beam. Additionally or alternatively, the beacon device may fully or partially be embodied as a passive beacon device comprising at least one reflective element adapted to reflect a primary light beam generated independently from the beacon device towards the detector.

The beacon device is at least one of attachable to the object, holdable by the object and integratable into the object. Thus, the beacon device may be attached to the object by an arbitrary attachment means, such as one or more connecting elements. Additionally or alternatively, the object may be adapted to hold the beacon device, such as by one or more appropriate holding means. Additionally or alternatively, again, the beacon device may fully or partially be integrated into the object and, thus, may form part of the object or even may form the object.

Generally, with regard to potential embodiments of the beacon device, reference may be made to one or more of U.S. provisional applications 61/739,173, filed on Dec. 19, 2012, and 61/749,964, filed on Jan. 8, 2013, and/or to European patent application number EP 13171901.5. Still, other embodiments are feasible.

As outlined above, the beacon device may fully or partially be embodied as an active beacon device and may comprise at least one illumination source. Thus, as an example, the beacon device may comprise a generally arbitrary illumination source, such as an illumination source selected from the group consisting of a light-emitting diode (LED), a light bulb, an incandescent lamp and a fluorescent lamp. Other embodiments are feasible.

Additionally or alternatively, as outlined above, the beacon device may fully or partially be embodied as a passive beacon device and may comprise at least one reflective device adapted to reflect a primary light beam generated by an illumination source independent from the object. Thus, in addition or alternatively to generating the light beam, the beacon device may be adapted to reflect a primary light beam towards the detector.

In case an additional illumination source is used by the optical detector, the at least one illumination source may be part of the optical detector. Additionally or alternatively, other types of illumination sources may be used. The illumination source may be adapted to fully or partially illuminate a scene. Further, the illumination source may be adapted to provide one or more primary light beams which are fully or partially reflected by the at least one beacon device. Further, the illumination source may be adapted to provide one or more primary light beams which are fixed in space and/or to provide one or more primary light beams which are movable, such as one or more primary light beams which scan through a specific region in space. Thus, as an example, one or more illumination sources may be provided which are movable and/or which comprise one or more movable mirrors to adjust or modify a position and/or orientation of the at least one primary light beam in space, such as by scanning the at least one primary light beam through a specific scene captured by the optical detector. In case one or more movable mirrors are used, the movable mirror may also comprise one or more spatial light modulators, such as one or more micro-mirrors, specifically one or more of the micro-mirrors based on DLP® technology, as disclosed above. Thus, as an example, a scene may be illuminated by using at least one first spatial light modulator, and the actual measurement via the optical detector may be performed by using at least one second spatial light modulator.

The detector system may comprise one, two, three or more beacon devices. Thus, generally, in case the object is a rigid object which, at least on a microscope scale, does not change its shape, preferably, at least two beacon devices may be used. In case the object is fully or partially flexible or is adapted to fully or partially change its shape, preferably, three or more beacon devices may be used. Generally, the number of beacon devices may be adapted to the degree of flexibility of the object. Preferably, the detector system comprises at least three beacon devices.

The object itself may be part of the detector system or may be independent from the detector system. Thus, generally, the detector system may further comprise the at least one object. One or more objects may be used. The object may be a rigid object and/or a flexible object.

The object generally may be a living or non-living object. The detector system even may comprise the at least one object, the object thereby forming part of the detector system. Preferably, however, the object may move independently from the detector, in at least one spatial dimension.

The object generally may be an arbitrary object. In one embodiment, the object may be a rigid object. Other embodiments are feasible, such as embodiments in which the object is a non-rigid object or an object which may change its shape.

As will be outlined in further detail below, the present invention may specifically be used for tracking positions and/or motions of a person, such as for the purpose of controlling machines, gaming or simulation of sports. In this or other embodiments, specifically, the object may be selected from the group consisting of: an article of sports equipment, preferably an article selected from the group consisting of a racket, a club, a bat; an article of clothing; a hat; a shoe.

The optional transfer device can, as explained above, be designed to feed light propagating from the object to the optical detector. As explained above, this feeding can optionally be effected by means of imaging or else by means of non-imaging properties of the transfer device. In particular the transfer device can also be designed to collect the electromagnetic radiation before the latter is fed to the spatial light modulator and/or the optical sensor. The optional transfer device can also be wholly or partly a constituent part of at least one optional illumination source, for example by the illumination source being designed to provide a light beam having defined optical properties, for example having a defined or precisely known beam profile, for example at least one Gaussian beam, in particular at least one laser beam having a known beam profile.

For potential embodiments of the optional illumination source, reference may be made to WO 2012/110924 A1. Still, other embodiments are feasible. Light emerging from the object can originate in the object itself, but can also optionally have a different origin and propagate from this origin to the object and subsequently toward the spatial light modulator and/or the optical sensor. The latter case can be effected for example by at least one illumination source being used. This illumination source can for example be or comprise an ambient illumination source and/or may be or may comprise an artificial illumination source. By way of example, the detector itself can comprise at least one illumination source, for example at least one laser and/or at least one incandescent lamp and/or at least one semiconductor illumination source, for example, at least one light-emitting diode, in particular an organic and/or inorganic light-emitting diode. On account of their generally defined beam profiles and other properties of handleability, the use of one or a plurality of lasers as illumination source or as part thereof, is particularly preferred. The illumination source itself can be a constituent part of the detector or else be formed independently of the optical detector. The illumination source can be integrated in particular into the optical detector, for example a housing of the detector. Alternatively or additionally, at least one illumination source can also be integrated into the at least one beacon device or into one or more of the beacon devices and/or into the object or connected or spatially coupled to the object.

The light emerging from the one or more beacon devices can accordingly, alternatively or additionally from the option that said light originates in the respective beacon device itself, emerge from the illumination source and/or be excited by the illumination source. By way of example, the electromagnetic light emerging from the beacon device can be emitted by the beacon device itself and/or be reflected by the beacon device and/or be scattered by the beacon device before it is fed to the detector. In this case, emission and/or scattering of the electromagnetic radiation can be effected without spectral influencing of the electromagnetic radiation or with such influencing. Thus, by way of example, a wavelength shift can also occur during scattering, for example according to Stokes or Raman. Furthermore, emission of light can be excited, for example, by a primary illumination source, for example by the object or a partial region of the object being excited to generate luminescence, in particular phosphorescence and/or fluorescence. Other emission processes are also possible, in principle. If a reflection occurs, then the object can have for example at least one reflective region, in particular at least one reflective surface. Said reflective surface can be a part of the object itself, but can also be for example a reflector which is connected or spatially coupled to the object, for example a reflector plaque connected to the object. If at least one reflector is used, then it can in turn also be regarded as part of the detector which is connected to the object, for example, independently of other constituent parts of the optical detector.

The beacon devices and/or the at least one optional illumination source independently from each other and generally may emit light in at least one of: the ultraviolet spectral range, preferably in the range of 200 nm to 380 nm; the visible spectral range (380 nm to 780 nm); the infrared spectral range, preferably in the range of 780 nm to 3.0 micrometers. Most preferably, the at least one illumination source is adapted to emit light in the visible spectral range, preferably in the range of 500 nm to 780 nm, most preferably at 650 nm to 750 nm or at 690 nm to 700 nm.

The feeding of the light beam to the optical sensor can be effected in particular in such a way that a light spot, for example having a round, oval or differently configured cross section, is produced on the optional sensor area of the optical sensor. By way of example, the detector can have a visual range, in particular a solid angle range and/or spatial range, within which objects can be detected. Preferably, the optional transfer device is designed in such a way that the light spot, for example in the case of an object arranged within a visual range of the detector, is arranged completely on a sensor region and/or on a sensor area of the optical sensor. By way of example, a sensor area can be chosen to have a corresponding size in order to ensure this condition.

The evaluation device can comprise in particular at least one data processing device, in particular an electronic data processing device, which can be designed to generate at least one item of information on the position of the object. Thus, the evaluation device may be designed to use one or more of: the number of illuminated pixels of the spatial light modulator; a beam width of the light beam on one or more of the optical sensors, specifically on one or more of the optical sensors having the above-mentioned FiP-effect; a number of illuminated pixels of a pixelated optical sensor such as a CCD or a CMOS chip. The evaluation device may be designed to use one or more of these types of information as one or more input variables and to generate the at least one item of information on the position of the object by processing these input variables. The processing can be done in parallel, subsequently or even in a combined manner. The evaluation device may use an arbitrary process for generating these items of information, such as by calculation and/or using at least one stored and/or known relationship. The relationship can be a predetermined analytical relationship or can be determined or determinable empirically, analytically or else semi-empirically. Particularly preferably, the relationship comprises at least one calibration curve, at least one set of calibration curves, at least one function or a combination of the possibilities mentioned. One or a plurality of calibration curves can be stored for example in the form of a set of values and the associated function values thereof, for example in a data storage device and/or a table. Alternatively or additionally, however, the at least one calibration curve can also be stored for example in parameterized form and/or as a functional equation.

By way of example, the evaluation device can be designed in terms of programming for the purpose of determining the items of information. The evaluation device can comprise in particular at least one computer, for example at least one microcomputer. Furthermore, the evaluation device can comprise one or a plurality of volatile or nonvolatile data memories. As an alternative or in addition to a data processing device, in particular at least one computer, the evaluation device can comprise one or a plurality of further electronic components which are designed for determining the items of information, for example an electronic table and in particular at least one look-up table and/or at least one application-specific integrated circuit (ASIC).

In a further aspect of the present invention, a human-machine interface for exchanging at least one item of information between a user and a machine is disclosed. The human-machine interface comprises at least one detector system according to the present invention, such as according to one or more of the embodiments disclosed above or disclosed in further detail below. The at least one beacon device of the detector system is adapted to be at least one of directly or indirectly attached to the user and held by the user. The human-machine interface is designed to determine at least one position of the user by means of the detector system and is designed to assign to the position at least one item of information.

As used herein, the term "human-machine interface" generally refers to an arbitrary device or combination of devices adapted for exchanging at least one item of information, specifically at least one item of electronic information, between a user and a machine such as a machine having at least one data processing device. The exchange of information may be performed in a unidirectional fashion and/or in a bidirectional fashion. Specifically, the human-machine interface may be adapted to allow for a user to provide one or more commands to the machine in a machine-readable fashion.

In a further aspect of the invention, an entertainment device for carrying out at least one entertainment function is disclosed. The entertainment device comprises at least one human-machine interface according to the present invention, such as disclosed in one or more of the embodiments disclosed above or disclosed in further detail below. The entertainment device is designed to enable at least one item of information to be input by a player by means of the human-machine interface, wherein the entertainment device is designed to vary the entertainment function in accordance with the information.

As used herein, an "entertainment device" is a device which may serve the purpose of leisure and/or entertainment of one or more users, in the following also referred to as one or more players. As an example, the entertainment device may serve the purpose of gaming, preferably computer gaming. Additionally or alternatively, the entertainment device may also be used for other purposes, such as for exercising, sports, physical therapy or motion tracking in general. Thus, the entertainment device may be implemented into a computer, a computer network or a computer system or may comprise a computer, a computer network or a computer system which runs one or more gaming software programs.

The entertainment device comprises at least one human-machine interface according to the present invention, such as according to one or more of the embodiments disclosed above and/or according to one or more of the embodiments disclosed below. The entertainment device is designed to enable at least one item of information to be input by a player by means of the human-machine interface. The at least one item of information may be transmitted to and/or may be used by a controller and/or a computer of the entertainment device.

The at least one item of information preferably may comprise at least one command adapted for influencing the course of a game. Thus, as an example, the at least one item of information may include at least one item of information on at least one orientation of the player and/or of one or more body parts of the player, thereby allowing for the player to simulate a specific position and/or orientation and/or action required for gaming. As an example, one or more of the following movements may be simulated and communicated to a controller and/or a computer of the entertainment device: dancing; running; jumping; swinging of a racket; swinging of a bat; swinging of a club; pointing of an object towards another object, such as pointing of a toy gun towards a target.

The entertainment device as a part or as a whole, preferably a controller and/or a computer of the entertainment device, is designed to vary the entertainment function in accordance with the information. Thus, as outlined above, a course of a game might be influenced in accordance with the at least one item of information. Thus, the entertainment device might include one or more controllers which might be separate from the evaluation device of the at least one detector and/or which might be fully or partially identical to the at least one evaluation device or which might even include the at least one evaluation device. Preferably, the at least one controller might include one or more data processing devices, such as one or more computers and/or microcontrollers.

In a further aspect of the present invention, a tracking system for tracking a position of at least one movable object is disclosed. The tracking system comprises at least one detector system according to the present invention, such as disclosed in one or more of the embodiments given above or given in further detail below. The tracking system further comprises at least one track controller, wherein the track controller is adapted to track a series of positions of the object at specific points in time.

As used herein, a "tracking system" is a device which is adapted to gather information on a series of past positions of the at least one object and/or at least one part of the object. Additionally, the tracking system may be adapted to provide information on at least one predicted future position and/or orientation of the at least one object or the at least one part of the object. The tracking system may have at least one track controller, which may fully or partially be embodied as an electronic device, preferably as at least one data processing device, more preferably as at least one computer or microcontroller. Again, the at least one track controller may fully or partially comprise the at least one evaluation device and/or may be part of the at least one evaluation device and/or may fully or partially be identical to the at least one evaluation device.

The tracking system comprises at least one detector according to the present invention, such as at least one detector as disclosed in one or more of the embodiments listed above and/or as disclosed in one or more of the embodiments below. The tracking system further comprises at least one track controller. The track controller is adapted to track a series of positions of the object at specific points in time, such as by recording groups of data or data pairs, each group of data or data pair comprising at least one position information and at least one time information.

The tracking system may further comprise the at least one detector system according to the present invention. Thus, besides the at least one detector and the at least one evaluation device and the optional at least one beacon device, the tracking system may further comprise the object itself or a part of the object, such as at least one control element comprising the beacon devices or at least one beacon device, wherein the control element is directly or indirectly attachable to or integratable into the object to be tracked.

The tracking system may be adapted to initiate one or more actions of the tracking system itself and/or of one or more separate devices. For the latter purpose, the tracking system, preferably the track controller, may have one or more wireless and/or wire-bound interfaces and/or other types of control connections for initiating at least one action. Preferably, the at least one track controller may be adapted to initiate at least one action in accordance with at least one actual position of the object. As an example, the action may be selected from the group consisting of: a prediction of a future position of the object; pointing at least one device towards the object; pointing at least one device towards the detector; illuminating the object; illuminating the detector.

As an example of application of a tracking system, the tracking system may be used for continuously pointing at least one first object to at least one second object even though the first object and/or the second object might move. Potential examples, again, may be found in industrial applications, such as in robotics and/or for continuously working on an article even though the article is moving, such as during manufacturing in a manufacturing line or assembly line. Additionally or alternatively, the tracking system might be used for illumination purposes, such as for continuously illuminating the object by continuously pointing an illumination source to the object even though the object might be moving. Further applications might be found in communication systems, such as in order to continuously transmit information to a moving object by pointing a transmitter towards the moving object.

In a further aspect of the present invention, a camera for imaging at least one object is disclosed. The camera comprises at least one optical detector according to the present invention, such as disclosed in one or more of the embodiments given above or given in further detail below.

Thus, specifically, the present application may be applied in the field of photography. Thus, the detector may be part of a photographic device, specifically of a digital camera. Specifically, the detector may be used for 3D photography, specifically for digital 3D photography. Thus, the detector may form a digital 3D camera or may be part of a digital 3D camera. As used herein, the term "photography" generally refers to the technology of acquiring image information of at least one object. As further used herein, a "camera" generally is a device adapted for performing photography. As further used herein, the term "digital photography" generally refers to the technology of acquiring image information of at least one object by using a plurality of light-sensitive elements adapted to generate electrical signals indicating an intensity and/or color of illumination, preferably digital electrical signals. As further used herein, the term "3D photography" generally refers to the technology of acquiring image information of at least one object in three spatial dimensions. Accordingly, a 3D camera is a device adapted for performing 3D photography. The camera generally may be adapted for acquiring a single image, such as a single 3D image, or may be adapted for acquiring a plurality of images, such as a sequence of images. Thus, the camera may also be a video camera adapted for video applications, such as for acquiring digital video sequences.

Thus, generally, the present invention further refers to a camera, specifically a digital camera, more specifically a 3D camera or digital 3D camera, for imaging at least one object. As outlined above, the term imaging, as used herein, generally refers to acquiring image information of at least one object. The camera comprises at least one optical detector according to the present invention. The camera, as outlined above, may be adapted for acquiring a single image or for acquiring a plurality of images, such as image sequence, preferably for acquiring digital video sequences. Thus, as an example, the camera may be or may comprise a video camera. In the latter case, the camera preferably comprises a data memory for storing the image sequence.

The optical detector or the camera including the optical detector, having the at least one optical sensor, specifically the above-mentioned FiP sensor, may further be combined with one or more additional sensors. Thus, at least one camera having the at least one optical sensor, specifically the at least one above-mentioned FiP sensor, may be combined with at least one further camera, which may be a conventional camera and/or e.g. a stereo camera. Further, one, two or more cameras having the at least one optical sensor, specifically the at least one above-mentioned FiP sensor, may be combined with one, two or more digital cameras. As an example, one or two or more two-dimensional digital cameras may be used for calculating the depth from stereo information and from the depth information gained by the optical detector according to the present invention.

Specifically in the field of automotive technology, in case a camera fails, the optical detector according to the present invention may still be present for measuring a longitudinal coordinate of an object, such as for measuring a distance of an object in the field of view. Thus, by using the optical detector according to the present invention in the field of automotive technology, a failsafe function may be implemented. Specifically for automotive applications, the optical detector according to the present invention provides the advantage of data reduction. Thus, as compared to camera data of conventional digital cameras, data obtained by using the optical detector according to the present invention, i.e. an optical detector having the at least one optical sensor, specifically the at least one FiP sensor, may provide data having a significantly lower volume. Specifically in the field of automotive technology, a reduced amount of data is favorable, since automotive data networks generally provide lower capabilities in terms of data transmission rate.

The optical detector according to the present invention may further comprise one or more light sources. Thus, the optical detector may comprise one or more light sources for illuminating the at least one object, such that e.g. illuminated light is reflected by the object. The light source may be a continuous light source or maybe discontinuously emitting light source such as a pulsed light source. The light source may be a uniform light source or may be a nonuniform light source or a patterned light source. Thus, as an example, in order for the optical detector to measure the at least one longitudinal coordinate, such as to measure the depth of at least one object, a contrast in the illumination or in the scene captured by the optical detector is advantageous. In case no contrast is present by natural illumination, the optical detector may be adapted, via the at least one optional light source, to fully or partially illuminate the scene and/or at least one object within the scene, preferably with patterned light. Thus, as an example, the light source may project a pattern into a scene, onto a wall or onto at least one object, in order to create an increased contrast within an image captured by the optical detector.

The at least one optional light source may generally emit light in one or more of the visible spectral range, the infrared spectral range or the ultraviolet spectral range. Preferably, the at least one light source emits light at least in the infrared spectral range.

The optical detector may also be adapted to automatically illuminate the scene. Thus, the optical detector, such as the evaluation device, may be adapted to automatically control the illumination of the scene captured by the optical detector or a part thereof. Thus, as an example, the optical detector may be adapted to recognize in case large areas provide low contrast, thereby making it difficult to measure the longitudinal coordinates, such as depth, within these areas. In these cases, as an example, the optical detector may be adapted to automatically illuminate these areas with patterned light, such as by projecting one or more patterns into these areas.

As used within the present invention, the expression "position" generally refers to at least one item of information regarding one or more of an absolute position and an orientation of one or more points of the object. Thus, specifically, the position may be determined in a coordinate system of the detector, such as in a Cartesian coordinate system. Additionally or alternatively, however, other types of coordinate systems may be used, such as polar coordinate systems and/or spherical coordinate systems.

As outlined above, the at least one spatial light modulator of the optical detector specifically may be or may comprise at least one reflective spatial light modulator such as a DLP. In case one or more reflective spatial light modulators are used, the optical detector may further be adapted to use this at least one reflective spatial light modulator for more than the above-mentioned purposes. Thus, specifically, the optical detector may be adapted for additionally using the at least one spatial light modulator, specifically the at least one reflective spatial light modulator, for projecting light into space, such as into a scene and/or onto a screen. Thus, the detector specifically may be adapted to additionally provide at least one projector function.

Thus, as an example, DLP technology was mainly developed for projectors, such as projectors in communication devices like mobile phones. Thereby, an integrated projector may be implemented into a wide variety of devices. In the present invention, the spatial light modulator specifically may be used for distance sensing and/or for determining at least one longitudinal coordinate of an object. These two functions, however, may be combined. Thus, a combination of a projector and a distance sensor in one device may be achieved.

This is due to the fact that the spatial light modulator, specifically the reflective spatial light modulator, in combination with the evaluation device, may fulfill both the task of distance sensing or determining at least one longitudinal coordinate of an object and the task of a projector, such as for projecting at least one image into space, into a scene or onto a screen. The at least one spatial light modulator, to fulfill both tasks, specifically may be modulated intermittently, such as by using modulation periods for distance sensing and modulation periods for projecting intermittently. Thus, reflective spatial light modulators such as DLPs are generally capable of being modulated at modulation frequencies of more than 1 kHz. Consequently, realtime video frequencies may be reached for projections and for distance measurements simultaneously with a single spatial light modulator such as a DLP. This allows, for example to use a mobile phone to record a 3D-scene and to project it at the same time.

In a further aspect of the present invention, a method of optical detection is disclosed, specifically a method for determining a position of at least one object. The method comprises the following steps, which may be performed in the given order or in a different order. Further, two or more or even all of the method steps may be performed simultaneously and/or overlapping in time. Further, one, two or more or even all of the method steps may be performed repeatedly. The method may further comprise additional method steps. The method comprises the following method steps:

- modifying at least one property of a light beam in a spatially resolved fashion by using at least one spatial light modulator, the spatial light modulator having a matrix of pixels, each pixel being controllable to individually modify the at least one optical property of a portion of the light beam passing the pixel;
- detecting the light beam after passing the matrix of pixels of the spatial light modulator by using at least one optical sensor and for generating at least one sensor signal;
- periodically controlling at least two of the pixels with different frequencies by using at least one modulator device; and
- performing a frequency analysis by using at least one evaluation device and to determining signal components of the sensor signal for the control frequencies.

The method preferably may be performed by using the optical detector according to the present invention, such as disclosed in one or more of the embodiments given above or given in further detail below. Thus, with regard to definitions and potential embodiments of the method, reference may be made to the optical detector. Still, other embodiments are feasible.

In a further aspect of the present invention, a use of the optical detector according to the present invention, such as disclosed in one or more of the embodiments discussed above and/or as disclosed in one or more of the embodiments given in further detail below, is disclosed, for a purpose of use, selected from the group consisting of: a position measurement in traffic technology; an entertainment application; a security application; a human-machine interface application; a tracking application; a photography application; a mapping application for generating maps of at least one space, such as at least one space selected from the group of a room, a building and a street; a mobile application; a webcam; a computer peripheral device; a gaming application; a camera or video application; a security application; a surveillance application; an automotive application; a transport application; a medical application; a sports application; a machine vision application; a vehicle application; an airplane application; a ship application; a spacecraft application; a building application; a construction application; a cartography application; a manufacturing application; a use in combination with at least one time-of-flight detector. Additionally or alternatively, applications in local and/or global positioning systems may be named, especially landmark-based positioning and/or indoor and/or outdoor navigation, specifically for use in cars or other vehicles (such as trains, motorcycles, bicycles, trucks for cargo transportation), robots or for use by pedestrians. Further, indoor positioning systems may be named as potential applications, such as for household applications and/or for robots used in manufacturing technology. Further, the optical detector according to the present invention may be used in automatic door openers, such as in so-called smart sliding doors, such as a smart sliding door disclosed in Jie-Ci Yang et al., Sensors 2013, 13(5), 5923-5936; doi:10.3390/s130505923. At least one optical detector according to the present invention may be used for detecting when a person or an object approaches the door, and the door may automatically open.

Further applications, as outlined above, may be global positioning systems, local positioning systems, indoor navigation systems or the like. Thus, the devices according to the present invention, i.e. one or more of the optical detector, the detector system, the human-machine interface, the entertainment device, the tracking system or the camera, specifically may be part of a local or global positioning system. Additionally or alternatively, the devices may be part of a visible light communication system. Other uses are feasible.

The devices according to the present invention, i.e. one or more of the optical detector, the detector system, the human-machine interface, the entertainment device, the tracking system or the camera, further specifically may be used in combination with a local or global positioning system, such as for indoor or outdoor navigation. As an example, one or more devices according to the present invention may be combined with software/database-combinations such as Google Maps® or Google Street View®. Devices according to the present invention may further be used to analyze the distance to objects in the surrounding, the position of which can be found in the database. From the distance to the position of the known object, the local or global position of the user may be calculated.

Thus, as for the optical detectors and devices disclosed in WO 2012/110924 A1 or in U.S. provisional applications 61/739,173, filed on Dec. 19, 2012, and 61/749,964, filed on Jan. 8, 2013, the optical detector, the detector system, the human-machine interface, the entertainment device, the tracking system or the camera according to the present invention (in the following simply referred to as "the devices according to the present invention" or—without restricting the present invention to the potential use of the FiP effect—"FiP-devices") may be used for a plurality of application purposes, such as one or more of the purposes disclosed in further detail in the following.

Thus, firstly, FiP-devices may be used in mobile phones, tablet computers, laptops, smart panels or other stationary or mobile computer or communication applications. Thus, FiP-devices may be combined with at least one active light source, such as a light source emitting light in the visible range or infrared spectral range, in order to enhance performance. Thus, as an example, FiP-devices may be used as cameras and/or sensors, such as in combination with mobile software for scanning environment, objects and living beings. FiP-devices may even be combined with 2D cameras, such as conventional cameras, in order to increase imaging effects. FiP-devices may further be used for surveillance and/or for recording purposes or as input devices to control mobile devices, especially in combination with gesture recognition. Thus, specifically, FiP-devices acting as human-machine interfaces, also referred to as FiP input devices, may be used in mobile applications, such as for controlling other electronic devices or components via the mobile device, such as the mobile phone. As an example, the mobile application including at least one FiP-device may be used for controlling a television set, a game console, a music player or music device or other entertainment devices.

Further, FiP-devices may be used in webcams or other peripheral devices for computing applications. Thus, as an example, FiP-devices may be used in combination with software for imaging, recording, surveillance, scanning or motion detection. As outlined in the context of the human-machine interface and/or the entertainment device, FiP-devices are particularly useful for giving commands by facial expressions and/or body expressions. FiP-devices can be combined with other input generating devices like e.g. mouse, keyboard, touchpad, etc. Further, FiP-devices may be used in applications for gaming, such as by using a webcam. Further, FiP-devices may be used in virtual training applications and/or video conferences Further, FiP-devices may be used in mobile audio devices, television devices and gaming devices, as partially explained above. Specifically, FiP-devices may be used as controls or control devices for electronic devices, entertainment devices or the like. Further, FiP-devices may be used for eye detection or eye tracking, such as in 2D- and 3D-display techniques, especially with transparent displays for augmented reality applications.

Further, FiP-devices may be used in or as digital cameras such as DSC cameras and/or in or as reflex cameras such as SLR cameras. For these applications, reference may be made to the use of FiP-devices in mobile applications such as mobile phones, as disclosed above.

Further, FiP-devices may be used for security and surveillance applications. Thus, as an example, FiP-sensors in general and, specifically, the present SLM-based optical detector, can be combined with one or more digital and/or analog electronics that will give a signal if an object is within or outside a predetermined area (e.g. for surveillance applications in banks or museums). Specifically, FiP-devices may be used for optical encryption. FiP-based detection can be combined with other detection devices to complement wavelengths, such as with IR, x-ray, UV-VIS, radar or ultrasound detectors. FiP-devices may further be combined with an active infrared light source to allow detection in low light surroundings. FiP-devices such as FIP-based sensors are generally advantageous as compared to active detector systems, specifically since FiP-devices avoid actively sending signals which may be detected by third parties, as is the case e.g. in radar applications, ultrasound applications, LIDAR or similar active detector device is. Thus, generally, FiP-devices may be used for an unrecognized and undetectable tracking of moving objects. Additionally, FiP-devices generally are less prone to manipulations and irritations as compared to conventional devices.

Further, given the ease and accuracy of 3D detection by using FiP-devices, FiP-devices generally may be used for facial, body and person recognition and identification. Therein, FiP-devices may be combined with other detection means for identification or personalization purposes such as passwords, finger prints, iris detection, voice recognition or other means. Thus, generally, FiP-devices may be used in security devices and other personalized applications.

Further, FiP-devices may be used as 3D-Barcode readers for product identification.

In addition to the security and surveillance applications mentioned above, FiP-devices generally can be used for surveillance and monitoring of spaces and areas. Thus, FiP-devices may be used for surveying and monitoring spaces and areas and, as an example, for triggering or executing alarms in case prohibited areas are violated. Thus, generally, FiP-devices may be used for surveillance purposes in building surveillance or museums, optionally in combination with other types of sensors, such as in combination with motion or heat sensors, in combination with image intensifiers or image enhancement devices and/or photomultipliers.

Further, FiP-devices may advantageously be applied in camera applications such as video and camcorder applications. Thus, FiP-devices may be used for motion capture and 3D-movie recording. Therein, FiP-devices generally provide a large number of advantages over conventional optical devices. Thus, FiP-devices generally require a lower complexity with regard to optical components. Thus, as an example, the number of lenses may be reduced as compared to conventional optical devices, such as by providing FiP-devices having one lens only. Due to the reduced complexity, very compact devices are possible, such as for mobile use. Conventional optical systems having two or more lenses with high quality generally are voluminous, such as due to the general need for voluminous beam-splitters. Further, FiP-devices generally may be used for focus/autofocus devices, such as autofocus cameras. Further, FiP-devices may also be used in optical microscopy, especially in confocal microscopy.

Further, FiP-devices generally are applicable in the technical field of automotive technology and transport technology. Thus, as an example, FiP-devices may be used as distance and surveillance sensors, such as for adaptive cruise control, emergency brake assist, lane departure warning, surround view, blind spot detection, rear cross traffic alert, and other automotive and traffic applications. Further, FiP-sensors in general and, more specifically, the present SLM-based optical detector, can also be used for velocity and/or acceleration measurements, such as by analyzing a first and second time-derivative of position information gained by using the FiP-sensor. This feature generally may be applicable in automotive technology, transportation technology or general traffic technology. Applications in other fields of technology are feasible.

In these or other applications, generally, FiP-devices may be used as standalone devices or in combination with other sensor devices, such as in combination with radar and/or ultrasonic devices. Specifically, FiP-devices may be used for autonomous driving and safety issues. Further, in these applications, FiP-devices may be used in combination with infrared sensors, radar sensors, which are sonic sensors, two-dimensional cameras or other types of sensors. In these applications, the generally passive nature of typical FiP-devices is advantageous. Thus, since FiP-devices generally do not require emitting signals, the risk of interference of active sensor signals with other signal sources may be avoided. FiP-devices specifically may be used in combination with recognition software, such as standard image recognition software. Thus, signals and data as provide by FiP-devices typically are readily processable and, therefore, generally require lower calculation power than established stereovision systems such as LIDAR. Given the low space demand, FiP-devices such as cameras using the FiP-effect may be placed at virtually any place in a vehicle, such as on a window screen, on a front hood, on bumpers, on lights, on mirrors or other places the like. Various detectors based on the FiP-effect can be combined, such as in order to allow autonomously driving vehicles or in order to increase the performance of active safety concepts. Thus, various FiP-based sensors may be combined with other FiP-based sensors and/or conventional sensors, such as in the windows like rear window, side window or front window, on the bumpers or on the lights.

A combination of a FiP-sensor with one or more rain detection sensors is also possible. This is due to the fact that FiP-devices generally are advantageous over conventional sensor techniques such as radar, specifically during heavy rain. A combination of at least one FiP-device with at least one conventional sensing technique such as radar may allow for a software to pick the right combination of signals according to the weather conditions.

Further, FiP-devices generally may be used as break assist and/or parking assist and/or for speed measurements. Speed measurements can be integrated in the vehicle or may be used outside the vehicle, such as in order to measure the speed of other cars in traffic control. Further, FiP-devices may be used for detecting free parking spaces in parking lots.

Further, FiP-devices may be used is the fields of medical systems and sports. Thus, in the field of medical technology, surgery robotics, e.g. for use in endoscopes, may be named, since, as outlined above, FiP-devices may require a low volume only and may be integrated into other devices. Specifically, FiP-devices having one lens, at most, may be used for capturing 3D information in medical devices such as in endoscopes. Further, FiP-devices may be combined with an appropriate monitoring software, in order to enable tracking and analysis of movements. These applications are specifically valuable e.g. in medical treatments and long-distance diagnosis and tele-medicine.

Further, FiP-devices may be applied in the field of sports and exercising, such as for training, remote instructions or competition purposes. Specifically, FiP-devices may be applied in the field of dancing, aerobic, football, soccer, basketball, baseball, cricket, hockey, track and field, swimming, polo, handball, volleyball, rugby, sumo, judo, fencing, boxing etc. FiP-devices can be used to detect the position of a ball, a bat, a sword, motions, etc., both in sports and in games, such as to monitor the game, support the referee or for judgment, specifically automatic judgment, of specific situations in sports, such as for judging whether a point or a goal actually was made.

FiP-devices further may be used in rehabilitation and physiotherapy, in order to encourage training and/or in order to survey and correct movements. Therein, the FiP-devices may also be applied for distance diagnostics.

Further, FiP-devices may be applied in the field of machine vision. Thus, one or more FiP-devices may be used e.g. as a passive controlling unit for autonomous driving and or working of robots. In combination with moving robots, FiP-devices may allow for autonomous movement and/or autonomous detection of failures in parts. FiP-devices may also be used for manufacturing and safety surveillance, such as in order to avoid accidents including but not limited to collisions between robots, production parts and living beings. Given the passive nature of FiP-devices, FiP-devices may be advantageous over active devices and/or may be used complementary to existing solutions like radar, ultrasound, 2D cameras, IR detection etc. One particular advantage of FiP-devices is the low likelihood of signal interference. Therefore multiple sensors can work at the same time in the same environment, without the risk of signal interference. Thus, FiP-devices generally may be useful in highly automated production environments like e.g. but not limited to automotive, mining, steel, etc. FiP-devices can also be used for quality control in production, e.g. in combination with other sensors like 2-D imaging, radar, ultrasound, IR etc., such as for quality control or other purposes. Further, FiP-devices may be used for assessment of surface quality, such as for surveying the surface evenness of a product or the adherence to specified dimensions, from the range of micrometers to the range of meters. Other quality control applications are feasible.

Further, FiP-devices may be used in the polls, airplanes, ships, spacecrafts and other traffic applications. Thus, besides the applications mentioned above in the context of traffic applications, passive tracking systems for aircrafts, vehicles and the like may be named. Detection devices based on the FiP-effect for monitoring the speed and/or the direction of moving objects are feasible. Specifically, the tracking of fast moving objects on land, sea and in the air including space may be named. The at least one FiP-detector specifically may be mounted on a still-standing and/or on a moving device. An output signal of the at least one FiP-device can be combined e.g. with a guiding mechanism for autonomous or guided movement of another object. Thus, applications for avoiding collisions or for enabling collisions between the tracked and the steered object are feasible. FiP-devices generally are useful and advantageous due to the low calculation power required, the instant response and due to the passive nature of the detection system which generally is more difficult to detect and to disturb as compared to active systems, like e.g. radar. FiP-devices are particularly useful but not limited to e.g. speed control and air traffic control devices.

FiP-devices generally may be used in passive applications. Passive applications include guidance for ships in harbors or in dangerous areas, and for aircrafts at landing or starting. Wherein, fixed, known active targets may be used for precise guidance. The same can be used for vehicles driving in dangerous but well defined routes, such as mining vehicles.

Further, as outlined above, FiP-devices may be used in the field of gaming. Thus, FiP-devices can be passive for use with multiple objects of the same or of different size, color, shape, etc., such as for movement detection in combination with software that incorporates the movement into its content. In particular, applications are feasible in implementing movements into graphical output. Further, applications of FiP-devices for giving commands are feasible, such as by using one or more FiP-devices for gesture or facial recognition. FiP-devices may be combined with an active system in order to work under e.g. low light conditions or in other situations in which enhancement of the surrounding conditions is required. Additionally or alternatively, a combination of one or more FiP-devices with one or more IR or VIS light sources is possible, such as with a detection device based on the FiP effect. A combination of a FiP-based detector with special devices is also possible, which can be distinguished easily by the system and its software, e.g. and not limited to, a special color, shape, relative position to other devices, speed of movement, light, frequency used to modulate light sources on the device, surface properties, material used, reflection properties, transparency degree, absorption characteristics, etc. The device can, amongst other possibilities, resemble a stick, a racquet, a club, a gun, a knife, a wheel, a ring, a steering wheel, a bottle, a ball, a glass, a vase, a spoon, a fork, a cube, a dice, a figure, a puppet, a teddy, a beaker, a pedal, a switch, a glove, jewelry, a musical instrument or an auxiliary device for playing a musical instrument, such as a plectrum, a drumstick or the like. Other options are feasible.

Further, FiP-devices generally may be used in the field of building, construction and cartography. Thus, generally, FiP-based devices may be used in order to measure and/or monitor environmental areas, e.g. country side or buildings. Therein, one or more FiP-devices may be combined with other methods and devices or can be used solely in order to monitor progress and accuracy of building projects, changing objects, houses, etc. FiP-devices can be used for generating three-dimensional models of scanned environments, in order to construct maps of rooms, streets, houses, communities or landscapes, both from ground or from air. Potential fields of application may be construction, cartography, real estate management, land surveying or the like.

FiP-based devices can further be used for scanning of objects, such as in combination with CAD or similar software, such as for additive manufacturing and/or 3D printing. Therein, use may be made of the high dimensional accuracy of FiP-devices, e.g. in x-, y- or z-direction or in any arbitrary combination of these directions, such as simultaneously. Further, FiP-devices may be used in inspections and maintenance, such as pipeline inspection gauges.

As outlined above, FiP-devices may further be used in manufacturing, quality control or identification applications, such as in product identification or size identification (such as for finding an optimal place or package, for reducing waste etc.). Further, FiP-devices may be used in logistics applications. Thus, FiP-devices may be used for optimized loading or packing containers or vehicles. Further, FiP-devices may be used for monitoring or controlling of surface damages in the field of manufacturing, for monitoring or controlling rental objects such as rental vehicles, and/or for insurance applications, such as for assessment of damages. Further. FiP-devices may be used for identifying a size of material, object or tools, such as for optimal material handling, especially in combination with robots. Further, FiP-devices may be used for process control in production, e.g. for observing filling level of tanks. Further, FiP-devices may be used for maintenance of production assets like, but not limited to, tanks, pipes, reactors, tools etc. Further, FiP-devices may be used for analyzing 3D-quality marks. Further, FiP-devices may be used in manufacturing tailor-made goods such as tooth inlays, dental braces, prosthesis, clothes or the like. FiP-devices may also be combined with one or more 3D-printers for rapid prototyping, 3D-copying or the like. Further, FiP-devices may be used for detecting the shape of one or more articles, such as for anti-product piracy and for anti-counterfeiting purposes.

As outlined above, the at least one optical sensor or, in case a plurality of optical sensors is provided, at least one of the optical sensors may be an organic optical sensor comprising a photosensitive layer setup having at least two electrodes and at least one photovoltaic material embedded in between these electrodes. In the following, examples of a preferred setup of the photosensitive layer setup will be given, specifically with regard to materials which may be used within this photosensitive layer setup. The photosensitive layer setup preferably is a photosensitive layer setup of a solar cell, more preferably an organic solar cell and/or a dye-sensitized solar cell (DSC), more preferably a solid dye-sensitized solar cell (sDSC). Other embodiments, however, are feasible.

Preferably, the photosensitive layer setup comprises at least one photovoltaic material, such as at least one photovoltaic layer setup comprising at least two layers, sandwiched between the first electrode and the second electrode. Preferably, the photosensitive layer setup and the photovoltaic material comprise at least one layer of an n-semiconducting metal oxide, at least one dye and at least one p-semiconducting organic material. As an example, the photovoltaic material may comprise a layer setup having at least one dense layer of an n-semiconducting metal oxide such as titanium dioxide, at least one nano-porous layer of an n-semiconducting metal oxide contacting the dense layer of the n-semiconducting metal oxide, such as at least one nano-porous layer of titanium dioxide, at least one dye sensitizing the nano-porous layer of the n-semiconducting metal oxide, preferably an organic dye, and at least one layer of at least one p-semiconducting organic material, contacting the dye and/or the nano-porous layer of the n-semiconducting metal oxide.

The dense layer of the n-semiconducting metal oxide, as will be explained in further detail below, may form at least one barrier layer in between the first electrode and the at least one layer of the nano-porous n-semiconducting metal oxide. It shall be noted, however, that other embodiments are feasible, such as embodiments having other types of buffer layers.

The at least two electrodes comprise at least one first electrode and at least one second electrode. The first electrode may be one of an anode or a cathode, preferably an anode. The second electrode may be the other one of an anode or a cathode, preferably a cathode. The first electrode preferably contacts the at least one layer of the n-semiconducting metal oxide, and the second electrode preferably contacts the at least one layer of the p-semiconducting organic material. The first electrode may be a bottom electrode, contacting a substrate, and the second electrode may be a top electrode facing away from the substrate. Alternatively, the second electrode may be a bottom electrode, contacting the substrate, and the first electrode may be the top electrode facing away from the substrate. Preferably, one or both of the first electrode and the second electrode are transparent.

In the following, some options regarding the first electrode, the second electrode and the photovoltaic material, preferably the layer setup comprising two or more photovoltaic materials, will be disclosed. It shall be noted, however, that other embodiments are feasible.

a) Substrate, First Electrode and n-Semiconductive Metal Oxide

Generally, for preferred embodiments of the first electrode and the n-semiconductive metal oxide, reference may be made to WO 2012/110924 A1, U.S. provisional application No. 61/739,173 or U.S. provisional application No. 61/708,058, the full content of all of which is herewith included by reference. Other embodiments are feasible.

In the following, it shall be assumed that the first electrode is the bottom electrode directly or indirectly contacting the substrate. It shall be noted, however, that other setups are feasible, with the first electrode being the top electrode.

The n-semiconductive metal oxide which may be used in the photosensitive layer setup, such as in at least one dense film (also referred to as a solid film) of the n-semiconductive metal oxide and/or in at least one nano-porous film (also referred to as a nano-particulate film) of the n-semiconductive metal oxide, may be a single metal oxide or a mixture of different oxides. It is also possible to use mixed oxides. The n-semiconductive metal oxide may especially be porous and/or be used in the form of a nanoparticulate oxide, nanoparticles in this context being understood to mean particles which have an average particle size of less than 0.1 micrometer. A nanoparticulate oxide is typically applied to a conductive substrate (i.e. a carrier with a conductive layer as the first electrode) by a sintering process as a thin porous film with large surface area.

Preferably, the optical sensor uses at least one transparent substrate. However, setups using one or more intransparent substrates are feasible.

The substrate may be rigid or else flexible. Suitable substrates (also referred to hereinafter as carriers) are, as well as metal foils, in particular plastic sheets or films and especially glass sheets or glass films. Particularly suitable electrode materials, especially for the first electrode according to the above-described, preferred structure, are conductive materials, for example transparent conductive oxides (TCOs), for example fluorine- and/or indium-doped tin oxide (FTO or ITO) and/or aluminum-doped zinc oxide (AZO), carbon nanotubes or metal films. Alternatively or additionally, it would, however, also be possible to use thin metal films which still have a sufficient transparency. In case an intransparent first electrode is desired and used, thick metal films may be used.

The substrate can be covered or coated with these conductive materials. Since generally, only a single substrate is required in the structure proposed, the formation of flexible cells is also possible. This enables a multitude of end uses which would be achievable only with difficulty, if at all, with rigid substrates, for example use in bank cards, garments, etc.

The first electrode, especially the TCO layer, may additionally be covered or coated with a solid or dense metal oxide buffer layer (for example of thickness 10 to 200 nm), in order to prevent direct contact of the p-type semiconductor with the TCO layer (see Peng et at, Coord. Chem. Rev. 248, 1479 (2004)). The use of solid p-semiconducting electrolytes, in the case of which contact of the electrolyte with the first electrode is greatly reduced compared to liquid or gel-form electrolytes, however, makes this buffer layer unnecessary in many cases, such that it is possible in many cases to dispense with this layer, which also has a current-limiting effect and can also worsen the contact of the n-semiconducting metal oxide with the first electrode. This enhances the efficiency of the components. On the other hand, such a buffer layer can in turn be utilized in a controlled manner in order to match the current component of the dye solar cell to the current component of the organic solar cell. In addition, in the case of cells in which the buffer layer has been dispensed with, especially in solid cells, problems frequently occur with unwanted recombinations of charge carriers. In this respect, buffer layers are advantageous in many cases specifically in solid cells.

As is well known, thin layers or films of metal oxides are generally inexpensive solid semiconductor materials (n-type semiconductors), but the absorption thereof, due to large bandgaps, is typically not within the visible region of the electromagnetic spectrum, but rather usually in the ultraviolet spectral region. For use in solar cells, the metal oxides therefore generally, as is the case in the dye solar cells, have to be combined with a dye as a photosensitizer, which absorbs in the wavelength range of sunlight, i.e. at 300 to 2000 nm, and, in the electronically excited state, injects electrons into the conduction band of the semiconductor. With the aid of a solid p-type semiconductor used additionally in the cell as an electrolyte, which is in turn reduced at the counter electrode, electrons can be recycled to the sensitizer, such that it is regenerated.

Of particular interest for use in organic solar cells are the semiconductors zinc oxide, tin dioxide, titanium dioxide or mixtures of these metal oxides. The metal oxides can be used in the form of microcrystalline or nanocrystalline porous layers. These layers have a large surface area which is coated with the dye as a sensitizer, such that a high absorption of sunlight is achieved. Metal oxide layers which are structured, for example nanorods, give advantages such as higher electron mobilities, improved pore filling by the dye, improved surface sensitization by the dye or increased surface areas.

The metal oxide semiconductors can be used alone or in the form of mixtures. It is also possible to coat a metal oxide with one or more other metal oxides. In addition, the metal oxides may also be applied as a coating to another semiconductor, for example GaP, ZnP or ZnS.

Particularly preferred semiconductors are zinc oxide and titanium dioxide in the anatase polymorph, which is preferably used in nanocrystalline form.

In addition, the sensitizers can advantageously be combined with all n-type semiconductors which typically find use in these solar cells. Preferred examples include metal oxides used in ceramics, such as titanium dioxide, zinc oxide, tin(IV) oxide, tungsten(VI) oxide, tantalum(V) oxide, niobium(V) oxide, cesium oxide, strontium titanate, zinc stannate, complex oxides of the perovskite type, for example barium titanate, and binary and ternary iron oxides, which may also be present in nanocrystalline or amorphous form.

Due to the strong absorption that customary organic dyes and ruthenium, phthalocyanines and porphyrins have, even thin layers or films of the n-semiconducting metal oxide are sufficient to absorb the required amount of dye. Thin metal oxide films in turn have the advantage that the probability of unwanted recombination processes falls and that the internal resistance of the dye subcell is reduced. For the n-semiconducting metal oxide, it is possible with preference to use layer thicknesses of 100 nm up to 20 micrometers, more preferably in the range between 500 nm and approx. 3 micrometers.

b) Dye

In the context of the present invention, as usual in particular for DSCs, the terms "dye", "sensitizer dye" and "sensitizer" are used essentially synonymously without any restriction of possible configurations. Numerous dyes which are usable in the context of the present invention are known from the prior art, and so, for possible material examples, reference may also be made to the above description of the prior art regarding dye solar cells. As a preferred example, one or more of the dyes disclosed in WO 2012/110924 A1, U.S. provisional application No. 61/739,173 or U.S. provisional application No. 61/708,058 may be used, the full content of all of which is herewith included by reference. Additionally or alternatively, one or more of the dyes as disclosed in WO 2007/054470 A1 and/or WO 2013/144177 A1 and/or WO 2012/085803 A1 may be used, the full content of which is included by reference, too.

Dye-sensitized solar cells based on titanium dioxide as a semiconductor material are described, for example, in U.S. Pat. No. 4,927,721, Nature 353, p. 737-740 (1991) and U.S. Pat. No. 5,350,644, and also Nature 395, p. 583-585 (1998) and EP-A-1 176 646. The dyes described in these documents can in principle also be used advantageously in the context of the present invention. These dye solar cells preferably comprise monomolecular films of transition metal complexes, especially ruthenium complexes, which are bonded to the titanium dioxide layer via acid groups as sensitizers.

Many sensitizers which have been proposed include metal-free organic dyes, which are likewise also usable in the context of the present invention. High efficiencies of more than 4%, especially in solid dye solar cells, can be achieved, for example, with indoline dyes (see, for example, Schmidt-Mende et al., Adv. Mater. 2005, 17, 813). U.S. Pat. No. 6,359,211 describes the use, also implementable in the context of the present invention, of cyanine, oxazine, thiazine and acridine dyes which have carboxyl groups bonded via an alkylene radical for fixing to the titanium dioxide semiconductor.

Preferred sensitizer dyes in the dye solar cell proposed are the perylene derivatives, terrylene derivatives and quaterrylene derivatives described in DE 10 2005 053 995 A1 or WO 2007/054470 A1. Further, as outlined above, one or more of the dyes as disclosed in WO 2012/085803 A1 may be used. Additionally or alternatively, one or more of the dyes as disclosed in WO 2013/144177 A1 may be used. The full content of WO 2013/144177 A1 and of EP 12162526.3 is herewith included by reference. Specifically, dye D-5 and/or dye R-3 may be used, which is also referred to as ID1338:

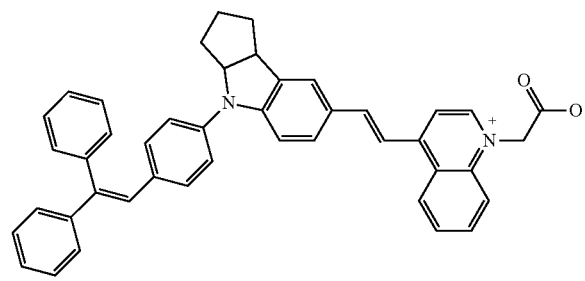

-continued

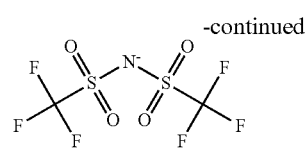

Preparation and properties of the Dye D-5 and dye R-3 are disclosed in WO 2013/144177 A1.

The use of these dyes, which is also possible in the context of the present invention, leads to photovoltaic elements with high efficiencies and simultaneously high stabilities.

Further, additionally or alternatively, the following dye may be used, which also is disclosed in WO 2013/144177 A1, which is referred to as ID1456:

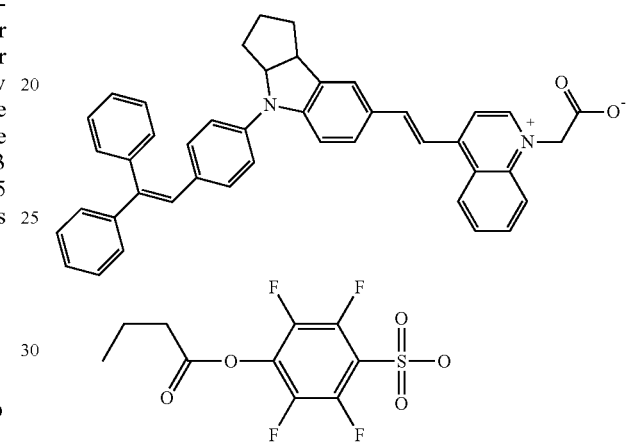

Further, one or both of the following rylene dyes may be used in the devices according to the present invention, specifically in the at least one optical sensor:
ID1187:

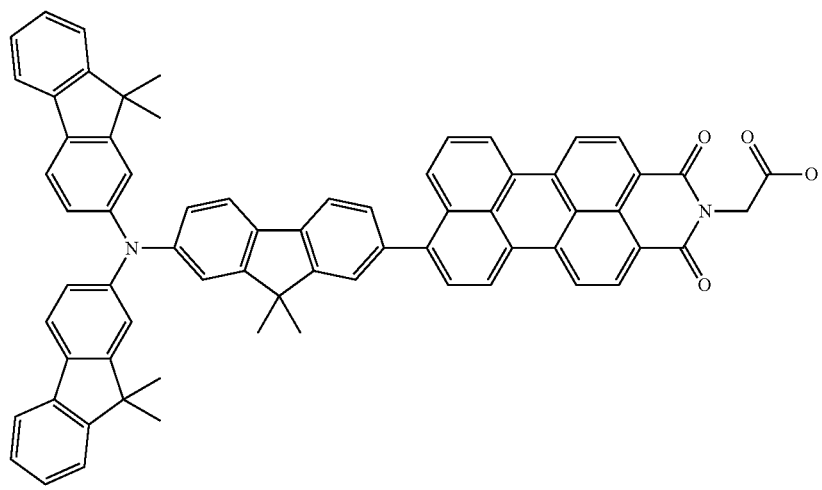 [SMILES: CC1(C)c2ccccc2-c2ccc(N(c3ccc4c(c3)C(C)(C)c3ccccc3-4)c3ccc4c(c3)C(C)(C)c3cc(-c5ccc6c7ccc8c9c(ccc(c%10cccc5c%106)c97)C(=O)N(CC(=O)O)C8=O)ccc3-4)cc21]

ID1167:

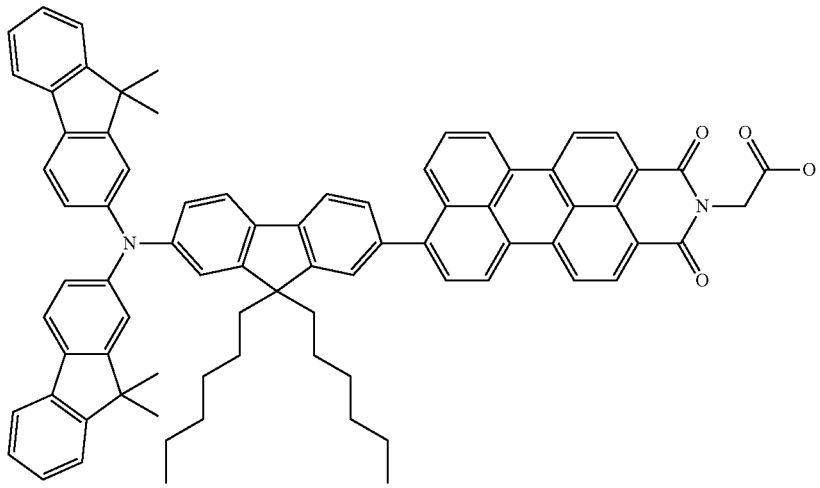 [SMILES: CCCCCCC1(CCCCCC)c2cc(-c3ccc4c5ccc6c7c(ccc(c8cccc3c84)c75)C(=O)N(CC(=O)O)C6=O)ccc2-c2ccc(N(c3ccc4c(c3)C(C)(C)c3ccccc3-4)c3ccc4c(c3)C(C)(C)c3ccccc3-4)cc21]

These dyes ID1187 and ID1167 fall within the scope of the rylene dyes as disclosed in WO 2007/054470 A1, and may be synthesized using the general synthesis routes as disclosed therein, as the skilled person will recognize.

The rylenes exhibit strong absorption in the wavelength range of sunlight and can, depending on the length of the conjugated system, cover a range from about 400 nm (perylene derivatives I from DE 10 2005 053 995 A1) up to about 900 nm (quaterrylene derivatives I from DE 10 2005 053 995 A1). Rylene derivatives I based on terrylene absorb, according to the composition thereof, in the solid state adsorbed onto titanium dioxide, within a range from about 400 to 800 nm. In order to achieve very substantial utilization of the incident sunlight from the visible into the near infrared region, it is advantageous to use mixtures of different rylene derivatives I. Occasionally, it may also be advisable also to use different rylene homologs.

The rylene derivatives I can be fixed easily and in a permanent manner to the n-semiconducting metal oxide film. The bonding is effected via the anhydride function (x1) or the carboxyl groups —COOH or —COO— formed in situ, or via the acid groups A present in the imide or condensate radicals ((x2) or (x3)). The rylene derivatives I described in DE 10 2005 053 995 A1 have good suitability for use in dye-sensitized solar cells in the context of the present invention.

It is particularly preferred when the dyes, at one end of the molecule, have an anchor group which enables the fixing thereof to the n-type semiconductor film. At the other end of the molecule, the dyes preferably comprise electron donors Y which facilitate the regeneration of the dye after the electron release to the n-type semiconductor, and also prevent recombination with electrons already released to the semiconductor.

For further details regarding the possible selection of a suitable dye, it is possible, for example, again to refer to DE 10 2005 053 995 A1. By way of example, it is possible especially to use ruthenium complexes, porphyrins, other organic sensitizers, and preferably rylenes.

The dyes can be fixed onto or into the n-semiconducting metal oxide film, such as the nano-porous n-semiconducting metal oxide layer, in a simple manner. For example, the n-semiconducting metal oxide films can be contacted in the freshly sintered (still warm) state over a sufficient period (for example about 0.5 to 24 h) with a solution or suspension of the dye in a suitable organic solvent. This can be accomplished, for example, by immersing the metal oxide-coated substrate into the solution of the dye.

If combinations of different dyes are to be used, they may, for example, be applied successively from one or more solutions or suspensions which comprise one or more of the dyes. It is also possible to use two dyes which are separated by a layer of, for example, CuSCN (on this subject see, for example, Tennakone, K. J., Phys. Chem. B. 2003, 107, 13758). The most convenient method can be determined comparatively easily in the individual case.

In the selection of the dye and of the size of the oxide particles of the n-semiconducting metal oxide, the organic solar cell should be configured such that a maximum amount of light is absorbed. The oxide layers should be structured such that the solid p-type semiconductor can efficiently fill the pores. For instance, smaller particles have greater surface areas and are therefore capable of adsorbing a greater amount of dyes. On the other hand, larger particles generally have larger pores which enable better penetration through the p-conductor.

c) p-Semiconducting Organic Material

As described above, the at least one photosensitive layer setup, such as the photosensitive layer setup of the DSC or sDSC, can comprise in particular at least one p-semiconducting organic material, preferably at least one solid p-semiconducting material, which is also designated hereinafter as p-type semiconductor or p-type conductor. Hereinafter, a description is given of a series of preferred examples of such organic p-type semiconductors which can be used individually or else in any desired combination, for example in a combination of a plurality of layers with a respective p-type semiconductor, and/or in a combination of a plurality of p-type semiconductors in one layer.

In order to prevent recombination of the electrons in the n-semiconducting metal oxide with the solid p-conductor, it is possible to use, between the n-semiconducting metal oxide and the p-type semiconductor, at least one passivating layer which has a passivating material. This layer should be very thin and should as far as possible cover only the as yet uncovered sites of the n-semiconducting metal oxide. The passivation material may, under some circumstances, also be applied to the metal oxide before the dye. Preferred passivation materials are especially one or more of the following substances: $Al_2O_3$; silanes, for example $CH_3SiCl_3$; $Al^{3+}$; 4-tert-butylpyridine (TBP); MgO; GBA (4-guanidinobutyric acid) and similar derivatives; alkyl acids; hexadecylmalonic acid (HDMA).

As described above, preferably one or more solid organic p-type semiconductors are used—alone or else in combination with one or more further p-type semiconductors which are organic or inorganic in nature. In the context of the present invention, a p-type semiconductor is generally understood to mean a material, especially an organic material, which is capable of conducting holes, that is to say positive charge carriers. More particularly, it may be an organic material with an extensive π-electron system which can be oxidized stably at least once, for example to form what is called a free-radical cation. For example, the p-type semiconductor may comprise at least one organic matrix material which has the properties mentioned. Furthermore, the p-type semiconductor can optionally comprise one or a plurality of dopants which intensify the p-semiconducting properties. A significant parameter influencing the selection of the p-type semiconductor is the hole mobility, since this partly determines the hole diffusion length (cf. Kumara, G., Langmuir, 2002, 18, 10493-10495). A comparison of charge carrier mobilities in different Spiro compounds can be found, for example, in T. Saragi, Adv. Funct. Mater. 2006, 16, 966-974.

Preferably, in the context of the present invention, organic semiconductors are used (i.e. one or more of low molecular weight, oligomeric or polymeric semiconductors or mixtures of such semiconductors). Particular preference is given to p-type semiconductors which can be processed from a liquid phase. Examples here are p-type semiconductors based on polymers such as polythiophene and polyarylamines, or on amorphous, reversibly oxidizable, nonpolymeric organic compounds, such as the spirobifluorenes mentioned at the outset (cf., for example, US 2006/0049397 and the spiro compounds disclosed therein as p-type semiconductors, which are also usable in the context of the present invention). Preference is also given to using low molecular weight organic semiconductors, such as the low molecular weight p-type semiconducting materials as disclosed in WO 2012/110924 A1, preferably spiro-MeOTAD, and/or one or more of the p-type semiconducting materials disclosed in Leijtens et al., ACS Nano, VOL. 6, NO. 2, 1455-1462 (2012). Additionally or alternatively, one or more of the p-type semiconducting materials as disclosed in WO 2010/094636 A1 may be used, the full content of which is herewith included by reference. In addition, reference may also be made to the remarks regarding the p-semiconducting materials and dopants from the above description of the prior art.

The p-type semiconductor is preferably producible or produced by applying at least one p-conducting organic material to at least one carrier element, wherein the application is effected for example by deposition from a liquid phase comprising the at least one p-conducting organic material. The deposition can in this case once again be effected, in principle, by any desired deposition process, for example by spin-coating, doctor blading, knife-coating, printing or combinations of the stated and/or other deposition methods.

The organic p-type semiconductor may especially comprise at least one spiro compound such as spiro-MeOTAD and/or at least one compound with the structural formula:

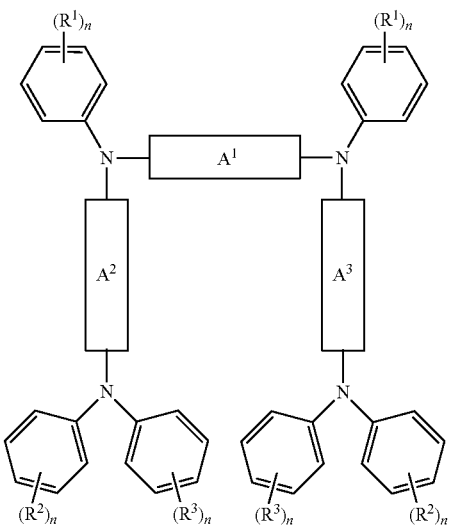

in which

A$^1$, A$^2$, A$^3$ are each independently optionally substituted aryl groups or heteroaryl groups, R$^1$, R$^2$, R$^3$ are each independently selected from the group consisting of the substituents —R, —OR, —NR$_2$, -A$^4$-OR and -A$^4$-NR$_2$, where R is selected from the group consisting of alkyl, aryl and heteroaryl, and where A$^4$ is an aryl group or heteroaryl group, and where n at each instance in formula I is independently a value of 0, 1, 2 or 3, with the proviso that the sum of the individual n values is at least 2 and at least two of the R$^1$, R$^2$ and R$^3$ radicals are —OR and/or —NR$_2$.

Preferably, A$^2$ and A$^3$ are the same; accordingly, the compound of the formula (I) preferably has the following structure (Ia)

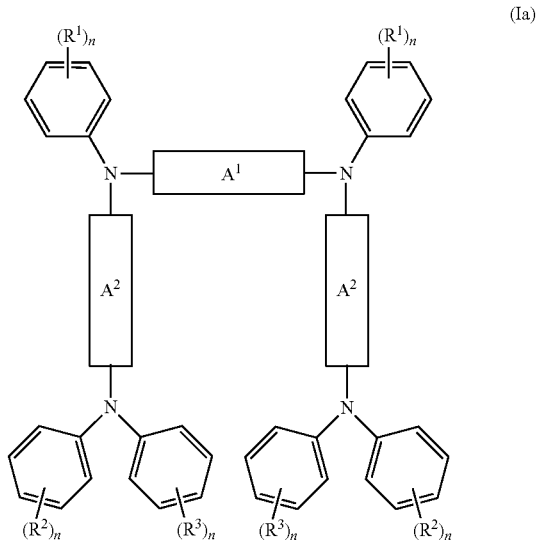

More particularly, as explained above, the p-type semiconductor may thus have at least one low molecular weight organic p-type semiconductor. A low molecular weight material is generally understood to mean a material which is present in monomeric, nonpolymerized or nonoligomerized form. The term "low molecular weight" as used in the present context preferably means that the p-type semiconductor has molecular weights in the range from 100 to 25 000 g/mol. Preferably, the low molecular weight substances have molecular weights of 500 to 2000 g/mol.

In general, in the context of the present invention, p-semiconducting properties are understood to mean the property of materials, especially of organic molecules, to form holes and to transport these holes and/or to pass them on to adjacent molecules. More particularly, stable oxidation of these molecules should be possible. In addition, the low molecular weight organic p-type semiconductors mentioned may especially have an extensive π-electron system. More particularly, the at least one low molecular weight p-type semiconductor may be processable from a solution. The low molecular weight p-type semiconductor may especially comprise at least one triphenylamine. It is particularly preferred when the low molecular weight organic p-type semiconductor comprises at least one Spiro compound. A spiro compound is understood to mean polycyclic organic compounds whose rings are joined only at one atom, which is also referred to as the Spiro atom. More particularly, the spiro atom may be spa-hybridized, such that the constituents of the Spiro compound connected to one another via the Spiro atom are, for example, arranged in different planes with respect to one another.

More preferably, the Spiro compound has a structure of the following formula:

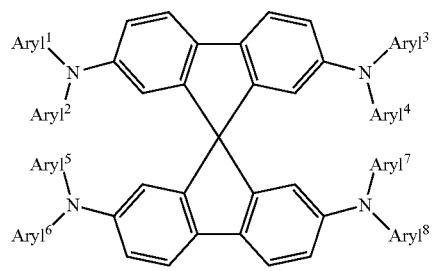

where the aryl$^1$, aryl$^2$, aryl$^3$, aryl$^4$, aryl$^5$, aryl$^6$, aryl$^7$ and aryl$^8$ radicals are each independently selected from substituted aryl radicals and heteroaryl radicals, especially from substituted phenyl radicals, where the aryl radicals and heteroaryl radicals, preferably the phenyl radicals, are each independently substituted, preferably in each case by one or more substituents selected from the group consisting of —O-alkyl, —OH, —F, —Cl, —Br and —I, where alkyl is preferably methyl, ethyl, propyl or isopropyl. More preferably, the phenyl radicals are each independently substituted, in each case by one or more substituents selected from the group consisting of —O-Me, —OH, —F, —Cl, —Br and —I.

Further preferably, the spiro compound is a compound of the following formula:

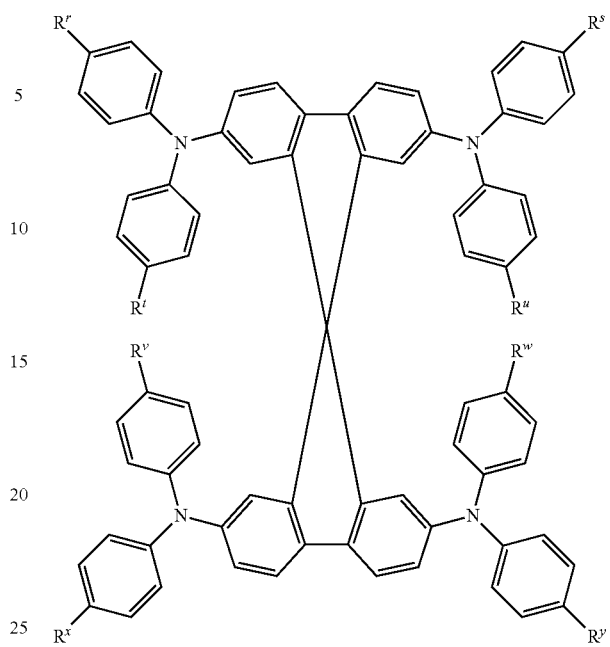

where $R^r$, $R^s$, $R^t$, $R^u$, $R^v$, $R^w$, $R^x$ and $R^y$ are each independently selected from the group consisting of —O-alkyl, —OH, —F, —Cl, —Br and —I, where alkyl is preferably methyl, ethyl, propyl or isopropyl. More preferably, $R^r$, $R^s$, $R^t$, $R^u$, $R^v$, $R^w$, $R^x$ and $R^y$ are each independently selected from the group consisting of —O-Me, —OH, —F, —Cl, —Br and —I.

More particularly, the p-type semiconductor may comprise spiro-MeOTAD or consist of spiro-MeOTAD, i.e. a compound of the formula below, commercially available from Merck KGaA, Darmstadt, Germany:

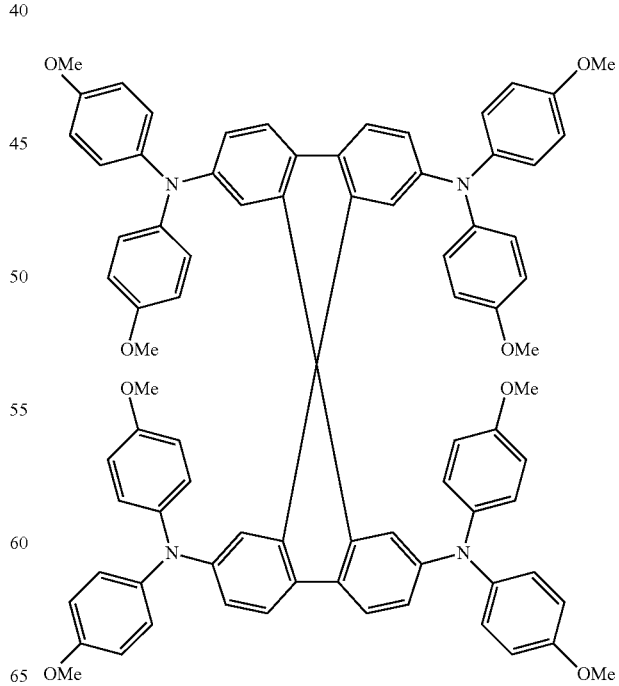

Alternatively or additionally, it is also possible to use other p-semiconducting compounds, especially low molecular weight and/or oligomeric and/or polymeric p-semiconducting compounds.

In an alternative embodiment, the low molecular weight organic p-type semiconductor comprises one or more compounds of the above-mentioned general formula I, for which reference may be made, for example, to PCT application number PCT/EP2010/051826. The p-type semiconductor may comprise the at least one compound of the above-mentioned general formula I additionally or alternatively to the spiro compound described above.

The term "alkyl" or "alkyl group" or "alkyl radical" as used in the context of the present invention is understood to mean substituted or unsubstituted $C_1$-$C_{20}$-alkyl radicals in general. Preference is given to $C_1$- to $C_{10}$-alkyl radicals, particular preference to $C_1$- to $C_8$-alkyl radicals. The alkyl radicals may be either straight-chain or branched. In addition, the alkyl radicals may be substituted by one or more substituents selected from the group consisting of $C_1$-$C_{20}$-alkoxy, halogen, preferably F, and $C_6$-$C_{30}$-aryl which may in turn be substituted or unsubstituted. Examples of suitable alkyl groups are methyl, ethyl, propyl, butyl, pentyl, hexyl, heptyl and octyl, and also isopropyl, isobutyl, isopentyl, sec-butyl, tert-butyl, neopentyl, 3,3-dimethylbutyl, 2-ethylhexyl, and also derivatives of the alkyl groups mentioned substituted by $C_6$-$C_{30}$-aryl, $C_1$-$C_{20}$-alkoxy and/or halogen, especially F, for example $CF_3$.

The term "aryl" or "aryl group" or "aryl radical" as used in the context of the present invention is understood to mean optionally substituted $C_6$-$C_{30}$-aryl radicals which are derived from monocyclic, bicyclic, tricyclic or else multicyclic aromatic rings, where the aromatic rings do not comprise any ring heteroatoms. The aryl radical preferably comprises 5- and/or 6-membered aromatic rings. When the aryls are not monocyclic systems, in the case of the term "aryl" for the second ring, the saturated form (perhydro form) or the partly unsaturated form (for example the dihydro form or tetrahydro form), provided the particular forms are known and stable, is also possible. The term "aryl" in the context of the present invention thus comprises, for example, also bicyclic or tricyclic radicals in which either both or all three radicals are aromatic, and also bicyclic or tricyclic radicals in which only one ring is aromatic, and also tricyclic radicals in which two rings are aromatic. Examples of aryl are: phenyl, naphthyl, indanyl, 1,2-dihydronaphthenyl, 1,4-dihydronaphthenyl, fluorenyl, indenyl, anthracenyl, phenanthrenyl or 1,2,3,4-tetrahydronaphthyl. Particular preference is given to $C_6$-$C_{10}$-aryl radicals, for example phenyl or naphthyl, very particular preference to $C_6$-aryl radicals, for example phenyl. In addition, the term "aryl" also comprises ring systems comprising at least two monocyclic, bicyclic or multicyclic aromatic rings joined to one another via single or double bonds. One example is that of biphenyl groups.

The term "heteroaryl" or "heteroaryl group" or "heteroaryl radical" as used in the context of the present invention is understood to mean optionally substituted 5- or 6-membered aromatic rings and multicyclic rings, for example bicyclic and tricyclic compounds having at least one heteroatom in at least one ring. The heteroaryls in the context of the invention preferably comprise 5 to 30 ring atoms. They may be monocyclic, bicyclic or tricyclic, and some can be derived from the aforementioned aryl by replacing at least one carbon atom in the aryl base skeleton with a heteroatom. Preferred heteroatoms are N, O and S. The hetaryl radicals more preferably have 5 to 13 ring atoms. The base skeleton of the heteroaryl radicals is especially preferably selected from systems such as pyridine and five-membered heteroaromatics such as thiophene, pyrrole, imidazole or furan. These base skeletons may optionally be fused to one or two six-membered aromatic radicals. In addition, the term "heteroaryl" also comprises ring systems comprising at least two monocyclic, bicyclic or multicyclic aromatic rings joined to one another via single or double bonds, where at least one ring comprises a heteroatom. When the heteroaryls are not monocyclic systems, in the case of the term "heteroaryl" for at least one ring, the saturated form (perhydro form) or the partly unsaturated form (for example the dihydro form or tetrahydro form), provided the particular forms are known and stable, is also possible. The term "heteroaryl" in the context of the present invention thus comprises, for example, also bicyclic or tricyclic radicals in which either both or all three radicals are aromatic, and also bicyclic or tricyclic radicals in which only one ring is aromatic, and also tricyclic radicals in which two rings are aromatic, where at least one of the rings, i.e. at least one aromatic or one nonaromatic ring, has a heteroatom. Suitable fused heteroaromatics are, for example, carbazolyl, benzimidazolyl, benzofuryl, dibenzofuryl or dibenzothiophenyl. The base skeleton may be substituted at one, more than one or all substitutable positions, suitable substituents being the same as have already been specified under the definition of $C_6$-$C_{30}$-aryl. However, the hetaryl radicals are preferably unsubstituted. Suitable hetaryl radicals are, for example, pyridin-2-yl, pyridin-3-yl, pyridin-4-yl, thiophen-2-yl, thiophen-3-yl, pyrrol-2-yl, pyrrol-3-yl, furan-2-yl, furan-3-yl and imidazol-2-yl and the corresponding benzofused radicals, especially carbazolyl, benzimidazolyl, benzofuryl, dibenzofuryl or dibenzothiophenyl.

In the context of the invention, the term "optionally substituted" refers to radicals in which at least one hydrogen radical of an alkyl group, aryl group or heteroaryl group has been replaced by a substituent. With regard to the type of this substituent, preference is given to alkyl radicals, for example methyl, ethyl, propyl, butyl, pentyl, hexyl, heptyl and octyl, and also isopropyl, isobutyl, isopentyl, sec-butyl, tert-butyl, neopentyl, 3,3-dimethylbutyl and 2-ethylhexyl, aryl radicals, for example $C_6$-$C_{10}$-aryl radicals, especially phenyl or naphthyl, most preferably $C_6$-aryl radicals, for example phenyl, and hetaryl radicals, for example pyridin-2-yl, pyridin-3-yl, pyridin-4-yl, thiophen-2-yl, thiophen-3-yl, pyrrol-2-yl, pyrrol-3-yl, furan-2-yl, furan-3-yl and imidazol-2-yl, and also the corresponding benzofused radicals, especially carbazolyl, benzimidazolyl, benzofuryl, dibenzofuryl or dibenzothiophenyl. Further examples include the following substituents: alkenyl, alkynyl, halogen, hydroxyl.

The degree of substitution here may vary from monosubstitution up to the maximum number of possible substituents.

Preferred compounds of the formula I for use in accordance with the invention are notable in that at least two of the $R^1$, $R^2$ and $R^3$ radicals are para-OR and/or —$NR_2$ substituents. The at least two radicals here may be only —OR radicals, only —$NR_2$ radicals, or at least one —OR and at least one —$NR_2$ radical.

Particularly preferred compounds of the formula I for use in accordance with the invention are notable in that at least four of the $R^1$, $R^2$ and $R^3$ radicals are para-OR and/or —$NR_2$ substituents. The at least four radicals here may be only —OR radicals, only —$NR_2$ radicals or a mixture of —OR and —$NR_2$ radicals.

Very particularly preferred compounds of the formula I for use in accordance with the invention are notable in that all of the $R^1$, $R^2$ and $R^3$ radicals are para-OR and/or —$NR_2$ substituents. They may be only —OR radicals, only —$NR_2$ radicals or a mixture of —OR and —$NR_2$ radicals.

In all cases, the two R in the —$NR_2$ radicals may be different from one another, but they are preferably the same.

Preferably, $A^1$, $A^2$ and $A^3$ are each independently selected from the group consisting of

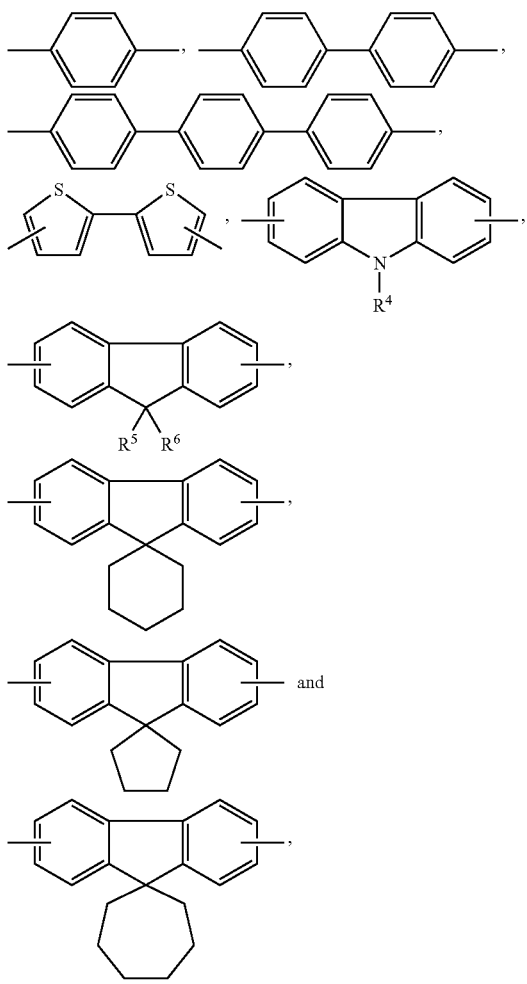

in which
m is an integer from 1 to 18, $R^4$ is alkyl, aryl or heteroaryl, where $R^4$ is preferably an aryl radical, more preferably a phenyl radical, $R^5$, $R^6$ are each independently H, alkyl, aryl or heteroaryl, where the aromatic and heteroaromatic rings of the structures shown may optionally have further substitution. The degree of substitution of the aromatic and heteroaromatic rings here may vary from monosubstitution up to the maximum number of possible substituents.

Preferred substituents in the case of further substitution of the aromatic and heteroaromatic rings include the substituents already mentioned above for the one, two or three optionally substituted aromatic or heteroaromatic groups.

Preferably, the aromatic and heteroaromatic rings of the structures shown do not have further substitution.

More preferably, $A^1$, $A^2$ and $A^3$ are each independently

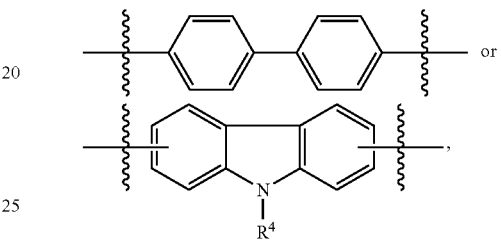

more preferably

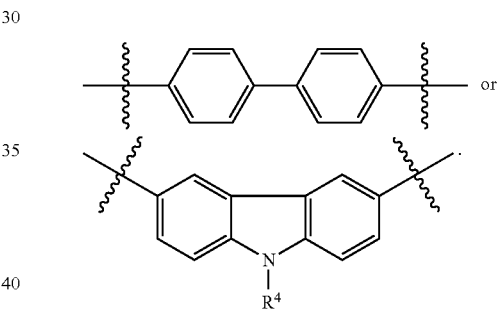

More preferably, the at least one compound of the formula (I) has one of the following structures

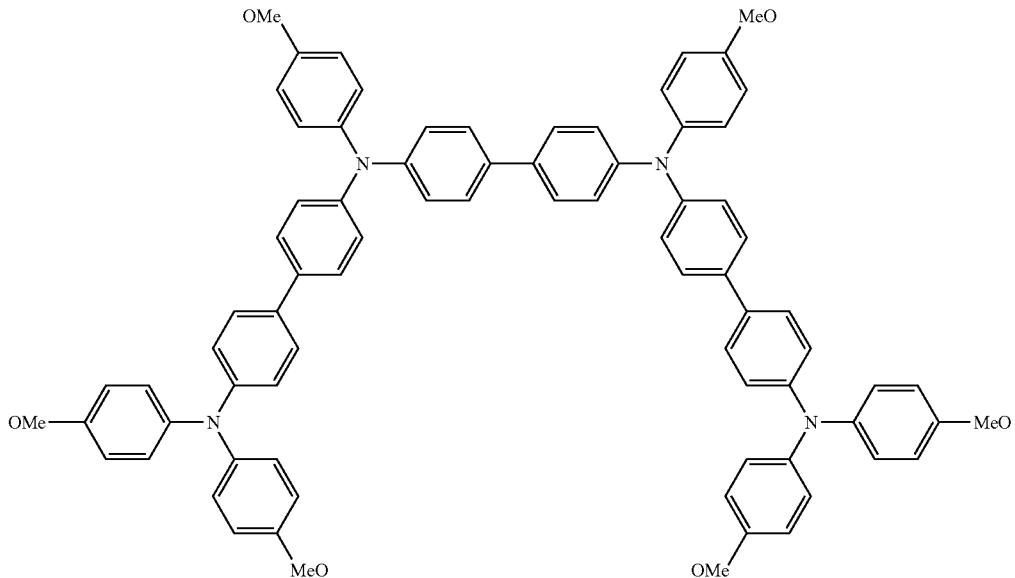

ID367

-continued

ID522

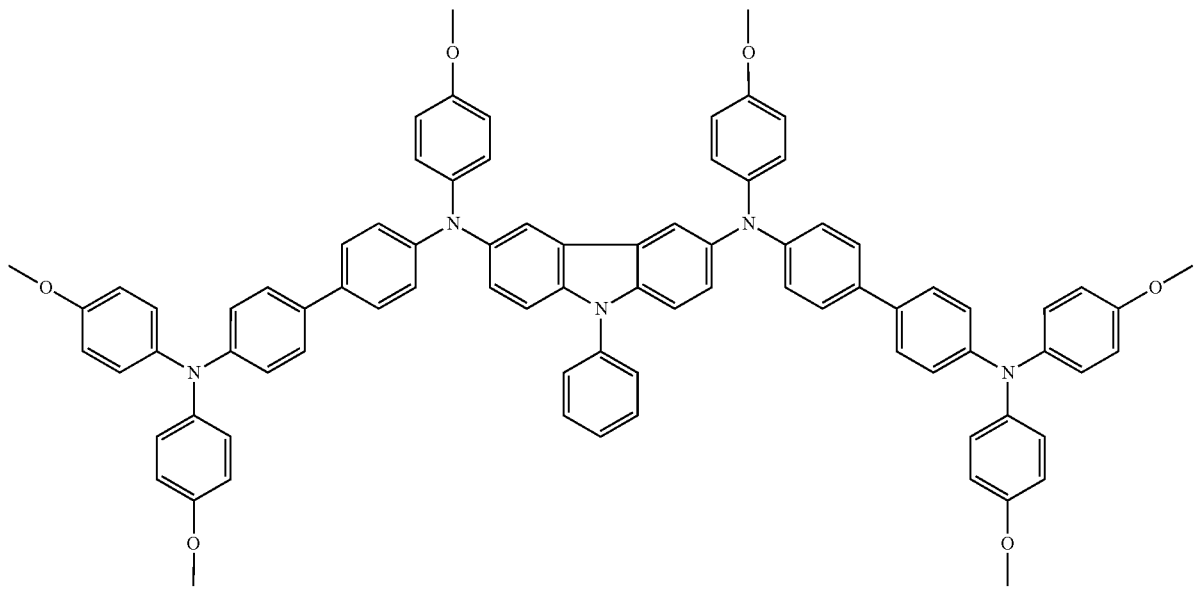

In an alternative embodiment, the organic p-type semiconductor comprises a compound of the type ID322 having the following structure:

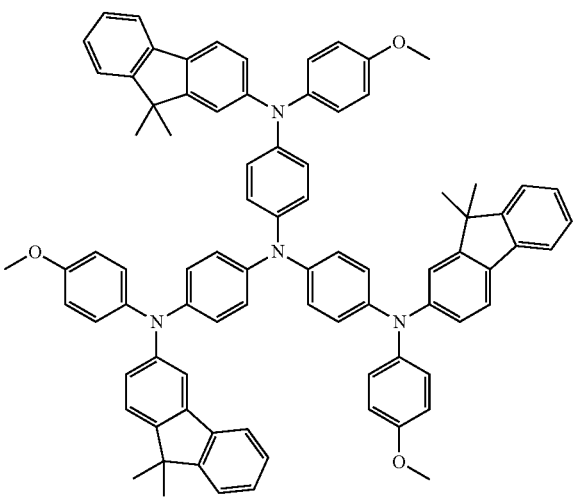 [SMILES: COc1ccc(N(c2ccc(N(c3ccc(N(c4ccc(OC)cc4)c4ccc5c(c4)C(C)(C)c4ccccc4-5)cc3)c3ccc(N(c4ccc(OC)cc4)c4ccc5c(c4)C(C)(C)c4ccccc4-5)cc3)cc2)c2ccc3c(c2)-c2ccccc2C3(C)C)cc1]

The compounds for use in accordance with the invention can be prepared by customary methods of organic synthesis known to those skilled in the art. References to relevant (patent) literature can additionally be found in the synthesis examples adduced below.

d) Second Electrode

The second electrode may be a bottom electrode facing the substrate or else a top electrode facing away from the substrate. As outlined above, the second electrode may be fully or partially transparent or, else, may be intransparent. As used herein, the term partially transparent refers to the fact that the second electrode may comprise transparent regions and intransparent regions.

One or more materials of the following group of materials may be used: at least one metallic material, preferably a metallic material selected from the group consisting of aluminum, silver, platinum, gold; at least one nonmetallic inorganic material, preferably LiF; at least one organic conductive material, preferably at least one electrically conductive polymer and, more preferably, at least one transparent electrically conductive polymer.

The second electrode may comprise at least one metal electrode, wherein one or more metals in pure form or as a mixture/alloy, such as especially aluminum or silver may be used.

Additionally or alternatively, nonmetallic materials may be used, such as inorganic materials and/or organic materials, both alone and in combination with metal electrodes. As an example, the use of inorganic/organic mixed electrodes or multilayer electrodes is possible, for example the use of LiF/Al electrodes. Additionally or alternatively, conductive polymers may be used. Thus, the second electrode of the optical sensor preferably may comprise one or more conductive polymers.

Thus, as an example, the second electrode may comprise one or more electrically conductive polymers, in combination with one or more layers of a metal. Preferably, the at least one electrically conductive polymer is a transparent electrically conductive polymer. This combination allows for providing very thin and, thus, transparent metal layers, by still providing sufficient electrical conductivity in order to render the second electrode both transparent and highly electrically conductive. Thus, as an example, the one or more metal layers, each or in combination, may have a thickness of less than 50 nm, preferably less than 40 nm or even less than 30 nm.

As an example, one or more electrically conductive polymers may be used, selected from the group consisting of: polyanaline (PANI) and/or its chemical relatives; a polythiophene and/or its chemical relatives, such as poly(3-hexylthiophene) (P3HT) and/or PEDOT:PSS (poly(3,4-ethylenedioxythiophene) poly(styrenesulfonate)). Additionally or alternatively, one or more of the conductive polymers as disclosed in EP2507286 A2, EP2205657 A1 or EP2220141 A1. For further exemplary embodiments, reference may be made to U.S. provisional application No. 61/739,173 or U.S. provisional application No. 61/708,058, the full content of all of which is herewith included by reference.

In addition or alternatively, inorganic conductive materials may be used, such as inorganic conductive carbon materials, such as carbon materials selected from the group consisting of: graphite, graphene, carbon nano-tubes, carbon nano-wires.

In addition, it is also possible to use electrode designs in which the quantum efficiency of the components is increased by virtue of the photons being forced, by means of appropriate reflections, to pass through the absorbing layers at least twice. Such layer structures are also referred to as "concentrators" and are likewise described, for example, in WO 02/101838 (especially pages 23-24).

The at least one second electrode of the optical sensor may be a single electrode or may comprise a plurality of partial electrodes. Thus, a single second electrode may be used, or more complex setups, such as split electrodes.

Further, the at least one second electrode of the at least one optical sensor, which specifically may be or may comprise at least one longitudinal optical sensor and/or at least one transversal optical sensor, preferably may fully or partially be transparent. Thus, specifically, the at least one second electrode may comprise one, two or more electrodes, such as one electrode or two or more partial electrodes, and optionally at least one additional electrode material contacting the electrode or the two or more partial electrodes.

Further, the second electrode may fully or partially be intransparent. Specifically, the two or more partial electrodes may be intransparent. It may be especially preferable to make the final electrode intransparent, such as the electrode facing away from the object and/or the last electrode of a stack of optical sensors. Consequently, this last electrode can then be optimized to convert all remaining light into a sensor signal. Herein, the "final" electrode may be the electrode of the at least one optical sensor facing away from the object. Generally, intransparent electrodes are more efficient than transparent electrodes.

Thus, it is generally beneficial to reduce the number of transparent sensors and/or the number of transparent electrodes to a minimum. In this context, as an example, reference may be made to the potential setups of the at least one longitudinal optical sensor and/or to the at least one transversal optical sensor as shown in WO2014/097181 A1. Other setups, however, are feasible.

The optical detector, the detector system, the method, the human-machine interface, the entertainment device, the tracking system, the camera and the uses of the optical detector provide a large number of advantages over known devices, methods and uses of this type.

Thus, generally, by combining one or more spatial light modulators with one or more optical sensors, in conjunction with the general idea of using modulation frequencies for separating signal components by frequency analysis, an optical detector may be provided which, in a technically simple fashion and without the necessity of using pixelated optical sensors, may provide the possibility of high-resolution imaging, preferably high-resolution 3D imaging, the possibility of determining transversal and/or longitudinal coordinates of an object, the possibility of separating colors in a simplified fashion and many other possibilities.

Thus, current setups of cameras, specifically 3D-cameras, typically require complex measurement setups and complex measurement algorithms. Within the present invention, large-area optical sensors may be used as a whole, such as solar cells and more preferably DSCs or sDSCs, without the necessity of subdividing these optical sensors into pixels. For the spatial light modulator, as an example, a liquid crystal screen as commonly used in displays and/or projection devices may be placed above one or more solar cells, such as a stack of solar cells, more preferably a stack of DSCs. The DSCs may have the same optical properties and/or differing optical properties. Thus, at least two DSCs having differing absorption properties may be used, such as at least one DSC having an absorption in the red spectral region, one DSC having an absorption in the green spectral region, and one DSC having an absorption in the blue spectral region. Other setups are feasible. The DSCs may be combined with one or more inorganic sensors, such as one or more CCD chips, specifically one or more intransparent CCD chips having a high resolution, such as used in standard digital cameras. Thus, a stack setup may be used, having a CCD chip at a position furthest away from the spatial light modulator, a stack of one, two or more at least partially transparent DSCs or sDSCs, preferably without pixels, specifically for the purpose of determining a longitudinal coordinate of the object by using the FiP-effect. This stack may be followed by one or more spatial light modulators, such as one or more transparent or semitransparent LCDs and/or one or more devices using the so-called DLP technology, as e.g. disclosed in www.dlp.com/de/technology/how-dlp-works. This stack may be combined with one or more transfer devices, such as one or more camera lens systems.

The frequency analysis may be performed by using standard Fourier transformation algorithms.

The optional intransparent CCD chip may be used at a high resolution, in order to obtain x-, y- and color information, as in regular camera systems. The combination of the SLM and the one or more large-area optical sensors may be used for obtaining longitudinal information (z-information). Each of the pixels of the SLM may oscillate, such as by opening and closing at a high frequency, and each of the pixels may oscillate a well-defined, unique frequency.

The photon-density-dependent transparent DSCs may be used to determine depth information, which is known as the above-mentioned FiP-effect. Thus, a light beam passing a concentrating lens and two transparent DSCs will cover different surface areas of the sensitive regions of the DSCs. This may cause different photocurrents, from which depth information may be deduced. The beams passing the solar cells may be pulsed by the oscillating pixels of the SLM, such as the LCD and/or the micro-mirror device. Current-voltage information obtained from the DSCs may be processed by frequency analysis, such as by Fourier transformation, in order to obtain the current-voltage information behind each pixel. The frequency uniquely may identify each pixel and, thus, its transversal position (x-y-position). The photocurrent of each pixel may be used in order to obtain the corresponding depth information, as discussed above.

Further, as discussed above, the optical detector may be realized as a multi-color or full-color detector, adapted for recognizing and/or determining colors of the at least one light beam. Thus, generally, the optical detector may be a multi-color and/or full-color optical detector, which may be used in cameras. Thereby, a simple setup may be realized, and a multi-color detector for imaging and/or determining a transversal and/or longitudinal position of at least one object may be realized, in a technically simple fashion. Thus, a spatial light modulator having at least two, preferably at least three different types of pixels of different color may be used.

As an example, a liquid crystal spatial light modulator, such as a thin-film transistor spectral light modulator, may be used, preferably having pixels of at least two, preferably at least three different colors. These types of spatial light modulators are commercially available with red, green and blue channels, each of which may be opened (transparent) and closed (black), preferably pixel by pixel. Additionally or alternatively, reflective SLMs may be used, such as by using the above-mentioned DLP® technology, available by Texas Instruments, having single-color or multi- or even full-color micro-mirrors. Again, additionally or alternatively, SLMs based on an acousto-optical effect and/or based on an electro-optical effect may be used, such as described in e.g. http://www.leysop.com/integrated_pockels_cell.htm. Thus, as an example, in liquid crystal technology or micro-mirrors, color filters may be used, such as color filters directly on top of the pixels. Thus, each pixel can open or close a channel wherein light can pass the SLM and proceed towards the at least one optical sensor. The at least one optical sensor, such as the at least one DSC or sDSC, may absorb fully or partially the light-beam passing the SLM. As an example, in case only the blue channel is open, only blue light may be absorbed by the optical sensor. When red, green and blue light are pulsed out of phase and/or at a differing frequency, the frequency analysis may allow for a detection of the three colors simultaneously. Thus, generally, the at least one optical sensor may be a broad-band optical sensor adapted to absorb in the spectral regions of the multi-color or full-color SLM. Thus, a broad-band optical sensor may be used which absorbs in the red, the green and the blue spectral region. Additionally or alternatively, different optical sensors may be used for different spectral regions. Generally, the above-mentioned frequency analysis may be adapted to identify signal components according to their frequency and/or phase of modulation. Thus, by identifying the frequency and/or the phase of the signal components, the signal components may be assigned to a specific color component of the light beam. Thus, the evaluation device may be adapted to separate the light beam into differing colors.

When two or more channels are pulsed at different modulation frequencies, i.e. at different frequencies and/or different phases, there may be times at which each channel may be individually open, all channels open and two different channels open simultaneously. This allows to detect a larger number of different colors simultaneously, with little additional post-processing. For detecting multiple channel signals, accuracy or color selectivity may be increased, when one-channel and multi-channel signals may be compared in the post-processing.

As outlined above, the spatial light modulator may be embodied in various ways. Thus, as an example, the spatial light modulator may use liquid crystal technology, preferably in conjunction with thin-film transistor (TFT) technology. Additionally or alternatively, micromechanical devices may be used, such as reflective micromechanical devices, such as micro-mirror devices according to the DLP® technology available by Texas Instruments. Additionally or alternatively, electrochromic and/or dichroitic filters may be used as spatial light modulators. Additionally or alternatively, one or more of electrochromic spatial light modulators, acousto-optical spatial light modulators or electro-optical spatial light modulators may be used. Generally, the spatial light modulator may be adapted to modulate the at least one optical property of the light beam in various ways, such as by switching the pixels between a transparent state and an intransparent state, a transparent state and a more transparent state, or a transparent state and a color state.

Further embodiments relate to a beam path of the light beam or a part thereof within the optical detector. As used herein and as used in the following, a "beam path" generally is a path along which a light beam or a part thereof may propagate. Thus, generally, the light beam within the optical detector may travel along a single beam path. The single beam path may be a straight single beam path or may be a beam path having one or more deflections, such as a folded beam path, a branched beam path, a rectangular beam path or a Z-shaped beam path. Alternatively, two or more beam paths may be present within the optical detector. Thus, the light beam entering the optical detector may be split into two or more partial light beams, each of the partial light beams following one or more partial beam paths. Each of the partial beam paths, independently, may be a straight partial beam path or, as outlined above, a partial beam path having one or more deflections, such as a folded partial beam path, a rectangular partial beam path or a Z-shaped partial beam path. Generally, any type of combination of various types of beam paths is feasible, as the skilled person will recognize. Thus, at least two partial beam paths may be present, forming, in total, a W-shaped setup.

By splitting the beam path into two or more partial beam paths, the elements of the optical detector may be distributed over the two or more partial beam paths. Thus, at least one optical sensor, such as at least one large-area optical sensor and/or at least one stack of large-area optical sensors, such as one or more optical sensors having the above-mentioned FiP-effect, may be located in a first partial beam path. At least one additional optical sensor, such as an intransparent optical sensor, e.g. an image sensor such as a CCD sensor and/or a CMOS sensor may be located in a second partial beam path. Further, the at least one spatial light modulator may be located in one or more of the partial beam paths and/or may be located in a common beam path before splitting the common beam path into two or more partial beam paths. Various setups are feasible. Further, the light beam and/or the partial light beam may travel along the beam path or the partial beam path in a unidirectional fashion, such as only once or in a single travel fashion. Alternatively, the light beam or the partial light beam may travel along the beam path or the partial beam path repeatedly, such as in ring-shaped setups, and/or in a bidirectional fashion, such as in a setup in which the light beam or the partial light beam is reflected by one or more reflective elements, in order to travel back along the same beam path or partial beam path. The at least one reflector element may be or may comprise the spatial light modulator itself. Similarly, for splitting the beam path into two or more partial beam paths, the spatial light modulator itself may be used. Additionally or alternatively, other types of reflective elements may be used.

By using two or more partial beam paths within the optical detector and/or by having the light beam or the partial light beam travelling along the beam path or the partial beam path repeatedly or in a bidirectional fashion, various setups of the optical detector are feasible, which allow for a high flexibility of the setup of the optical detector. Thus, the functionalities of the optical detector may be split and/or distributed over different partial beam paths. Thus, a first partial beam path may be dedicated to a z-detection of an object, such as by using one or more optical sensors having the above-mentioned FiP-effect, and a second beam path may be used for imaging, such as by providing one or more image sensors such as one or more CCD chips or CMOS chips for imaging. Thus, within one, more than one or all of the partial beam paths, independent or dependent coordinate systems may be defined, wherein one or more coordinates of the object may be determined within these coordinate systems. Since the general setup of the optical detector is known, the coordinate systems may be correlated, and a simple coordinate transformation may be used for combining the coordinates in a common coordinate system of the optical detector.

The above-mentioned possibilities may be embodied in various ways. Thus, generally, the spatial light modulator, as outlined above, may be a reflective spatial light modulator. Thus, as discussed above, the reflective spatial light modulator may be or may comprise a micro-mirror system, such as by using the above-mentioned DLP® technology. Thus, the spatial light modulator may be used for deflecting or for reflecting the light beam and/or a part thereof, such as for reflecting the light beam into its direction of origin. Thus, the at least one optical sensor of the optical detector may comprise one transparent optical sensor. The optical detector may be setup such that the light beam passes through the transparent optical sensor before reaching the spatial light modulator. The spatial light modulator may be adapted to at least partially reflect the light beam back towards the optical sensor. In this embodiment, the light beam may pass the transparent optical sensor twice. Thus, firstly, the light beam may pass through the transparent optical sensor for the first time in an unmodulated fashion, reaching the spatial light modulator. The spatial light modulator, as discussed above, may be adapted to modulate the light beam and, simultaneously, reflect the light beam back towards the transparent optical sensor such that the light beam passes the transparent optical sensor for the second time, this time in a modulated fashion, in order to be detected by the optical sensor.

As outlined above, additionally or alternatively, the optical detector may contain at least one beam-splitting element adapted for dividing the beam path of the light beam into at least two partial beam paths. The beam-splitting element may be embodied in various ways and/or by using combinations of beam-splitting elements. Thus, as an example, the beam-splitting element may comprise at least one element selected from the group consisting of: the spatial light modulator, a beam-splitting prism, a grating, a semitransparent mirror, a dichroitic mirror. Combinations of the named elements and/or other elements are feasible. Thus, generally, the at least one beam splitting element may comprise the at least one spatial light modulator. In this embodiment, specifically, the spatial light modulator may be a reflective spatial light modulator, such as by using the above-mentioned micro-mirror technology, specifically the above-mentioned DLP® technology. As outlined above, the elements of the optical detector may be distributed over the beam paths, before and/or after splitting the beam path. Thus, as an example, at least one optical sensor may be located in each of the partial beam paths. Thus, e.g., at least one stack of optical sensors, such as at least one stack of large-area optical sensors and, more preferably, at least one stack of optical sensors having the above-mentioned FiP-effect, may be located in at least one of the partial beam paths, such as in a first one of the partial beam paths. Additionally or alternatively, at least one intransparent optical sensor may be located in at least one of the partial beam paths, such as in at least a second one of the partial beam paths. Thus, as an example, at least one inorganic optical sensor may be located in a second partial beam path, such as an inorganic semiconductor optical sensor, such as an imaging sensor and/or a camera chip, more preferably a CCD chip and/or a CMOS chip, wherein both monochrome chips and/or multi-chrome or full-color chips may be used. Thus, as outlined above, the first partial beam path, by using the stack of optical sensors, may be used for detecting the z-coordinate of the object, and the second partial beam path may be used for imaging, such as by using the imaging sensor, specifically the camera chip.

As outlined above, the spatial light modulator may be part of the beam-splitting element. Additionally or alternatively, the at least one spatial light modulator and/or at least one of a plurality of spatial light modulators may, itself, be located in one or more of the partial beam paths. Thus, as an example, the spatial light modulator may be located in the first one of the partial beam paths, i.e. in the partial beam path having the stack of optical sensors, such as the stack of optical sensors having the above-mentioned FiP-effect. Thus, the stack of optical sensors may comprise at least one large-area optical sensor, such as at least one large-area optical sensor having the FiP-effect.

In case one or more intransparent optical sensors are used, such as in one or more of the partial beam paths, such as in the second partial beam path, the intransparent optical sensor preferably may be or may comprise a pixelated optical sensor, preferably an inorganic pixelated optical sensor and more preferably a camera chip, and most preferably at least one of a CCD chip and CMOS chip. However, other embodiments are feasible, and combinations of pixelated and non-pixelated intransparent optical sensors in one or more of the partial optical beam paths are feasible.

By using the above-mentioned possibilities of more complex setups of the optical sensor and/or the optical detector, specifically, use may be made of the high flexibility of spatial light modulators, with regard to their transparency, reflective properties or other properties. Thus, as outlined above, the spatial light modulator itself may be used for reflecting or deflecting the light beam or a partial light beam. Therein, linear or non-linear setups of the optical detector may be feasible. Thus, as outlined above, W-shaped setups, Z-shaped setups or other setups are feasible. In case a reflective spatial light modulator is used, use may be made of the fact that, specifically in micro-mirror systems the spatial light modulator is generally adapted to reflect or deflect the light beam into more than one direction. Thus, a first partial beam path may be setup in a first direction of deflection or reflection of the spatial light modulator, and at least one second partial beam path may be setup in at least one second direction of deflection or reflection of the spatial light modulator. Thus, the spatial light modulator may form a beam-splitting element adapted for splitting an incident light beam into at least one first direction and at least one second direction. Thus, as an example, the micro-mirrors of the spatial light modulator may either be positioned to reflect or deflect the light beam and/or parts thereof towards at least one first partial beam path, such as towards a first partial beam path having a stack of optical sensors such as a stack of FiP-sensors, or towards at least one second partial beam path, such as towards at least one second partial beam path having the intransparent optical sensor, such as the imaging sensor, specifically the at least one CCD chip and/or the at least one CMOS chip. Thereby, the general amount of light illuminating the elements in the various beam paths may be increased. Furthermore, this construction may allow obtaining identical pictures, such as pictures having an identical focus, in the two or more partial beam paths, such as on the stack of optical sensors and the imaging sensor, such as the full-color CCD or CMOS sensor.

As opposed to a linear setup, a non-linear setup such as a setup having two or more partial beam paths, such as a branched setup and/or a W-setup, may allow for individually optimizing the setups of the partial beam paths. Thus, in case the imaging function by the at least one imaging sensor and the function of the z-detection are separated in separate partial beam paths, an independent optimization of these partial beam paths and the elements disposed therein is feasible. Thus, as an example, different types of optical sensors such as transparent solar cells may be used in the partial beam path adapted for z-detection, since transparency is less important as in the case in which the same light beam has to be used for imaging by the imaging detector. Thus, combinations with various types of cameras are feasible. As an example, thicker stacks of optical detectors may be used, allowing for a more accurate z-information. Consequently, even in case the stack of optical sensors should be out of focus, a detection of the z-position of the object is feasible.

Further, one or more additional elements may be located in one or more of the partial beam paths. As an example, one or more optical shutters may be disposed within one or more of the partial beam paths. Thus, one or more shutters may be located between the reflective spatial light modulator and the stack of optical sensors and/or the intransparent optical sensor such as the imaging sensor. The shutters of the partial beam paths may be used and/or actuated independently. Thus, as an example, one or more imaging sensors, specifically one or more imaging chips such as CCD chips and/or CMOS chips, and the large-area optical sensor and/or the stack of large area optical sensors generally may exhibit different types of optimum light responses. In a linear arrangement, only one additional shutter may be possible, such as between the large-area optical sensor or stack of large-area optical sensors and the imaging sensor. In a split setup having two or more partial beam paths, such as in the above-mentioned W-setup, one or more shutters may be placed in front of the stack of optical sensors and/or in front of the imaging sensor. Thereby, optimum light intensities for both types of sensors may be feasible.

Additionally or alternatively, one or more lenses may be disposed within one or more of the partial beam paths. Thus, one or more lenses may be located between spatial light modulator, specifically the reflective spatial light modulator, and the stack of optical sensors and/or between the spatial light modulator and the intransparent optical sensor such as the imaging sensor. Thus, as an example, by using the one or more lenses in one or more or all of the partial beam paths, a beam shaping may take place for the respective partial beams path or partial beam paths comprising the at least one lens. Thus, the imaging sensor, specifically the CCD or CMOS sensor, may be adapted to take a 2D picture, whereas the at least one optical sensor such as the optical sensor stack may be adapted to measure a z-coordinate or depth of the object. The focus or the beam shaping in these partial beam paths, which generally may be determined by the respective lenses of these partial beam paths, not necessarily has to be identical. Thus, the beam properties of the partial light beams propagating along the partial beam paths may be optimized individually, such as for imaging, xy-detection or z-detection.

Further embodiments generally refer to the at least one optical sensor. Generally, for potential embodiments of the at least one optical sensor, as outlined above, reference may be made to one or more of the prior art documents listed above, such as to WO 2012/110924 A1 and/or to WO 2014/097181 A1. Thus, as outlined above, the at least one optical sensor may comprise at least one longitudinal optical sensor and/or at least one transversal optical sensor, as described e.g. in WO 2014/097181 A1. Specifically, the at least one optical sensor may be or may comprise at least one organic photodetector, such as at least one organic solar cell, more preferably a dye-sensitized solar cell, further preferably a solid dye sensitized solar cell, having a layer setup comprising at least one first electrode, at least one n-semiconducting metal oxide, at least one dye, at least one p-semiconducting organic material, preferably a solid p-semiconducting organic material, and at least one second electrode. For potential embodiments of this layer setup, reference may be made to one or more of the above-mentioned prior art documents.

The at least one optical sensor may be or may comprise at least one large-area optical sensor, having a single optically sensitive sensor area. Still, additionally or alternatively, the at least one optical sensor may as well be or may comprise at least one pixelated optical sensor, having two or more sensitive sensor areas, i.e. two or more sensor pixels. Thus, the at least one optical sensor may comprise a sensor matrix having two or more sensor pixels.

As outlined above, the at least one optical sensor may be or may comprise at least one intransparent optical sensor. Additionally or alternatively, the at least one optical sensor may be or may comprise at least one transparent or semi-transparent optical sensor. Generally, however, in case one or more pixelated transparent optical sensors are used, in many devices known in the art, the combination of transparency and pixelation imposes some technical challenges. Thus, generally, optical sensors known in the art both contain sensitive areas and appropriate driving electronics. Still, in this context, the problem of generating transparent electronics generally remains unsolved.

As it turned out in the context of the present invention, it may be preferable to split an active area of the at least one optical sensor into an array of 2×N sensor pixels, with N being an integer, wherein, preferably, N≥1, such as N=1, N=2, N=3, N=4 or an integer >4. Thus, generally, the at least one optical sensor may comprise a matrix of sensor pixels having 2×N sensor pixels, with N being an integer. The matrix, as an example, may form two rows of sensor pixels, wherein, as an example, the sensor pixels of a first row are electrically contacted from a first side of the optical sensor and wherein the sensor pixels of a second row are electrically contacted from a second side of the optical sensor opposing the first side. In a further embodiment, the first and last pixels of the two rows of N pixels may further be split up into pixels that are electrically contacted from the third and fourth side of the sensor. As an example, this would lead to a setup of 2×M+2×N pixels. Further embodiments are feasible.

In case two or more optical sensors are comprised in the optical detector, one, two or more optical sensors may comprise the above-mentioned array of sensor pixels. Thus, in case a plurality of optical sensors is provided, one optical sensor, more than one optical sensor or even all optical sensors may be pixelated optical sensors. Alternatively, one optical sensor, more than one optical sensor or even all optical sensors may be non-pixelated optical sensors, i.e. large area optical sensors.

In case the above-mentioned setup of the optical sensor is used, including at least one optical sensor having a layer setup comprising at least one first electrode, at least one n-semiconducting metal oxide, at least one dye, at least one p-semiconducting organic material, preferably a solid p-semiconducting organic material, and at least one second electrode, the use of a matrix of sensor pixels is specifically advantageous. As outlined above, these types of devices specifically may exhibit the FiP-effect.

In these devices, such as FiP-devices, especially for SLM-based cameras as disclosed herein, a 2×N-array of sensor pixels is very well suited. Thus, generally, at least one first, transparent electrode and at least one second electrode, with one or more layers sandwiched in between, a pixelation into two or more sensor pixels specifically may be achieved by splitting one or both of the first electrode and the second electrode into an array of electrodes. As an example, for the transparent electrode, such as a transparent electrode comprising fluorinated tin oxide and/or another transparent conductive oxide, preferably disposed on a transparent substrate, a pixelation may easily be achieved by appropriate patterning techniques, such as patterning by using lithography and/or laser patterning. Thereby, the electrodes may easily be split into an area of partial electrodes, wherein each partial electrode forms a pixel electrode of a sensor pixel of the array of sensor pixels. The remaining layers, as well as optionally the second electrode, may remain unpatterned, or may, alternatively, be patterned as well. In case a split transparent conductive oxide such as fluorinated tin oxide is used, in conjunction with unpatterned further layers, cross conductivities in the remaining layers may generally be neglected, at least for dye-sensitized solar cells. Thus, generally, a crosstalk between the sensor pixels may be neglected. Each sensor pixel may comprise a single counter electrode, such as a single silver electrode.

Using at least one optical sensor having an array of sensor pixels, specifically a 2×N array, provides several advantages within the present invention, i.e. within one or more of the devices disclosed by the present invention. Thus, firstly, using the array may improve the signal quality. The modulator device of the optical detector may modulate each pixel of the spatial light modulator, such as with a distinct modulation frequency, thereby e.g. modulating each depth area with a distinct frequency. At high frequencies, however, the signal of the at least one optical sensor, such as the at least one FiP-sensor, generally decreases, thereby leading to a low signal strength. Therefore, generally, only a limited number of modulation frequencies may be used in the modulator device. If the optical sensor, however, is split up into sensor pixels, the number of possible depth points that can be detected may be multiplied with the number of pixels. Thus, as an example, two pixels may result in a doubling of the number of modulation frequencies which may be detected and, thus, may result in a doubling of the number of pixels or superpixels of the SLM which may be modulated and/or may result in a doubling of the number of depth points.

Further, as opposed to a conventional camera, the shape of the pixels is not relevant for the appearance of the picture. Thus, generally, the shape and/or size of the sensor pixels may be chosen with no or little constraints, thereby allowing for choosing an appropriate design of the array of sensor pixels.

Further, the sensor pixels generally may be chosen rather small. The frequency range which may generally be detected by a sensor pixel is typically increased by decreasing the size of the sensor pixel. The frequency range typically improves, when smaller sensors or sensor pixels are used. In a small sensor pixel, more frequencies may be detected as compared to a large sensor pixel. Consequently, by using smaller sensor pixels, a larger number of depth points may be detected as compared to using large pixels.

Summarizing the above-mentioned findings, the following embodiments are preferred within the present invention:

Embodiment 1

An optical detector, comprising:
at least one spatial light modulator being adapted to modify at least one property of a light beam in a spatially resolved fashion, having a matrix of pixels, each pixel being controllable to individually modify the at least one optical property of a portion of the light beam passing the pixel;
at least one optical sensor adapted to detect the light beam after passing the matrix of pixels of the spatial light modulator and to generate at least one sensor signal;
at least one modulator device adapted for periodically controlling at least two of the pixels with different modulation frequencies; and
at least one evaluation device adapted for performing a frequency analysis in order to determine signal components of the sensor signal for the modulation frequencies.

Embodiment 2

The optical detector according to the preceding embodiment, wherein the evaluation device is further adapted to assign each signal component to a respective pixel in accordance with its modulation frequency.

Embodiment 3

The optical detector according to any one of the preceding embodiments, wherein the modulator device is adapted such that each of the pixels is controlled at a unique modulation frequency.

Embodiment 4

The optical detector according to any one of the preceding embodiments, wherein the modulator device is adapted for periodically modulating the at least two pixels with the different modulation frequencies.

Embodiment 5

The optical detector according to any one of the preceding embodiments, wherein the evaluation device is adapted for performing the frequency analysis by demodulating the sensor signal with different modulation frequencies.

Embodiment 6

The optical detector according to any one of the preceding embodiments, wherein the at least one property of the light beam modified by the spatial light modulator in a spatially resolved fashion is at least one property selected from the group consisting of: an intensity of the portion of the light beam; a phase of the portion of the light beam; a spectral property of the portion of the light beam, preferably a color; a polarization of the portion of the light beam; a direction of propagation of the portion of the light beam.

Embodiment 7

The optical detector according to any one of the preceding embodiments, wherein the spatial light modulator, for each pixel, is adapted to switch on or off the portion of light passing the respective pixel.

Embodiment 8

The optical detector according to any one of the preceding embodiments, wherein the at least one spatial light modulator comprises at least one spatial light modulator selected from the group consisting of: a transmissive spatial light modulator, wherein the light beam passes through the matrix of pixels and wherein the pixels are adapted to modify the optical property for each portion of the light beam passing through the respective pixel in an individually controllable fashion; a reflective spatial light modulator, wherein the pixels have individually controllable reflective properties and are adapted to individually change a direction of propagation for each portion of the light beam being reflected by the respective pixel; an electrochromic spatial light modulator, wherein the pixels have controllable spectral properties individually controllable by an electric voltage applied to the respective pixel; an acousto-optical spatial light modulator, wherein a birefringence of the pixels is controllable by acoustic waves; an electro-optical spatial light modulator, wherein a birefringence of the pixels is controllable by electric fields, preferably a spatial light modulator based on the Pockels effect and/or on the Kerr effect; a spatial light modulator comprising at least one array of tunable optical elements, such as one or more of an array of focus-tunable lenses, an area of adaptive liquid microlenses, an array of transparent micro-prisms.

Embodiment 9

The optical detector according to any one of the preceding embodiments, wherein the at least one spatial light modulator comprises at least one spatial light modulator selected from the group consisting of: a liquid crystal device, preferably an active matrix liquid crystal device, wherein the pixels are individually controllable cells of the liquid crystal device; a micro-mirror device, wherein the pixels are micro-mirrors of the micro-mirror device individually controllable with regard to an orientation of their reflective surfaces; an electrochromic device, wherein the pixels are cells of the electrochromic device having spectral properties individually controllable by an electric voltage applied to the respective cell; an acousto-optical device, wherein the pixels are cells of the acousto-optical device having a birefringence individually controllable by acoustic waves applied to the cells; an electro-optical device, wherein the pixels are cells of the electro-optical device having a birefringence individually controllable by electric fields applied to the cells.

Embodiment 10

The optical detector according to any one of the preceding embodiments, wherein the capability of the pixels to modify the at least one property of the portion of the light beam passing the respective pixel is dependent on the spectral properties of the light beam, specifically of the color of the light beam.

Embodiment 11

The optical detector according to any one of the preceding embodiments, wherein the spatial light modulator is a transparent spatial light modulator.

Embodiment 12

The optical detector according to any one of the preceding embodiments, wherein a transmissivity of the pixels is switchable.

Embodiment 13

The optical detector according to any one of the preceding embodiments, wherein the spatial light modulator comprises a transparent liquid crystal display.

Embodiment 14

The optical detector according to any one of the preceding embodiments, wherein the evaluation device is adapted to assign each of the signal components to a pixel of the matrix.

Embodiment 15

The optical detector according any one of the preceding embodiments, wherein the evaluation device is adapted to determine which pixels of the matrix are illuminated by the light beam by evaluating the signal components.

Embodiment 16

The optical detector according to the preceding embodiment, wherein the evaluation device is adapted to compare the signal components with at least one threshold in order to determine the illuminated pixels.

Embodiment 17

The optical detector according to any of the preceding embodiments, wherein the evaluation device is adapted to identify at least one of a transversal position of the light beam and an orientation of the light beam, by identifying a transversal position of pixels of the matrix illuminated by the light beam.

Embodiment 18

The optical detector according to the preceding embodiment, wherein the evaluation device is adapted to identify one or more of a transversal position of an object from which the light beam propagates towards the detector and a relative direction of an object from which the light beam propagates towards the detector, by evaluating at least one of the transversal position of the light beam and the orientation of the light beam.

Embodiment 19

The optical detector according to any one of the preceding embodiments, wherein the transversal position of the pixels of the matrix illuminated by the light beam is determined by determining one or more pixels having the highest illumination by the light beam.

Embodiment 20

The optical detector according to any one of the preceding embodiments, wherein the evaluation device is adapted to determine a width of the light beam by evaluating the signal components.

Embodiment 21

The optical detector according to any one of the preceding embodiments, wherein the evaluation device is adapted to identify the signal components assigned to pixels being illuminated by the light beam and to determine the width of the light beam at the position of the spatial light modulator from known geometric properties of the arrangement of the pixels.

Embodiment 22

The optical detector according to any one of the preceding embodiments, wherein the evaluation device, using a known or determinable relationship between a longitudinal coordinate of an object from which the light beam propagates towards the detector and one or both of a width of the light beam at the position of the spatial light modulator or a number of pixels of the spatial light modulator illuminated by the light beam, is adapted to determine a longitudinal coordinate of the object.

Embodiment 23

The optical detector according to any one of the preceding embodiments, wherein the capability of the pixels to modify the at least one optical property of the portion of the light beam passing the respective pixel is dependent on the spectral properties of the light beam, specifically of the color of the light beam.

Embodiment 24

The optical detector according to the preceding embodiment, wherein the evaluation device is adapted to assign the signal components to components of the light beam having differing spectral properties.

Embodiment 25

The optical detector according to any one of the two preceding embodiments, wherein the evaluation device is adapted to determine a color of the light beam by comparing signal components being assigned to components of the light beam having differing spectral properties, specifically being assigned to components of the light beam having differing wavelengths.

Embodiment 26

The optical detector according to any one of the three preceding embodiments, wherein the matrix of pixels comprises pixels having differing spectral properties, preferably having differing color, wherein the evaluation device is adapted to assign signal components to the respective pixels having differing spectral properties.

Embodiment 27

The optical detector according to the preceding embodiment, wherein the modulator device is adapted to control pixels having a first color in a different way than pixels having a second color.

Embodiment 28

The optical detector according to any one of the preceding embodiments, wherein the at least one optical sensor comprises at least one large-area optical sensor being adapted to detect a plurality of portions of the light beam passing through a plurality of the pixels.

Embodiment 29

The optical detector according to the preceding embodiment, wherein the large area-optical sensor has a sensor region, wherein the sensor signal is a uniform sensor signal for all portions of the sensor region.

Embodiment 30

The optical detector according to the preceding embodiment, wherein the sensor region has a sensitive area of at least 25 mm$^2$, preferably of at least 100 mm$^2$ and more preferably of at least 400 mm$^2$.

Embodiment 31

The optical detector according to any one of the preceding embodiments, wherein the at least one optical sensor comprises at least one at least partially transparent optical sensor such that the light beam at least partially may pass through the transparent optical sensor.

Embodiment 32

The optical detector according to any one of the preceding embodiments, wherein the at least one optical sensor comprises a stack of at least two optical sensors.

Embodiment 33

The optical detector according to the preceding embodiment, wherein at least one of the optical sensors of the stack is an at least partially transparent optical sensor.

Embodiment 34

The optical detector according to any one of the two preceding embodiments, wherein at least one of the optical sensors of the stack is a pixelated optical sensor having a plurality of light-sensitive pixels.

Embodiment 35

The optical detector according to the preceding embodiment, wherein the pixelated optical sensor is an inorganic pixelated optical sensor, preferably a CCD chip or a CMOS chip.

Embodiment 36

The optical detector according to any one of the two preceding embodiments, wherein the pixelated optical sensor is a camera chip, preferably a full-color camera chip.

Embodiment 37

The optical detector according to any one of the three preceding embodiments, wherein the pixelated optical sensor is located on a position of the stack furthest away from the spatial light modulator.

Embodiment 38

The optical detector according to any one of the four preceding embodiments, wherein the pixelated optical sensor is color-sensitive.

Embodiment 39

The optical detector according to the preceding embodiment, wherein the pixelated optical sensor is a full-color imaging sensor.

Embodiment 40

The optical detector according to any one of the preceding embodiments, wherein the at least one optical sensor has at least one sensor region, wherein the sensor signal of the optical sensor is dependent on an illumination of the sensor region by the light beam, wherein the sensor signal, given the same total power of the illumination, is dependent on a width of the light beam in the sensor region, wherein the evaluation device preferably is adapted to determine the width by evaluating the sensor signal.

Embodiment 41

The optical detector according to the preceding embodiment, wherein the at least one optical sensor contains at least two optical sensors, wherein the evaluation device is adapted to determine the widths of the light beam in the sensor regions of the at least two optical sensors, wherein the evaluation device is further adapted to generate at least one item of information on a longitudinal position of an object from which the light beam propagates towards the optical detector, by evaluating the widths.

Embodiment 42

The optical detector according to any one of the two preceding embodiments, wherein the sensor signal of the optical sensor is further dependent on a modulation frequency of the light beam.

Embodiment 43

The optical detector according to any one of the preceding embodiments, wherein the at least one optical sensor comprises at least one semiconductor detector.

Embodiment 44

The optical detector according to the preceding embodiment, wherein the semiconductor detector is an organic semiconductor detector comprising at least one organic material.

Embodiment 45

The optical detector according to any one of the two preceding embodiments, wherein the semiconductor detector is selected from the group consisting of an organic solar cell, a dye solar cell, a dye-sensitized solar cell, a solid dye solar cell, a solid dye-sensitized solar cell.

Embodiment 46

The optical detector according to any one of the preceding embodiments, wherein the at least one optical sensor comprises at least one optical sensor having a layer setup comprising at least one first electrode, at least one n-semiconducting metal oxide, at least one dye, at least one p-semiconducting organic material, preferably a solid p-semiconducting organic material, and at least one second electrode.

Embodiment 47

The optical detector according to the preceding embodiment, wherein both the first electrode and the second electrode are transparent.

Embodiment 48

The optical detector according to any one of the preceding embodiments, wherein the optical detector further comprises at least one transfer device adapted for feeding light into the optical detector.

Embodiment 49

The optical detector according to the preceding embodiment, wherein the transfer device is adapted to focus and/or collimate light onto one or more of the spatial light modulator and the optical sensor.

Embodiment 50

The optical detector according to any one of the two preceding embodiments, wherein the transfer device comprises one or more devices selected from the group consisting of: a lens, a focusing mirror, a defocusing mirror, a reflector, a prism, an optical filter, a diaphragm.

Embodiment 51

The optical detector according to any one of the preceding embodiments, wherein the spatial light modulator comprises pixels of different colors, wherein the evaluation device is adapted to assign the signal components to the different colors.

Embodiment 52

The optical detector according to any one of the preceding embodiments, wherein the spatial light modulator is a reflective spatial light modulator, wherein the optical sensor comprises at least one transparent optical sensor, wherein the optical detector is set up such that the light beam passes through the transparent optical sensor before reaching the spatial light modulator, wherein the spatial light modulator is adapted to at least partially reflect the light beam back towards the optical sensor.

Embodiment 53

The optical detector according to any one of the preceding embodiments, wherein the optical detector contains at least one beam-splitting element adapted for dividing a beam path of the light beam into at least two partial beam paths.

Embodiment 54

The optical detector according to the preceding embodiment, wherein the beam-splitting element comprises at least one element selected from the group consisting of: the spatial light modulator, a beam-splitting prism, a grating, a semi-transparent mirror, a dichroitic mirror.

Embodiment 55

The optical detector according to any one of the two preceding embodiments, wherein the beam-splitting element comprises the spatial light modulator.

Embodiment 56

The optical detector according to the preceding embodiment, wherein the spatial light modulator is a reflective spatial light modulator.

Embodiment 57

The optical detector according to any one of the four preceding embodiments, wherein at least one optical sensor is located in each of the partial beam paths.

Embodiment 58

The optical detector according to the preceding embodiment, wherein at least one stack of optical sensors is located in at least one of the partial beam paths.

Embodiment 59

The optical detector according to any one of the two preceding embodiments, wherein at least one intransparent optical sensor is located in at least one of the partial beam paths.

Embodiment 60

The optical detector according to the two preceding embodiments, wherein the stack of optical sensors is located in a first one of the partial beam paths and wherein the intransparent optical sensor is located in a second one of the partial beam paths.

Embodiment 61

The optical detector according to the preceding embodiment, wherein the spatial light modulator is located in the first one of the partial beam paths.

Embodiment 62

The optical detector according to any one of the two preceding embodiments, wherein the stack of optical sensors comprises at least one large-area optical sensor.

Embodiment 63

The optical detector according to any one of the three preceding embodiments, wherein the intransparent optical sensor is a pixelated optical sensor, preferably an inorganic pixelated optical sensor, more preferably a camera chip and most preferably at least one of a CCD chip and a CMOS chip.

Embodiment 64

The optical detector according to any one of the 11 preceding embodiments, wherein the beam-splitting element is adapted to divide a light beam into at least two portions having different intensities.

Embodiment 65

The optical detector according to the preceding embodiment, wherein the beam-splitting element is adapted to divide the light beam into a first portion traveling along a first partial beam path and at least one second portion traveling along at least one second partial beam path, wherein the first portion has a lower intensity than the second portion.

Embodiment 66

The optical detector according to the preceding embodiment, wherein the optical detector contains at least one imaging device, preferably an inorganic imaging device, more preferably a CCD chip and/or a CMOS chip, the at least one imaging device being located in the first partial beam path.

Embodiment 67

The optical detector according to any one of the two preceding embodiments, wherein the first portion has an intensity of lower than one half the intensity of the second portion.

Embodiment 68

The optical detector according to any one of the 15 preceding embodiments, wherein the beam-splitting element is a polarization-selective beam-splitting element, preferably a polarization beam-splitting cube.

Embodiment 69

The optical detector according to any one of the 16 preceding embodiments, wherein the optical detector is adapted to back-reflect partial light beams traveling along the partial beam paths towards the beam-splitting element, wherein the beam-splitting element is adapted to recombine the partial light beams to form a common light beam.

Embodiment 70

The optical detector according to the preceding embodiment, wherein the optical detector is adapted to feed the common light beam into at least one optical sensor, preferably into at least one FiP sensor, more preferably into a stack of optical sensors.

Embodiment 71

The optical detector according to any one of the 18 preceding embodiments, wherein the optical detector comprises at least two spatial light modulators, wherein the at least two spatial light modulators are arranged in different partial beam paths.

Embodiment 72

The optical detector according to the preceding embodiment, wherein the optical detector is adapted to recombine partial light beams passing the spatial light modulators to form a common light beam.

Embodiment 73

The optical detector according to any one of the preceding embodiments, wherein the optical detector is adapted to capture at least one image, preferably a 2D-image, wherein the optical detector, preferably the at least one evaluation device, is adapted to define at least two regions in the image and to assign corresponding superpixels of the matrix of pixels of the spatial light modulator to at least one of the regions, preferably to each of the regions.

Embodiment 74

The optical detector according to the preceding embodiment, wherein the optical detector comprises at least one pixelated optical sensor for capturing the at least one image, preferably at least one inorganic pixelated optical sensor and more preferably at least one of a CCD sensor and a CMOS sensor.

Embodiment 75

The optical detector according to any one of the two preceding embodiments, wherein the optical detector, preferably the at least one evaluation device, is adapted to define the at least two regions in the image by using at least one image recognition algorithm.

Embodiment 76

The optical detector according to the preceding embodiment, wherein the at least one image recognition algorithm is adapted to define the at least two regions by recognizing boundaries of at least one of: contrast, color or intensity.

Embodiment 77

The optical detector according to any one of the two preceding embodiments, wherein the at least one image recognition algorithm is selected from the group consisting of: Felzenszwalb's efficient graph based segmentation; Quickshift image segmentation; SLIC—K-Means based image segmentation; Energy-Driven sampling; an edge detection algorithm such as a Canny algorithm; a Mean-shift algorithm, such as a Cam shift algorithm; a Contour extraction algorithm; an edge, ridge, corner, blob, or feature detection; a dimensionality reduction; a texture classification; a texture segmentation.

Embodiment 78

The optical detector according to any one of the three preceding embodiments, wherein the at least one image recognition algorithm is adapted to recognize objects in the image.

Embodiment 79

The optical detector according to any one of the six preceding embodiments, wherein the optical detector, preferably the at least one evaluation device, is adapted to assign the superpixels of the matrix of pixels of the spatial light modulator to at least one of the regions or even each of the regions, such that each component of the light beam passing a specific pixel of the matrix of pixels, the specific pixel belonging to a specific superpixel, subsequently hits the specific region of the at least two regions, the specific region corresponding to the specific superpixel.

Embodiment 80

The optical detector according to any one of the seven preceding embodiments, wherein the optical detector, preferably the at least one evaluation device, is adapted to assign at least one first modulation frequency to at least a first superpixel of the superpixels and at least one second modulation frequency to at least a second superpixel of the superpixels, wherein the first modulation frequency is different from the second modulation frequency, and wherein the at least one modulator device is adapted for periodically controlling the pixels of the first superpixel with the at least one first modulation frequency and for periodically controlling the pixels of the second superpixel with the at least one second modulation frequency.

Embodiment 81

The optical detector according to any one of the eight preceding embodiments, wherein the optical detector, preferably the at least one evaluation device, is adapted to individually determine z-coordinates for at least one of the regions, preferably for each of the regions.

Embodiment 82

The optical detector according to the preceding embodiment, wherein the at least one optical sensor of the optical detector has at least one sensor region, wherein the sensor signal of the optical sensor is dependent on an illumination of the sensor region by the light beam, wherein the sensor signal, given the same total power of the illumination, is dependent on a width of the light beam in the sensor region, wherein the evaluation device is adapted to determine the z-coordinates for at least one of the regions, preferably for each of the regions, by individually evaluating the sensor signal in a frequency-selective way.

Embodiment 83

The optical detector according to the preceding embodiment, wherein the at least one optical sensor contains at least two optical sensors arranged in a stack.

Embodiment 84

The optical detector according to any one of the two preceding embodiments, wherein the optical detector contains at least one beam-splitting element adapted for dividing a beam path of the light beam into at least two partial beam paths, wherein the at least one optical sensor having the at least one sensor region, the sensor signal of the optical sensor being dependent on the illumination of the sensor region by the light beam, the sensor signal, given the same total power of the illumination, being dependent on the width of the light beam in the sensor region, is arranged in a first partial beam path of the beam paths, and wherein at least one pixelated optical sensor for capturing the at least one image, preferably the at least one inorganic pixelated optical sensor and more preferably the at least one of a CCD sensor and/or CMOS sensor, is arranged in a second partial beam path of the beam paths.

Embodiment 85

The optical detector according to any one of the twelve preceding embodiments, where the optical detector, preferably the at least one evaluation device, is adapted to iteratively refine the at least two regions in the image.

Embodiment 86

The optical detector according to any one of the thirteen preceding embodiments, wherein the optical detector is adapted to detect at least one object in the at least one image and wherein the optical detector is adapted to track and/or follow the object within a series of images.

Embodiment 87

The optical detector according to the preceding embodiment, wherein the optical detector is adapted to assign the at least one object a region within the image.

Embodiment 88

The optical detector according to the preceding embodiment, wherein the optical detector, preferably the at least one evaluation device, is adapted to assign at least one superpixel of the matrix of pixels of the spatial light modulator to the at least one region corresponding to the at least one object.

Embodiment 89

The optical detector according to the preceding embodiment, wherein the optical detector is adapted to adjust the assignment of the at least one superpixel for the images of the series of images.

Embodiment 90

The optical detector according to any one of the seventeen preceding embodiments, wherein the optical detector is adapted to detect at least one first area within the image, the first area having a first illumination, such as a first average illumination, wherein the optical detector is further adapted to detect at least one second area within the image, the second area having a second illumination, such as a second average illumination, wherein the second illumination is lower than the first illumination, wherein the first area is assigned at least one first superpixel, wherein the second area is assigned at least one second superpixel, wherein the optical detector is further adapted to modulate the pixels of the first superpixel with at least one first modulation frequency, wherein the optical detector is further adapted to modulate the pixels of the second superpixel with at least one second modulation frequency, wherein the first modulation frequency is higher than the second modulation frequency.

Embodiment 91

The optical detector according to any one of the preceding embodiments, wherein the optical detector comprises at least one stack of optical sensors, wherein the optical detector is adapted to acquire a three-dimensional image of a scene within a field of view of the optical detector.

Embodiment 92

The optical detector according to the preceding embodiment, wherein the optical sensors of the stack have differing spectral properties.

Embodiment 93

The optical detector according to the preceding embodiment, wherein the stack comprises at least one first optical sensor having a first spectral sensitivity and at least one second optical sensor having a second spectral sensitivity, wherein the first spectral sensitivity and the second spectral sensitivity are different.

Embodiment 94

The optical detector according to any one of the two preceding embodiments, wherein the stack comprises optical sensors having differing spectral properties in an alternating sequence.

Embodiment 95

The optical detector according to any one of the three preceding embodiments, wherein the optical detector is adapted to acquire a multicolor three-dimensional image, preferably a full-color three-dimensional image, by evaluating sensor signals of the optical sensors having differing spectral properties.

Embodiment 96

The optical detector according to any one of the preceding embodiments, wherein the optical detector further comprises at least one time-of-flight detector adapted for detecting at least one distance between the at least one object and the optical detector by performing at least one time-of-flight measurement.

Embodiment 97

The optical detector according to any one of the preceding embodiments, wherein the optical detector further comprises at least one active distance sensor, having at least one active optical sensor adapted to generate a sensor signal when illuminated by a light beam propagating from the object to the active optical sensor, wherein the sensor signal, given the same total power of the illumination, is dependent on a geometry of the illumination, the active distance sensor further comprising at least one active illumination source for illuminating the object.

Embodiment 98

The optical detector according to any one of the preceding embodiments, wherein the spatial light modulator comprises at least one reflective spatial light modulator, wherein the optical detector is further adapted to additionally use the reflective spatial light modulator as a projector.

Embodiment 99

The optical detector according to any one of the preceding embodiments, wherein the optical detector is adapted to detect, and preferably to track, at least one eye of a creature within a scene captured by the detector.

Embodiment 100

The optical detector according to the preceding embodiment, wherein the optical detector is adapted to determine at least one longitudinal coordinate of the at least one eye.

Embodiment 101

The optical detector according to any one of the preceding embodiments, wherein the at least one optical sensor comprises at least one array of sensor pixels, preferably an array containing 2×N sensor pixels with N being an integer.

Embodiment 102

A detector system for determining a position of at least one object, the detector system comprising at least one optical detector according to any one of the preceding embodiments, the detector system further comprising at least one beacon device adapted to direct at least one light beam towards the optical detector, wherein the beacon device is at least one of attachable to the object, holdable by the object and integratable into the object.

Embodiment 103

The detector system according to the preceding embodiment, wherein the beacon device comprises at least one illumination source.

Embodiment 104

The detector system according to any one of the two preceding embodiments, wherein the beacon device comprises at least one reflective device adapted to reflect a primary light beam generated by an illumination source independent from the object.

Embodiment 105

The detector system according to any one of the three preceding embodiments, wherein the detector system comprises at least two beacon devices, preferably at least three beacon devices.

Embodiment 106

The detector system according to any one of the four preceding embodiments, wherein the detector system further comprises the at least one object.

Embodiment 107

The detector system according to the preceding embodiment, wherein the object is a rigid object.

Embodiment 108

The detector system according to any of the two preceding embodiments, wherein the object is selected from the group consisting of: an article of sports equipment, preferably an article selected from the group consisting of a racket, a club, a bat; an article of clothing; a hat; a shoe.

Embodiment 109

A human-machine interface for exchanging at least one item of information between a user and a machine, wherein the human-machine interface comprises at least one detector system according to any of the preceding embodiments referring to a detector system, wherein the at least one beacon device is adapted to be at least one of directly or indirectly attached to the user and held by the user, wherein the human-machine interface is designed to determine at least one position of the user by means of the detector system, wherein the human-machine interface is designed to assign to the position at least one item of information.

Embodiment 110

An entertainment device for carrying out at least one entertainment function, wherein the entertainment device comprises at least one human-machine interface according to the preceding embodiment, wherein the entertainment device is designed to enable at least one item of information to be input by a player by means of the human-machine interface, wherein the entertainment device is designed to vary the entertainment function in accordance with the information.

Embodiment 111

A tracking system for tracking a position of at least one movable object, the tracking system comprising at least one detector system according to any of the preceding embodiments referring to a detector system, the tracking system further comprising at least one track controller, wherein the track controller is adapted to track a series of positions of the object at specific points in time.

Embodiment 112

A camera for imaging at least one object, the camera comprising at least one optical detector according to any of the preceding embodiments referring to a detector.

Embodiment 113

A method of optical detection, specifically for determining a position of at least one object, the method comprising the following steps:
  modifying at least one property of a light beam in a spatially resolved fashion by using at least one spatial light modulator, the spatial light modulator having a matrix of pixels, each pixel being controllable to individually modify the at least one optical property of a portion of the light beam passing the pixel;
  detecting the light beam after passing the matrix of pixels of the spatial light modulator by using at least one optical sensor and for generating at least one sensor signal;
  periodically controlling at least two of the pixels with different frequencies by using at least one modulator device; and
  performing a frequency analysis by using at least one evaluation device and to determining signal components of the sensor signal for the control frequencies.

Embodiment 114

The method according to the preceding embodiment, wherein the optical detector according to one of the preceding embodiments referring to an optical detector is used.

Embodiment 115

A use of the optical detector according to any one of the preceding embodiments relating to an optical detector, for a purpose of use, selected from the group consisting of: a position measurement in traffic technology; an entertainment application; a security application; a human-machine interface application; a tracking application; a photography application; a mapping application for generating maps of at least one space; a mobile application; a webcam; a computer peripheral device; a gaming application; a camera or video application; a security application; a surveillance application; an automotive application; a transport application; a medical application; a sports application; a machine vision application; a vehicle application; an airplane application; a ship application; a spacecraft application; a building application; a construction application; a cartography application; a manufacturing application; a use in combination with at least one time-of-flight detector; an application in a local positioning system; an application in a global positioning system; an application in a landmark-based positioning system; an application in an indoor navigation system; an application in an outdoor navigation system; an application in a household application; a robot application; an application in an automatic door opener; an application in a light communication system, specifically in a visible light communication system, i.e. a communication system based on the use of visible light.

BRIEF DESCRIPTION OF THE FIGURES

Further optional details and features of the invention are evident from the description of preferred exemplary embodiments which follows in conjunction with the dependent claims. In this context, the particular features may be implemented alone or in any reasonable combination. The invention is not restricted to the exemplary embodiments. The exemplary embodiments are shown schematically in the figures. Identical reference numerals in the individual figures refer to identical elements or elements with identical function, or elements which correspond to one another with regard to their functions.

In the figures.

EXEMPLARY EMBODIMENTS

Figure 1:
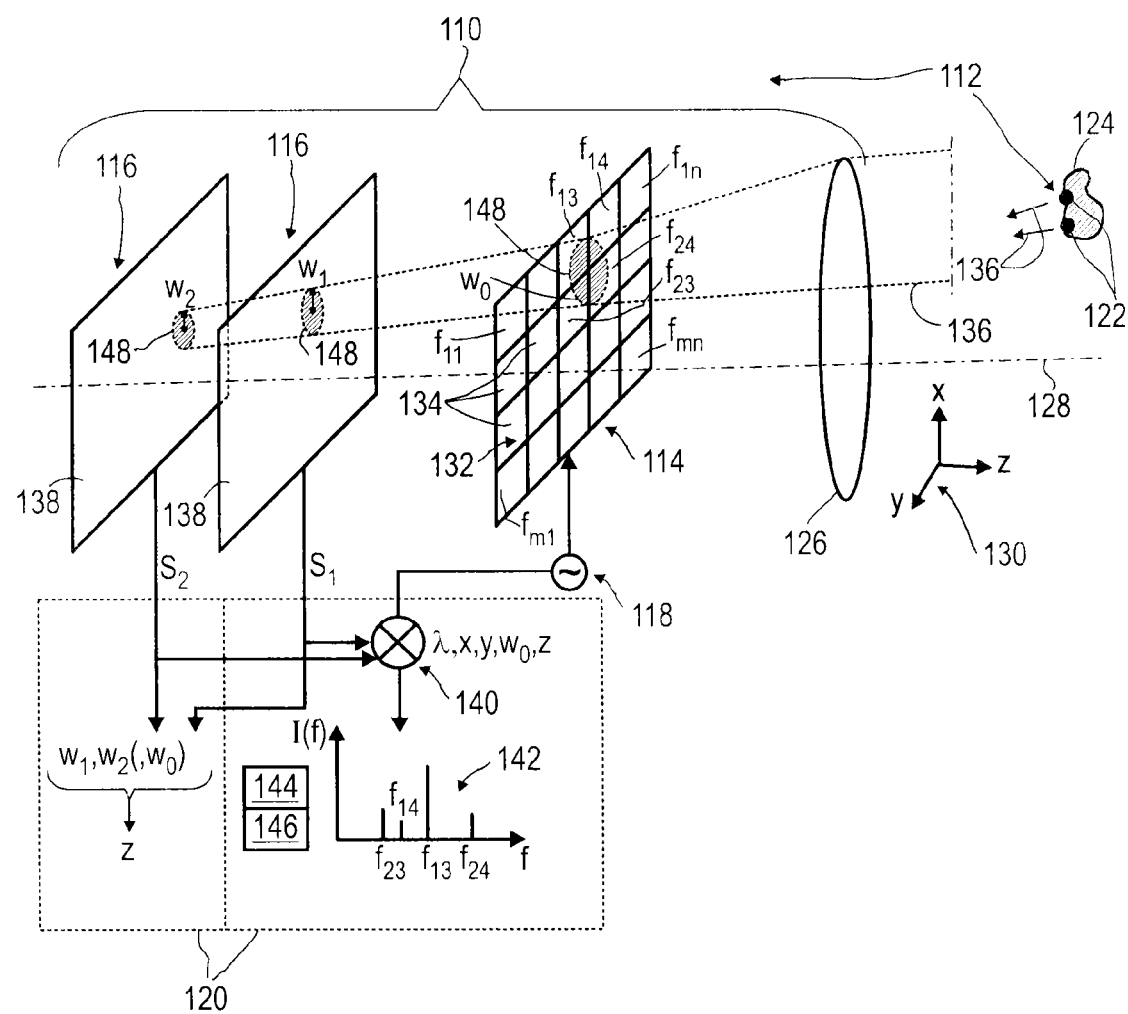
FIG. 1 shows an exemplary embodiment of an optical detector according to the present invention.

In FIG. 1, an exemplary embodiment of an optical detector 110 and of a detector system 112 is disclosed. The optical detector 110 comprises at least one spatial light modulator 114, at least one optical sensor 116, at least one modulator device 118 and at least one evaluation device 120. The detector system 112, besides the at least optical detector 110, comprises at least one beacon device 122 which is at least one of attachable to an object 124, holdable by the object 124 and integratable into the object 124. The optical detector 110, in this embodiment, furthermore may comprise one or more transfer devices 126, such as one or more lenses, preferably one or more camera lenses. In the exemplary embodiment shown in FIG. 1, the spatial light modulator 114, the optical sensor 116 and the transfer device 126 are arranged along an optical axis 128 in a stacked fashion. The optical axis 128 defines a longitudinal axis or z-axis, wherein a plane perpendicular to the optical axis 128 defines a x-y-plane. Thus, in FIG. 1, a coordinate system 130 is shown, which may be a coordinate system of the optical detector 110 and in which, fully or partially, at least one item of information regarding a position and/or orientation of the object 124 may be determined.

The spatial light modulator 114 in the exemplary embodiment shown in FIG. 1 may be a transparent spatial light modulator, as shown, or may be an intransparent, such as a reflective, spatial light modulator 114. For further details, reference may be made to the potential embodiments discussed above. The spatial light modulator comprises a matrix 132 of pixels 134 which preferably are individually controllable to individually modify at least one optical property of a portion of a light beam 136 passing the respective pixel 134. In the exemplary and schematic embodiment shown in FIG. 1, the light beam is denoted by reference number 136 and may be emitted and/or reflected by the one or more beacon devices 122. As an example, the pixels 134 may be switched between a transparent state or an intransparent state and/or a transmission of the pixels may be switched between two or more transparent states. In case a reflective and/or any other type of spatial light modulator 114 is used, other types of optical properties may be switched. In the embodiment shown in FIG. 1, four pixels are illuminated, such that the light beam 136 is split into four portions, each of the portions passing through a different pixel 134. Thus, the optical property of the portions of the light beam may be controlled individually by controlling the state of the respective pixels.

The modulator device 118 is adapted to individually control the pixels 134, preferably all of the pixels 134, of the matrix 132. Thus, as shown in the exemplary embodiment of FIG. 1, the pixels 134 may be controlled at different modulation frequencies, which, for the sake of simplicity, are denoted by the position of the respective pixel 134 in the matrix 132. Thus, modulation frequencies $f_{11}$ to $f_{mn}$ are provided for an m×n matrix 132. As outlined above, the term "modulation frequency" may refer to the fact that one or more of the actual frequency and the phase of the modulation may be controlled.

Having passed the spatial light modulator 114, the light beam 136, now being influenced by the spatial light modulator 114, reaches the one or more optical sensors 116. Preferably, the at least one optical sensor 116 may be or may comprise a large-area optical sensor having a single and uniform sensor region 138. Due to the beam propagation properties, a beam width w will vary, when the light beam 136 propagates along the optical axis 128.

The at least one optical sensor 116 generates at least one sensor signal S, which, in the embodiment shown in FIG. 1, is denoted by $S_1$ and $S_2$. At least one of the sensor signals (in the embodiment shown in FIG. 1 the sensor Signal $S_1$) is provided to the evaluation device 120 and, therein, to a demodulation device 140. The demodulation device 140, which, as an example, may contain one or more frequency mixers and/or one or more frequency filters, such as a low pass filter, may be adapted to perform a frequency analysis. As an example, the demodulation device 118 may contain a lock-in device and/or a Fourier analyzer. The modulator device 118 and/or a common frequency generator may further provide the modulation frequencies to the demodulation device 140. As a result, a frequency analysis may be provided which contains signal components of the at least one sensor signal for the modulation frequencies. In FIG. 1, the result of the frequency analysis symbolically is denoted by reference number 142. As an example, the result of the frequency analysis 142 may contain a histogram, in two or more dimensions, indicating signal components for each of the modulation frequencies, i.e. for each of the frequencies and/or phases of the modulation.

The evaluation device 120, which may contain one or more data processing devices 144 and/or one or more data memories 146, may further be adapted to assign the signal components of the result 142 of the frequency analysis to their respective pixels 134, such as by a unique relationship between the respective modulation frequency and the pixels 134. Consequently, for each of the signal components, the respective pixel 134 may be determined, and the portion of the light beam 136 passing through the respective pixel 134 may be derived.

Thus, even though a large-area optical sensor 116 may be used, various types of information may be derived from the frequency analysis, using the preferred unique relationship between the modulation of the pixels 134 and the signal components.

Thus, as a first example, an information on a lateral position of the illuminated area or light spot 148 on the spatial light modulator 114 may be determined (x-y-position). Thus, as symbolically shown in FIG. 1, significant signal components arise for modulation frequencies $f_{23}$, $f_{14}$, $f_{13}$ and $f_{24}$. This exemplary embodiment allows for determining the positions of the illuminated pixels and the degree of illumination. In this embodiment, pixels 13, 14, 23 and 24 are illuminated. Since the position of the pixels 134 in the matrix 132 generally is known, it may be derived that the center of illumination is located somewhere in between these pixels, mainly within pixel 13. A more thorough analysis of the illumination may be performed, specifically if (which usually is the case) a larger number of pixels 134 is illuminated. Thus, by identifying the signal components having the highest amplitude, the center of illumination and/or a radius of the illumination and/or a spot-size or spot-shape of the light spot 148 may be determined. This option of determining the transversal coordinates is generally denoted by x, y in FIG. 1. The option of determining a width of the light spot 148 on the spatial light modulator 114 is symbolically depicted by $w_0$.

By determining a transversal or lateral position of the light spot 148 on the spatial light modulator 114, using known imaging properties of the transfer device 126, a transversal coordinate of the object 124 and/or of the at least one beacon device 122 may be determined. Thus, at least one item of information regarding a transversal position of the object 124 may be generated.

Further, since the beam width $w_0$ generally, at least if the beam properties of the light beam 136 are known or may be determined (such as by using one or more beacon devices 122 emitting light beams 136 having well-defined propagation properties), the beam width $w_0$ may further be used, alone or in conjunction with beam waist $w_1$ and/or $w_2$ determined by using the optical sensors 116, in order to determine a longitudinal coordinate (z-coordinate) of the object 124 and/or the at least one beacon device 122, as disclosed e.g. in WO 2012/110924 A1.

In addition or alternatively to the option of determining one or both of at least one transversal coordinate x, y and/or determining at least one longitudinal coordinate z, the information derived by the frequency analysis may further be used for deriving color information. Thus, as will be outlined in further detail below, the pixels 134 may have differing spectral properties, specifically different colors. Thus, as an example, the spatial light modulator 114 may be a multi-color or even full-color spatial light modulator 114. Thus, as an example, at least two, preferably at least three different types of pixels 134 may be provided, wherein each type of pixels 134 has a specific filter characteristic, having a high transmission e.g. in the red, the green or the blue spectral range. As used herein, the term red spectral range refers to a spectral range of 600 to 780 nm, the green spectral range refers to a range of 490 to 600 nm, and the blue spectral range refers to a range of 380 nm to 490 nm. Other embodiments, such as embodiments using different spectral ranges, may be feasible.

By identifying the respective pixels 134 and assigning each of the signal components to a specific pixel 134, the color components of the light beam 136 may be determined. Thus, specifically by analyzing signal components of neighboring pixels 134 having different transmission spectra, assuming that the intensity of the light beam 136 on these neighboring pixels is more or less identical, the color components of the light beam 136 may be determined. Thus, generally, the evaluation device 120, in this embodiment or other embodiments, may be adapted to derive at least one item of color information regarding the light beam 136, such as by providing at least one wavelength and/or by providing color coordinates of the light beam 136, such as CIE-coordinates.

As outlined above, for determining at least one longitudinal coordinate of the object 124 and/or the at least one beacon device 122, a relationship between the width w of the beam and a longitudinal coordinate may be used, such as the relationship of a Gaussian light beam as disclosed in formula (3) above. The formula assumes a focus of the light beam 136 at position z=0. From a shift of the focus, i.e. from a coordinate transformation along the z-axis, a longitudinal position of the object 128 may be derived.

In addition or alternatively to using the beam width $w_0$ at the position of the spatial light modulator 114, a beam width w at the position of the at least one optical sensor 116 may be derived and/or used for determining the longitudinal position of the object 124 and/or the beacon device 122.

Thus, as outlined in further detail above, one or more of the at least one optical sensors 116 may be a pixelated optical sensor 116, allowing for a pixel count and, thus, similar to the equations given above, to allow for determining a number of illuminated pixels and, thus, deriving a beam width thereof. Additionally or alternatively, at least one of the one or more optical sensors 116 may be a FiP-sensor, as discussed above and as discussed in further detail e.g. in WO 2012/110924 A1. Thus, given the same total power of illumination, the signal S may depend on the beam width w of the respective light spot 148 on the optical sensor 116. This effect may be pronounced by modulating the light beam 136, by the spatial light modulator 114 and/or any other modulation device. The modulation may be the same modulation as provided by the modulator device 118 and/or may be a different modulation, such as a modulation at higher frequencies. Thus, as an example, the emission and/or reflection of the at least one light beam 136 by the at least one beacon device 122 may take place in a modulated way. Thus, as an example, the at least one beacon device 122 may comprise at least one illumination source which may be modulated individually.

Due to the FiP-effect, the signal $S_1$ and/or $S_2$ may depend on a beam width $w_1$ or $w_2$, respectively. Thus, e.g. by using equation (3) given above, beam parameters of the light beam 136 may be derived, such as $z_0$ and/or the origin of the z-axis (z=0). From these parameters, as symbolically depicted in FIG. 1, the longitudinal coordinate z of the object 124 and/or of one or more of the beacon devices 122 may be derived.

Figure 2:
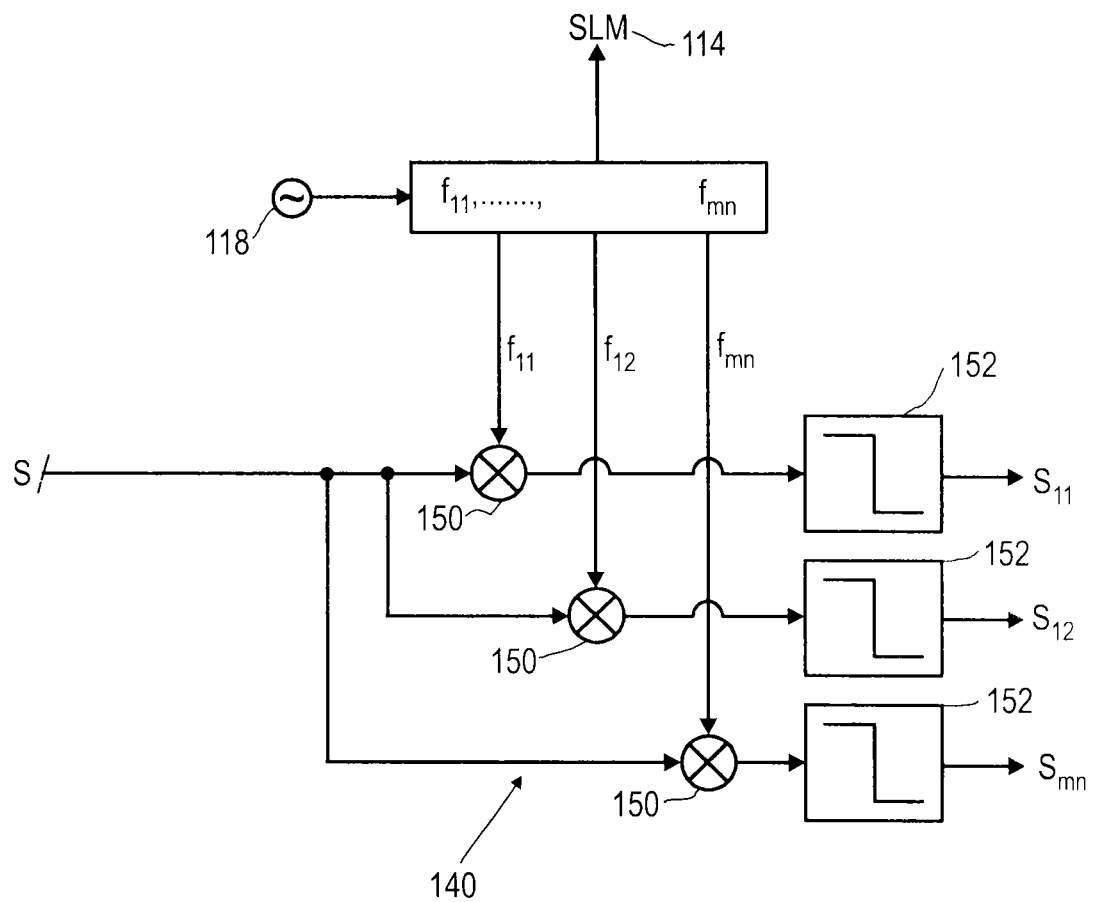
FIG. 2 shows an exemplary embodiment of a demodulator which may be part of an evaluation device adapted for frequency analysis in order to determine signal components.

In FIG. 2, symbolically, a setup of the modulator device 118 and of a demodulation device 140 is disclosed in a symbolic fashion, which allows for separating signal components (indicated by $S_{11}$ to $S_{mn}$) for the pixels 134 of the m×n matrix 132. Thus, the modulator device 118 may be adapted for generating a set of modulation frequencies $f_{11}$ to $f_{mn}$, for the entire matrix 132 and/or for a part thereof. As outlined above, each of the modulation frequencies $f_{11}$ to $f_{mn}$ may include a respective frequency and/or a respective phase for the pixel 134 indicated by the indices i, j, with i= 1 . . . m and j=1 . . . n. The set of frequencies $f_{11}$ to $f_{mn}$ is both provided to the spatial light modulator 114, for modulating the pixels 134, and to the demodulation device 140. In the demodulation device 140, simultaneously or subsequently, the modulation frequencies $f_{11}$ to $f_{mn}$ are mixed with the respective signal S to be analyzed, such as by using one or more frequency mixers 150. The mixed signal, subsequently, may be filtered by one or more frequency filters, such as one or more low pass filters 152, preferably with well-defined cutoff frequencies. The setup comprising the one or more frequency mixers 150 and the one or more low pass filters 152 generally is used in lock-in analyzers and is well-known to the skilled person.

By using the demodulation device 140, signal components $S_{11}$ to $S_{mn}$ may be derived, wherein each signal component is assigned to a specific pixel 134, according to its index. It shall be noted, however, that other types of frequency analyzers may be used, such as Fourier analyzers, and/or that one or more of the components shown in FIG. 2 may be combined, such as by subsequently using one and the same frequency mixer 150 and/or one and the same low pass filter 152 for the different channels.

As outlined above, various setups of the optical detector 110 are possible. Thus, as an example, the optical detector 110 as shown in FIG. 1 may comprise one or more optical sensors 116. These optical sensors 116 may be identical or different. Thus, as an example, one or more large-area optical sensors 116 may be used, providing a single sensitive area 138. Additionally or alternatively, one or more pixelated optical sensors 116 may be used. Further, in case a plurality of optical sensors 116 is provided, the optical sensors 116 may provide identical or different spectral properties, such as identical or different absorption spectra. Further, in case a plurality of optical sensors 116 is provided, one or more of the optical sensors 116 may be organic and/or one or more of the optical sensors 116 may be inorganic. A combination of organic and inorganic optical sensors 116 may be used.

Figure 3:
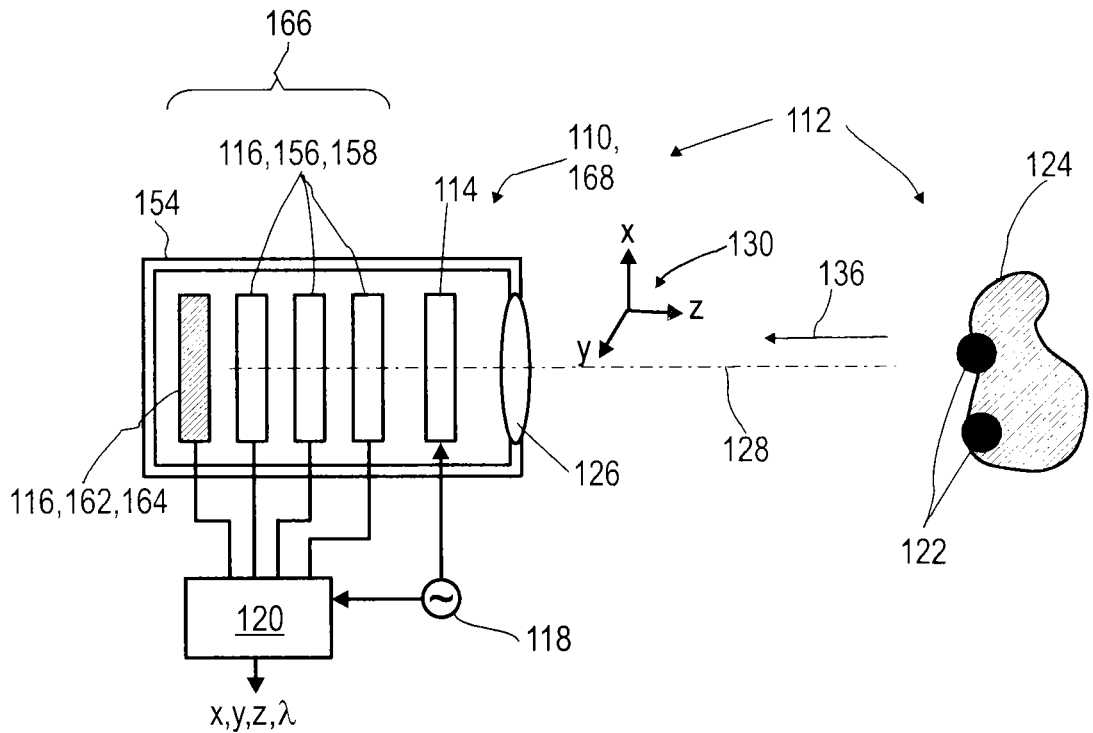
FIGS. 3 and 4 show alternative setups of an optical detector having a transparent spatial light modulator (FIG. 3) and a reflective spatial light modulator (FIG. 4)

Thus, as an example, in FIG. 3, a schematic setup of an optical detector 110 and a detector system 112 similar to the setup shown in FIG. 1 is given. While FIG. 1 shows the setup in a simplified perspective view, FIG. 3 shows the setup in a cross-sectional view of the detector 110. For most of the details of the detector 110, reference may be made to the potential embodiments discussed above with regard to FIG. 1. The components of the optical detector 110 may fully or partially be embodied in one or more housings 154. Thus, the transfer device 126, the spatial light modulator 114, the at least one optical sensor 116 and the evaluation device 120 may be encased fully or partially within the same housing 154 and/or may fully or partially be encased within separate housings 154.

In the setup shown in FIG. 3, the spatial light modulator 114, again, may be a transparent spatial light modulator 114, which may be located behind the transfer device 126, such as the lens. Further, the optical detector 110 may comprise one or more optical sensors 116 embodied as large-area optical sensors 156. Further, the at least one optical sensor 116 may fully or partially be embodied as a transparent optical sensor 158. Further, the at least one optical sensor 116 may fully or partially be embodied as an organic optical sensor 160, preferably a DSC or sDSC. Additionally or alternatively, at least one inorganic optical sensor 162 may be provided, preferably a pixelated inorganic optical sensor and, more preferably, a CCD chip and/or a CMOS chip. Further, at least one intransparent optical sensor 164 may be provided.

Thus, in case a plurality of optical sensors 116 is provided, the optical sensors 116 may form a stack 166 of optical sensors 116, wherein at least one of the optical sensors 116 is fully or partially embodied as an at least partially transparent optical sensor 158 and wherein at least one of the optical sensors 116 is fully or partially embodied as an intransparent optical sensor 164. In the setup of the stack 166 shown in FIG. 3, as an example, on a side of the stack 166 furthest away from the spatial light modulator 114 and/or the object 124, an intransparent optical sensor 164 is located, whereas in between the intransparent optical sensor 164 and the spatial light modulator 114 one or more transparent optical sensors 158 are located. This setup of the stack 166 may easily be embodied by using one or more organic optical sensors 160 as the transparent optical sensors 158, such as by using one or more large-area transparent DSCs or sDSCs, and by using an inorganic camera chip as the intransparent optical sensor 164, preferably a CCD and/or CMOS chip, preferably a full-color camera chip. Thus, the setup of the optical detector 110 as shown in FIG. 3 may be an embodiment of a camera 168 which may be used for taking 2D images by a pixelated optical sensor 116, preferably the inorganic pixelated camera chip, at the far end of the stack 166, and, additionally, providing longitudinal information (z-information) by evaluating the signal components and/or the beam widths, as discussed above with regard to FIG. 1. Thereby, a 3D camera 168 may be realized, preferably a full-color 3D camera.

Figure 4:
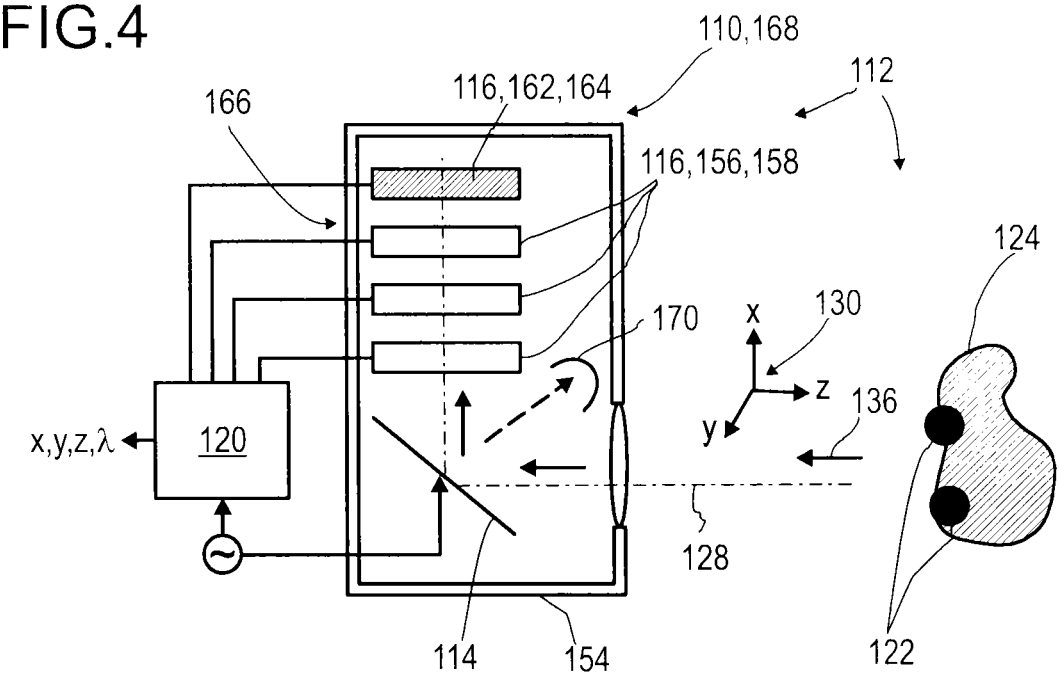

In FIG. 4, an alternative setup of the detector 110, the detector system 112 and the camera 168 is shown. Thus, as discussed above, the spatial light modulator 114 may be a transparent or intransparent spatial light modulator. Thus, as an example, spatial light modulators 114 based on liquid crystal technology may be used as transparent spatial light modulators 114. Alternatively, as shown in FIG. 4, micromirror devices may be used as reflective spatial light modulators 114, thereby deflecting the optical axis 128 and/or the light path. As an example, the reflective spatial light modulator 114 shown in FIG. 14 may have a matrix of pixels shaped as micro-mirrors either adapted to transmit the respective portion of the light beam 136 towards the stack 166 of optical sensors 116 and/or to block the respective portions, such as by directing these portions towards a beam dump 170 depicted in FIG. 4. Except for these modifications, the setup of the detector 110 and the camera 168 of FIG. 4, including its optional variations, may be identical to the setup disclosed with regard to FIG. 3.

Figure 5:
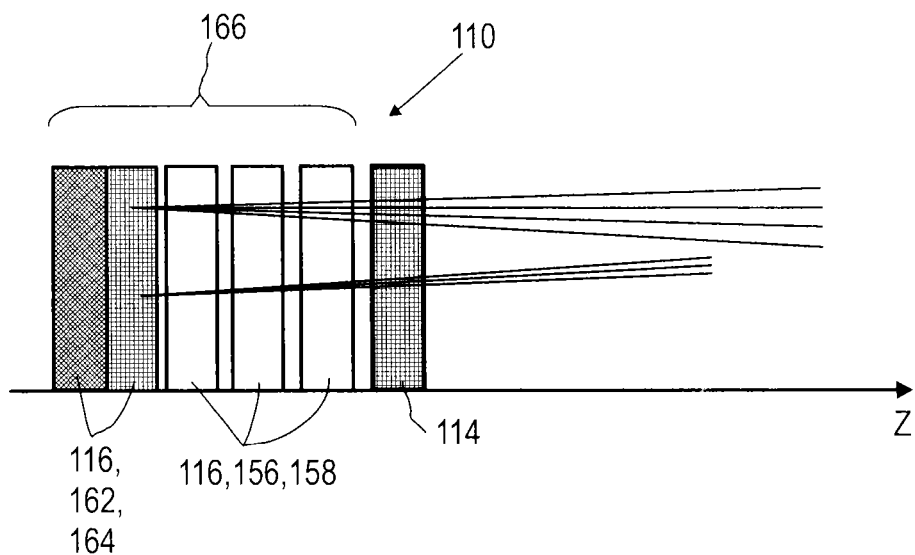
FIG. 5 shows an exemplary embodiment of an optical detector adapted for 3D imaging.
Figure 6:
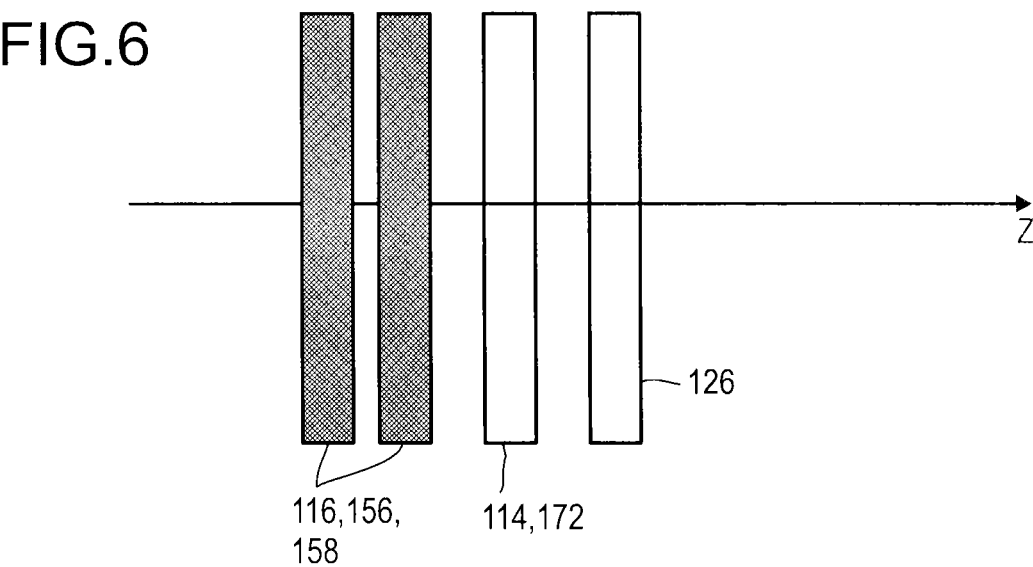
FIG. 6 shows an exemplary embodiment of an optical detector for color recognition.
Figure 7:
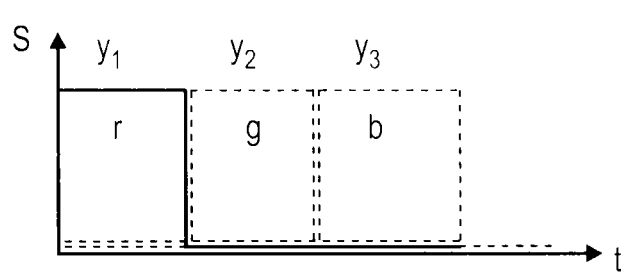
FIG. 7 shows an exemplary embodiment of phase separation of color signals in the setup of FIG. 6.

In FIGS. 5 to 7, various functions of the setups of FIGS. 1 to 4, which may be realized in isolation or in any arbitrary combination, are repeated. Thus, FIG. 5 shows a setup of the optical detector 110 as e.g. given in FIG. 3, indicating a combination of an intransparent optical sensor 164 in a stack 166 with a plurality of transparent optical sensors 158. Thus, the intransparent optical sensor 164 may be used for imaging, generating high-resolution images of an object 124 (not shown). The transparent optical sensors 158 of the stack 166 may be used, as outlined above, for generating additional longitudinal position information (z-information).

In the setup shown in FIG. 6, in conjunction with a pulse scheme shown in FIG. 7, color recognition is disclosed in further detail. Thus, a spatial light modulator 114 embodied as a full-color spatial light modulator 172 may be used, such as a transparent RGB TFT display with pixels. Further, one or more transparent, semitransparent or intransparent optical sensors 116 may be used, preferably large-area optical sensors 156, which may be able to provide signal components. The evaluation device 120 (not shown) may be adapted to assign the signal components to pixels 134 having different colors, by their modulation frequency, i.e. by their frequency and/or their phase. The option of phase separation symbolically is shown in FIG. 7. As can be seen therein, the signal components S may be separated according to their phase, by red, green and blue (r, g, b) pixels emitting at different times t, i.e. having differing phases $\phi_1$, $\phi_2$ and $\phi_3$. Thus, by evaluating the signal components, color components of the light beam 136 may be identified.

Figure 8:
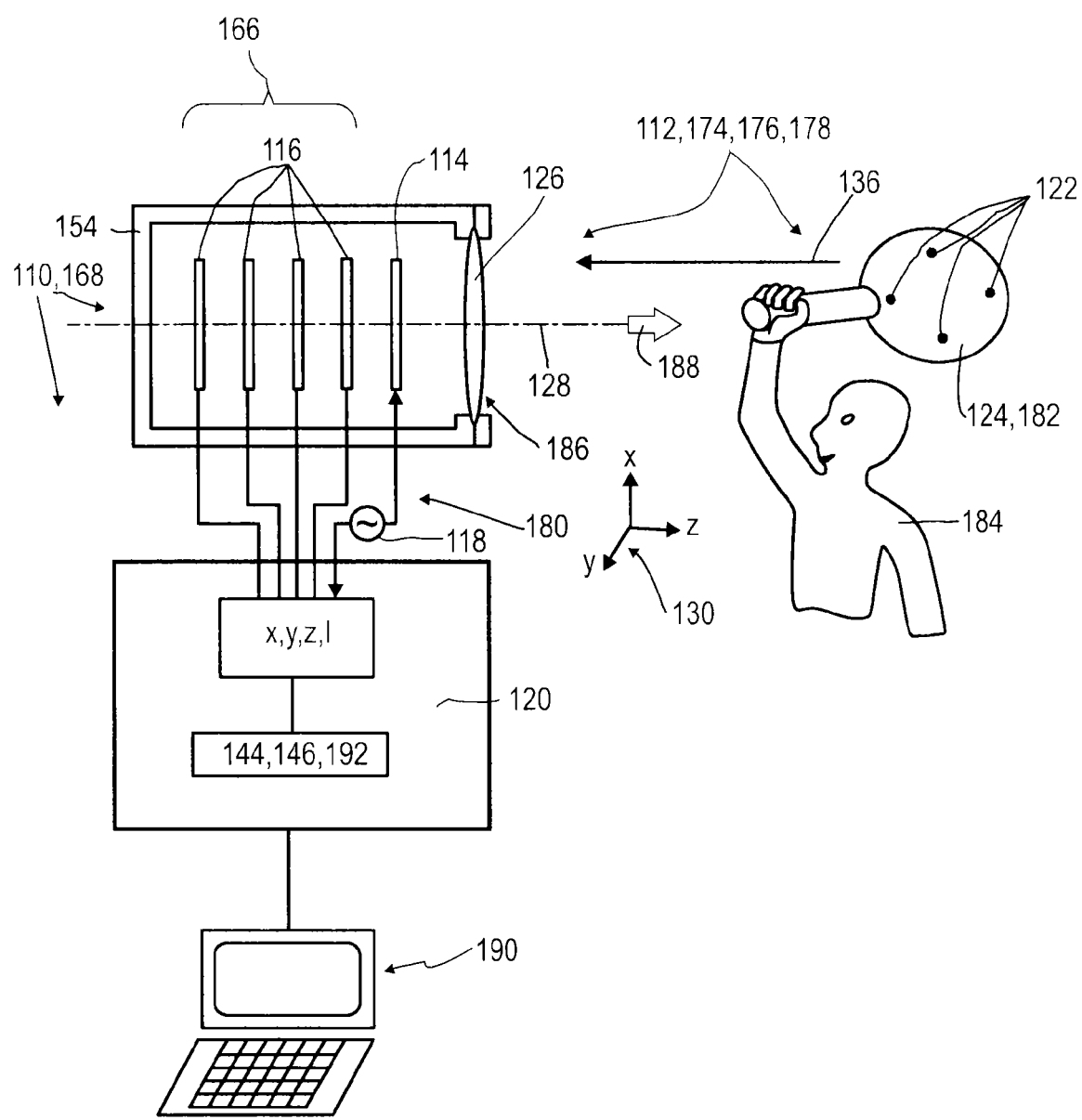
FIG. 8 shows an exemplary embodiment of an optical detector used in a human-machine interface, a detector system, an entertainment device and a tracking system.

As outlined above, the optical detector 110, the detector system 112 and the camera 168 may be used in various other devices and systems. Thus, the camera 168 may be used for imaging, specifically for 3D imaging, and may be made for acquiring standstill images and/or image sequences such as digital video clips. FIG. 8, as an exemplary embodiment, shows a detector system 112, comprising at least one optical detector 110, such as the optical detector 110 as disclosed in one or more of the embodiments shown in FIGS. 1 through 6. In this regard, specifically with regard to potential embodiments, reference may be made to the disclosure given above. FIG. 8 further shows an exemplary embodiment of a human-machine interface 174, which comprises the at least one detector system 112, and, further, an exemplary embodiment of an entertainment device 176 comprising the human-machine interface 174. The figure further shows an embodiment of a tracking system 178 adapted for tracking a position of at least one object 124, which comprises the detector system 112.

With regard to the optical detector 110 and the detector system 112, reference may be made to the disclosure given above.

The evaluation device 120 may be connected to the optical sensors 116 and the modulator device 118 and/or the spatial light modulator 112, by one or more connectors 180 and/or one or more interfaces. Further, the connector 180 may comprise one or more drivers and/or one or more measurement devices for generating sensor signals. Further, the evaluation device 120 may fully or partially be integrated into the optical sensors 116 and/or into the housing 154 and/or into the spatial light modulator 114. Additionally or alternatively, the evaluation device 120 may fully or partially be designed as a separate, independent device.

In this exemplary embodiment shown in FIG. 8, the object 124 to be detected may be designed as an article of sports equipment and/or or may form a control element 182, the position and/or orientation of which may be manipulated by a user 184. As an example, the object 124 may be or may comprise a bat, a racket, a club or any other article of sports equipment and/or fake sports equipment. Other types of objects 124 are possible. Further, the user 184 himself or herself may be considered as the object 124, the position of which shall be detected. As an example, the user 184 may carry one or more of the beacon devices 122 attached directly or indirectly to his or her body.

As discussed above with regard to the potential options of FIG. 1, the optical detector 110 may be adapted to determine one or more of a transversal position and a longitudinal position of one or more of the beacon devices 122 and/or of the object 124. Additionally or alternatively, the optical detector 110 may be adapted for identifying colors and/or for imaging the object 124. An opening 186 inside the housing 154, which, preferably, is located concentrically with regard to the optical axis 128 of the detector 110, preferably defines a direction of view 188 of the optical detector 110.

The detector 110 may be adapted for determining a position of the at least one object 124. Additionally, the optical detector 110 may be adapted for acquiring an image of the object 124, preferably a 3D image.

As outlined above, the determination of a position of the object 118 and/or a part thereof by using the detector 110 and/or the detector system 112 may be used for providing a human-machine interface 174, in order to provide at least one item of information to a machine 190. In the embodiment schematically depicted in FIG. 8, the machine 190 may be a computer and/or may comprise a computer. Other embodiments are feasible. The evaluation device 120 may be fully or partially embodied as a separate device and/or may fully or partially be integrated into the machine 180, such as into the computer. The same holds true for a track controller 192, of the tracking system 178, which may fully or partially form a part of the evaluation device 120 and/or the machine 190.

Similarly, as outlined above, the human-machine interface 174 may form part of an entertainment device 176. The machine 190, specifically the computer, may also form part of the entertainment device 176. Thus, by means of the user 184 functioning as the object 118 and/or by means of the user 184 handling the control element 182 functioning as the object 124, the user 184 may input at least one item of information, such as at least one control command, into the computer, thereby varying the entertainment function, such as controlling the course of a computer game.

As outlined above, the optical detector 110 may have a straight beam path, as e.g. in the setup of FIG. 3, or may be tilted, angulated, branched, deflected or split, such as in the rectangular setup shown in FIG. 4. Further, the light beam 136 may travel along each beam path or partial beam path once or repeatedly, unidirectionally or bidirectionally. Thereby, the spatial light modulator 114 may fully or partially be located in front of the at least one optical sensor 116 and/or behind the at least one optical sensor 116.

Figure 9:
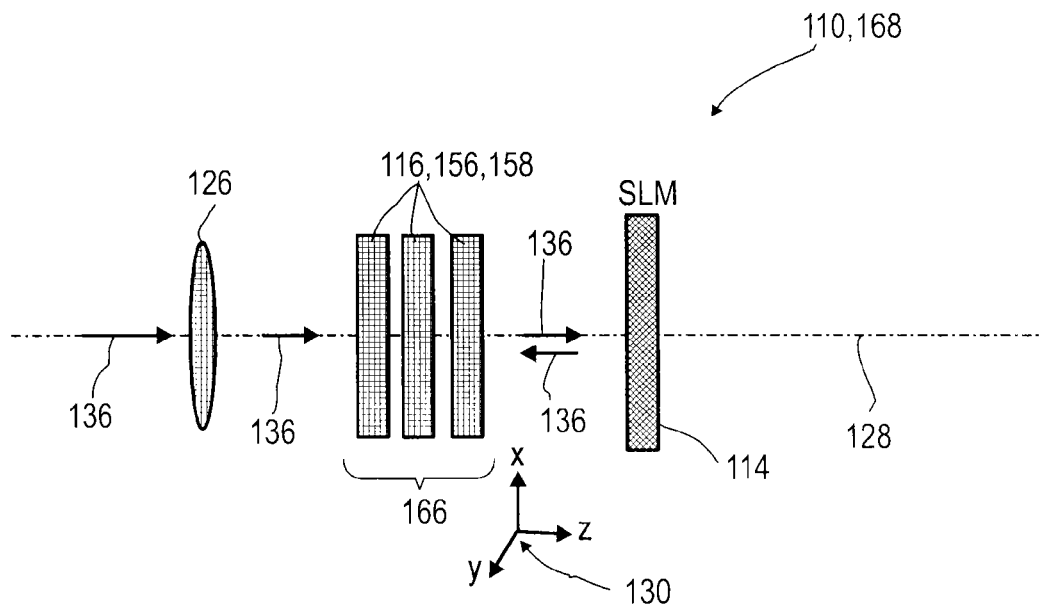
FIGS. 9-11 show alternative setups of the optical detector.

In FIG. 9, an alternative setup of the optical detector 110 is shown, which may generally be used in the setup of FIG. 3. The modulator device 118 and the evaluation device 120 as well as the object 124 and the beacon devices 122 are not shown in the setup and may be embodied as e.g. shown in FIG. 3.

In the setup of FIG. 9, an incoming light beam 136 enters the optical detector 110 from the left, passes towards the right, passes the at least one optional transfer device 126 such as the at least one lance, and passes a stack 166 of transparent optical sensors 158 for the first time, in an unmodulated fashion. Subsequently, the light beam 136 hits the spatial light modulator 114 and, as outlined above, is modulated by the spatial light modulator 114. The spatial light modulator 114, in this setup, is a reflective spatial light modulator adapted for reflecting the light beam 136 back towards the stack 166. Thus, the reflected light beam 136, traveling towards the left in FIG. 9, hits the stack 166 for the second time, thereby allowing for the above-mentioned z-detection of the object 124 and/or the beacon devices 122.

Figure 10:
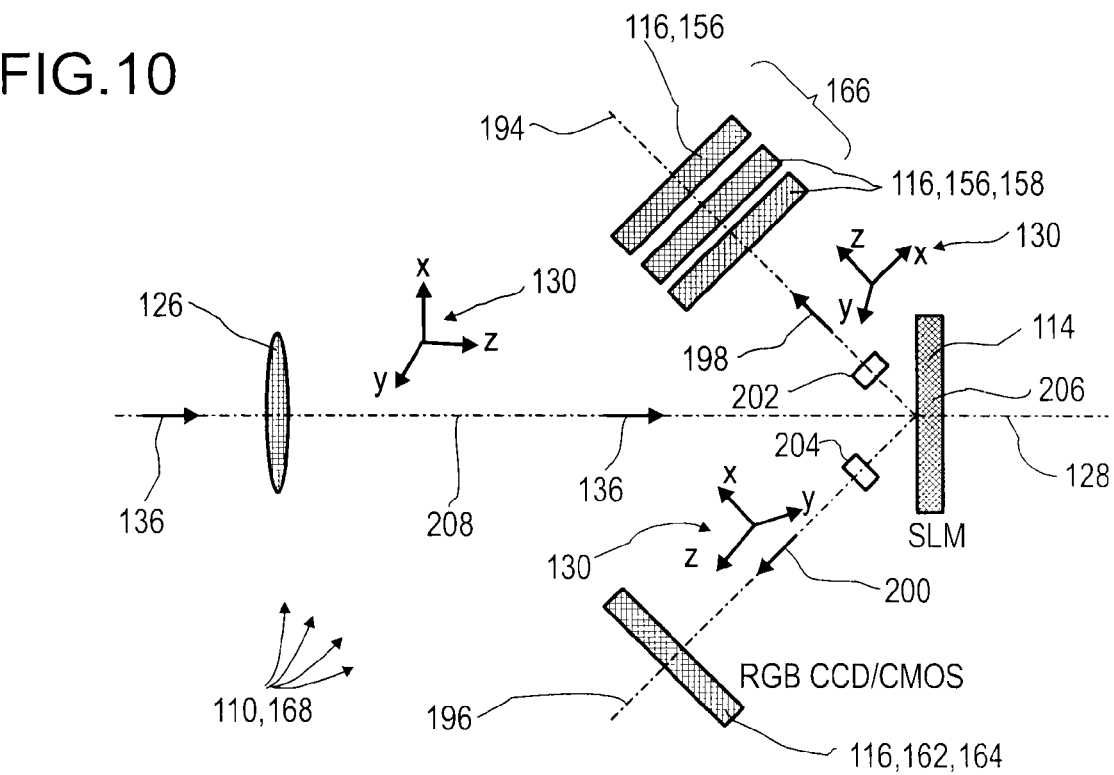

Further, as discussed above, the optical detector 110 may have a beam path which is split into a plurality of partial beam paths. A first exemplary embodiment of a split beam path setup is shown in FIG. 10. Again, an optical detector 110 is shown, without the modulator device 118 and the evaluation device 120 and without the object 124 and the beacon devices 122, which may be embodied as e.g. shown in FIG. 3.

Again, the light beam 136 enters the optical detector 110 from the left, by passing the at least one optional transfer device 126. Subsequently, the light beam 136 hits the spatial light modulator 114, which, again, is embodied as a reflective spatial light modulator and which, in this case, is adapted to deflect the light beam 136 into a direction of a first partial beam path 194 and into a direction of a second partial beam path 196. Thus, as an example, the reflective spatial light modulator 114 may comprise, as discussed above, a matrix of pixels having micro-mirrors, wherein each micro-mirror may be adapted to deflect the incident light beam 136 either into the direction of the first partial beam path 194 or into the direction of the second partial beam path 196. Thereby, the light beam 136 may be split into a first partial light beam 198 travelling along the first beam path 194, and a second partial light beam 200 travelling along the second partial beam path 196.

Each one of the partial beam paths 194, 196 may define a coordinate system 130 of its own, wherein, since the setup of the optical detector is known, these coordinate systems 130 of the partial beam paths 194, 196 may be correlated to one another and/or may be correlated to a common coordinate system 130 of the optical detector 110.

Within each one of the at least two partial beam paths 194, 196, one or more optical elements may be located. Thus, in the setup shown in FIG. 10, which may be called a W-shaped setup of the beam paths 164, 196, a stack 196 of optical sensors 116 is located in the first partial beam path 194. Thus, the first partial beam path 194 may be dedicated to z-detection of the object 124. The second partial beam path 196 may be dedicated to imaging, and, consequently, may contain one or more inorganic optical sensors 162 and/or intransparent optical sensors 164, such as one or more camera chips. Thus, as an example, the second partial beam path may contain at least one pixelated imaging sensor, specifically in imaging sensor chip, such as at least one CCD- and/or CMOS-chip, preferably at least one full-color or RGB CCD- or CMOS-chip.

Further, optionally, one or more additional optical elements 202, 204 may be located within the first partial beam path 194 and/or within the second partial beam path 196. Thus, as an example, the additional optical elements 202, 204 may be adapted for individually controlling an intensity and/or a focus and/or other optical properties of the partial light beams 198, 200. Thus, as an example, one or more shutters and/or one or more attenuators such as one or more diaphragms may be present for individually controlling e.g. an intensity of the partial light beams 198, 200. Further, one or more lenses may be present within the additional optical elements 202, 204.

In the setup of FIG. 10, the spatial light modulator 114 itself acts as a beam splitting element 206. Additionally or alternatively, other beam splitting elements may be used for splitting a beam path 208 into at least one first partial beam path 194 and at least one second beam path 196. Thus, in FIG. 11, a setup of the optical detector is shown having a beam splitting element 206 being independent from the spatial light modulator 114. Again, as for FIGS. 9 and 10, the modulator device 118, the evaluation device 120, the object 124 and the beacon devices 122 are not shown and may be embodied as e.g. shown in FIGS. 3 and/or 4.

Figure 11:
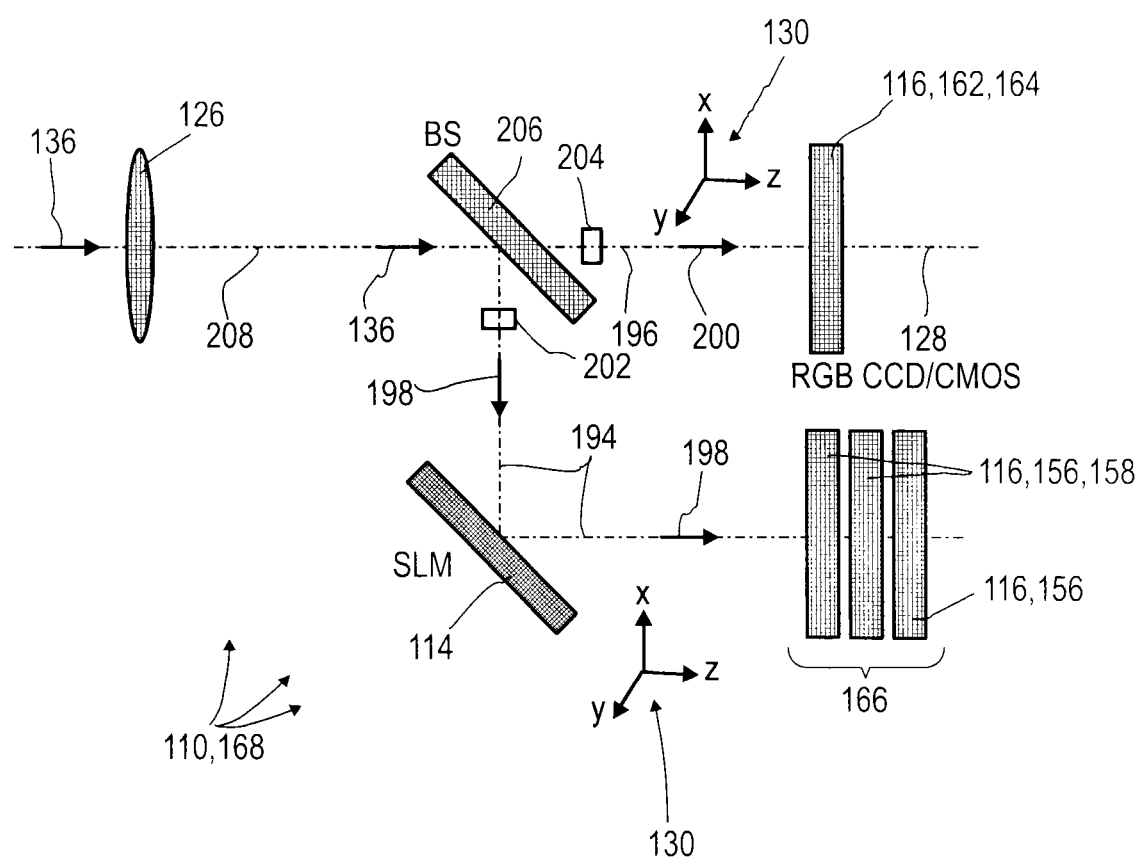

Again, in FIG. 11, the light beam 136 enters the optical detector 110 from the left, by passing the at least one transfer device 126, propagating along an optical axis and/or a beam path 208. Subsequently, by one or more beam splitting elements 206 such as one or more prisms, one or more semi-transparent mirrors or one or more dichroitic mirrors, the light beam 136 is split into a first partial light beam 198 travelling along a first partial beam path, and a second partial light beam 200, propagating along a second partial beam path 196. In this embodiment, the spatial light modulator is depicted as a reflective spatial light modulator, deflecting the first partial light beam 198 towards the stack of optical sensors 116. Alternatively, however, a transparent spatial light modulator 114 may be used, as in the setup of FIG. 3, thereby rendering the first partial beam path 194 straight. Alternatively, again, the setup as shown in FIG. 9 may be used for the first partial beam path 194.

As in the setup of FIG. 10, in the second partial beam path 196, at least one intransparent optical sensor 164 may be located, such as an imaging sensor, more preferably a CCD- and/or CMOS-chip, more preferably a full-color or RGB CCD- or CMOS chip. Thus, as in the setup of FIG. 10, the second partial beam path 169 may be dedicated to imaging and/or determining x- and/or y-coordinates, whereas the first partial beam path 194 may be dedicated to determining a z-coordinate, wherein, still, in this embodiment or other embodiments, an x-y-detector may be present in the first partial beam path 194. Again, as in the setup of FIG. 10, individual additional optical elements 202, 204 may be present within the partial beam paths, 194, 196.

Figure 12:
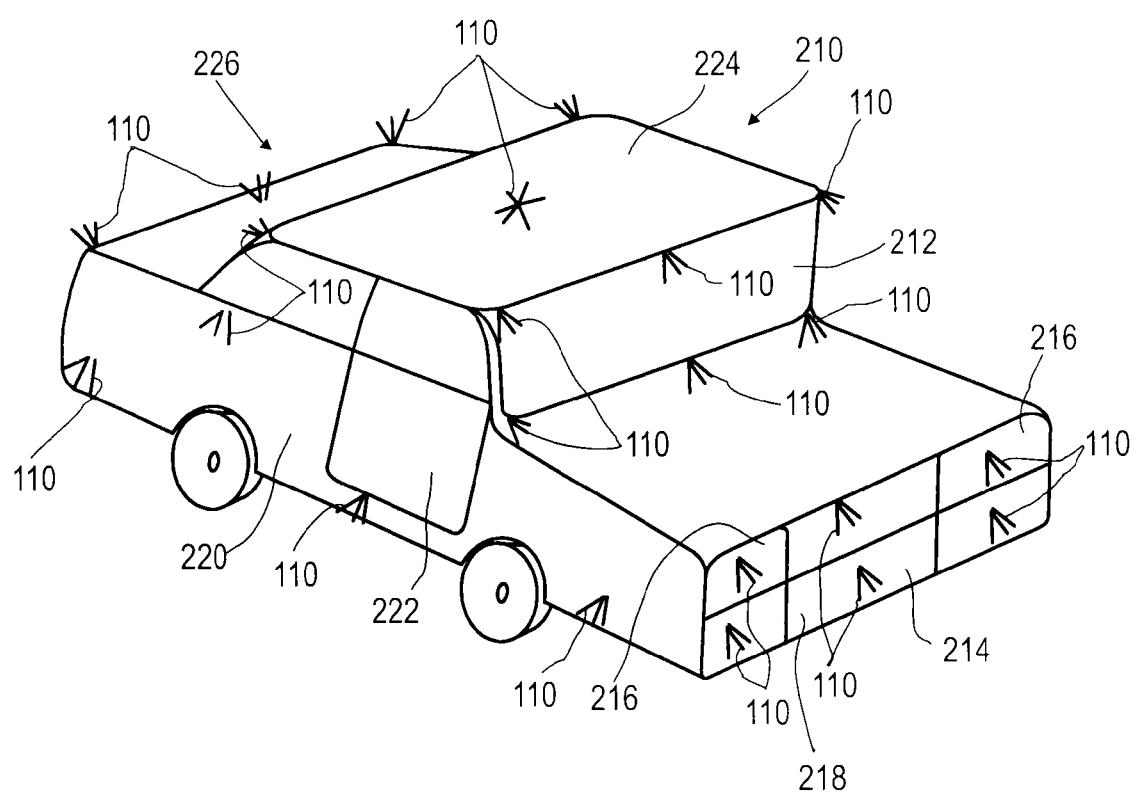
FIG. 12 shows potential application positions of the optical detector in a vehicle.

In FIG. 12, potential application positions of the optical detector 110 and/or the detector system 112 according to the present invention in automotive systems are shown. For potential applications, reference may be made to the disclosure given above.

Thus, in FIG. 12, as an exemplary embodiment of potential uses in automotive systems, a car 210 is shown in a simplified perspective view. Therein, various potential positions of optical detectors 110 and/or detectors systems 112 are shown, which may be used individually or in any arbitrary combination.

Thus, one or more optical detectors 110 may be used in the region of a windshield 212 of the car 210, such as in various positions surrounding the windshield 212 and/or even within the windshield 212, such as for use as rain sensors.

Further, one or more optical detectors 110 in the region of a front part 214 of car 210 may be present. These optical detectors 110 may be used as sensors in headlights 216 and/or bumpers 218. Similarly, which is not shown, one or more optical detectors 110 may be present in the rear bumpers and/or as sensors in the backlights. Thus, one or more of the optical detectors 110 may be used as distance sensors and/or for other assistance applications, such as one or more of the applications listed above. Thus, as an example, lane departure warning may be named as a potential application of one or more of the optical detectors 110.

Further, one or more optical detectors 110 may be present in the side region 220 of car 210. Thus, one or more optical detectors may be present at or near passenger doors 222, such as in order to avoid collisions of the doors with a solid objects.

Further, one or more optical detectors 110 may be present on a roof 224 of the car 210 and/or at a rear part 226. Thus, similar to the sensors in the front part 214, one or more optical detectors 110 in the rear part 226 may be used as a distance sensor, such as for parking assistance.

Figure 13:
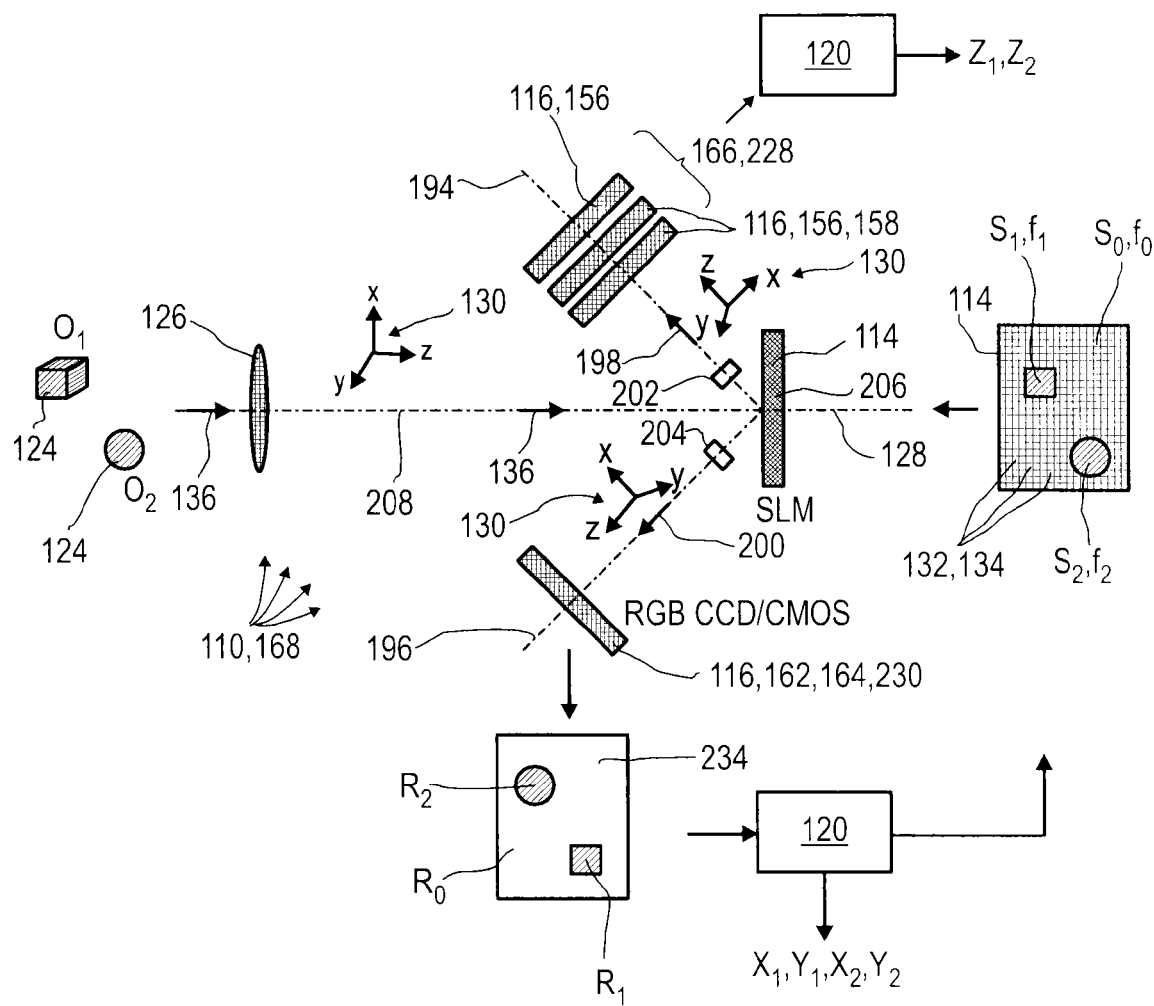
FIG. 13 shows a setup of an embodiment of the optical detector adapted for defining superpixels.
Figure 14:
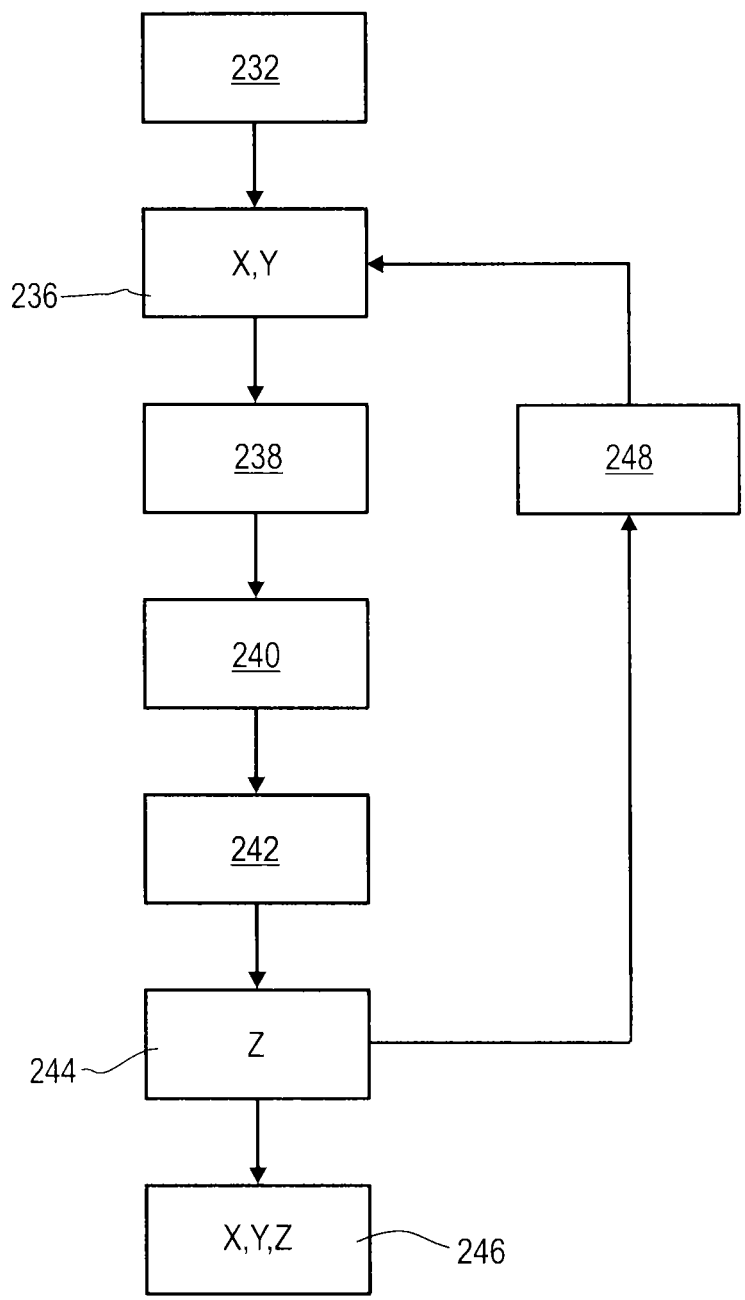
FIG. 14 shows a flow diagram of a method for detecting an object by using the optical detector of FIG. 13.

In FIGS. 13 and 14, a further embodiment of the present invention is shown which makes use of subdividing the matrix 132 of pixels 134 of the spatial light modulator 114 into superpixels. Therein, FIG. 13 shows a setup of the optical detector 110, whereas FIG. 14 shows a flow of a method for using the optical detector 110 and of a method of optical detection. Both figures will be explained in the following.

In this exemplary embodiment, the optical detector 110 is generally setup, in terms of hardware, as in the exemplary embodiment shown in FIG. 10. Thus, for details of the setup, reference may be made to the description of FIG. 10 above. Thus, a split beam path is used in the setup, specifically a W-shaped setup. Still, it shall be noted that other setups are feasible, such as the split beam path setup shown in FIG. 11 or the non-split beam path setup is shown in the embodiments of FIG. 3, 4 or 9.

As outlined above, the optical detector 110 comprises the stack 166 of optical sensors 116 which, individually or in common, act as at least one FiP-sensor 228 for z-detection, i.e. for determining at least one z-coordinate of at least one object 124. In this embodiment, stack 166 is arranged in the first partial beam path 194. Further, the optical detector 110 comprises, for example in the second beam path 196, an image sensor 230, which may be a pixelated optical sensor 116 and which may also be referred to as an image detector or an imaging device. As an example and as outlined above, image sensor 230 may be or may comprise one or more CCD and/or CMOS sensors, such as monochrome CCD and/or CMOS sensors, multi-chrome CCD and/or CMOS sensors or full-color CCD and/or CMOS sensors. Thus, by using the at least one FiP-sensor 228, a determination of at least one longitudinal coordinate or z-coordinate of at least one object 124 detected by the optical detector 110 is possible, whereas, by using the at least one image sensor 228, a 2D imaging of the at least one object 124 is possible.

In the exemplary setup shown in FIG. 13, a scene comprising two objects, denoted by $O_1$ and $O_2$, is captured by the optical detector 110. As can be seen in FIG. 14, in a first method step 232, a 2D image 234 of the scene is captured by using the at least one image sensor 228. In a subsequent method step, referred to as method step 236 in FIG. 14, two or more regions are detected in the 2D image 234. Thus, corresponding to objects $O_1$ and $O_2$ in FIG. 13, two or more regions may be defined in the 2D image 234, which are denoted by $R_1$ and $R_2$. Further, optionally, a background region may be defined, denoted by $R_0$. The regions may be defined by determining their respective transversal coordinates or coordinate ranges in the 2D image 234, as symbolically denoted by $x_1$, $y_1$, $x_2$, $y_2$ in FIG. 13 or by x, y in step 236 of FIG. 14. Consequently, image sensor 230 may act as a transversal optical sensor. For potential techniques of defining the regions, reference may be made to the above-mentioned algorithms. As an example, boundaries of regions $R_1$ and $R_2$ may be detected by detecting gradients of intensity or color. As depicted in FIG. 13, the detection of the regions may take place within the at least one evaluation device 120, which may provide at least one data processing device with an appropriate software for image recognition and/or image analysis.

In a further step, denoted by reference number 238 in FIG. 14, superpixels are assigned to the regions. For this purpose, pixels 134 of the spatial light modulator 114 are defined which correspond to regions $R_0$, $R_1$ and $R_2$ in the 2D image 234. Thus, due to known transmission properties, it is generally known or may generally be determined which components of the light beam 136 or partial light beam 200 pass which pixels 134 before hitting corresponding pixels of the image sensor 230. Consequently, a known or determinable relationship, which, e.g. may be a calculated analytical relationship or an empirical or semi-empirically relationship, between pixels of the spatial light modulator 114 and the image sensor 230 may be used.

By defining superpixels, in FIG. 13 referred to as $S_0$, $S_1$ and $S_2$, modulation frequencies may be assigned to the corresponding superpixels, as denoted by $f_0$, $f_1$ and $f_2$ in FIG. 13. The step of assigning modulation frequencies to the superpixels is denoted by reference number 240 in FIG. 14. Subsequently (step 242 in FIG. 14), the superpixels are modulated with their corresponding modulation frequencies. Consequently, each pixel 134 of a superpixel is modulated with the corresponding modulation frequency assigned to the respective superpixels. Further, sub-modulations, i.e. subdivisions of each superpixels and assigning additional modulations to the subdivisions, are possible.

Further, in step 244 in FIG. 14, a z-detection of one or more than one or even all of the superpixels takes place. For this purpose, the at least one optical sensor 116 acting as a FiP-sensor 228 is used, which may also be referred to as a longitudinal optical sensor since a longitudinal coordinate is determined by using this optical sensor. Thus, as an example and as shown in FIG. 13, the stack 166 may be used. The at least one signal of the stack 166 is demodulated in a frequency-selective way, by using $f_0$, $f_1$ and $f_2$ as demodulation frequencies and by individually evaluating the signal components corresponding to these demodulation frequencies, in order to determine the z-coordinates. Thus, for example, z-coordinates $z_1$ and $z_2$ may be determined for objects $O_1$ and $O_2$. Thereby (step 246 in FIG. 14), a 3D image of the scene captured by the optical detector 110 or a part of this scene, such as of one or more of the objects 124 comprise therein, may be generated, by combining the transversal coordinates generated in step 236 with the longitudinal coordinates determined in step 244. Thus, as an example, for each object 124 or for one or more of objects 124 comprised within a scene, transversal coordinates or coordinate ranges $x_1$, $y_1$, $x_2$, $y_2$ may be combined with corresponding z-coordinates $z_1$ and $z_2$, thereby generating 3D coordinates $(x_1, y_1, z_1)$ and $(x_2, y_2, z_2)$ of objects $O_1$ and $O_2$. Again, steps 244 and/or 246 may be performed by the at least one evaluation device 120.

As will be evident to the skilled person, the setup and scheme shown in FIGS. 13 and 14 simply denotes a simplified way of 3D imaging. More complex scenes may be captured by the optical detector 110. Further, more complex objects 124 as schematically depicted in FIG. 13 may be used, such as objects 124 which, in itself, comprise a plurality of parts or components. These parts are components of the at least one object 112 themselves may be regarded as objects 112 and, consequently, their 2D images may be defined as separate regions in the 2D image 234. Consequently, separate superpixels may be assigned to these object parts.

Further, as symbolically depicted by reference number 248 in FIG. 14, the procedure shown in FIG. 14, the procedure, as a whole or partly, may be performed iteratively. Thus, as an example, a refining of the regions and/or superpixels may take place, such as in case a large range of z-coordinates is detected in step 244 within one superpixel. Thus, detecting a large range of z-coordinates for one region and/or superpixel may indicate that a corresponding object 124 has a depth along a z-axis. Consequently, the corresponding region and/or superpixel may be refined or subdivided into a plurality of regions and/or superpixels. As an example, region $R_7$ corresponding to spherical object $O_2$ may be subdivided into two or more concentric annular regions in order to fully recognize the depth of this spherical object. This refining 248 may take place for one or more of the object or components contained within a scene or for the full scene. Thereby, the detection procedure may start with a simplified setup and with a simplified approach, such as with a few regions and/or superpixels, followed by one or more iterations for refining the findings and for obtaining more detailed information for one, more than one or even all objects contained within the scene.

Figure 15:
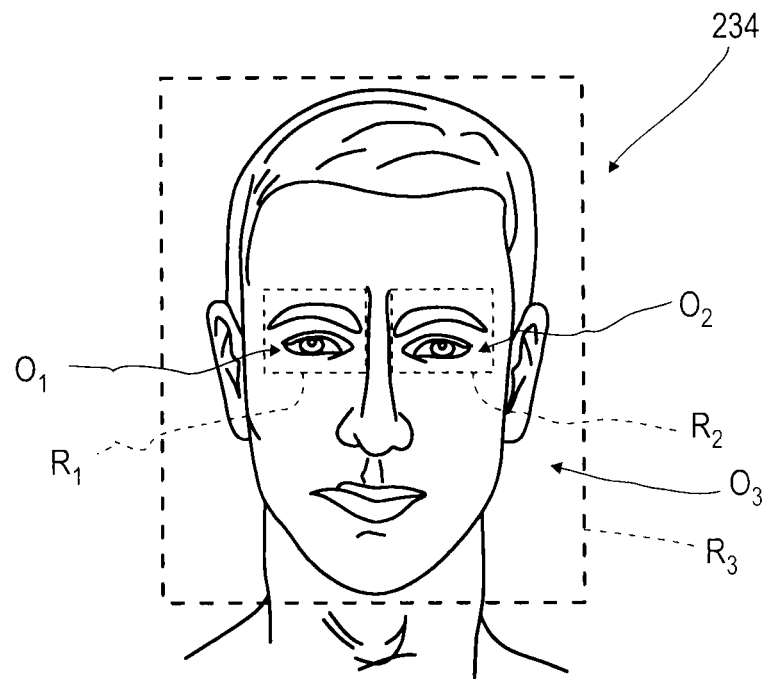
FIGS. 15 and 16 show embodiments of object following.
Figure 16:
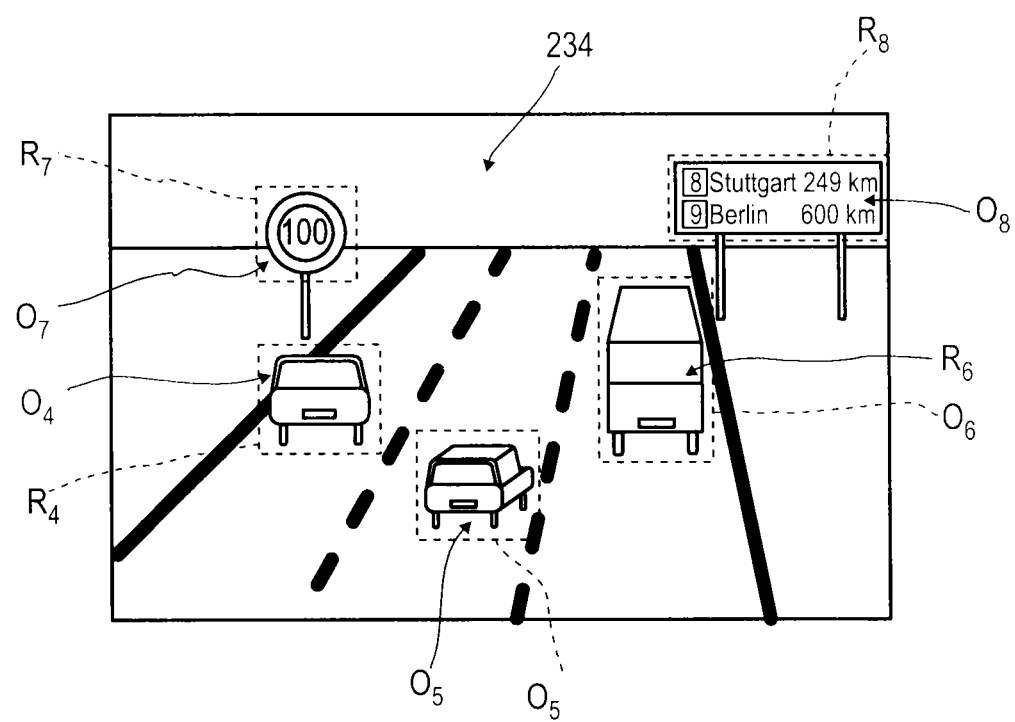

In FIGS. 15 and 16, the principle of object following, as possible with the optical detector 110 according to the present invention, shall be explained. Thus, by using an image sensor 230 such as in a setup as explained with reference to FIG. 13, an image 234 is taken. In the exemplary embodiment shown in FIG. 15, the image may be the image of a human head or face. In the embodiment shown in FIG. 16, the image may be a scene in traffic, such as in a field of view of a front camera in a vehicle on a motorway.

Within the image 234, by using appropriate image recognition algorithms and/or by using a specific training, one or more objects may be recognized. As an example, eyes may be recognized, marked by $O_1$ and $O_2$ in FIG. 15. Similarly, a facial region may be recognized, marked by $O_3$ in FIG. 15. In the traffic scene of FIG. 16, various vehicles $O_4$-$O_6$ may be recognized. Additionally or alternatively, road signs Or, 08 may be recognized, such as road signs indicating speed limits and/or indicating distances to various cities along the road. These objects $O_1$-$O_8$ each may be assigned corresponding regions $R_1$-$R_8$, in the images 234, wherein the regions might be simplified geometric patterns of various shapes within the images 234, such as boxes, rectangles or squares.

As explained above with reference to FIG. 13, each of these regions $R_1$-$R_8$ may be assigned to corresponding superpixels of the spatial light modulator 114. Consequently, instead of analyzing the entire image 234, image analysis may be reduced to a following or tracking of objects $O_1$-$O_8$. For this purpose, the superpixels corresponding to the regions $R_1$-$R_8$ may be tracked by retrieving z-coordinates for the at least one frequency assigned to the at least one region or, in this embodiment, regions $R_1$-$R_8$, only. For each of the objects, a distance may thus be determined. In a series of images such as an ongoing camera movie capturing a scene, in each image or in a plurality of the images, the one or more objects of interest may be detected, followed by assigning one or more superpixels to these objects and determining z-coordinates and/or distances for these objects only, by using the longitudinal optical sensor, specifically the FiP-sensor 228.

Figure 17:
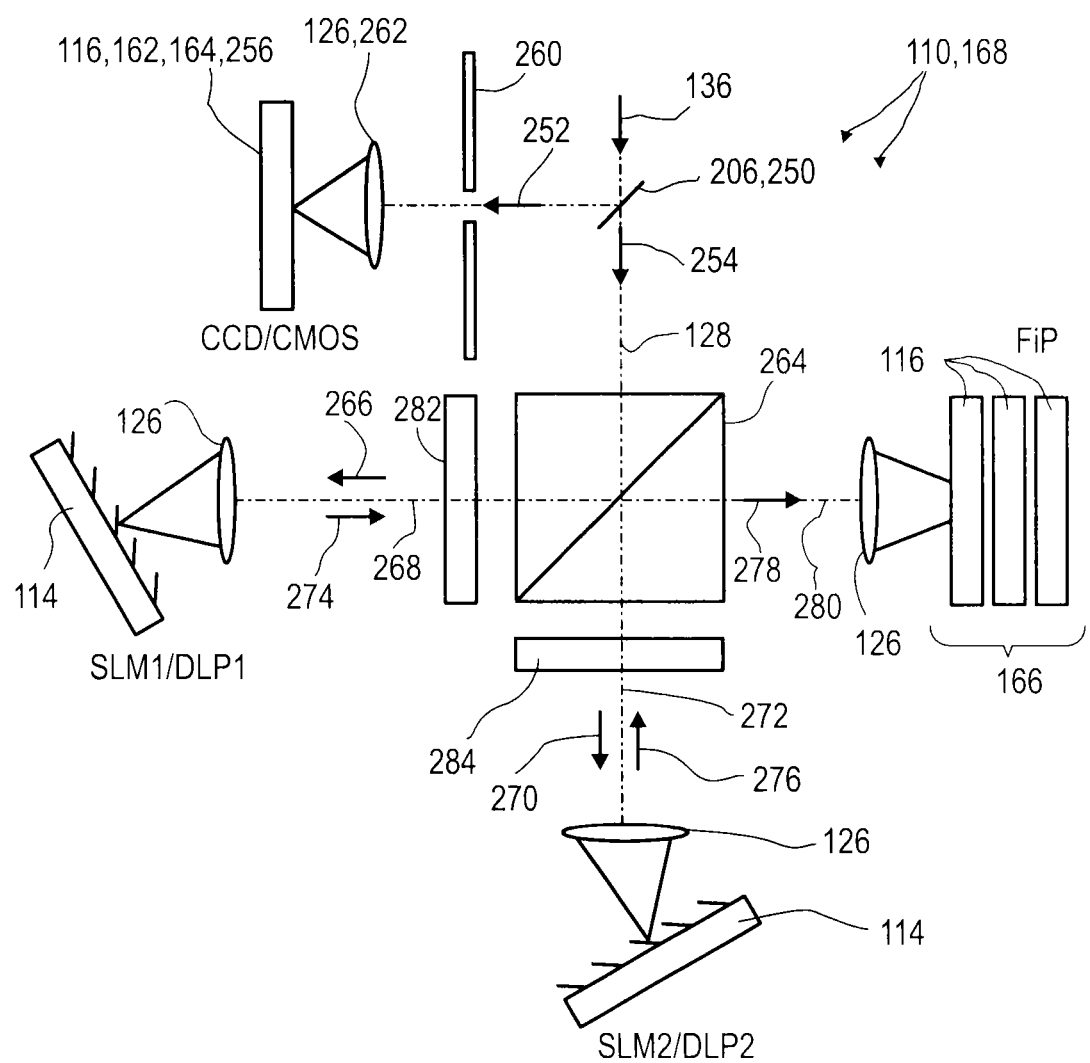
FIG. 17 shows an embodiment of a cross-shaped setup of an optical detector having to beam splitters.
Figure 18:
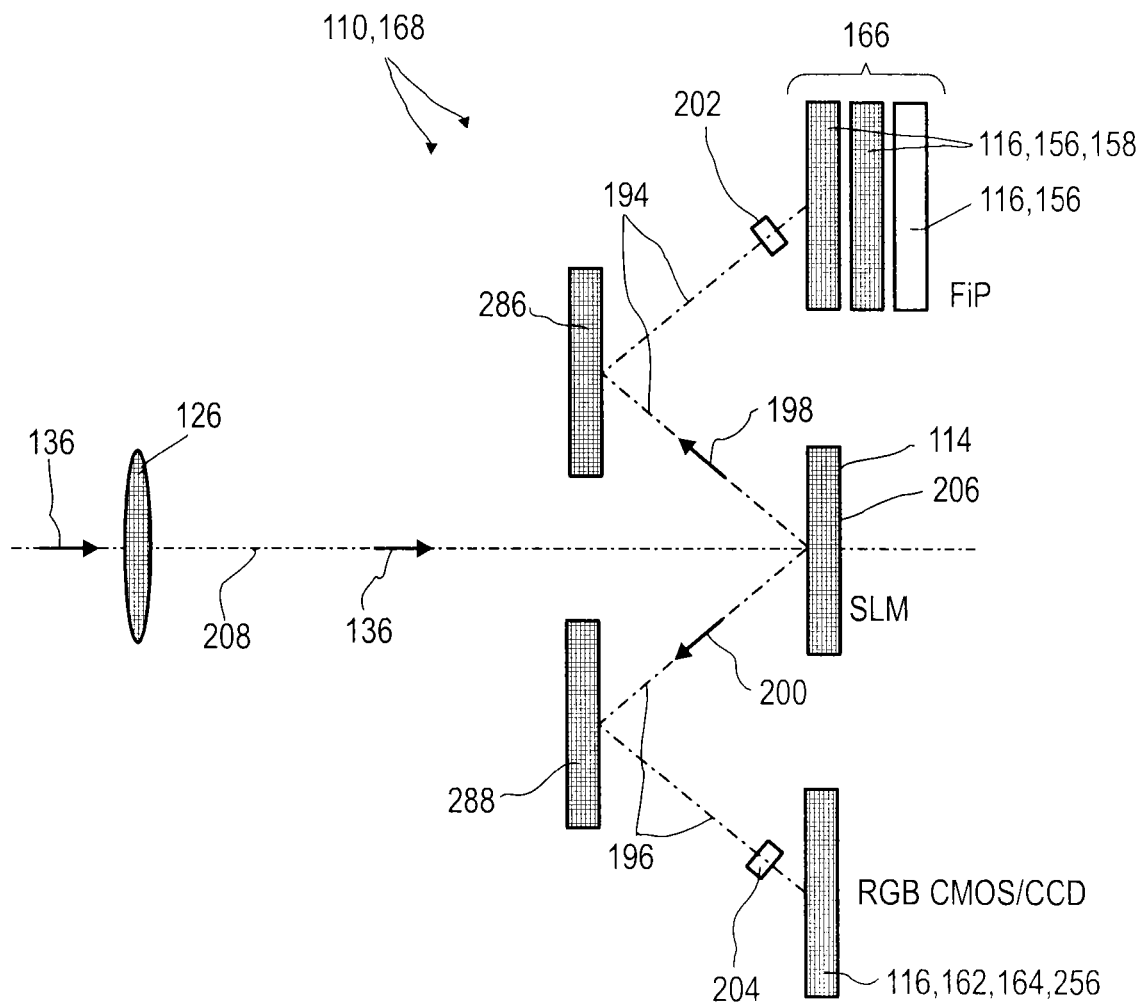
FIG. 18 shows an alternative embodiment of a W-shaped setup of an optical detector.

In FIGS. 17 and 18, alternative setups of the optical detector 110 and/or the camera 168 are shown. Again, as for the setup in FIG. 11, an incoming light beam 136 is split up into a plurality of partial light beams. In the embodiment of FIG. 17, an optical detector 110 is shown which may also serve as an exemplary embodiment of a camera 168. An incoming light beam 136, traveling along an optical axis 128 of the optical detector 110, hits a first beam-splitting element 250 which is adapted to separate a first partial light beam 252 from a main light beam 254. The first partial light beam 252 may have an intensity significantly lower as compared to the main light beam 254, since the first partial light beam 252 serves the purpose of observation of an object, from which the light beam 136 originates, by an imaging device 256, such as a CCD and/or CMOS chip, as in the embodiment of FIG. 11. As an example, the first partial light beam 252 may have an intensity of less than one half of the main light beam 254. As an example, the first beam-splitting element 250 may divide the incoming light beam 136 by a ratio of 10 to 90. For this purpose, the transparency of the first beam-splitting element 250 may be adjusted and/or an overall surface area of the first beam-splitting element may be adjusted.

The first partial light beam 252 may be modified by various optical elements. As an example, in a first partial beam path 258, between the first beam-splitting element 250 and the imaging device 256, at least one diaphragm 260 and/or at least one transfer device 126, such as at least one lens system 262, may be located. Other embodiments are feasible.

The main light beam 254 continues traveling along the optical axis 128 and meets a second beam-splitting element 264. As an example, the second beam-splitting element 264 may be or may comprise a beam-splitter cube, preferably a polarizing beam-splitter cube. The second beam-splitting element 264 splits up the main light beam 254 into a second partial light beam 266 traveling along a second partial beam path 268 and a third partial light beam 270 traveling along a third partial beam path 272. The second partial light beam 266 hits a first spatial light modulator 114, referred to as SLM 1 or DLP 1 in FIG. 17. Similarly, the third partial light beam 270 hits a second spatial modulator 114, referred to as SLM 2 or DLP 2 in FIG. 17. The first and second spatial light modulators, in this specific embodiment, specifically may be reflective spatial light modulators, specifically reflective spatial light modulators based on the DLP® technology. Other types of spatial light modulators are feasible. By the first and second spatial light modulators, the second and third partial light beams 266 and 270 are back-reflected along the second and third partial beam path 268 and 272, respectively, to form back-reflected partial light beams 274 and 276. In the second beam-splitting element 264, the back-reflected partial light beams 274, 276 are re-united to form a common light beam 278 traveling along a fourth partial beam path 280 towards a stack 166 of optical sensors 116, which may act as a longitudinal optical sensor for determining a z-coordinate of an object from which the light beam 136 travels towards the optical detector 110.

Before being re-united to form the common light beam 278, the partial light beams 266, 270 may be subject to various operations. Thus, generally, the partial light beam 266 may have a polarization perpendicular to the plane of view of FIG. 17. By using a first half-wave-plate 282, the polarization of partial light beam 266 may be turned into the plane of view of FIG. 17. The back-reflection by SLM 1 may, again, turn the direction of polarization of this partial light beam 266, such that back-reflected partial light beam 274 may, again, have a polarization perpendicular to the plane of view in FIG. 17. The first half-wave-plate 282, however, again, turns polarization into the plane of view of FIG. 17, thereby allowing a transmission of the back-reflected partial light beam 274 towards the stack 166.

Similarly, the third partial light beam 270, after passing the polarization beam splitter cube 264, has a polarization parallel to the plane of view of FIG. 17. After passing second half-wave-plate 284, after back-reflection at SLM 2 and after, again, passing the second half-wave-plate 284, the back-reflected third partial light beam 276 has a polarization perpendicular to the plane of view in FIG. 17 and, consequently, is deflected by the second beam-splitting element 264 towards the stack 166. Thus, back-reflected partial light beams 274, 276 are both deflected towards stack 166 and may form the common light beam 278.

Further, various types of transfer devices 126 may be located within the second and third partial beam path 268 and 272, such as one or more lenses, as depicted in FIG. 17. Other embodiments are feasible.

The first and second spatial light modulators SLM 1, SLM 2 may be adapted to modulate partial light beams 266, 270, in the same way or in a different way. Thus, generally, in case a plurality of spatial light modulators 114 is used, as e.g. in the embodiment of FIG. 17, the plurality of spatial light modulators 114 may be driven in a synchronized way. However, other modes of operation are feasible.

The setup as shown in FIG. 17 implies various advantages. Thus, the setup generally makes use of the fact that, typically, less light is needed for imaging device 256, as compared e.g. to the detection of the z-coordinate by using the FiP-sensor. Thus, by using the first beam-splitting element 250, 10% or a similar energy or intensity of the incoming light beam 136 may be separated off, for the purpose of the imaging device 256. 90% or a similar, larger amount of the incoming light beam 136 may continue towards the longitudinal optical sensor, such as the FiP.

Typically, a picture of the object from which light beam 136 travels towards the optical detector 110, should be in focus with the spatial light modulators SLM 1, SLM 2. However, most commercial versions of reflective spatial light modulators, such as DLP® chips, are generally not designed for a straight back-reflection but for a back-reflection under a certain angle. Therefore, it might be necessary to use asymmetrical lens systems allowing for an in-focus picture on each of the spatial light modulators SLM 1, SLM 2, which are not perpendicular to the optical axis. These options, however, shall be included when referring to a "back reflection".

It shall be noted that the various ideas shown in the embodiment of FIG. 17 may be combined in an arbitrary fashion. Thus, generally, the idea of splitting off a minor part of the incoming light beam 136 for the purpose of imaging by at least one imaging device 256 may be used independently from the idea of using a plurality of spatial light modulators 114 and/or may be used independently from the further treatment of main light beam 254. Similarly, the idea of using a plurality of spatial light modulators 114, which may fully or partially be transmissive or reflective spatial light modulators 114, may be used independently from the idea of imaging by using at least one imaging device 262 and/or independently from the idea of re-uniting partial light beams 266, 270 by spatial light modulators SLM 1, SLM 2. Further, it shall be noted that various additional optical elements may be present in the setup of FIG. 17, such as one or more additional transfer devices 126. Thus, as shown in FIG. 17, an additional transfer device 126, such as an additional lens system, may be located in front of the stack 166. Further, the optical elements shown in FIG. 17 may fully or partially have non-reflecting properties, such as using one or more anti-reflection coatings. Thus, as an example, the half-wave-plates 282, 284 each may have appropriate anti-reflection coatings, as well as the transfer devices 126. Further, modifications of the setup of FIG. 17 as well as of other setups using one or more imaging devices, such as the setup shown in FIGS. 10 and 11, refer to the type of imaging device which may be used. Thus, generally, the CCD/CMOS devices shown in FIGS. 10, 11 and 17 may generally be replaced by other types of imaging devices, such as infrared cameras, e.g. thermographic cameras. Thus, in addition or as alternatives to the imaging devices shown in the figures, infrared cameras may be used, in order to record heat radiation and/or in order to combine a depth picture with an infrared or heat information. A thermographic camera may generally be integrated into the optical system by using wavelength-dependent beam-splitting elements. Thus, as an example, an infrared camera or thermographic camera may be integrated into the optical detector 110 by separating infrared partial light beams off the incoming light beam 136 by using wavelength-selective beam-splitting elements, such as infrared beam splitter or a hot plate. This setup of the optical detector 110 may generally be useful for tracking living beings, such as for gaming applications. The same modifications as discussed with regard to FIGS. 10, 11 and 17 may as well be applied to other setups of the present invention, such as the setup of the optical detector 110 as shown in FIG. 18, which will be discussed below.

In FIG. 18, a modification of the setup of the optical detector of FIG. 10 is shown. Thus, generally, reference may be made to the disclosure of FIG. 10 above. Thus, based on the W-shaped setup of FIG. 10, the setup of FIG. 18 contains additional reflective elements 286, 288 located within the first and second partial beam path 194, 196. Thus, first and second partial light beams 198, 200 may be deflected by these reflective elements 286, 288, which may be or may comprise one or more mirrors. Thus, in the optical setup of optical detector 110, lens systems, as e.g. contained within the optional additional optical elements, e.g. 202, 204, typically require some considerable space. Still, in most commercial reflective spatial light modulators 114, the angle of reflection is limited and rather small. Consequently, a placement of lens systems of incoming light beams in close proximity to the lens systems may be located in front of the stack 166 and/or in front of the imaging device 256 and may not be feasible in the setup of FIG. 10. By using the additional reflective element 286, 288, additional space may be gained, for the purpose of the placement of additional optical elements 202, 204, specifically in front of the longitudinal optical sensor such as the FiP-sensor and/or in front of the imaging device 256.

Specifically, the at least one reflective element 286, 288 may comprise at least one mirror. The at least one mirror may be or may comprise at least one planar mirror. Additionally, or alternatively, the at least one reflective element 286, 288 may as well comprise on or more curved mirrors, such as one or more convex and/or concave mirrors. Thus, one or more lenses may be replaced by one or more curved mirrors. Consequently, optical detector 110 may even replace one or more lenses by curved mirrors, in order to save additional space, reflective elements 286, 288 each may have focusing properties in order to focus partial light beams 198, 200, respectively, onto the longitudinal optical sensor stack 166 and/or onto the imaging device 256.

Figure 19:
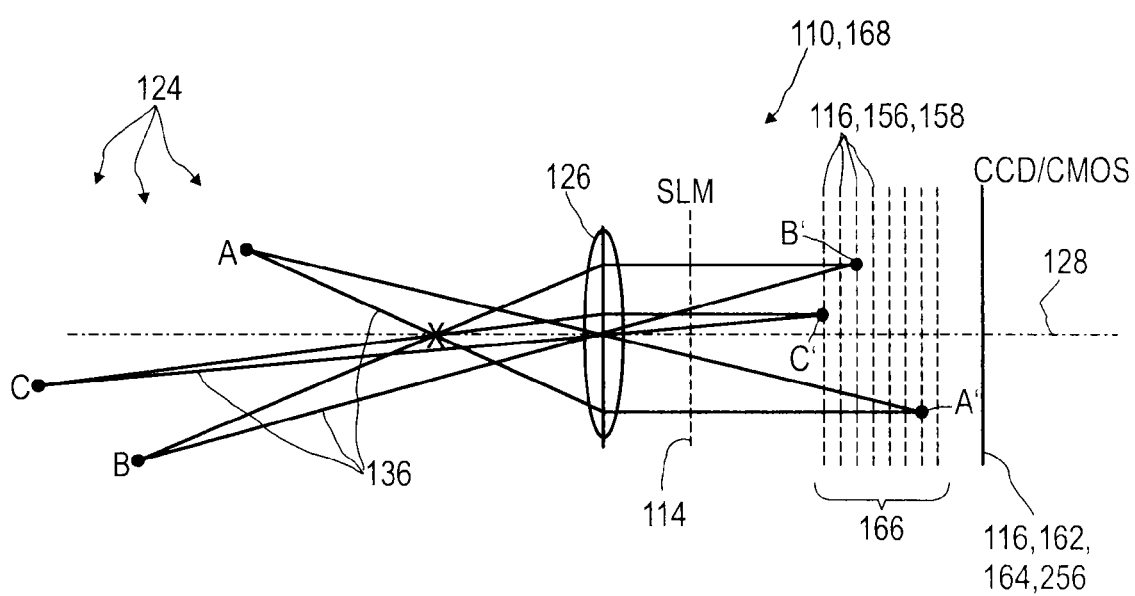
FIG. 19 shows an arrangement of the optical detector to be used as a light-field camera.

In FIG. 19, a schematic setup of an optical detector 110 to be used as a light-field camera is shown. Basically, the setup shown in FIG. 19 may correspond to one or more of the embodiments shown in FIG. 3 or 4 or any other of the embodiments shown herein. The optical detector 110 comprises at least one spatial light modulator 114 and a stack 166 of optical detectors 110, preferably large-area optical sensors 156, more preferably transparent optical sensors 158. As an example, organic optical sensors 160, such as organic solar cells, specifically sDSCs may be used. In addition, the optical detector 110 may comprise at least one transfer device 126 such as at least one lens or lens system, adapted for imaging objects 124. Additionally, the optical detector 110 may comprise at least one imaging device 256, such as a CCD and/or a CMOS imaging device.

As outlined above, the optical detector 110 in the embodiment shown herein is suited to act as a light-field camera. Thus, light-beams 136 propagating from various objects 124, symbolically denoted by A, B and C in FIG. 19, are focused by the transfer device 126 into corresponding images, denoted by A', B' and C' in FIG. 19. By using the stack of optical sensors 116, in combination with the above-mentioned action of the spatial light modulator 114, a three-dimensional image may be captured. Thus, specifically in case the optical sensors 116 are FiP-sensors, i.e. sensors for which the sensor signals are dependent on the photon density, the focal points for each of the light beams 136 may be determined, by evaluating sensor signals of neighboring optical sensors. Thus, by evaluating the sensor signals of the stack 166, beam parameters of the various light beams 136 may be determined, such as a focal position, spreading parameters or other parameters. Thus, as an example, each light beam 136 and/or one or more light beams of interest may be determined in terms of their beam parameters and may be represented by a parameter representation and/or vector representation. Thus, since the optical qualities and properties of the transfer device 126 are known, as soon as the beam parameters of the light beams 136 are determined by using the stack 166, a scene captured by the optical detector 110, containing objects 124, may be represented by a simplified set of beam parameters. For further details of the light-field camera shown in FIG. 19, reference may be made to the description of the various possibilities given above.

Figure 20:
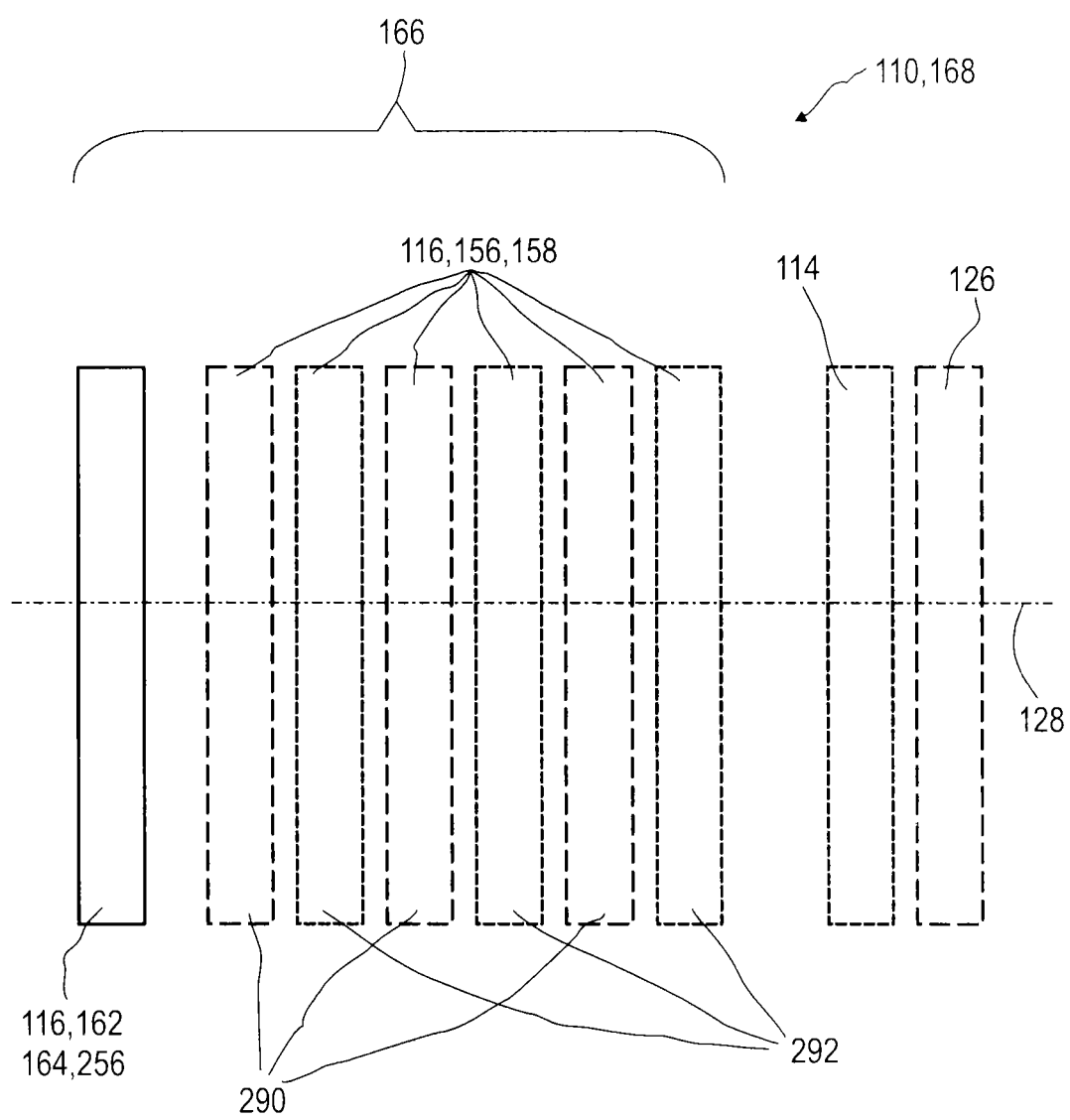
FIG. 20 shows an exemplary arrangement of a stack of colored optical sensors for use in the setup of FIG. 19.

Further, as outlined above, the optical sensors 116 of the stack 166 of optical sensors may have different wavelength sensitivities. Thus, the stack 166 may, besides the optional imaging device 256, comprise two types of optical sensors 116. This possibility is schematically shown in FIG. 20. Therein, a first type 290 and a second type 292 of optical sensors 116 is provided in the stack 166. The optical sensors 116 of the first type 290 and the second type 292 specifically may be arranged in an alternating fashion along the optical axis 128, as shown in FIG. 20. The optical sensors 116 of the first type 290 may have a first spectral sensitivity, such as a first absorption spectrum, such as a first absorption spectrum defined by a first dye, and the optical sensors 116 of the second type 292 may have a second spectral sensitivity different from the first spectral sensitivity, such as a second absorption spectrum, such as a second absorption spectrum defined by a second dye. By evaluating sensor signals of these two types of optical sensors 116, color information may be obtained. Thus, in addition to the beam parameters which may be derived, as explained above with reference to FIG. 19, the two or more types of optical sensors 116 allow for deriving additional color information, such as for deriving a full-color three-dimensional image. Thus, as an example, color information may be derived by comparing the sensor signals of the optical sensors 116 of different color with values stored in a look-up table. Thus, the setup of FIG. 19, by implementing the color recognition as shown in FIG. 20, may be embodied as a full-color or multicolor light-field camera.

Figure 21:
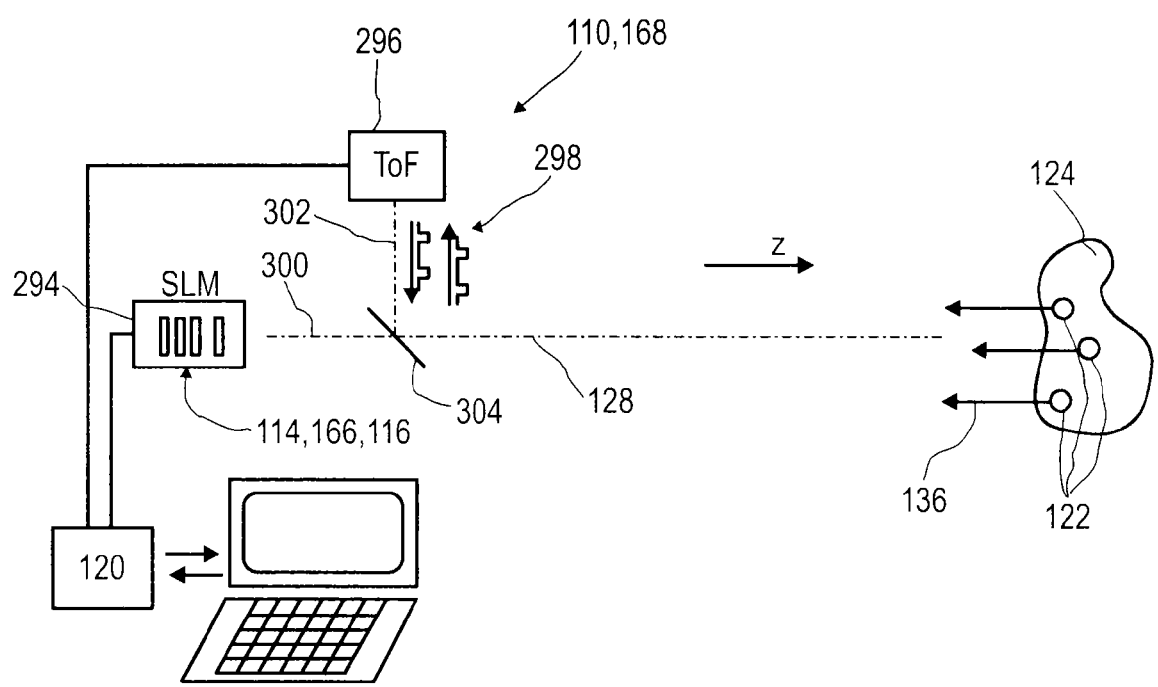
FIG. 21 shows an exemplary arrangement of an implementation of a time-of-flight detector into the optical detector.

As outlined above, the optical detector 110 may further comprise one or more time-of-flight detectors. This possibility is shown in FIG. 21. The optical detector 110, firstly, comprises at least one SLM detector 294, including the SLM 114 and the stack 166 of optical sensors 116, optionally including an imaging device 256. For details of potential setups of the SLM detector 294, reference may be made to the embodiments shown in e.g. in FIG. 3 or 4 or other embodiments of the optical detector 110. Basically any setup of the optical detector 110 as disclosed above may also be used in the context of the embodiment shown in FIG. 21.

Further, the optical detector 110 comprises at least one time-of-flight (ToF) detector 296. As shown in FIG. 21, the ToF detector 296 may be connected to the evaluation device 120 of the optical detector 110 or may be provided with a separate evaluation device. As outlined above, the ToF detector 296 may be adapted, by emitting and receiving pulses 298, as symbolically depicted in FIG. 21, to determine a distance between the optical detector 110 and the object 124 or, in other words, a z-coordinate along the optical axis 128.

The at least one optional ToF detector 296 may be combined with the at least one SLM detector 294 in various ways. Thus, as an example and as shown in FIG. 21, the at least one SLM detector 294 may be located in a first partial beam path 300, and the ToF detector 296 may be located in a second partial beam path 302. The partial beam path 300, 302 may be separated and/or combined by at least one beam-splitting element 304. As an example, the beam-splitting element 304 may be a wavelength-indifferent beam-splitting element 304, such as a semi-transparent mirror. Additionally or alternatively, a wavelength-dependency may be provided, thereby allowing for separating different wavelengths. As an alternative, or in addition to the setup shown in FIG. 21, other setups of the ToF detector 296 may be used. Thus, the SLM detector 294 and the ToF detector 296 may be arranged in line, such as by arranging the ToF detector 296 behind the SLM detector 294. In this case, preferably, no intransparent optical sensor 164 is provided in the SLM detector 294. Again, as an alternative or in addition, the ToF detector 296 may also be arranged independently from the SLM detector 294, and different light paths may be used, without combining the light paths. Various setups are feasible.

As outlined above, the ToF detector 296 and the SLM detector 294 may be combined in a beneficial way, for various purposes, such as for resolving ambiguities, for increasing the range of weather conditions in which the optical detector 110 may be used, or for extending a distance range between the object 124 and the optical detector 110. For further details, reference may be made to the description above.

Figure 22:
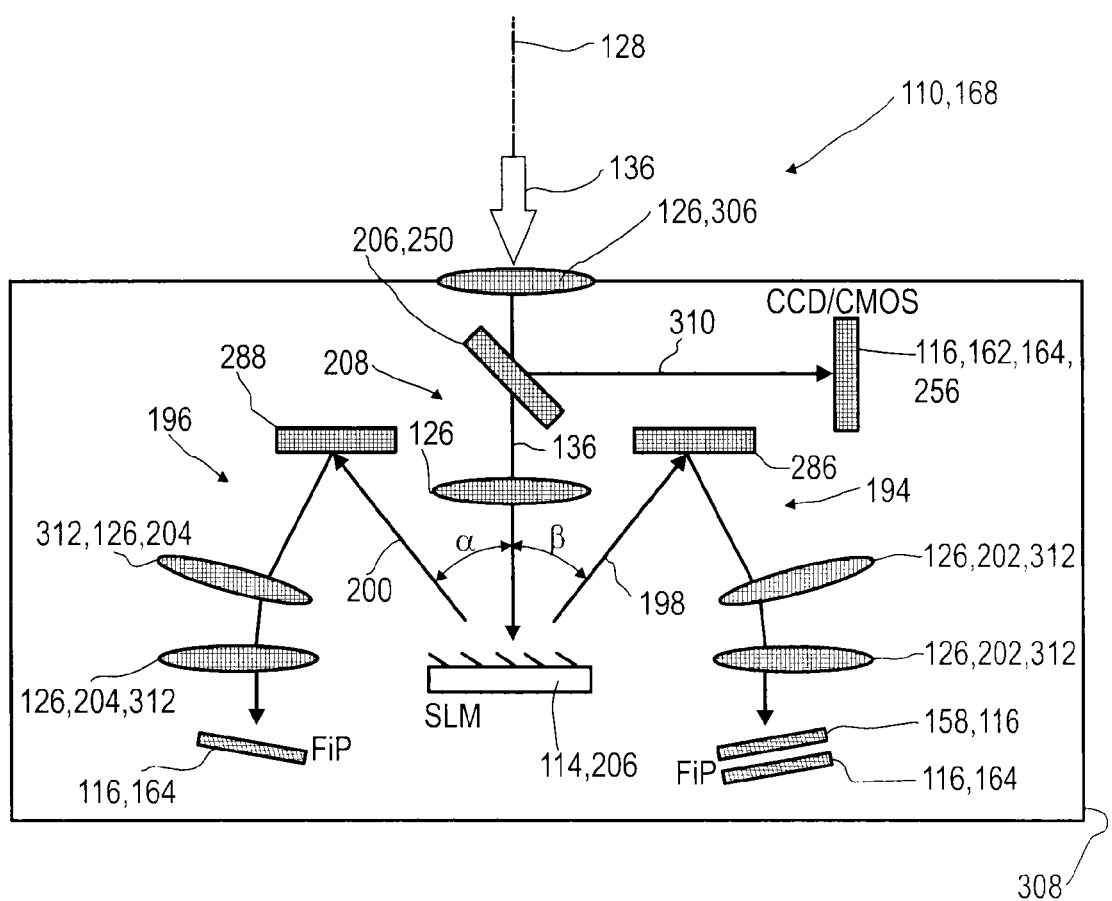
FIGS. 22 and 23 show alternative embodiments of the W-shaped setup of the optical detector of FIG. 18.

In FIG. 22, a modification of the embodiment of the optical detector 110 and the camera 168 of FIG. 18 is shown. The setup widely corresponds to the setup of FIG. 18, so for most parts reference may be made to the description of FIG. 18. The light beam 136 may enter the detector 110 via a first lens 306 which may form part of the transfer device 126. The detector 110, as an example, in this embodiment as well as other embodiments may comprise a casing 308, and the first lens 306 may form an entry lens.

Having passed the first lens 306, optionally, as in the setup of FIG. 17, an imaging partial light beam 310 may be split off by a beam-splitting element 206 which, in this case, may form a first beam-splitting element 250. The imaging partial light beam 310 may be analyzed by at least one imaging device 256, as in FIG. 17, with or without an additional lens. In this regard, reference may be made to the description of FIG. 17 above.

The remaining main light beam 136 transmitted by the first beam-splitting element 250 is split up into first and second partial light beams 198, 200, as in FIG. 18, by the reflective spatial light modulator 114, the first and second partial light beams 198, 200 propagating along first and second partial beam paths 194, 196, respectively.

The optical setup of the first and second partial beam paths 194, 196, in the embodiment shown in FIG. 22 is slightly modified as compared to the setup of FIG. 18. Thus, firstly, both partial beam paths 194, 196 may contain optical sensors 116 configured as FiP sensors, i.e. sensors exhibiting the above-mentioned FiP effect. As outlined above, an imaging function may be performed by splitting off the imaging partial light beam 310 and analyzing the site being by using imaging device 256. Consequently, optionally, both partial beam paths 194, 196, large-area optical sensors 116 may be used.

Generally, transparent optical sensors 158 are less sensitive than intransparent optical sensors 164. The setup of the detector 110 depicted in FIG. 22 allows for reducing the number of transparent optical sensors 158, such as by using only one transparent optical sensor 158. Thus, in the exemplary embodiment shown in FIG. 22, at the end of the second partial beam path 196, and intransparent optical sensor 164 is placed, such as an intransparent HP sensor. At the end of the first partial beam path 194, a combination of optical sensors 116 may be placed, having one transparent optical sensor 158, followed by an intransparent optical sensor 164. Both the transparent optical sensor 158 and the intransparent optical sensor 164 may be embodied as FiP sensors. Consequently, the setup of FIG. 22 may contain only one transparent optical sensor 158.

Generally, most preferably, both the reflective spatial light modulator 114, such as the DLP, and the optical sensors 116 are oriented perpendicular to the incoming light beam 136 in their respective positions, i.e. are oriented perpendicular to a local optical axis and/or are oriented perpendicular to the main direction of incoming light. This is generally due to the fact that a picture of only one focal plane should be reflected by the spatial light modulator 114 and/or detected by the at least one optical sensor 116. Still, this preferred setup generally is impeded by the technical challenge that the angle of deflection of the spatial light modulator 140 is generally rather small. Thus, as an example, a deflection by a DLP, relative to an optical axis 128 (such as an angle α or β in FIG. 22), typically is the range of 10° to 20°. This constraint, however, generally does not allow for placing both the spatial light modulator 114 and the optical sensors 160 perpendicular to the local optical axis.

In order to overcome the technical challenge, generally, in this embodiment or other embodiments, specifically embodiments having a W-shaped beam path, additional optical elements 202, 204 may be used, which are adapted to provide appropriate deflection and/or beam shaping. Specifically, as shown in FIG. 22, asymmetric lenses 312 may be used in the first and second partial beam paths 194, 196. These asymmetric lenses 312 are asymmetric with regard to the local optical axis and, thus, are tilted towards the incoming light beam, thereby deflecting the light. Consequently, the plane of the asymmetric lenses 312 and the plane of the optical sensors 116 at the end of the partial beam paths 194, 196 are not necessarily parallel. Thus, generally, in the embodiment shown in FIG. 22 as well as other embodiments of the present invention, one or more symmetric lenses perpendicular to the local optical axis may be used and/or one or more asymmetric lenses which are tilted towards the local optical axis.

The setup shown in FIG. 22 thus provides several advantages. Thus, firstly, by using the asymmetric lenses 312, the above-mentioned design constraints resulting from the small angle of deflection of typical DLPs may be overcome. Further, the setup reduces the number of transparent optical sensors 158 and improves the usage of light that is reflected by the spatial light modulator 114, since deflections in both directions are considered. The use of additional mirrors and the positioning of the reflective spatial light modulator 114 perpendicular to the optical axis 128 allow for using a large variety of optical elements and transfer devices 126 such as lens systems, objectives or other optical elements, specifically for shaping the incoming light beam 136.

Figure 23:
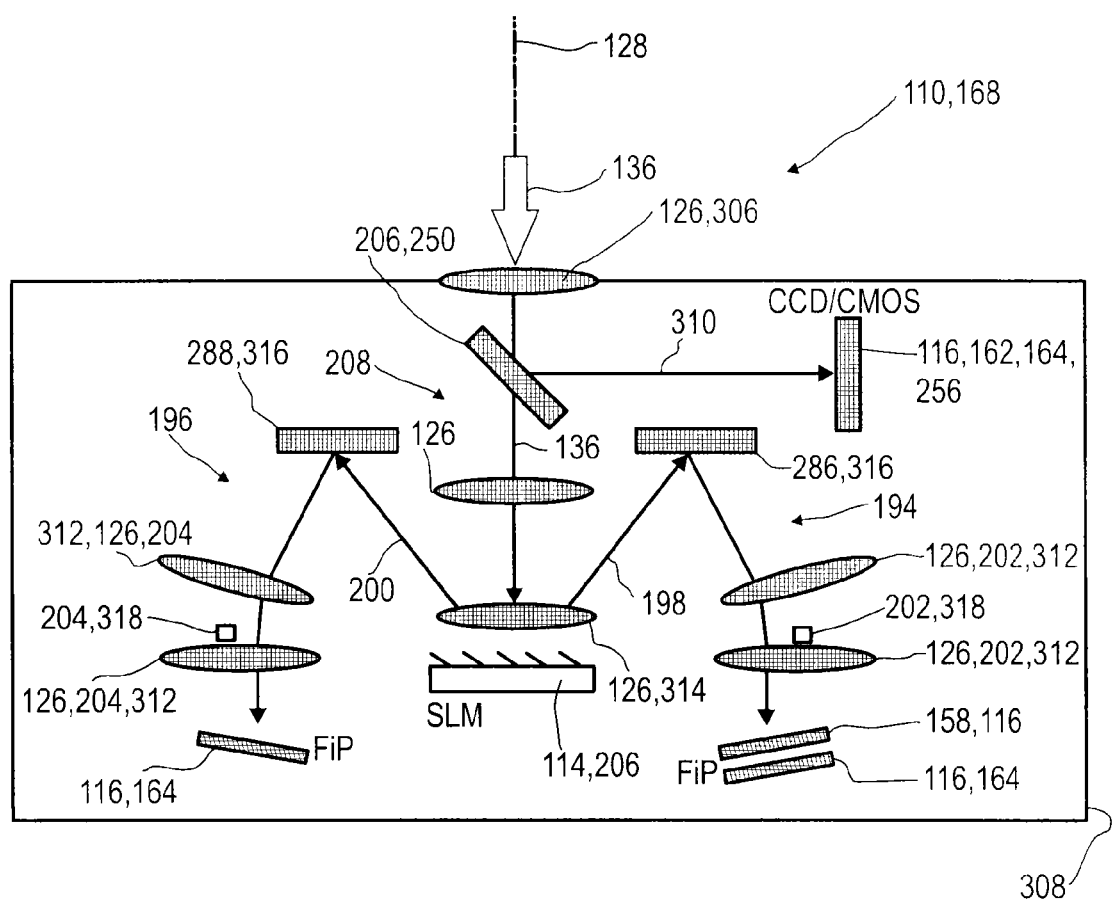

The setup of the optical detector 110 and the camera 168 as shown in FIG. 18 or 22 may further be modified in various ways, some of which will be explained with respect to FIG. 23. In this Figure, a setup of an optical detector 110 and a camera 168 is depicted which widely corresponds to the setup of FIG. 22. Still, the embodiment comprises several optional modifications.

Thus, firstly, the transfer device 126 and/or the additional optical elements 202, 204 in the partial beam paths 194, 196 may contain additional and/or alternative optical elements. Thus, as an example, a field lens 314 may be placed in front of the spatial light modulator 114 such as in front of the DLP. By using this field lens 314, an image on the spatial light modulator 114 may be modified, and/or a size of an image and/or a size of a light spot on the spatial light modulator 114 may be modified or corrected.

As an additional or alternative modification of the setup, the reflective elements 286, 288 may be modified. Thus, one or both of these reflective elements 286, 288, which specifically may be embodied as mirrors, may be flat and planar reflective elements. Alternatively, one or both of these reflective elements 286, 288 may be embodied non-planar or curved. Consequently, one or both of these reflective elements 286, 288 may comprise one or more curved mirrors 316. Thereby, the beam properties of the partial light beams 198, 200 may be modified, such as by focusing and/or defocusing these partial light beams 198, 200.

Further, additionally or alternatively, the additional optical elements 202, 204 may contain one or more apertures or diaphragms, as outlined above. This includes the possibility that so-called inverted apertures are used. As used herein, an inverted aperture is aperture which comprises one or more openings other than simple hole-shaped openings. Specifically, as depicted in FIG. 23, one or more inverted apertures 318 may be provided in the partial beam paths 194, 196 which block a central part of the partial light beams 198, 200. Specifically, this central part of the partial light beams 198, 200 may not be focused and, therefore, may not be adapted to give depth information and, thus, may not contribution to gaining information about a longitudinal coordinate. Consequently, this part of the partial light beams 198, 200 may be blocked by using one or more inverted apertures 318. It shall be noted that other types of apertures may be used in order to block unwanted parts of the light beam 136 or of one or more partial light beams derived thereof.

Figure 24:
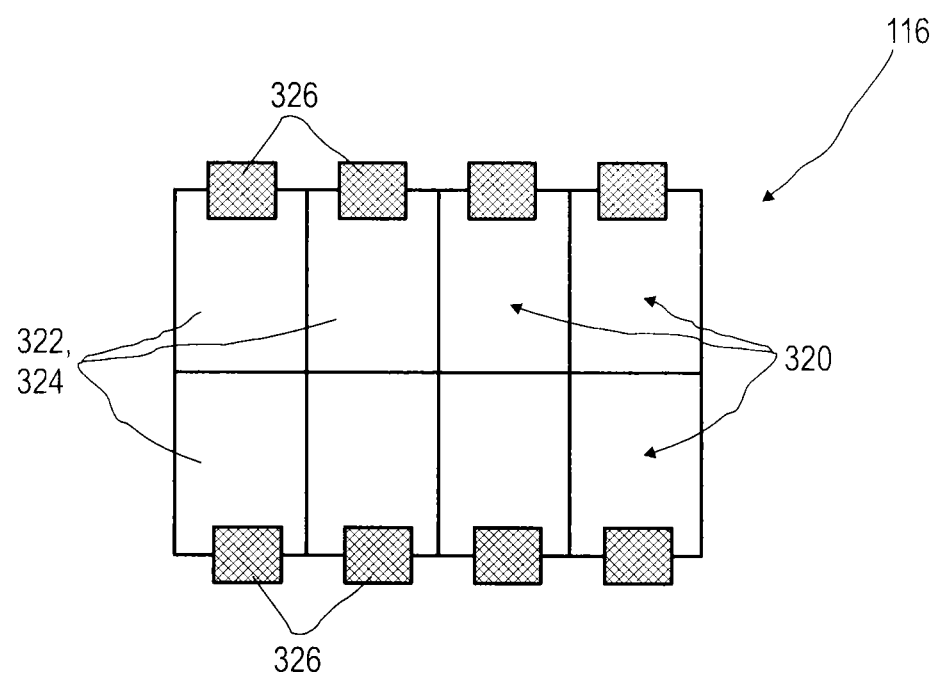
FIG. 24 shows an embodiment of an optical sensor comprising an array of 2×4 sensor pixels.

As outlined above, in some embodiments, it might be preferable if the at least one optical sensor 116 comprises an array of 2×N sensor pixels. Thus, these types of pixelated optical sensors 116 may provide advantages regarding manufacturing and/or evaluation of signals. An example of an embodiment of an optical sensor 116 having 2×4 sensor pixels 320 is shown in FIG. 24. For the general setup of the optical sensor 116, as an example, reference may be made to WO 2012/110924 A1, such as to FIG. 2 and the corresponding description, and/or to WO 2014/097181 A1, such as to FIG. 4a and the corresponding description.

In FIG. 24, only a transparent first electrode 322 of a layer setup of the optical sensor 116 is shown which is, as an example, made of a transparent conductive oxide (TCO) such as fluorinated tin oxide. The first electrode 322 is split into a plurality of electrode fields 324, such as by laser patterning and/or by using lithographic techniques. The electrode fields 324 form an array of 2 rows and 4 columns, i.e., in this example, a 2×4 array. As the skilled person will recognize, a different number of columns may be used, such as 2, 3, 5, 6, 7 or more columns. Each electrode fields 324 may be contacted by an electrical contact 326, such that the first row and the second row are electrically contacted from opposing sides, with the electrical contacts 326 being located at an outer rim of the optical sensor 116.

The first electrode 322 and the electrode contacts 326 may be deposited on a transparent substrate such as a glass substrate. On top of the first electrode 322, the remaining layers of the optical sensor 116 may be deposited, such as by using methods and/or materials as disclosed in one or both of the above-mentioned documents WO 2012/110924 A1 and/or to WO 2014/097181 A1 and/or any other methods or materials disclosed herein. Further, the optical sensor 116 may be encapsulated, as also disclosed in one or both of the mentioned documents. The negligible cross conductivities in the remaining layers generally prevent cross talk between neighboring sensor pixels 320. Thus, the layer setup of the optical sensor 116 may contain a common top electrode or second electrode (not depicted), such as a silver electrode, contacting all sensor pixels 320. Additionally or alternatively, two or more or even all of the sensor pixels 320 may be contacted by individual top electrodes or second electrodes.

An optical sensor 116 having an array of sensor pixels 320, such as a 2×N array, is especially suitable for devices as disclosed in the present invention, such as for an SLM camera, for various reasons:

(1) The SLM-camera may modulate each depth-area with a distinct frequency. At high frequencies, the FiP-signal gets weak. Thus, only a limited number of frequencies, and thus depth points can be used. If the sensor is split up into sensor pixels, the number of possible depth points that can be detected, multiplies with the number of sensor pixels 2 sensor pixels results in twice the number of depth points.

(2) As opposed to a normal camera, the shape of the sensor pixels generally is not relevant for the appearance of the picture.

(3) The frequency range improves, when smaller sensors (or sensor pixels) are used. In a small sensor pixel, more frequencies (depth points) can be sensed than in a large sensor pixel.

LIST OF REFERENCE NUMBERS 110 optical detector
112 detector system
114 spatial light modulator
116 optical sensor
118 modulator device
120 evaluation device
122 beacon device
124 Object
126 transfer device
128 optical axis
130 coordinate system
132 Matrix
134 Pixel
136 light beam
138 sensor region
140 demodulation device
142 result of frequency analysis
144 data processing device
146 data memory
148 light spot
150 frequency mixers
152 low pass filter
154 housing
156 large-area optical sensor
158 transparent optical sensor
160 organic optical sensor
162 inorganic optical sensor
164 intransparent optical sensor
166 Stack
168 camera
170 beam dump
172 full-color spatial light modulator
174 human-machine interface
176 entertainment device
178 tracking system
180 connector
182 control element
184 User
186 opening
188 direction of view
190 machine
192 track controller
194 first partial beam path
196 second partial beam path
198 first partial light beam
200 second partial light beam
202 additional optical element
204 additional optical element
206 beam-splitting element
208 beam path
210 Car
212 windshield
214 front part
216 headlights
218 bumpers
220 side region
222 passenger doors 224 Roof
226 rear part
228 FiP-sensor
230 image sensor
232 capture 2D image
234 2D image
236 detect regions
238 define superpixels
240 assign modulation frequencies to superpixels
242 modulate superpixels
244 z-detection
246 generate 3D image
248 refine regions and/or superpixels
250 first beam-splitting element
252 first partial light beam
254 main light beam
256 imaging device
258 first partial beam path
260 diaphragm
262 lens system
264 second beam-splitting element
266 second partial light beam
268 second partial beam path
270 third partial light beam
272 third partial beam path
274 back-reflected second partial light beam
276 back-reflected third partial light beam
278 common light beam
280 fourth partial beam path
282 first half-wave-plate
284 second half-wave-plate
286 reflective element
288 reflective element
290 first type of optical sensor
292 second type of optical sensor
294 SLM detector
296 time-of-flight (ToF) detector
298 pulses
300 first partial beam path
302 second partial beam path
304 beam-splitting element
306 first lens
308 casing
310 imaging partial light beam
312 asymmetric lens
314 field lens
316 curved mirror
318 inverted aperture
320 sensor pixel
322 first electrode
324 electrode field
326 electrical contact

The invention claimed is:

1. An optical detector, comprising:
at least one spatial light modulator within the optical detector and which modifies at least one property of a light beam in a spatially resolved fashion, said modulator comprising a matrix of pixels, each pixel being controllable to individually modify the at least one optical property of a portion of the light beam passing the pixel;
at least one optical sensor which detects the light beam after passing the matrix of pixels of the spatial light modulator and for generating at least one sensor signal;
at least one modulator device which periodically controls at least two of the pixels with different modulation frequencies for activation of the at least two of the pixels; and
at least one evaluation device which performs a frequency analysis in order to determine signal components of the sensor signal for the modulation frequencies.

2. The optical detector according to claim 1,
wherein the evaluation device assigns each signal component to a respective pixel in accordance with a modulation frequency of the signal component.

3. The optical detector according to claim 1,
wherein each of the pixels is controlled at a unique modulation frequency.

4. The optical detector according to claim 1,
wherein the modulator device periodically modulates the at least two pixels with the different modulation frequencies.

5. The optical detector according to claim 1,
wherein the evaluation device performs the frequency analysis by demodulating the sensor signal with different modulation frequencies.

6. The optical detector according to claim 1,
wherein the at least one property of the light beam modified by the spatial light modulator in a spatially resolved fashion is at least one property selected from the group consisting of: an intensity of the portion of the light beam; a phase of the portion of the light beam; a spectral property of the portion of the light beam; a polarization of the portion of the light beam; and a direction of propagation of the portion of the light beam.

7. The optical detector according to claim 1,
wherein the at least one spatial light modulator comprises at least one spatial light modulator selected from the group consisting of:
a transmissive spatial light modulator,
wherein the light beam passes through the matrix of pixels and
wherein the pixels modifies the optical property for each portion of the light beam passing through the respective pixel in an individually controllable fashion;
a reflective spatial light modulator,
wherein the pixels have individually controllable reflective properties
and individually change a direction of propagation for each portion of the light beam being reflected by the respective pixel;
an electrochromic spatial light modulator, and
wherein the pixels have controllable spectral properties individually
controllable by an electric voltage applied to the respective pixel;
an acousto-optical spatial light modulator,
wherein a birefringence of the pixels is controllable by acoustic waves;
an electro-optical spatial light modulator,
wherein a birefringence of the pixels is controllable by electric fields.

8. The optical detector according to claim 1,
wherein the at least one spatial light modulator comprises at least one spatial light modulator selected from the group consisting of:
a liquid crystal device,
wherein the pixels are individually controllable cells of the liquid crystal device;

a micro-minor device,
wherein the pixels are micro-mirrors of the micro-mirror device individually controllable with regard to an orientation of their reflective surfaces;
an electrochromic device,
wherein the pixels are cells of the electrochromic device having spectral properties individually controllable by an electric voltage applied to the respective cell;
an acousto-optical device,
wherein the pixels are cells of the acousto-optical device having a birefringence individually controllable by acoustic waves applied to the cells;
an electro-optical device,
wherein the pixels are cells of the electro-optical device having a birefringence individually controllable by electric fields applied to the cells.

9. The optical detector according to claim 1,
wherein the evaluation device assigns each of the signal components to a pixel of the matrix.

10. The optical detector according to claim 1,
wherein the evaluation device determines which pixels of the matrix are illuminated by the light beam by evaluating the signal components.

11. The optical detector according to claim 1,
wherein the evaluation device identifies at least one of a transversal position of the light beam and an orientation of the light beam, by identifying a transversal position of pixels of the matrix illuminated by the light beam.

12. The optical detector according to claim 1,
wherein the evaluation device determines a width of the light beam by evaluating the signal components.

13. The optical detector according to claim 1,
wherein the evaluation device identifies the signal components assigned to pixels being illuminated by the light beam and to determine the width of the light beam at the position of the spatial light modulator from known geometric properties of the arrangement of the pixels.

14. The optical detector according to claim 1,
wherein the evaluation device, using a known or determinable relationship between a longitudinal coordinate of an object from which the light beam propagates towards the detector and one or both of a width of the light beam at the position of the spatial light modulator or a number of pixels of the spatial light modulator illuminated by the light beam determines a longitudinal coordinate of the object.

15. The optical detector according to claim 1,
wherein the spatial light modulator comprises pixels of different colors,
wherein the evaluation device assigns the signal components to the different colors.

16. The optical detector according to claim 1,
wherein the at least one optical sensor comprises at least one large-area optical sensor for detecting a plurality of portions of the light beam passing through a plurality of the pixels.

17. The optical detector according to claim 1,
wherein the at least one optical sensor comprises a stack of at least two optical sensors.

18. The optical detector according to claim 17,
wherein at least one of the optical sensors of the stack is an at least partially transparent optical sensor.

19. The optical detector according to claim 17,
wherein at least one of the optical sensors of the stack is a pixelated optical sensor having a plurality of light-sensitive pixels.

20. The optical detector according to claim 1,
wherein the at least one optical sensor has at least one sensor region, wherein the sensor signal of the optical sensor is dependent on an illumination of the sensor region by the light beam,
wherein the sensor signal, given the same total power of the illumination, is dependent on a width of the light beam in the sensor region.

21. The optical detector according to claim 1,
wherein the at least one optical sensor comprises at least one optical sensor having a layer setup comprising at least one first electrode, at least one n-semiconducting metal oxide, at least one dye, at least one p-semiconducting organic material, and at least one second electrode.

22. The optical detector according to claim 1,
further comprising:
at least one transfer device which feeds light into the optical detector.

23. The optical detector according to claim 1,
wherein the spatial light modulator is a reflective spatial light modulator,
wherein the optical sensor comprises at least one transparent optical sensor,
wherein the optical detector is set up such that the light beam passes through the transparent optical sensor before reaching the spatial light modulator, and
wherein the spatial light modulator at least partially reflects the light beam back towards the optical sensor.

24. The optical detector according to claim 1,
comprising:
at least one beam-splitting element which divides a beam path of the light beam into at least two partial beam paths.

25. The optical detector according to claim 24,
wherein the beam-splitting element comprises the spatial light modulator.

26. The optical detector according to claim 1,
wherein at least one stack of optical sensors is located in at least one of the partial beam paths.

27. The optical detector according to claim 1,
wherein at least one intransparent optical sensor is located in at least one of the partial beam paths.

28. A detector system for determining a position of at least one object, the detector system comprising:
the optical detector according to claim 1, and
at least one beacon device which directs at least one light beam towards the optical detector,
wherein the beacon device is at least one of attachable to the object, holdable by the object and integratable into the object.

29. A human-machine interface for exchanging at least one item of information between a user and a machine, the human-machine interface comprising:
the detector system according to claim 28,
wherein the at least one beacon device is at least one of directly or indirectly attached to the user and held by the user,
wherein the human-machine interface determines at least one position of the user with the detector system, and
wherein the human-machine interface assigns to the position at least one item of information.

30. An entertainment device for carrying out at least one entertainment function, the entertainment device comprising:
the human-machine interface according to claim 29,
wherein the entertainment device enables at least one item of information to be input by a player with the human-machine interface, and
wherein the entertainment device varies the entertainment function in accordance with the information.

31. A tracking system for tracking a position of at least one movable object, the tracking system comprising:
the detector system according to claim 28; and at least one track controller,
wherein the track controller tracks a series of positions of the object at specific points in time.

32. A camera for imaging at least one object, the camera comprising:
the optical detector according to claim 1.

33. A method for producing an item of information, the method comprising:
producing the item with the optical detector according to claim 1,
wherein the item is suitable for utilization with at least one selected from the group consisting of: a position measurement in traffic technology; an entertainment application; a security application; a human-machine interface application; a tracking application; a photography application; an imaging application or camera application; a mapping application for generating maps of at least one space; a mobile application; a webcam; a computer peripheral device; a gaming application; a camera or video application; a security application; a surveillance application; an automotive application; a transport application; a medical application; a sports application; a machine vision application; a vehicle application; an airplane application; a ship application; a spacecraft application; a building application; a construction application; a cartography application; a manufacturing application; an application in combination with at least one time-of-flight detector; an application in a local positioning system; an application in a global positioning system; an application in a landmark-based positioning system; an application in an indoor navigation system; an application in an outdoor navigation system; an application in a household application; a robot application; an application in an automatic door opener; and an application in a light communication system.

34. A method of optical detection, the method comprising:
modifying within an optical detector at least one property of a light beam in a spatially resolved fashion with at least one spatial light modulator, the spatial light modulator having a matrix of pixels, each pixel being controllable to individually modify the at least one optical property of a portion of the light beam passing the pixel;
detecting the light beam after passing the matrix of pixels of the spatial light modulator with at least one optical sensor and for generating at least one sensor signal;
periodically controlling at least two of the pixels with different frequencies with at least one modulator device for activation of the at least two of the pixels; and
performing a frequency analysis by using at least one evaluation device and
determining signal components of the sensor signal for the control frequencies.

\* \* \* \* \*